(12) United States Patent
Taylor et al.

(10) Patent No.: US 9,738,707 B2
(45) Date of Patent: Aug. 22, 2017

(54) HETERODIMERIC FC REGIONS, BINDING MOLECULES COMPRISING SAME, AND METHODS RELATING THERETO

(75) Inventors: Frederick R. Taylor, Milton, MA (US); Justin A. Caravella, Cambridge, MA (US); Alexey A. Lugovskoy, Woburn, MA (US); Amna Saeed-Kothe, Medway, MA (US); Ellen A. Garber, Cambridge, MA (US)

(73) Assignee: Biogen MA Inc., Cambridge, MA (US)

( * ) Notice: Subject to any disclaimer, the term of this patent is extended or adjusted under 35 U.S.C. 154(b) by 319 days.

(21) Appl. No.: 14/232,868

(22) PCT Filed: Jul. 13, 2012

(86) PCT No.: PCT/US2012/046702
§ 371 (c)(1),
(2), (4) Date: Jul. 24, 2014

(87) PCT Pub. No.: WO2013/012733
PCT Pub. Date: Jan. 24, 2013

(65) Prior Publication Data
US 2014/0341906 A1 Nov. 20, 2014

Related U.S. Application Data

(60) Provisional application No. 61/508,583, filed on Jul. 15, 2011.

(51) Int. Cl.
*C07K 16/00* (2006.01)
*C07K 16/18* (2006.01)
*C07K 16/28* (2006.01)

(52) U.S. Cl.
CPC ............ *C07K 16/18* (2013.01); *C07K 16/00* (2013.01); *C07K 2317/31* (2013.01); *C07K 2317/522* (2013.01); *C07K 2317/524* (2013.01); *C07K 2317/53* (2013.01); *C07K 2317/60* (2013.01); *C07K 2317/66* (2013.01)

(58) Field of Classification Search
CPC .... C07K 16/00; C07K 16/18; C07K 16/3007; C07K 16/2851; C07K 16/3092; C07K 16/2884; C07K 16/2887; C07K 16/2806; C07K 16/2809; C07K 16/22; C07K 16/2878; C07K 16/2896; C07K 16/2863; C07K 2317/66; C07K 2317/31; C07K 2317/60; C07K 2317/53; C07K 2317/522; C07K 2317/524; C07K 2317/526; C07K 2317/56
See application file for complete search history.

(56) References Cited

U.S. PATENT DOCUMENTS

| 6,737,056 | B1 * | 5/2004 | Presta | C07K 16/28 424/133.1 |
| 2009/0252729 | A1 * | 10/2009 | Farrington | A61K 47/48338 424/135.1 |
| 2013/0095097 | A1 * | 4/2013 | Blankenship | C07K 16/2818 424/133.1 |

FOREIGN PATENT DOCUMENTS

| EP | 2 281 845 | 2/2011 |
| WO | WO 2009/080254 | 7/2009 |
| WO | WO 2010/145792 | 12/2010 |

OTHER PUBLICATIONS

Stancovski et al., Proc. Natl. Acad. Sci 88: 8691-8695, 1991.*
Wu et al., J Mol Biol 294: 151-162, 1999.*
Rudikoff et al., Proc. Natl. Acad. Sci. USA 79: 1979-1983, 1982.*
Paul, Fundamental Immunology, (textbook), 1993, pp. 292-295.*
Jubala et al., Vet Pathol 42: 468-476, 2005.*
Yu et al., Investigative Ophthalmology & Visual Science 49(2): 522-527, Feb. 2008.*
Golay et al., Archives of Biochemistry and Biophysics 526: 146-153, 2012.*
International Search Report and Written Opinion in International Application No. PCT/US2012/046702, dated Sep. 5, 2012, 10 pages.
International Preliminary Report on Patentability in International Application No. PCT/US2012/046702, dated Jan. 21, 2014, 7 pages.
Capon et al., "Designing CD4 immunoadhesins for AIDS therapy," Nature. Feb. 9, 1989;337(6207):525-31.
Dall'Acqua et al., "Increasing the affinity of a human IgG1 for the neonatal Fc receptor: biological consequences," J Immunol Nov. 1, 2002;169(9):5171-80.
Ghetie et al., "Increasing the serum persistence of an IgG fragment by random mutagenesis," Nat Biotechnol. Jul. 1997;15(7):637-40.
Gunasekaran et al., "Enhancing antibody Fc heterodimer formation through electrostatic steering effects: applications to bispecific molecules and monovalent IgG," J Biol Chem. Jun. 18, 2010;285(25):19637-46.
Kim et. al., "Identifying amino acid residues that influence plasma clearance of murine IgG1 fragments by site-directed mutagenesis," Eur J Immunol Mar. 1994;24(3):542-8.
Merchant et al., "An efficient route to human bispecific IgG," Nat Biotechnol. Jul. 1998;16(7):677-81.
Muda et al., "Therapeutic assessment of SEED: a new engineered antibody platform designed to generate mono- and bispecific antibodies," Protein Eng Des Sel. May 2011;24(5):447-54.
Ward and Ghetie, "The effector functions of immunoglobulins: implications for therapy," Ther Immunol. Apr. 1995;2(2):77-94.

* cited by examiner

*Primary Examiner* — Phuong Huynh
(74) *Attorney, Agent, or Firm* — Fish & Richardson P.C.

(57) ABSTRACT

The present invention features inter alia polypeptides comprising heterodimeric Fc regions. In addition, the instant invention provides methods for treating or preventing a disease or disorder in subject by administering the polypeptides of the invention to said subject.

33 Claims, 19 Drawing Sheets

CH1CL

Fc

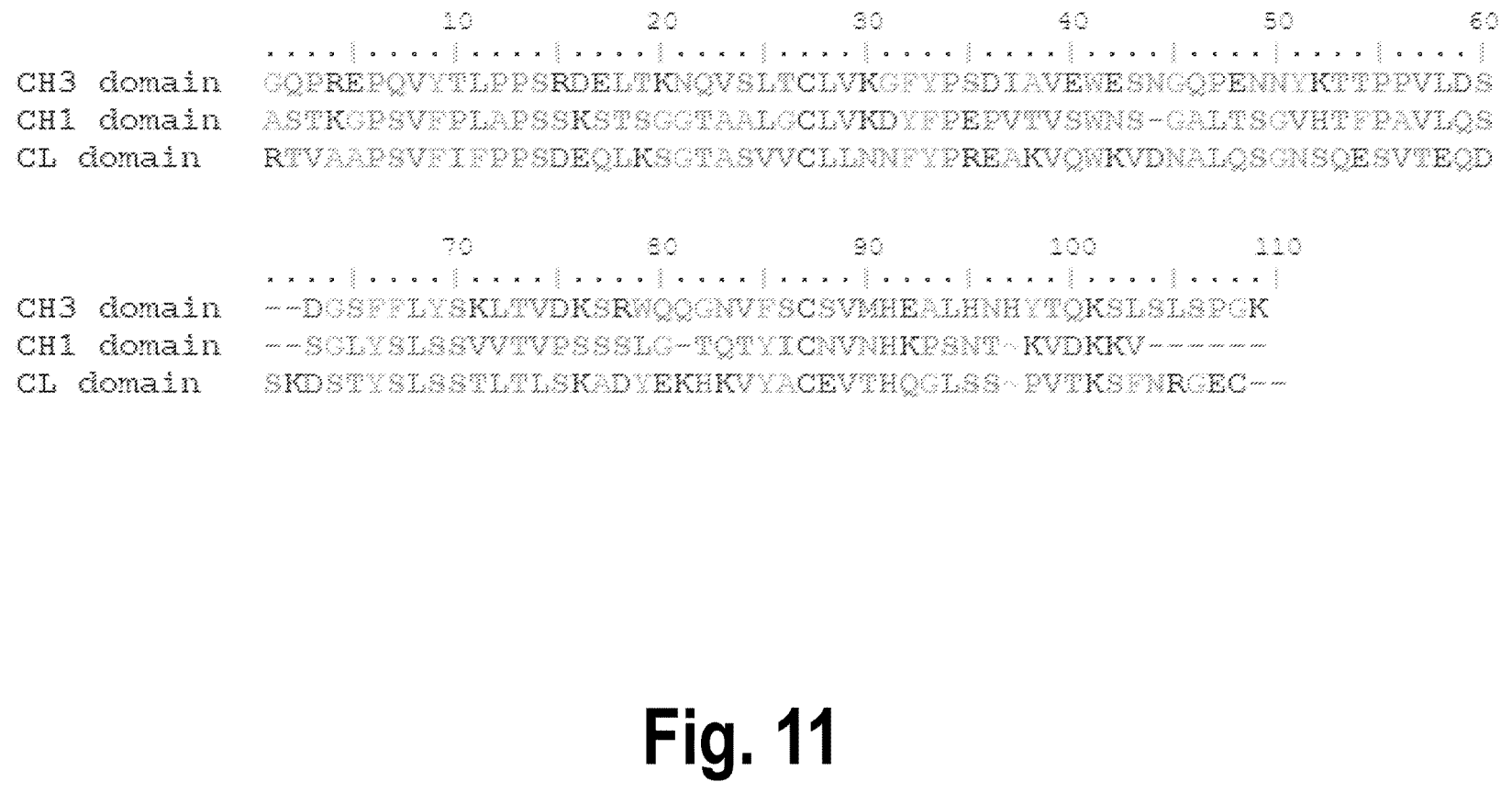

```
                 10         20         30         40         50         60
            ....|....|....|....|....|....|....|....|....|....|....|....|
CH3 domain  CQPREPQVYTLPPSRDELTKNQVSLTCLVKGFYPSDIAVEWESNGQPENNYKTTPPVLDS
CH1 domain  ASTKGPSVFPLAPSSKSTSGGTAALGCLVKDYFPEPVTVSWNS-GALTSGVHTFPAVLQS
CL  domain  RTVAAPSVFIFPPSDEQLKSGTASVVCLLNNFYPREAKVQWKVDNALQSGNSQESVTEQD 70         80         90        100        110
            ....|....|....|....|....|....|....|....|....|....|
CH3 domain  --DGSFFLYSKLTVDKSRWQQGNVFSCSVMHEALHNHYTQKSLSLSPGK
CH1 domain  -SGLYSLSSVVTVPSSSLG-TQTYICNVNHKPSNT-KVDKKV------
CL  domain  SKDSTYSLSSTLTLSKADYEKHKVYACEVTHQGLSS-PVTKSFNRGEC---
```

Fig. 11

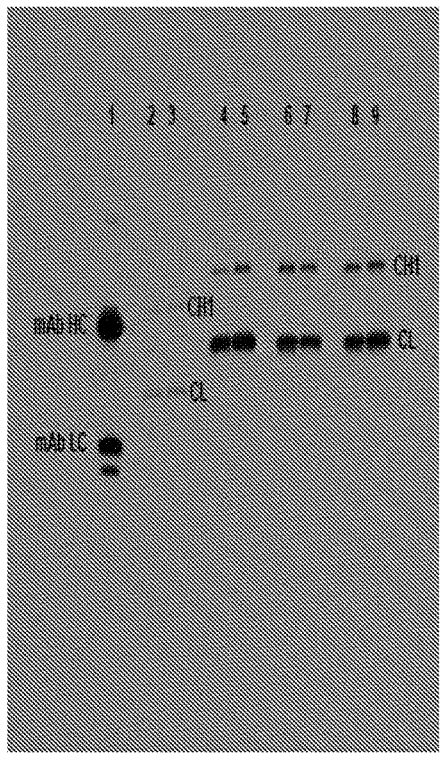
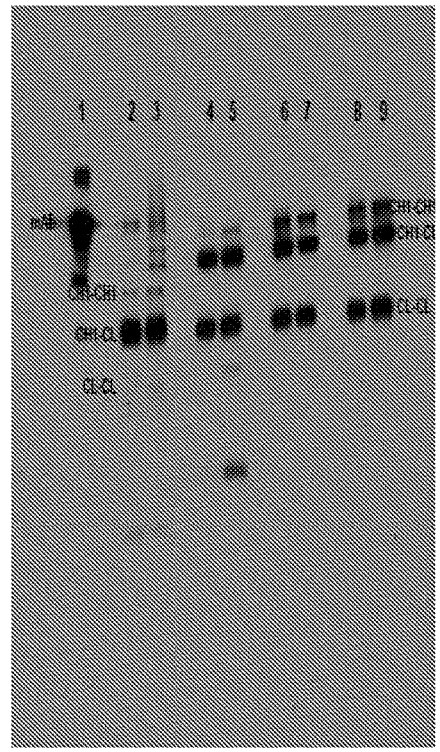
Fig. 12
Fig. 13
| Lane # | Construct | Expression medium |
|---|---|---|
| 1 | Human IgG1 mAb | |
| 2 | C0/D0, Table 6 | CHOII |
| 3 | C0/D0, Table 6 | CHO39 |
| 4 | Design 2, Table 8 | CHOII |
| 5 | Design 2, Table 8 | CHO39 |
| 6 | Design 3, Table 8 | CHOII |
| 7 | Design 3, Table 8 | CHO39 |
| 8 | Design 3, Table 8 | CHOII |
| 9 | Design 3, Table 8 | CHO39 |

Western blot of pairs of constructs that bind FcRn

FcRn binding of CL-CH1 heterodimers

Protein A binding of CL-CH1 heterodimers

SDS-PAGE demonstrating heterodimer formation by constructs with modification of potential T cell epitopes Lanes 1-5 non-reducing
Lanes 6-11 reducing

| Lanes | Construct |
|---|---|
| 1, 7 | huIgG1 standard |
| 2, 8 | C2 / D2 |
| 3, 9 | C2.2 / D2.2 |
| 4, 10 | C2.2 / D2.3 |
| 5, 11 | C2.2 / D2.4 |

Fig. 19

FcRn binding by constructs with modification of potential T cell epitopes

Hu IgG1 mAb standard

C2.2
D2.2

C2.2
D2.3

C2.2
D2.4

Binding to FcRn by Octet.
Association and dissociation conducted at pH 5.9

Fig. 20

HETERODIMERIC FC REGIONS, BINDING MOLECULES COMPRISING SAME, AND METHODS RELATING THERETO

SEQUENCE LISTING

The instant application contains a Sequence Listing which has been submitted electronically in ASCII format and is hereby incorporated by reference in its entirety. Said ASCII copy, created on Mar. 20, 2017, is named 13751-0173US1_SL.txt and is 187,740 bytes in size.

BACKGROUND OF THE INVENTION

The native structure of the IgG immunoglobulin class consists of a covalently linked homodimer comprised of two heavy and two light chains. Thus a monoclonal IgG will bind two molecules of antigen simultaneously (monospecific bivalency). It is preferred for some therapeutic purposes that the IgG bind only a single antigen molecule (monovalency) or bind two different antigens simultaneously (bispecific bivalency) while retaining the long half-life and potential for effector function of the native IgG immunoglobulin. For these purposes the molecular properties of the IgG need to be engineered to prevent homodimerization. Methods described in the art for preventing homodimerization have either not been adequately efficient or give less stable products (Merchant et al 1998 Nature Biotechnology 16:677; Gunasekaran et al 2010 J. Biol. Chem. 285:19637; Muda et al 2011 Proten Engineering, Design, and Selection 24:447).

It is critical in designing a new method for achieving heterodimerization versus homodimerization that the desirable attributes of the Fc domain of the IgG be retained. The Fc region of an immunoglobulin mediates effector functions that have been divided into two categories. In the first are functions that occur independently of antigen binding; these functions confer persistence in circulation and the ability to be transferred across cellular barriers by transcytosis (see Ward and Ghetie, *Therapeutic Immunology* 2:77-94, 1995, Capon et al. *Nature* 1989). The circulatory half-life of the IgG subclass of immunoglobulins is regulated by the affinity of the Fc region for the neonatal Fc receptor or FcRn (see Ghetie et al., *Nature Biotechnol.* 15:637-640, 1997; Kim et. al., *Eur. J. Immunol.* 24:542-548, 1994; Dall'Acqua et al. (*J. Immunol.* 169:5171-5180, 2002). The second general category of effector functions include those that operate after an immunoglobulin binds an antigen. In the case of IgG, these functions involve the participation of the complement cascade or Fc gamma receptor (FcγR)-bearing cells. Binding of the Fc region to an FcγR causes certain immune effects, for example, endocytosis of immune complexes, engulfment and destruction of immunoglobulin-coated particles or microorganisms (also called antibody-dependent phagocytosis, or ADCP), clearance of immune complexes, lysis of immunoglobulin-coated target cells by killer cells (called antibody-dependent cell-mediated cytotoxicity, or ADCC), release of inflammatory mediators, regulation of immune system cell activation, and regulation of immunoglobulin production.

Certain engineered binding polypeptides (e.g., antibody variants (e.g., scFvs) or antibody fragments (e.g., Fab fragments)), while benefiting from their smaller molecular size and/or monovalency, also suffer several disadvantages attributable to the absence of a functional Fc region. For example, Fab fragments have short half-lives in vivo because they lack the Fc region that is required for FcRn binding and are rapidly filtered out of the blood by the kidneys owing to their small size.

Accordingly, there is a need for Fc-containing binding molecules which can be produced and isolated efficiently and robustly while retaining desired Fc effector function(s) and providing desired valencies and specificities.

SUMMARY OF THE INVENTION

The present invention features inter alia binding molecules comprising one or more heterodimeric Fc regions. The subject binding molecules exhibit a spontaneous pairing interaction between a CH1 moiety in a first polypeptide chain and a CL moiety in a second polypeptide chain. Thus, the first and second constituent polypeptides of the binding molecule form a CH1:CL heterodimer via CH1:CL heterodimerization.

While CH1:CL heterodimers can be found in conventional antibodies and antibody fragments (e.g., Fab fragments), the binding molecules of the invention differ significantly from such molecules at least in that they comprise an CH1:CL heterodimer located in a heterodimeric Fc region. In certain embodiments, one or more component Fc moieties of the Fc region are fused to a terminus (preferably the N-terminus) of a CL moiety of a first polypeptide. In one embodiment, the one or more component Fc moieties (e.g., a CH2 and/or CH3 moiety) are interposed between the CL moiety and a binding moiety (e.g., an antigen binding site). In additional or alternative embodiments, one or more Fc moieties (e.g., CH2 and/or CH3 moieties) of the Fc region are fused to a terminus (preferably the N-terminus) of the CH1 moiety of a second polypeptide. In some embodiments, the one or more component Fc moieties are interposed between the CH1 moiety and a binding moiety (e.g., an antigen binding site). In one embodiment, the heterodimeric Fc region of a binding molecule of the invention lacks CH3 domains.

The heterodimeric binding molecules of the invention provide several advantages over conventional binding molecules (e.g., engineered binding molecules comprising peptide sequences derived or originating from immunoglobulins, such as scFv and Fab fragments). In certain aspects, the heterodimeric Fc regions of the molecules of the invention may be operably linked to a target binding moiety (e.g., to an antigen binding fragment (e.g., a Fab) or an scFv molecule) to form a heteromeric binding molecule, thereby imparting an effector function to the binding moiety. Heteromeric binding molecules of the invention may be monovalent (i.e., comprise a single binding site) or multivalent (i.e., comprise multiple binding sites). Additionally, the binding molecules may be monospecific (i.e., have binding specificity for a single target molecule or epitope) or multispecific (i.e., having binding specificity for two or more target molecules or epitopes).

In certain embodiments, novel heteromeric binding molecules of the invention combine the advantages of a monovalent binding polypeptide (e.g., the lack of cell-surface receptor crosslinking that can lead to unwanted cell signaling and/or endocytosis) with the advantages of Fc-mediated effector functions (e.g. longer half-life due to binding by FcRn, FcγRI, FcγRII, and FcγRIII, increase in molecular size, and/or complement activation). Moreover, the heteromeric binding molecules of the invention may be readily expressed in highly homogenous preparations that are readily scaled-up for high-yield manufacturing. For example, expression of a first polypeptide chain comprising an Fc moiety or moieties interposed between one or more target binding moieties (e.g., antigen binding sites, such as one or more scFv or Fab fragments) and a CL moiety can be co-expressed with a second polypeptide chain comprising a CH1 moiety such that the CL and CH1 moieties spontaneously interact and drive heterodimerization of the polypeptides. Since the dimerization of CH1 and CL domains is thermodynamically favored, the homogeneity of desired heterodimeric expression products is enhanced. Thus, the diversity of expression products resulting from conventional coexpression of two or more dissimilar chains (e.g., due to homodimerization of the same chain type) is reduced.

The heterodimeric binding molecules of the invention also afford the opportunity to produce molecules having heteromeric Fc regions with highly tailored effector function. It is currently very difficult to create and purify heteromeric molecules in which the two Fc moieties which make up a conventional Fc region are different from each other, for example in which only one of the two Fc moieties comprises an amino acid modification (e.g., a single point mutation within a single CH2 and/or CH3 domain and not in both chains of the Fc region). Given the teachings of the instant application, heteromeric binding molecules in which fewer than all of the Fc moieties of the Fc region comprise a mutation can now be readily obtained due to CH1:CL heterodimerization creating heterodimers preferentially and efficiently. Such molecules are readily scaled up for manufacturing.

In one embodiment, the invention pertains to heterodimeric Fc regions, polypeptides comprising heterodimeric Fc regions and the nucleic acid molecules encoding them.

In one embodiment, the invention pertains to a polypeptide comprising
 (i) at least one binding moiety,
 (ii) a first polypeptide chain comprising at least one Fc moiety operably linked to the N-terminus of a CL moiety (Fc-CL), and
 (iii) a second polypeptide chain comprising at least one Fc moiety operably linked to the N-terminus of a CH1 moiety (Fc-CH1),
wherein said at least one binding moiety is linked to one or both of the polypeptide chains, and
wherein said first and second polypeptide chains form a heterodimeric Fc region via CL:CH1 heterodimerization.

In one embodiment, the first polypeptide chain further comprises at least one Fc moiety operably linked to the C-terminus of the CL moiety (Fc-CL-Fc) and said second polypeptide chain further comprises at least one Fc moiety operably linked to the C-terminus of the CH1 moiety (Fc-CH1-Fc).

In one embodiment, the CL moiety consists of a sequence having at least 90% sequence homology with a wild type human CL amino acid sequence.

In one embodiment, the CL moiety comprises residues corresponding to F:116, F:118, S:121, E:123, Q:124, S:127, S:131, V:133, L:135, L:136, N:137, N:138, Q:160, S:162, E:165, D:167, S:174, S:176, T:178 and T:180.

In one embodiment, the CH1 moiety consists of a sequence having at least 90% sequence homology with a wild type human CH1 amino acid sequence.

In one embodiment, the CH1 moiety comprises residues corresponding to F:126, L:128, A:129, A:141, L:142, L:145, K:147, H:168, F:170, P:171, V:173, Q:175, L:182, S:183, V:185 and K:213.

In one embodiment, heterodimerization is stabilized by one or more interchain bonds between said first and second polypeptide chains.

In one embodiment, at least one interchain bond is a covalent bond or an ionic bond.

In one embodiment, the interchain bond is selected from the group consisting of a disulfide bond, a salt bridge and a covalent bond formed by chemical conjugation.

In one embodiment, the CH1 moiety comprises a sequence selected from the group consisting of C0-C9 and wherein the CL moiety is selected from a group consisting essentially of D0-D8.

In one embodiment, a polypeptide of the invention comprises an Fc moiety comprising an amino acid sequence having at least 90% sequence homology with a wild type human CH2 amino acid sequence.

In one embodiment, a polypeptide of the invention comprises an Fc moiety comprising an amino acid sequence having at least 90% sequence homology with a wild type human CH3 Fc amino acid sequence.

In one embodiment, a polypeptide of the invention comprises an amino acid linker.

In one embodiment, a polypeptide of the invention comprises an amino acid sequence derived from an immunoglobulin hinge. In one embodiment, the hinge is a chimeric hinge.

In one embodiment, a polypeptide of the invention comprises one or more additional binding sites.

In one embodiment, the first polypeptide chain and the second polypeptide chain comprise one or more identical Fc moieties.

In one embodiment, one or more Fc moieties of the first polypeptide chain and one or more Fc moieties of the second polypeptide chain have at least 90% homology with a single immunoglobulin Fc domain sequence.

In one embodiment, one or more Fc moieties imparts at least one effector function to said binding molecule.

In one embodiment, one or more Fc moieties of a polypeptide of the invention comprise amino acids 280-299 (EU numbering) from a human immunoglobulin heavy chain sequence.

In one embodiment, one or more Fc moieties comprise amino acids 243-261, 275-280, 282-293, 302-319, 336-348, 367, 369, 372-389, 391, 393, 408, 424, 425-440 (EU numbering) from a human immunoglobulin heavy chain sequence.

In one embodiment, one or more FcRn-interacting Fc moieties comprise one or more of amino acids 243-261, 275-280, 282-293, 302-319, 336-348, 367, 369, 372-389, 391, 393, 408 or 424-440 (EU numbering) from a human immunoglobulin heavy chain sequence.

In one embodiment, comprising one or more FcRn-interacting Fc moieties comprising one or more mutations corresponding to amino acids 256, 277-281, 283-288, 303-309, 313, 338, 342, 376, 381, 384, 385, 387, 434 or 438 (EU numbering) from a human immunoglobulin heavy chain sequence.

In one embodiment, either of the first or second polypeptide chains are aglycosylated.

In one embodiment, both the first and second polypeptide chains are aglycosylated.

In one embodiment, a polypeptide of the invention comprises additional Fc portions operably linked to the C-terminus of the Fc-CH1 and Fc-CL.

In one embodiment, a polypeptide of the invention comprises the sequence of an immunoglobulin Fc region operably linked to the N-terminus of a Fab constant domain moiety.

In one embodiment, the binding moiety is operably linked to the N-terminus or the C-terminus of the first polypeptide chain.

In one embodiment, a binding moiety is operably linked to the N-terminus or the C-terminus of the second polypeptide chain.

In one embodiment, a polypeptide of the invention is monovalent.

In one embodiment, a polypeptide of the invention is multivalent.

In one embodiment, the binding moiety is selected from the group consisting of an antigen binding region, a receptor binding portion of a ligand, and a ligand binding portion of a receptor.

In one embodiment, the antigen binding moiety is derived from an antibody.

In one embodiment, the antibody is selected from the group consisting of a monoclonal antibody, a chimeric antibody, a human antibody, and a humanized antibody.

In one embodiment, the antigen binding moiety is derived from an antibody variant selected from the group consisting of a conventional scFv, a stabilized scFv, a Fab, a minibody, a diabody, a triabody, a nanobody, a camelid, and a Dab.

In one embodiment, at least one binding moiety comprises at least one CDR from an antibody selected from the group consisting of M13-C06, M14-C03, M14-G11, P1E2, αIR3, CBE11, 14A2, B3F6, 2B8, Lym 1, Lym 2, LL2, Her2, B1, MB1, BH3, B4, B72.3, CC49, 5E10 and 1D5.

In one embodiment, the site is a ligand binding portion of a receptor is derived a receptor selected from the group consisting of a receptor of the Immunoglobulin (Ig) superfamily, a receptor of the TNF receptor superfamily, a receptor of the G-protein coupled receptor (GPCR) superfamily, a receptor of the Tyrosine Kinase (TK) receptor superfamily, a receptor of the Ligand-Gated (LG) superfamily, a receptor of the chemokine receptor superfamily, IL-1/Toll-like Receptor (TLR) superfamily, and a cytokine receptor superfamily.

In one embodiment, the binding site is a receptor binding portion of a ligand and is derived from an inhibitory ligand.

In one embodiment, the binding site is a receptor binding portion of a ligand is derived from an activating ligand.

In one embodiment, the ligand binds a receptor selected from the group consisting of a receptor of the Immunoglobulin (Ig) superfamily, a receptor of the TNF receptor superfamily, a receptor of the G-protein coupled receptor (GPCR) superfamily, a receptor of the Tyrosine Kinase (TK) receptor superfamily, a receptor of the Ligand-Gated (LG) superfamily, a receptor of the chemokine receptor superfamily, IL-1/Toll-like Receptor (TLR) superfamily, and a cytokine receptor superfamily.

In one aspect, the invention pertains to a multivalent binding molecule comprising:

(i) a first binding moiety operably linked or fused to a first polypeptide chain comprises at least one binding moiety comprising at least a first Fc moiety, wherein said Fc moiety is operably linked to the N-terminus of a CL moiety (Fc-CL), and (ii) a second binding moiety operably linked or fused to a second polypeptide chain comprising at least a second Fc moiety operably linked to the N-terminus of a CH1 moiety (Fc-CH1), wherein said first and second polypeptide chains form a heterodimeric Fc region via CL:CH1 heterodimerization.

In one embodiment, heterodimerization is stabilized by one or more interchain disulfide bonds between said Fc-CL moiety and said Fc-CH1 moiety.

In one embodiment, the Fc-CL moiety comprises an Fc portion comprising a hinge region and a CH2 domain.

In one embodiment, the Fc-CH1 moiety comprises an Fc portion comprising a hinge region and a CH2 domain.

In one embodiment, the Fc portion of the first polypeptide and/or the Fc portion of the second polypeptide lacks all or part of a CH3 domain.

In one embodiment, the Fc portion of the first polypeptide or the Fc portion of the second polypeptide comprises at least one Fc mutation at an EU convention amino acid position within said Fc portion.

In one embodiment, the hinge is a chimeric hinge.

In one embodiment, the hinge domain of the Fc-CH1 moiety forms at least one interchain disulfide bond with the hinge domain of said Fc-CL moiety.

In one embodiment, the Fc-CL moiety and the Fc-CH1 moiety form a homomeric Fc region.

In one embodiment, the Fc-CL moiety and the Fc-CH1 moiety form a heteromeric Fc region.

In one embodiment, the homomeric Fc region or said heteromeric Fc region imparts at least one effector function to said binding molecule.

In one embodiment, the Fc region comprises a mutation located in a CH2 domain.

In one embodiment, the Fc region comprises a mutation located in a CH3 domain.

In one embodiment, the either the Fc-CL portion or the Fc-CH1 portion is aglycosylated.

In one embodiment, the both the Fc-CL portion and the Fc-CH1 portion are aglycosylated.

In one embodiment, the binding moieties have the same specificity.

In one embodiment, the binding moieties have different specificities.

In one embodiment, the specificities are for epitopes which reside on different target molecules.

In one embodiment, the specificities are for eptitopes which reside on the same target molecule.

In one embodiment, the first binding moiety is operably linked to the N-terminus or C-terminus of the first polypeptide.

In one embodiment, the second binding moiety is operably linked to the N-terminus or C-terminus of the second polypeptide.

In one embodiment, a polypeptide of the invention is a tetravalent binding molecule.

In one embodiment, the binding molecule is a scFv2 tetravalent antibody molecule.

In one embodiment, the binding molecule is a C-scFv tetravalent antibody molecule.

In one embodiment, the binding molecule is a NH-scFv tetravalent antibody molecule.

In one embodiment, the binding molecule is a NL-scFv tetravalent antibody molecule.

In one embodiment, a polypeptide of the invention comprises a third binding moiety operably linked to the C-terminus of the first polypeptide and a fourth binding moiety operably linked to the C-terminus of the second polypeptide.

In one embodiment, the the first and third binding moieties have a first binding specificity and the second and fourth binding moieties have a second binding specificity.

In one embodiment, the first and second binding moieties have a first binding specificity and the third and fourth binding moieties have a second binding specificity.

In one embodiment, a polypeptide of the invention is conjugated to at least one functional moiety.

In one embodiment, the functional moiety is selected from the group consisting of a blocking moiety, a detectable moiety, a diagnostic moiety, and a therapeutic moiety.

In one embodiment, the blocking moiety is selected from the group consisting of a cysteine adduct, mixed disulfide, polyethylene glycol, and polyethylene glycol maleimide.

In one embodiment, the detectable moiety is selected from the group consisting of a fluorescent moiety and isotopic moiety.

In one embodiment, the the diagnostic agent is capable of revealing the presence of a disease or disorder.

In one embodiment, the therapeutic moiety is selected from the group consisting of an anti-inflammatory agent, an anticancer agent, an anti-neurodegenerative agent, and an anti-infective agent.

In one embodiment, the first or second binding site binds to an antigen present on an immune cell or a tumor cell.

In one embodiment, the Fc domains are of the IgG isotype. In one embodiment, the the IgG isotype is of the IgG1 subclass. In one embodiment, the IgG isotype is of the IgG4 subclass.

In one aspec, the invention pertains to a composition comprising a population of the binding molecule of the invention, wherein at least 90% of binding molecules in the population are in heterodimeric form.

In one embodiment, a pharmaceutical composition comprises the binding molecule of any of the preceding claims.

In one embodiment, the invention pertains to a nucleic acid molecule comprising a nucleotide sequence encoding the first polypeptide of a heterodimeric polypeptide of the invention. In one embodiment, the invention pertains to a nucleic acid molecule comprising a nucleotide sequence encoding the second polypeptide of a heterodimeric polypeptide of the invention.

In one embodiment, a nucleic acid molecule of the invention is present in an expression vector. In one embodiment, the invention pertains to host cells comprising an expression vector of the invention.

In one embodiment, the invention pertains to a disease or disorder in a subject, comprising administering the pharmaceutical composition of the invention to the subject.

In one embodiment, the disease or disorder is selected from the group consisting of an inflammatory disorder, an autoimmune disorder, and a neoplastic disorder.

In one embodiment, the invention pertains to a method for producing a heteromultimeric binding molecule said method comprising the steps of:
(a) expressing in a host cell a recombinant DNA construct encoding a first polypeptide chain comprising an Fc-CL moiety; and
(b) expressing in a host cell a recombinant DNA construct encoding a second polypeptide chain comprising an Fc-CH1 moiety;
(c) combining the first and second polypeptide chains under conditions such that the Fc-CH1 moiety stably associates with the Fc-CH1 moiety vian Fc-CL:Fc-CH1 heterodimerization; and
(d) recovering said heteromultimeric binding molecule, wherein the binding molecule comprises at least one binding moiety which is operably linked to said first or second polypeptide chain.
In one embodiment, the constructs are on the same expression vector. In one embodiment, the constructs are on different expression vectors. In one embodiment, the constructs are expressed in different host cells. In one embodiment, the constructs are expressed in the same host cell.

In one embodiment, the host cell is a mammalian cell.

In one embodiment, the binding molecule comprises a first binding moiety that is operably linked to said first polypeptide and a second binding moiety that is operably linked to said second polypeptide.

Heterodimerization of the binding molecule is driven by the spontaneous pairing interaction exhibited by the CH1 and CL moieties. This pairing interaction can be further stabilized by the inclusion of interchain disulfide bonds (e.g., between (i) the CH1 and CL moieties and/or (ii) hinge portions of Fc moieties). Inclusion of Fc moieties facilitate robust protein expression and Fc effector functionality (e.g., enhanced FcRn binding for increased half-life).

Figure 3:
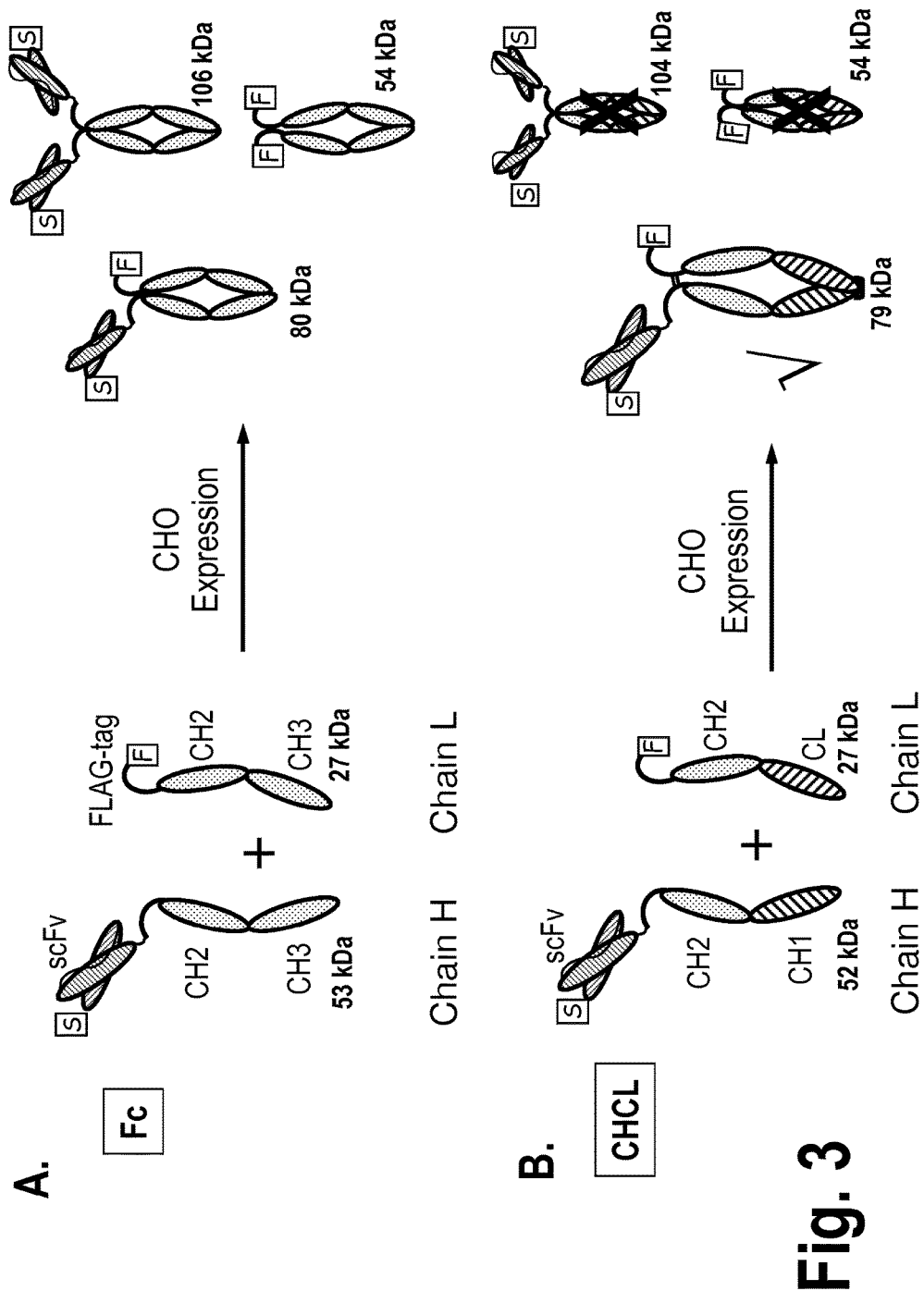

FIGS. 3A and B depict the expression heterogeneity of conventional heterodimeric constructs ("Fc", FIG. 3A) as compared to the homogeneous expression of heterodimeric binding molecules of the invention ("CHCL", FIG. 3B). Expression of conventional molecules leads to a heterogeneous mixture containing equal amounts of the desired heterodimeric species (80 kDa) and two undesired homodimers (106 kDa and 54 kDa). In contrast, co-expression of the component polypeptide chains of the heterodimeric binding molecules of the invention leads to the desired heterodimer (79 kDa) in high yield, relative to undesired homodimeric species (104 kDa and 54 kDa).

Figure 4A:
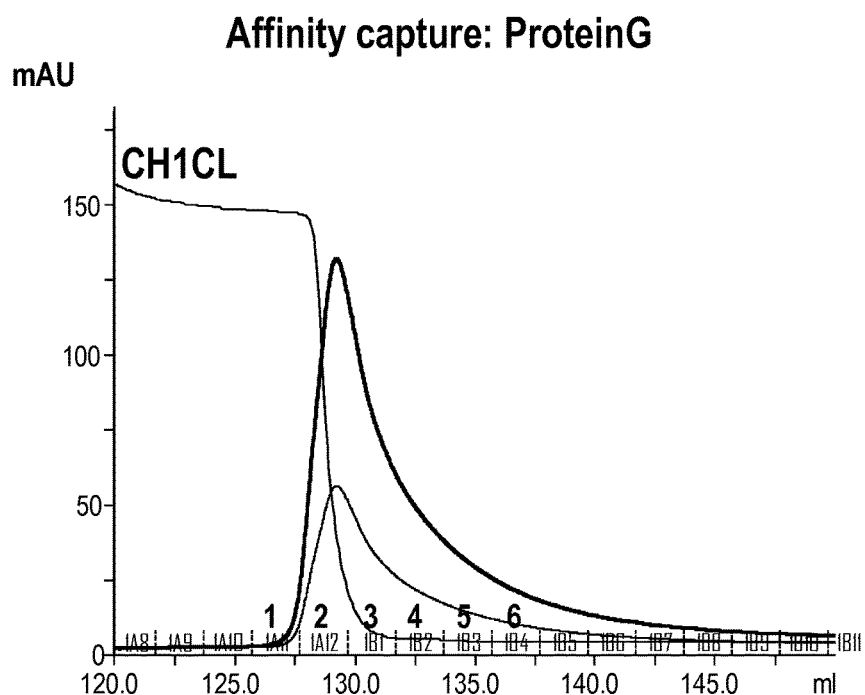

FIGS. 4A and B shows that the CHCL construct of the invention enriches for heterodimers as compared to a conventional Fc construct as determined by affinity chromatography. FIG. 4A shows the absorbance profile of fractions eluted from a Protein G affinity column of CHCL (top panel) and Fc expression products (bottom panel). Figure B shows the corresponding SDS PAGE analysis under reducing and non-reducing conditions (top panel=CHCL construct; bottom panel=Fc construct).

Figure 5A:
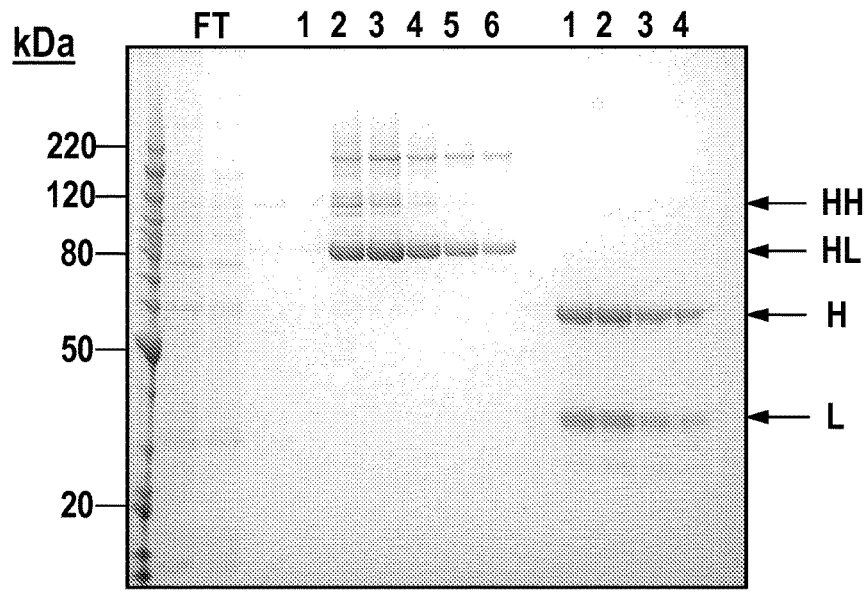

FIGS. 5A and B shows that the CHCL construct of the invention enriches for heterodimers as compared to a conventional Fc construct as determined by gel-filtration chromatography.

Figure 6A:
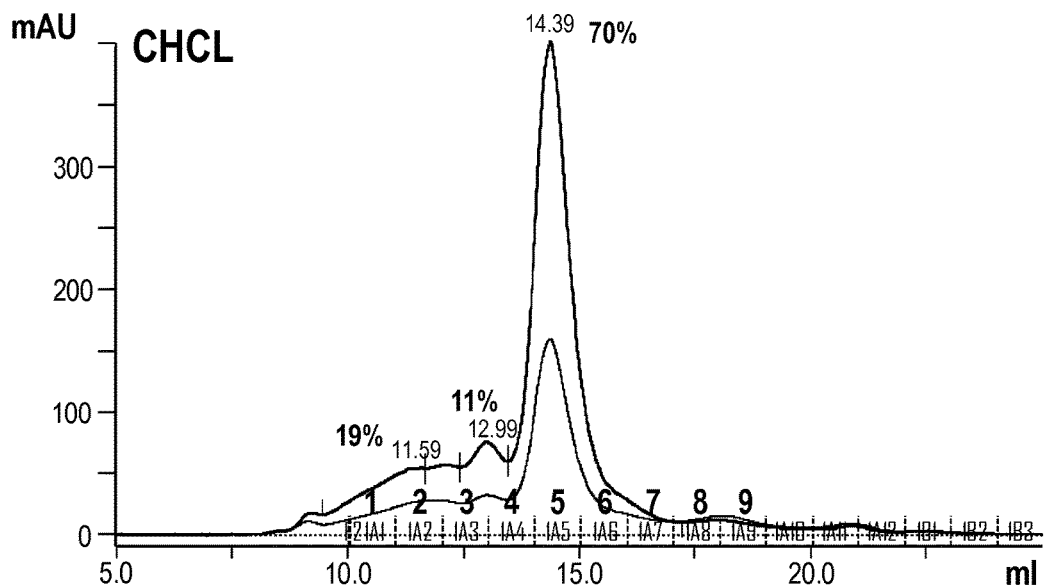
Figure 6B:
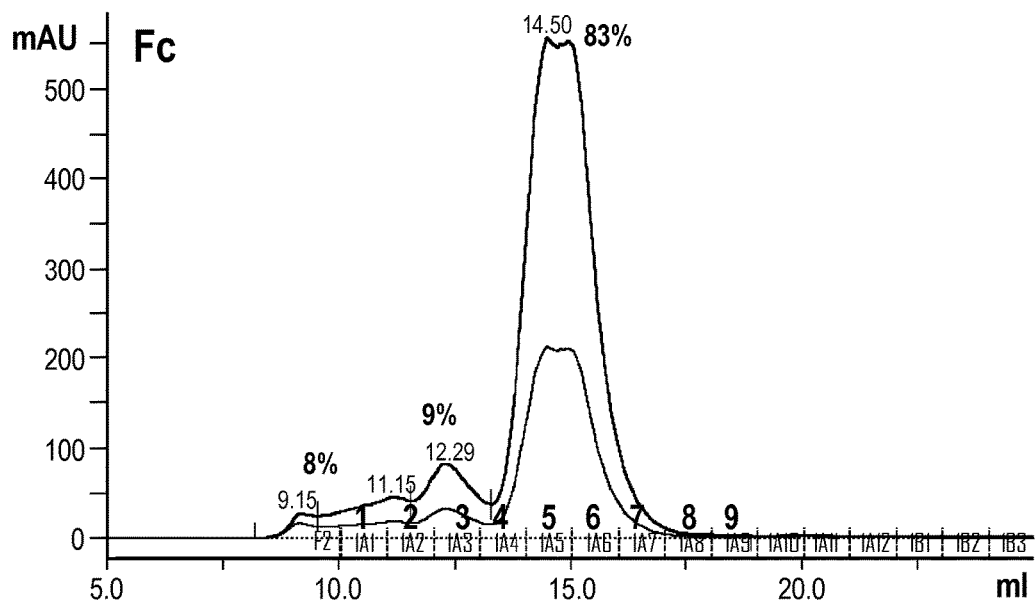

FIG. 6A shows the absorbance profile of fractions eluted from a Superdex 200 size exclusion column of CHCL (top panel) and 6B shows Fc expression products (bottom panel).

Figure 7A:
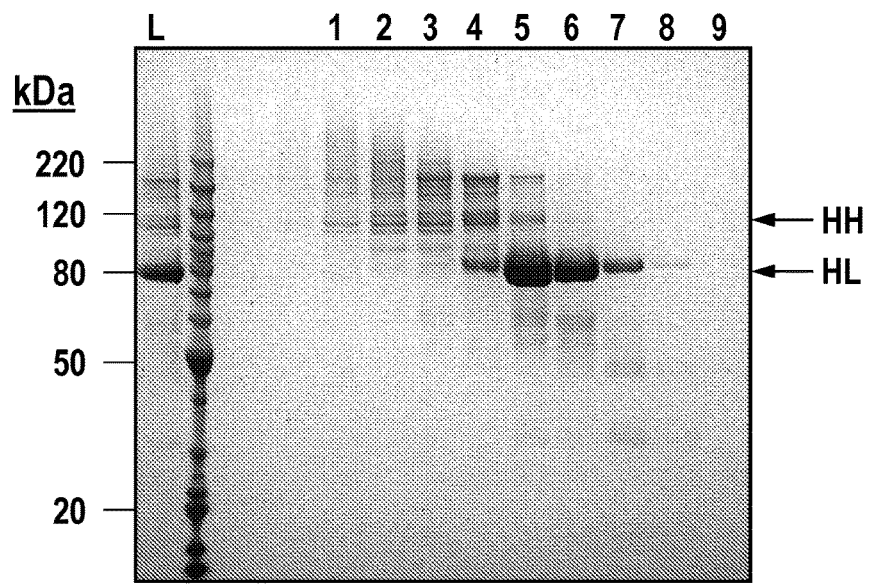
Figure 7B:
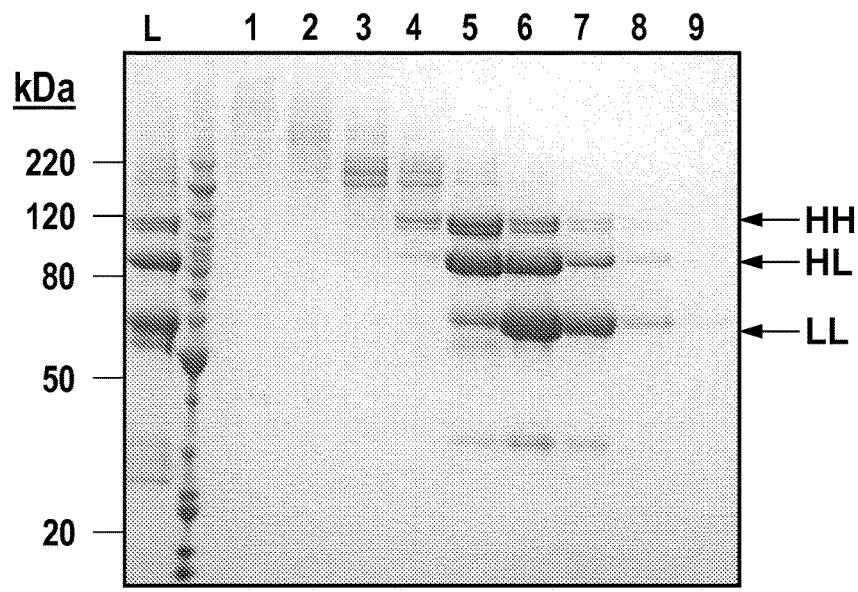

FIG. 7A shows the corresponding SDS PAGE analysis (top panel=CHCL construct; and 7B bottom panel=Fc construct).

Figure 8:
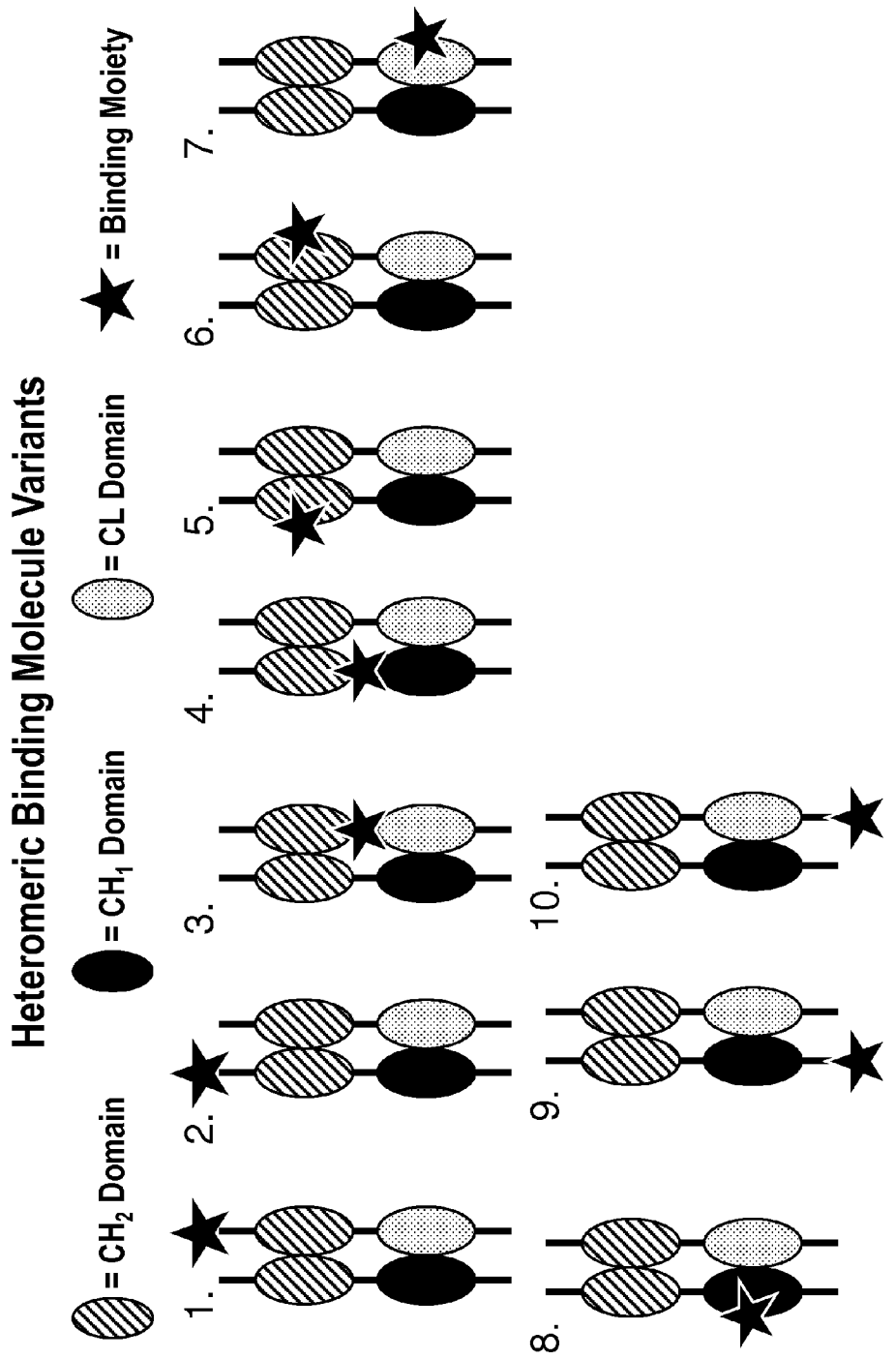

FIG. 8 shows exemplary heteromeric molecules of the invention: 1) N-terminal CH2-CL fused Binding Moiety; 2) N-terminal CH2-CH1 fused Binding Moiety; 3) Binding Moiety in the CH2-CL loop; 4) Binding Moiety in the CH2-CH1 loop; 5) Binding Moiety is veneered onto CH2 domain fused to CH1; 6) Binding Moiety is veneered onto CH2 domain fused to CL; 7) Binding Moiety is veneered onto CL domain; 8) Binding Moiety is veneered onto CH1 domain; 9) C-terminal CH2-CH1 fused Binding Moiety; 10) C-terminal CH2-CL fused Binding Moiety. Not shown: combinations of the above (e.g., heteromeric molecules with two or more binding sites) and single chain versions of heteromeric binding molecules (e.g. a first polypeptide chain genetically-fused with a second polypeptide chain (e.g., expressed as a single polypeptide chain)).

Figure 9:
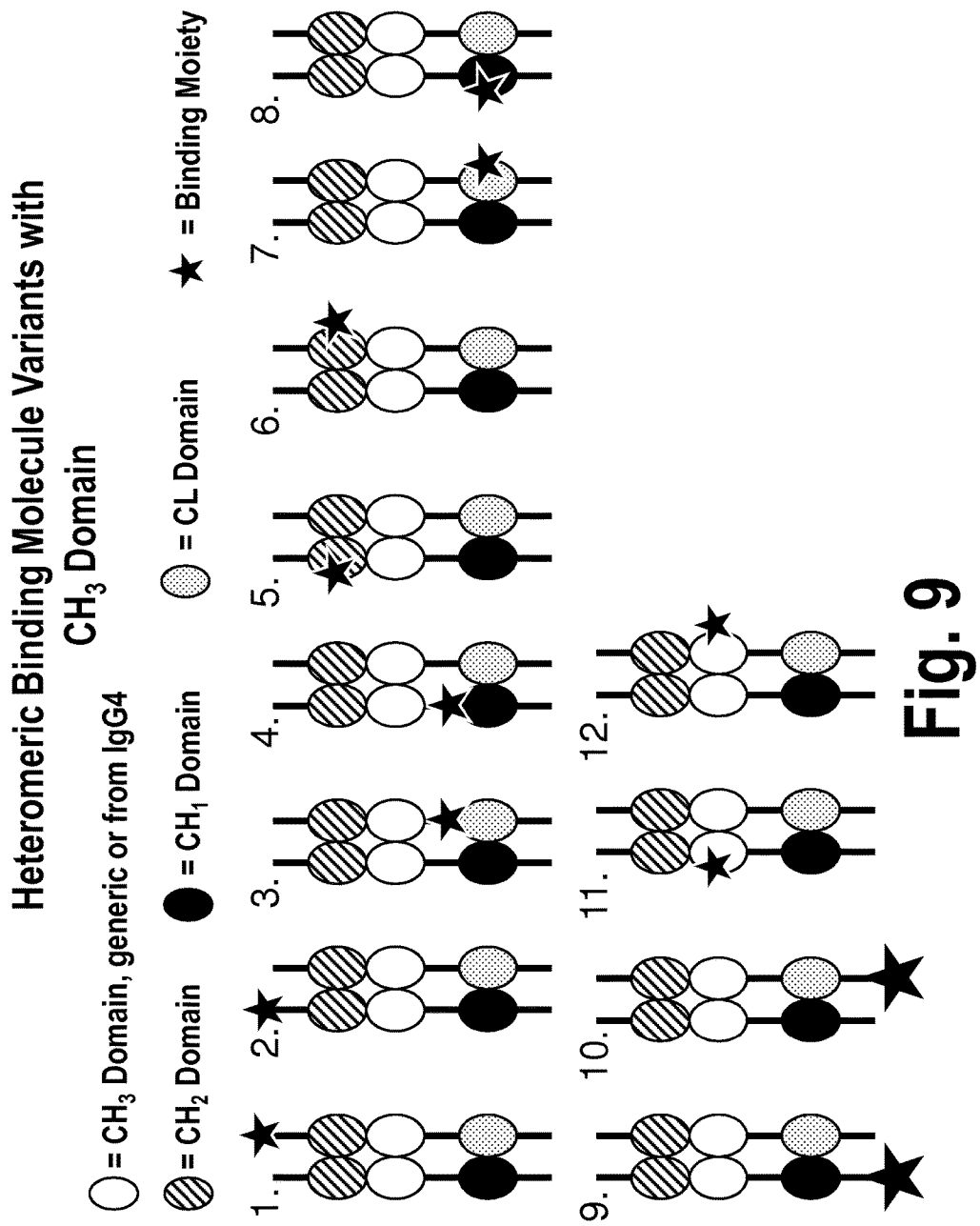

FIG. 9 shows exemplary heteromeric CH3 domain-containing binding molecules of the invention: 1) N-terminal CH2-CH3-CL fused Binding Moiety; 2) N-terminal CH2-CH3-CH1 fused Binding Moiety; 3) Binding Moiety in the CH3-CL loop; 4) Binding Moiety in the CH3-CH1 loop; 5) Binding Moiety is veneered onto CH2 domain fused to CH3-CH1; 6) Binding Moiety is veneered onto CH2 domain fused to CH3-CL; 7) Binding Moiety is veneered onto CL domain; 8) Binding Moiety is veneered onto CH1 domain; 9) C-terminal CH2-CH3-CH1 fused Binding Moiety; 10) C-terminal CH2-CH3-CL fused Binding Moiety; 11) Binding Moiety is veneered onto CH3 domain fused to CH1; 12) Binding Moiety is veneered onto CH3 domain fused to CL. Not shown: combinations of the above (e.g., heteromeric molecules with two or more binding sites) and single chain versions of heteromeric binding molecules (e.g. a first polypeptide chain genetically-fused with a second polypeptide chain (e.g., expressed as a single polypeptide chain)).

Figure 10:
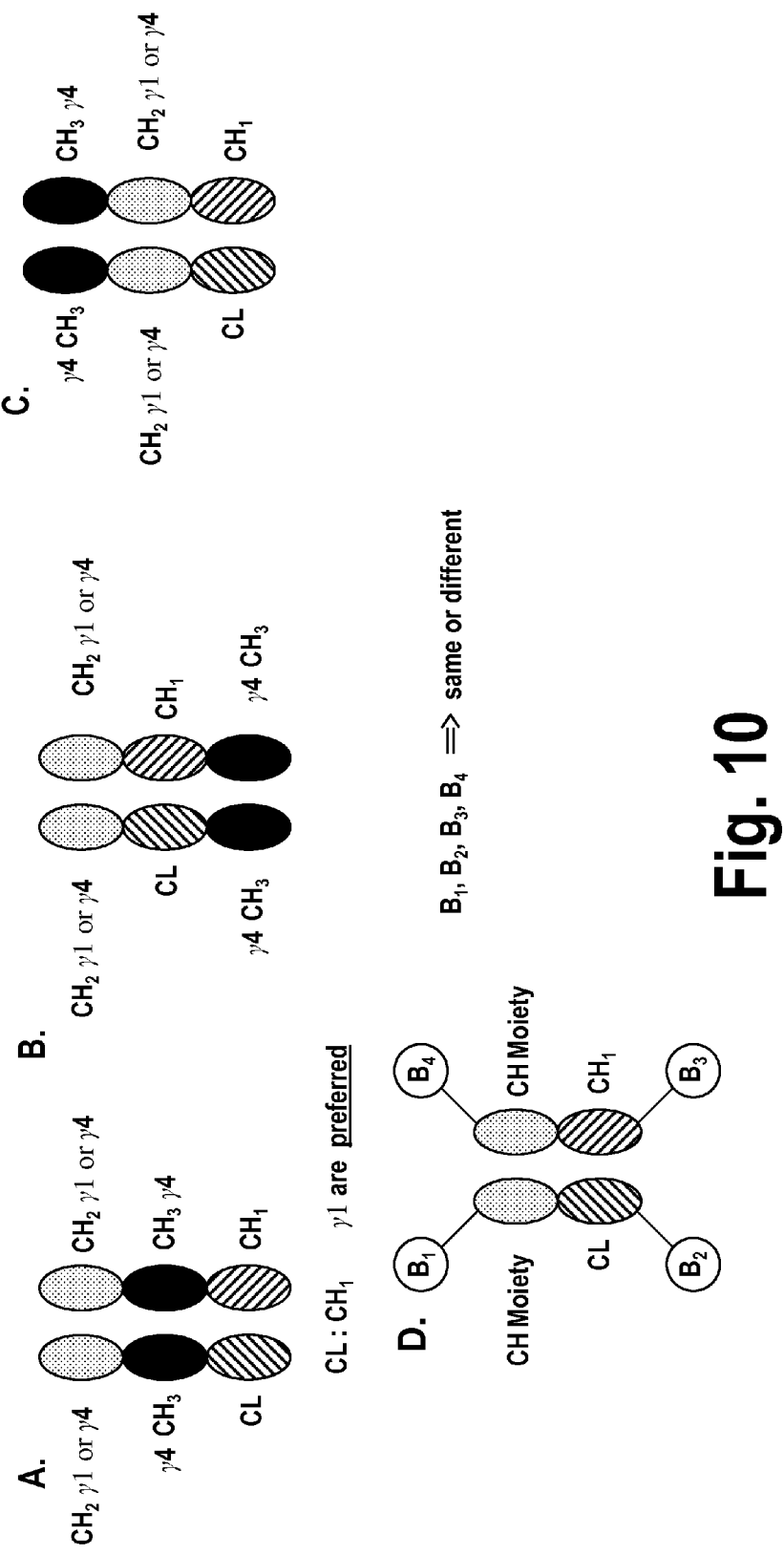

FIG. 10 shows the structure of additional heteromeric binding molecules of the invention, with a variety of Fc and Fab constant moiety arrangements and a molecule with two constituent polypeptide chains and four binding sites.

FIG. 11 shows the amino acid sequence alignment between the CH1 (SEQ ID NO: 101) and CL (SEQ ID NO: 61) domains of heterodimeric binding molecules and the native IgG1 CH3 domain (SEQ ID NO: 100) after alignment adjustments were made based on comparisons of the domains' three-dimensional structures.

FIG. 12 shows the immunoblot results from a reducing gel, which provides information about relative expression levels of the two chains, irrespective of heterodimer pairing. Since one member of each pair has a ~25 kDa single-chain Fv at the N-terminus and the other does not, the two chains are of different molecular weight and the CL-CL, CL-CH1, and CH1-CH1 pairings can be readily distinguished by electrophoretic mobility.

FIG. 13 shows the immunoblot results from a non-reducing gel, which provides information on the degree of heterodimer pairing. For the CH3-containing constructs all three pairings are visible (ie CL-C, CL-CH1, and CH1-CH1). The ratio is skewed toward the CL-CL and CL-CH1 pairings as expected if pairing were random and the CL-containing construct were expressed at much higher levels than the CH1-containing constructs. For the constructs not containing CH3 domains the CL-CH1 heterodimer is clearly favored over the other two pairings, demonstrating that the CL-CH1 interaction is favorable enough to drive the desired heterodimerization.

Figure 14:
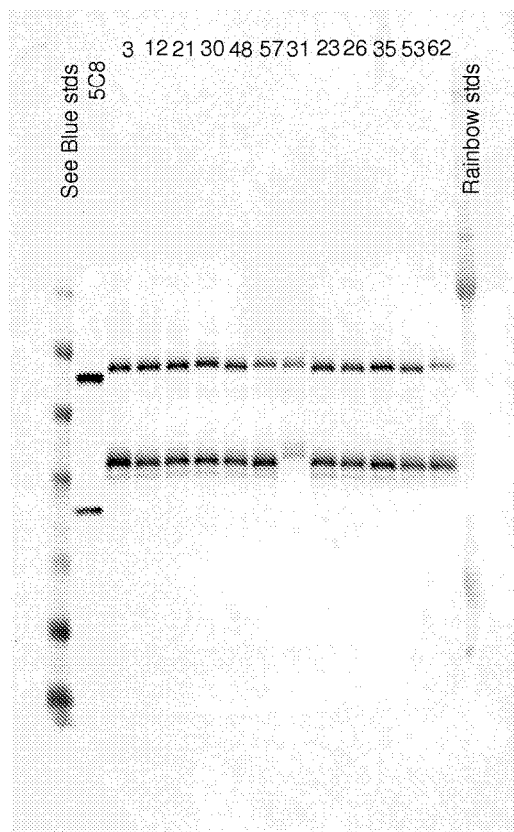

FIG. 14 is a representative Western blot from a reducing gel, which shows several different patterns of expression of the various constructs made.

Figure 15:
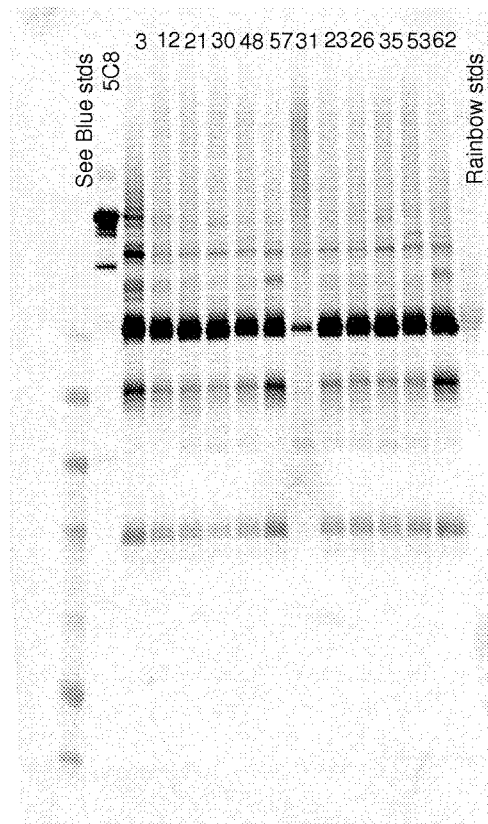

FIG. 15 shows a non-reducing gel. As shown in the gel, most supernatants showed a predominance of the CL-CH1 heterodimer although in lanes 3, 57, and 62 the CL-CL form appears a bit more prominent and in lane 31 a considerable degree of high molecular weight aggregate is evident.

Figure 16:
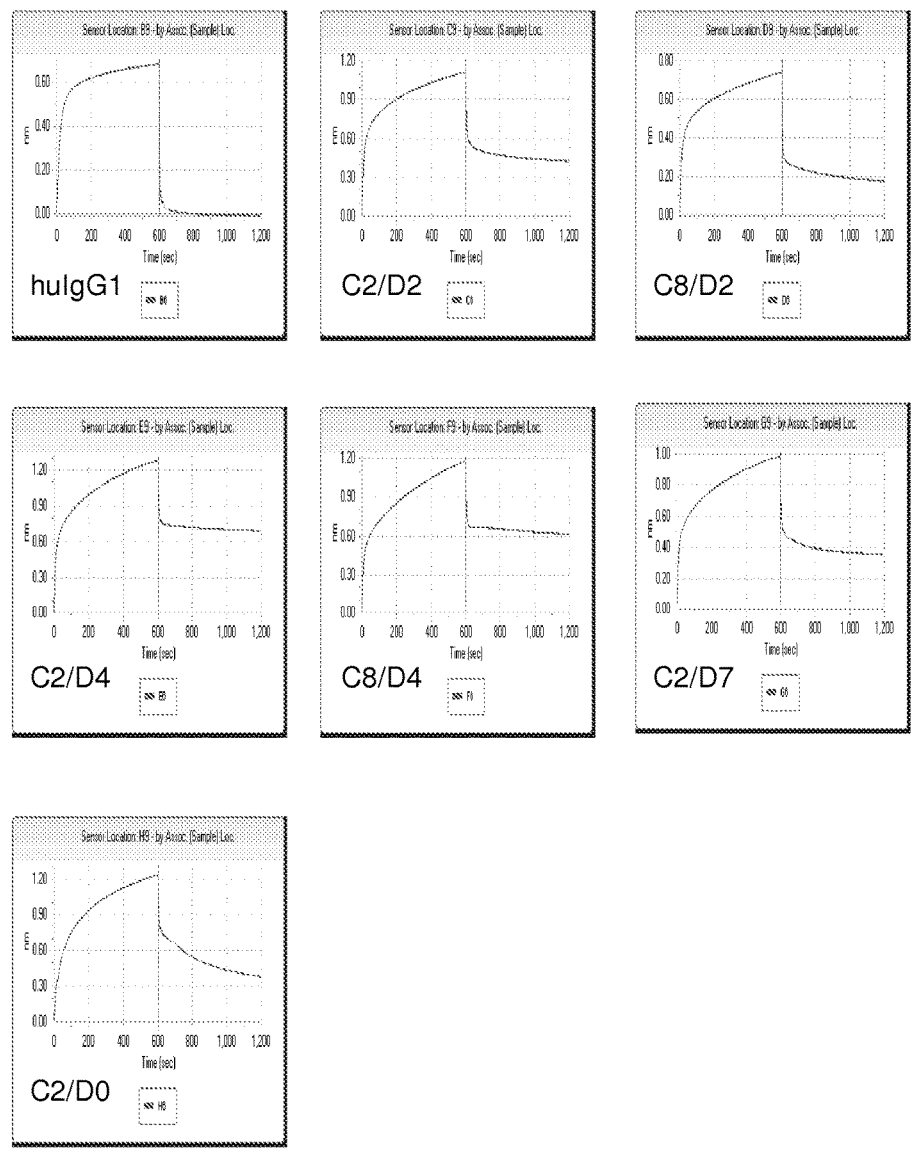

FIG. 16 shows the results of an FcRn binding assay carried out on a Fortebio Octet instrument with biotin-labeled FcRn-Fc fusion protein bound to streptavidin tips. The parental CL-CH1 construct (C0/D0) did not show binding to the FcRn loaded Octet tips, nor did constructs with the first segment of the CH3 domain incorporated into each chain (C1/D1). If one chain had two segments, while the second chain had only one segment (C2/D1 or C1D2), intermediate binding was found. Full binding to FcRn was restored when two segments were present on both chains (for example C2/D2). MAbs with more than two segments in both chains also bound well to FcRn.

Figure 17:
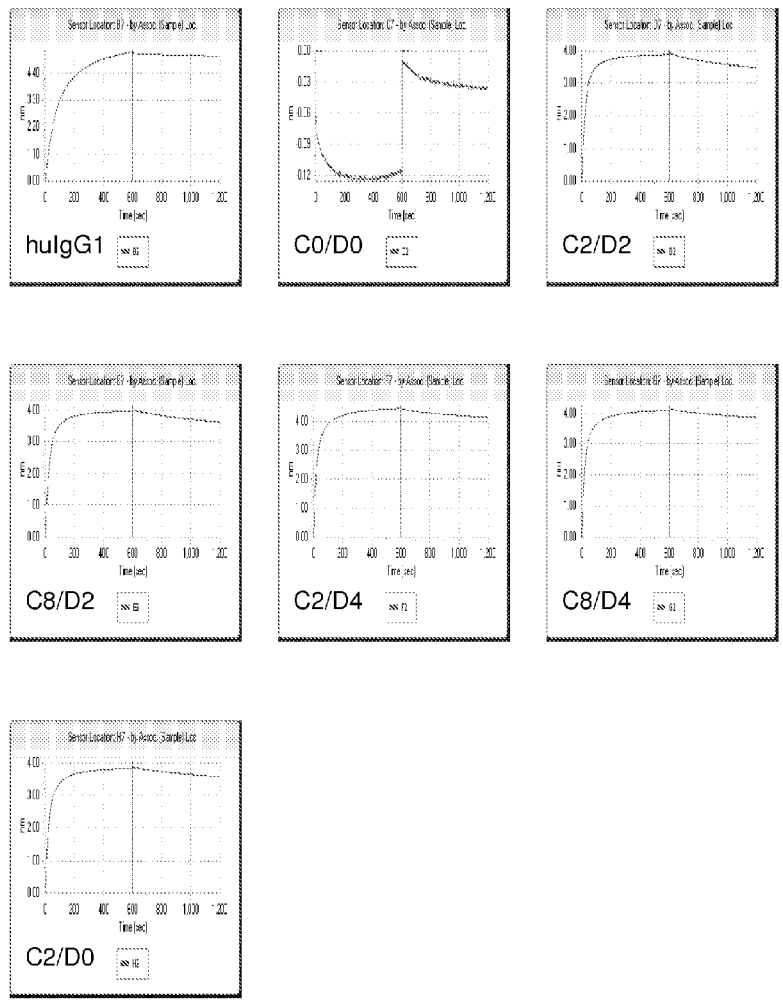

FIG. 17 shows the results of Protein A binding assays carried out on a Fortebio Octet instrument using Protein A tips provided by the vendor. The Protein A binding results were similar to the FcRn binding with two CH3 segments on each chain providing the optimum binding interactions.

Figure 18:
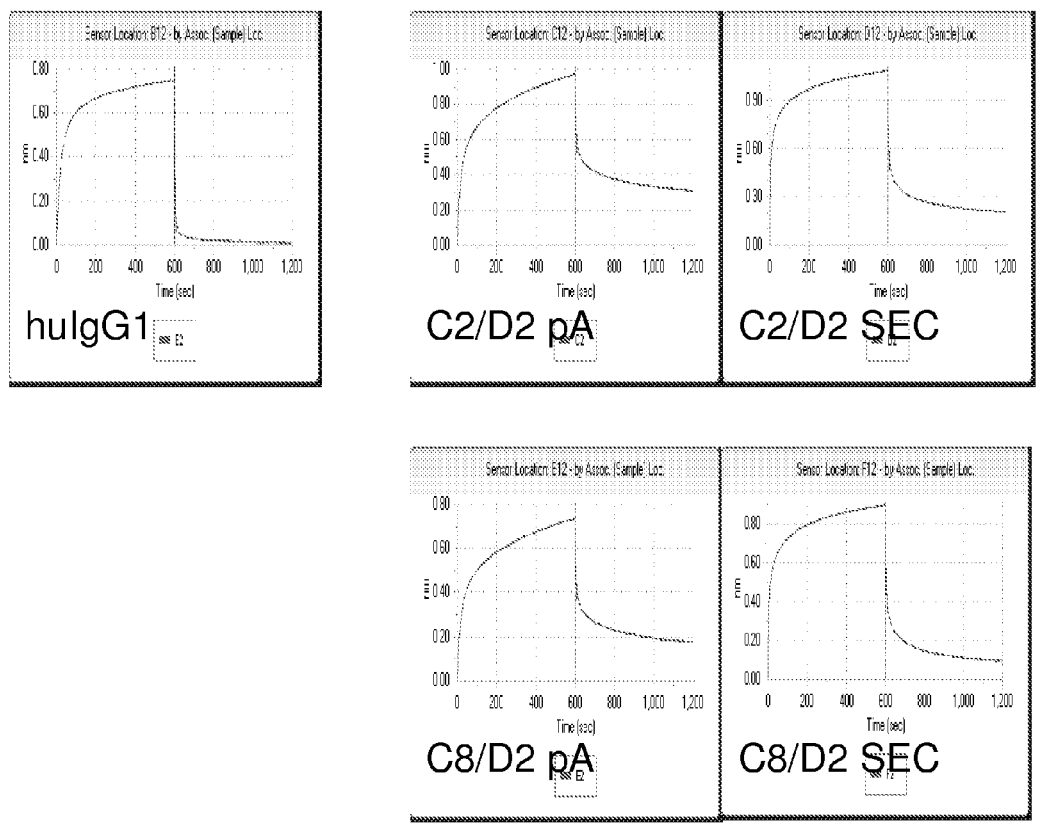

FIG. 18 shows FcRn binding results for top two constructs when tested for FcRn and Protein A binding. Extra purification steps removed contaminants that contributed to background binding, such that the binding curves were now very similar to the wild type IgG1 mAb control.

FIG. 19 shows the results of SDS-PAGE demonstrating heterodimer formation by constructs with modification of potential t cell epitopes.

FIG. 20 shows FcRn binding by constructs with modification of potential T cell epitopes as measured by Octet.

Figure 21:
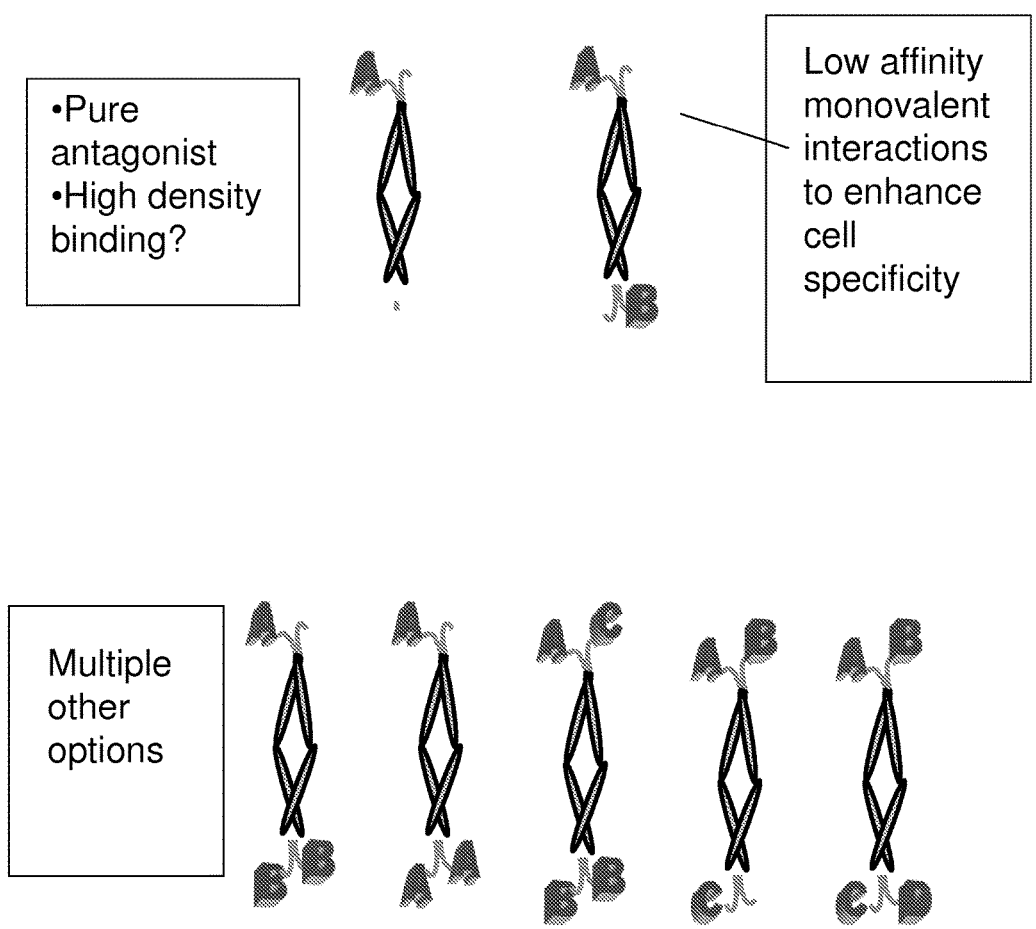

FIG. 21 shows some examples of binding molecules of the present invention.

DETAILED DESCRIPTION OF THE INVENTION

The present invention advances the art by providing inter alia binding molecules comprising, e.g., (i) at least one binding moiety (or binding domain); and (ii) at least one heterodimeric Fc region (i.e., two or more constituent Fc-containing polypeptide chains each comprising at least one Fc moiety, which chains exhibit a pairing interaction between a CH1 moiety in a first polypeptide chain and a CL moiety in a second polypeptide chain). In preferred embodiments, a constituent polypeptide chain of a binding molecule of the invention comprises at least one Fc moiety which is fused to the N terminus of a CH1 or CL moiety. In some embodiments, a constituent polypeptide chain of the invention comprises at least one Fc moiety fused to the C terminus of a CH1 or CL moiety. In one embodiment, the binding moiety may comprise, e.g., an F(ab) or scFv molecule which is fused (e.g., via either the VH or VL of the Fab) to either or both N- and C-termini of one or both constituent polypeptide chains of the binding molecule of the invention. In another embodiment, the target binding moiety may comprise a receptor fusion protein fused to either or both N- and C-termini of one or both constituent polypeptide chains of the binding molecule of the invention. Such fusions can be made either C-terminally or N-terminally to the desired binding moiety.

Expression of the non-identical constituent polypeptide chains to form heterodimeric binding molecules (FIG. 3B)

has numerous advantages over conventional protein expression methods, e.g., methods that involve the co-expression of two genes, one expressing a first Fc domain fused to a first binding moiety and a separate second gene consisting of a second binding moiety fused to a second Fc domain with disulfide bonds linking the two polypeptide chains (FIG. 3A). The problems of such conventional constructs include significant heterogeneity within the population of resulting molecules (homodimers and heterodimers), such that the desired molecule comprising both a first and second binding moiety must be purified away from undesired molecules, thereby resulting in a decline in total yield of the desired molecule. Exemplary advantages of the polypeptides of the invention include the following:

Preferential Production of Heteromeric Binding Molecules:

Heteromeric binding molecules of the invention comprise two or more distinct polypeptide chains, with at least one chain comprising a CH1 moiety and at least one chain comprising a CL moiety. In a preferred embodiment, the CH1 moiety or the CL moiety is found at the C-terminus of the polypeptide chain. The presence of the CH1 and CL moieties in the constituent polypeptide chains promotes the dimerization of heteromeric binding molecules and reduces the production of homomeric molecules. For example, in one embodiment of the invention, a first polypeptide chain comprises an Fc region consisting of a CH1 moiety fused at its N terminus to the C-terminus of a CH2 moiety and a second polypeptide chain comprises an Fc region consisting of a CL moiety fused at its N terminus to the C-terminus of a CH2 moiety. Upon co-expression, the two chains will exhibit preferential heterodimeric assembly, driven by the interaction between the CH1 and CL moieties, and the production of homodimeric molecules will be reduced. In contrast, current methods of generating binding proteins do not feature preferential heterodimerization, leading to a mixture of products. For example, in a system expressing two chains without preferential heteromerization, an undesirably complex mixture of molecules will be produced ($1^{st}$ chain+$1^{st}$ chain, $1^{st}$ chain+$2^{nd}$ chain, and $2^{nd}$ chain+$2^{nd}$ chain) in a theoretical ratio of 1:2:1. (The ratios of products observed from these systems, however, can very greatly from this theoretical prediction, leading to further reduction in yields of the desired product.)

Enhancement of F(ab) Half-Life Via Addition of FcRn Binding:

The therapeutic application of F(ab)s is often desirable because it enables blocking of cell surface receptors without target receptor crosslinking and subsequent undesirable signaling upon receptor engagement by a bivalent antibody. Such crosslinking of surface receptors can cause clustering of receptors and down regulation of the target receptor from the surface of the cell. One of the significant drawbacks to the application of F(ab)s in vivo, however, is their poor serum persistence or half-life. The addition of an Fc region, such as a heteromeric Fc region, to a F(ab) fragment results in pharmacokinetic half-life similar to an intact mAb. Typically the half-life of F(ab)s is prolonged by the chemical addition of a PEG moiety to a specific thiol after preparation and purification of the F(ab). The PEGylation reaction adds a significant complication to the preparation of the product. The PEGylation chemistry has to be optimized for each F(ab) and decreases the product yield. The pegylation also complicates the final product analysis since PEGylated materials are of heterogeneous molecular weight.

In some embodiments of the invention, coding sequences of constituent polypeptide chains of binding molecules of the invention are altered to enhance binding to Fc receptors. For example, key FcRn binding residues from the CH3 domain of a wild type immunoglobulin can be veneered onto Fc moieties, such as CH2, CH1 and CL moieties present in binding molecules of the invention. The resulting heterodimeric Fc region of the binding molecule will exhibit binding to FcRn.

Addition of FcγRI, FcγRII and FcγRIII Functionalities to a F(Ab):

F(ab)s and pegylated F(ab)s lack the ability to interact with FcγRI, FcγRII and FcγRIII. These Fc receptors can be responsible for the functionality of drugs, for example certain antibodies depend on the Fc functionality for the ADCC dependent depletion of unwanted cancerous B-cells. In one embodiment, heteromeric binding molecules of the invention include binding molecules that comprise one or more Fc moieties (e.g., CH2 moieties and/or CH3 moieties) and have the ability to interact with FcγRI, FcγRII and/or FcγRIII In some embodiments, one or more Fc moieties can comprise amino acid sequences that have been altered from a naturally occurring Fc amino acid sequence to alter effector functionality, such as Fc receptor binding. In some embodiments, a non-CH3 constant chain moiety sequence is altered to incorporate one or more CH3 loops with corresponding functionality. In some embodiments, key residues from a CH2 or CH3 moiety are veneered onto an Fc moiety of a binding molecule of the invention to alter effector function or a binding moiety is veneered into an Fc moiety, thereby adding a binding functionality to the binding molecule of the invention.

Heteromeric Binding Molecules Allow for Heterogeneous Point Mutations in the Fc Region:

Site-specific mutations within Fc moieties of binding molecules are useful in creating Fc-variant mAbs with improved Fc functionality. Examples are mutations that enhance the affinity to FcγRI, FcγRII and/or FcγRIII Alterations in the Fc moieties of binding molecules of the invention can be used to create a heteromeric Fc region in a binding molecule containing one or more specific point mutations in only one polypeptide chain of the heterodimeric Fc region, or to create a heteromeric Fc region in a binding molecule containing different combinations of point mutations in the two constituent polypeptide chains of the heteromeric Fc region. An example would be the expression of a first polypeptide comprising an Fc construct containing Asn 297 glycosylation, a point mutation that is correlated with somewhat decreased FcR affinity, but is not inactive in FcγRIII binding, and a second polypeptide having a wild type Fc moiety sequence.

In order to provide a clear understanding of the specification and claims, the following definitions are conveniently provided below.

I. Definitions

As used herein, the terms "polypeptide" or "polypeptide chain" refer to a polymer of two or more of the natural amino acids or non-natural amino acids.

The term "amino acid" includes alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (Ile or I): leucine (Leu or L); lysine (Lys or K); methionine (Met or M); phenylalanine (Phe or F); proline (Pro or P); serine (Ser or S); threonine (Thr or T); tryptophan (Trp or W); tyrosine (Tyr or Y); and valine (Val or V). Non-traditional amino acids are also within the scope of the invention and include norleucine, ornithine, norvaline, homoserine, and other amino acid residue analogues such as those described in Ellman et al. Meth. Enzym. 202:301-336 (1991). To generate such non-naturally occurring amino acid residues, the procedures of Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA. Introduction of the non-traditional amino acid can also be achieved using peptide chemistries known in the art. As used herein, the term "polar amino acid" includes amino acids that have net zero charge, but have non-zero partial charges in different portions of their side chains (e.g. M, F, W, S, Y, N, Q, C). These amino acids can participate in hydrophobic interactions and electrostatic interactions. As used herein, the term "charged amino acid" include amino acids that can have non-zero net charge on their side chains (e.g. R, K, H, E, D). These amino acids can participate in hydrophobic interactions and electrostatic interactions. As used herein the term "amino acids with sufficient steric bulk" includes those amino acids having side chains which occupy larger 3 dimensional space. Exemplary amino acids having side chain chemistries of sufficient steric bulk include tyrosine, tryptophan, arginine, lysine, histidine, glutamic acid, glutamine, and methionine, or analogs or mimetics thereof.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, the present larger "peptide insertions", can be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

As used herein, the term "moiety" refers to a component part or group present in a molecule. For example, in one embodiment, the term moiety refers to an immunoglobulin domain or a portion of an immunoglobulin domain incorporated into a binding molecule of the invention. For example, one or more "CH3 moieties" of an Fc region polypeptide chain may be included a binding molecule. Other immunoglobulin domains that may be incorporated into a constituent polypeptide chain include inter alia CL, CH1, CH2, VH, VL and hinge domains. As used herein the term "Fc moiety" refers to domains from an immunoglobulin Fc region, e.g., CH2 or CH3 domains. A polypeptide sequence comprising a moiety that is derived from a domain of an immunoglobulin may comprise at least 50%, at least 55%, at least 60%, at least 65%, at least 70%, at least 75%, at least 80%, at least 85%, at least 90%, at least 95%, at least 96%, at least 97%, at least 98% or at least 99% sequence identity with the domain from which it was derived.

As used herein, the term "Fc region" shall be defined as the portion of a binding molecule of the invention formed by the multimerization of the C-terminal portions of constituent peptides, which preferably comprise CH2 moieties from a native immunoglobulin (or a portion thereof). In one embodiment, an Fc region comprises any sequence attached to the C terminus of a CH2 moiety. For example, embodiments of the invention feature binding molecules with heterodimeric Fc regions formed by constituent polypeptide chains that comprise CH2 moieties along with CH1 or CL moieties fused at their N terminal ends to the C terminal end of the CH2 moieties. Additional embodiments of the invention feature binding molecules with heterodimeric Fc regions formed by peptide chains that comprise CH2 moieties, CH3 moieties and sequences from CH1 or CL immunoglobulin domains fused at their N-terminal ends to the C-terminal end of the CH2/CH3 moiety of the Fc domain. For example, in some embodiments of the invention, a first polypeptide chain of a heterodimer comprises an Fc region that begins C-terminal to the papain cleavage site in the hinge region, is genetically fused to a CH2 moiety, which is genetically fused to by a CH3 moiety, which is genetically fused to by a CH1 moiety (i.e., the CH1 moiety is found at the C-terminal end of the peptide). A second polypeptide of a heterodimer comprises an Fc region that begins C-terminal to the papain cleavage site in the hinge region, is genetically fused to a CH2 moiety, which is genetically fused to by a CH3 moiety, which is genetically fused to by a CL moiety (i.e., the CL moiety is found at the C-terminal end of the peptide). Upon expression, the two constituent polypeptide chains will dimerize with each other, the CH2 moieties of each strand interacting, the CH3 moieties of each strand interacting, and the CH1 moiety of one strand and the CL moiety of the other stand interacting with each other; the two strands thus form a heterodimer, with the interacting Fc moieties (i.e., the CH2 moieties, CH3 moieties and CH1-CL moieties) comprising the Fc region of the heterodimer.

As used herein, the term "constituent polypeptide chain" refers to a single polypeptide chain which is a component of a heteromeric binding molecule of the invention. In a preferred embodiment, a heterodimeric binding molecule of the invention comprises two non-identical constituent polypeptide chains. The two constituent polypeptide chains of a binding molecule of the invention differ at least in that one constituent polypeptide chain comprises a CH1 moiety (e.g., at its C-terminal end) and the other constituent polypeptide chain comprises a CL moiety (e.g., at its C-terminal end). In a preferred embodiment, the CH1 or CL moiety is fused at its N-terminal end to the C-terminal end of a CH2 or CH3 moiety.

As used herein, the term "binding molecule" refers to molecules that comprise at least one target binding site, binding domain or binding moiety that specifically binds to a target molecule (such as an antigen or binding partner). For example, in one embodiment, a binding molecule of the invention comprises an immunoglobulin antigen binding moiety or the portion of a receptor molecule responsible for ligand binding or the portion of a ligand molecule that is responsible for receptor binding. The binding molecules of the invention preferably also comprise at least two Fc moieties derived from one or more immunoglobulin (Ig) molecules. For example, in preferred embodiments, the binding molecule is a heterodimeric molecule comprising constituent polypeptide chains that exhibit a spontaneous pairing interaction between a CH1 moiety in the first polypeptide chain and a CL moiety in the second polypeptide chain. In one embodiment, a binding molecule of the invention comprises additional modifications. Exemplary modifications are described in more detail below.

For example, in certain preferred embodiments, a constituent polypeptide chain of a binding molecule of the invention may optionally comprise a flexible polypeptide linker interposed between at least two moieties derived from a native immunoglobulin peptide sequence. For example, a constituent polypeptide chain of the invention may comprise a flexible polypeptide linker between a CH2 moiety and a variable region moiety (e.g., a VL or VH moiety), between two CH2 moieties, between a CH2 moiety and a CH3 moiety, between a CH2 moiety and a CH1 moiety, between a CH2 moiety and a CL moiety, between a CH3 moiety and a variable region moiety (e.g., a VL or VH moiety), between two CH3 moieties, between a CH3 moiety and a CH1 moiety, and/or between a CH3 moiety and a CL moiety. In another embodiment, a binding molecule may be modified to add a functional moiety (e.g., PEG, a functional moiety such as a drug or isotope, or a detectable label).

In a preferred embodiment, a binding molecule of the invention comprises two non-identical constituent polypeptide chains that form a heterodimer through interactions between the CH1 moiety (e.g., at the C-terminal end of one constituent polypeptide chain) and the CL moiety (e.g., at the C-terminal end of another constituent polypeptide chain). Hence the binding molecule of the invention is a protein dimer comprising two non-identical constituent polypeptides. Modifications made to binding molecules of the invention as described below may be made to an individual constituent polypeptide chain or to the binding molecule as a whole.

As used herein, the term "heterodimer" refers to a polypeptide comprising at least two non-identical polypeptide chains which comprise one or more immunoglobulin constant domain moiety and/or moieties, that may combine with each other to form a multimeric molecule. The term "heterodimer" may refer to a multimeric molecule that comprises more than two constituent polypeptide chains and may refer to a multimeric molecule that comprises more than two moieties that originate from or are derived from the native sequence of a immunoglobulin chain.

In preferred embodiments, the binding molecules of the invention comprise at least one binding moiety. In one embodiment, the binding molecules of the invention comprise at least two binding sites. In one embodiment, the binding molecules comprise two binding sites. In another embodiment, the binding molecules comprise three binding sites. In another embodiment, the binding molecules comprise four binding sites. In another embodiment, the binding molecules comprise more than four binding sites. In one embodiment, one or more binding moieties are present within a linker sequence. In one embodiment, the binding moieties are linked to each other in tandem. In other embodiments, the binding moieties are located at different positions of a single constituent polypeptide chain of a binding molecule of the invention. In other embodiments, the binding moieties are located on two or more separate constituent polypeptide chains of a binding molecule of the invention. For example, one or more binding moieties may be linked to either one or both ends of a of a single constituent polypeptide chain or may be linked to either one or both ends of two or more separate constituent polypeptide chains. In some embodiments, a binding moiety may be created by the interaction, pairing, dimerization and/or multimerization of constituent polypeptide chains of a binding molecule of the invention.

The term "binding site" (used interchangeably with "binding domain" or "binding moiety") as used herein, shall refer to the portion, region, or site of binding molecule that mediates specific binding with a target molecule (e.g. an antigen, ligand, receptor, substrate or inhibitor). Exemplary binding domains include an antigen binding site, a receptor binding domain of a ligand, a ligand binding domain of a receptor or an enzymatic domain. The term "ligand binding domain" as used herein refers to a native receptor (e.g., cell surface receptor) or any region or derivative thereof retaining at least a qualitative ligand binding ability, and preferably the biological activity of a corresponding native receptor. The term "receptor binding domain" as used herein refers to a native ligand or any region or derivative thereof retaining at least a qualitative receptor binding ability, and preferably the biological activity of a corresponding native ligand. In one embodiment, the binding molecules of the invention have at least one binding moiety specific for a molecule targeted for reduction or elimination, e.g., a cell surface antigen or a soluble antigen. In preferred embodiments, the binding moiety is an antigen binding moiety.

A binding moiety may be a molecule or peptide attached to a constituent polypeptide chain, may be a part of or formed by a constituent polypeptide chain of the invention, or may be formed by the dimerization of constituent polypeptides of the invention. A portion of a polypeptide chain that comprises a binding moiety need not be comprised of contiguous amino acids in a sequence. In other words, a binding moiety may be comprised of non-contiguous amino acids that are part of a single constituent polypeptide chain, or may be comprised of amino acids that are parts of distinct constituent polypeptide chains of a binding molecule of the invention.

As used herein, "veneering" refers to using genetic engineering techniques known in the art to alter the sequence of a polypeptide so that residues exposed to the surface of the peptide molecule (once synthesized and folded) are altered preferentially (as opposed to residues that are not exposed to the surface, e.g. interior residues). As known in the art, veneering techniques can be used to humanize a domain from a non-human immunoglobulin constant region, so that the surface epitopes resemble those from a human immunoglobulin while some or all interior residues are unchanged. By minimizing changes to interior residues, core structure and folding activities can remain unaltered while simultaneously changing the immunogenicity, binding activities, or biological activity of a protein or domain. Veneering techniques can also be used to confer an effector function of one constant chain moiety to a constant chain moiety of a different type (e.g., an effector function of a CH3 moiety conferred to a CH2 moiety, by substituting particular amino acid residues found on the surface of the CH2 moiety with residues from a CH3 moiety). In one embodiment, key residues (described infra) of a CH3 moiety can be included in a CH2 moiety of a constituent polypeptide chain in order to confer properties of the CH3 moiety to the CH2 moiety.

The term "binding affinity", as used herein, includes the strength of a binding interaction and therefore includes both the actual binding affinity as well as the apparent binding affinity. The actual binding affinity is a ratio of the association rate over the disassociation rate. Therefore, conferring or optimizing binding affinity includes altering either or both of these components to achieve the desired level of binding affinity. The apparent affinity can include, for example, the avidity of the interaction.

The term "binding free energy" or "free energy of binding", as used herein, includes its art-recognized meaning, and, in particular, as applied to binding site-ligand or Fc-FcR interactions in a solvent. Reductions in binding free energy enhance affinities, whereas increases in binding free energy reduce affinities.

The term "specificity" includes the number of potential binding moieties which specifically bind (e.g., immunoreact with) a given target. A binding molecule may be monospecific and contain one or more binding moieties which specifically bind the same target (e.g., the same epitope) or the binding molecule may be multispecific and contain two or more binding moieties which specifically bind different regions of the same target (e.g., different epitopes) or different targets. In one embodiment, a multispecific binding molecule (e.g., a bispecific molecule) having binding specificity for more than one target molecule (e.g., more than one antigen or more than one epitope on the same antigen) can be made. In another embodiment, the multispecific binding molecule has at least one binding moiety specific for a molecule (such as a molecule expressed on the surface of a cell or in soluble form (e.g., a molecule which is targeted for reduction or elimination in a subject)). In another embodiment, the multispecific binding molecule has at least two binding moieties specific for a molecule on a cell. In another embodiment, the multispecific binding molecule has at least two binding moieties specific for a soluble molecule. In another embodiment, the multispecific binding molecule has at least one binding moiety specific for a target molecule and at least one binding moiety specific for a drug. In yet another embodiment, the multispecific binding molecule has at least one binding moiety specific for a target molecule and at least one binding moiety specific for a prodrug. In another embodiment, the multispecific binding molecule has at least one binding moiety specific for a molecule may be used to isolate and/or purify the molecule. In particular embodiments, binding moieties that may be used to isolate and/or purify the molecule include strepII-tags and FLAG-tags. In yet another embodiment, the multispecific binding molecules are tetravalent antibodies that have two binding moieties specific for one target molecule and two binding moieties specific for the second target molecule.

As used herein the term "valency" refers to the number of potential binding moieties in a binding molecule, polypeptide or protein. Each binding moiety specifically binds one target molecule. When a binding molecule comprises more than one binding site, each binding moiety may specifically bind the same or different molecules (e.g., may bind to different ligands or different antigens, or different epitopes on the same antigen). In one embodiment, the binding molecules of the invention are monovalent. In another embodiment, the binding molecules of the invention are bivalent. In another embodiment, the binding molecules of the invention are trivalent. In yet another embodiment, the binding molecules of the invention are tetravalent. Additional embodiments feature binding molecules with greater valencies than tetravalent.

In certain aspects, the binding molecules of invention employ polypeptide linkers. As used herein, the term "polypeptide linkers" refers to a peptide or polypeptide sequence (e.g., a synthetic peptide or polypeptide sequence) which connects two sites or moieties in a linear amino acid sequence of a polypeptide chain. For example, polypeptide linkers may be used to connect a binding moiety to an Fc region or moiety. Preferably, such polypeptide linkers provide flexibility to a constituent polypeptide molecule of the invention. For example, in one embodiment, a VH moiety or VL moiety is fused or linked to an Fc region (i.e., a heterodimeric Fc region) via a polypeptide linker (the N- or C-terminus of the polypeptide linker is attached to the C- or N-terminus of the one constituent polypeptide of the heterodimeric Fc region and the N-terminus of the polypeptide linker is attached to the N- or C-terminus of the VH or VL domain).

In certain embodiments the polypeptide linker is used to connect (e.g., genetically fuse) two Fc moieties or an Fc moiety and a CH1 or CL moiety. Such polypeptide linkers are also referred to herein as Fc connecting polypeptides. As used herein, the term "Fc connecting polypeptide" refers specifically to a linking polypeptide which connects (e.g., genetically fuses) two Fc moieties (e.g., CH2 or CH3 moieties) or an Fc moiety and a Fab constant domain moiety (e.g., a CH1 or CL moiety).

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence.

Polypeptides derived from another peptide may have one or more mutations relative to the starting polypeptide, e.g., one or more amino acid residues which have been substituted with another amino acid residue or which has one or more amino acid residue insertions or deletions. Preferably, the polypeptide comprises an amino acid sequence which is not naturally occurring. Such variants necessarily have less than 100% sequence identity or similarity with the starting antibody. In a preferred embodiment, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%. In one embodiment, there is one amino acid difference between a starting polypeptide sequence and the sequence derived therefrom. Identity or similarity with respect to this sequence is defined herein as the percentage of amino acid residues in the candidate sequence that are identical (i.e. same residue) with the starting amino acid residues, after aligning the sequences and introducing gaps, if necessary, to achieve the maximum percent sequence identity.

Preferred binding molecules of the invention comprise an amino acid sequence (e.g., at least one Fc moiety) derived from a human immunoglobulin sequence. However, binding molecules may comprise one or more amino acids from another mammalian species. For example, one or more primate Fc moieties or binding moieties may be included in the subject constituent polypeptide chains of the binding molecules. Alternatively, one or more murine amino acids may be present in a polypeptide chain.

It will also be understood by one of ordinary skill in the art that the binding molecules of the invention may be altered such that they vary in amino acid sequence from the naturally occurring or native proteins from which they were derived, while retaining the desirable activity of the native proteins. For example, nucleotide or amino acid substitutions leading to conservative substitutions or changes at "non-essential" amino acid residues may be made. An isolated nucleic acid molecule encoding a non-natural sequence variant derived from an immunoglobulin (e.g., an Fc domain or antigen binding site) within a coding sequence for a constituent polypeptide chain can be created by introducing one or more nucleotide substitutions, additions or deletions into the immunoglobulin-derived nucleotide sequence such that one or more amino acid substitutions, additions or deletions are introduced into the encoded protein. Mutations may be introduced by standard techniques, such as site-directed mutagenesis and PCR-mediated mutagenesis.

The binding molecules of the invention may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a constituent polypeptide chain is preferably replaced with another amino acid residue from the same R group (amino acid side chain) family. In another embodiment, a string of amino acids can be replaced with a structurally similar string that differs in order and/or composition of side chain family members. Alternatively, in another embodiment, mutations may be introduced randomly along all or part of a coding sequence, such as by saturation mutagenesis, and the resultant mutants can be incorporated into binding molecules of the invention and screened for their ability to bind to the desired target.

In the context of the constituent polypeptide chains of binding molecules of the invention, a "linear sequence" or a "sequence" is the order of amino acids in a polypeptide in an amino to carboxyl terminal direction in which residues that neighbor each other in the sequence are contiguous in the primary structure of the polypeptide.

As used herein, the terms "linked," "fused", or "fusion", are used interchangeably. These terms refer to the joining together of two more elements or components, by whatever means including chemical conjugation or recombinant means.

As used herein, the term "genetically fused" or "genetic fusion" refers to the co-linear, covalent linkage or attachment of two or more proteins, polypeptides, or fragments thereof via their individual peptide backbones, through genetic expression of a single polynucleotide molecule encoding those proteins, polypeptides, or fragments. Such genetic fusion results in the expression of a single contiguous genetic sequence. Preferred genetic fusions are in frame, i.e., two or more open reading frames (ORFs) are fused to form a continuous longer ORF, in a manner that maintains the correct reading frame of the original ORFs. Thus, the resulting recombinant fusion protein is a single polypeptide containing two or more protein segments that correspond to polypeptides encoded by the original ORFs (which segments are not normally so joined in nature). Although the reading frame is thus made continuous throughout the fused genetic segments, the protein segments may be physically or spatially separated by, for example, an in-frame polypeptide linker.

As used herein, the term "Fc domain" refers to the portion of a single immunoglobulin heavy chain beginning in the hinge region just upstream of the papain cleavage site (i.e. residue 216 in IgG, taking the first residue of heavy chain constant region to be 118) and ending at the C-terminus of the antibody. Accordingly, a complete Fc domain comprises at least a hinge domain, a CH2 domain, and a CH3 domain.

As used herein, the term "Fab domain" refers to the portion of a single immunoglobulin light chain, or to a portion of a single immunoglobulin heavy chain sequence beginning at the N-terminus of the native heavy chain immunoglobulin polypeptide and ending in the hinge region just upstream of the papain cleavage site (i.e. residue 216 in IgG, taking the first residue of heavy chain constant region to be 118). The term "Fab constant domain" refers to a CH1 or CL domain of a single immunoglobulin chain or a portion thereof.

As used herein, the term "Fc moiety" comprises an amino acid sequence of an Fc domain of an immunoglobulin or derived from an Fc domain of an immunoglobulin. In certain embodiments, an Fc moiety comprises a portion of the hinge domain, a CH2 domain, a CH3 domain, a CH4 domain, or a variant, portion, or fragment thereof.

The Fc moieties of a polypeptide of the invention may be derived from different immunoglobulin molecules. For example, Fc moieties of a single constituent polypeptide chain may comprise a CH2 and a CH3 domain derived from an IgG1 molecule or may comprise a CH2 derived from an IgG1 molecule and a CH3 domain from a IgG4 molecule (see, for example, FIGS. 8A and 8C).

As used herein, the term "Fab moiety" refers to an amino acid sequence of an Fab domain or derived from an Fab domain. In preferred embodiments, a Fab moiety consists of constant domain sequences from a CH1 domain of a native heavy chain immunoglobulin molecule, constant domain sequences from a CL domain of a native light chain immunoglobulin molecule or sequences derived from those domains.

As used herein, the terms "CH2 domain sequence", "CH3 domain sequence", "CH1 domain sequence", and "CL domain sequence" refer to polypeptide sequences that are derived from the CH2 domain, CH3 domain, CH1 domain and CL domain, respectively, of a native immunoglobulin molecule.

As will be discussed in more detail below, the term "antibody" or "immunoglobulin" includes five distinct classes of antibody that can be distinguished biochemically. All five classes of antibodies are clearly within the scope of the present invention, the following discussion will generally be directed to the IgG class of immunoglobulin molecules. With regard to IgG, immunoglobulins comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable domain.

As used herein, the term "native" refers to immunoglobulin epitopes, regions, domains, moieties or structures as found in naturally occurring (i.e., not engineered) immunoglobulins.

Light chains of an immunoglobulin are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc. are well characterized and are known to confer functional specialization. Modified versions of each of these classes and isotypes are readily discernable to the skilled artisan in view of the instant disclosure and, accordingly, are within the scope of the instant invention.

Both the light and heavy chains are divided into regions of structural and functional homology. The term "region" refers to a part or portion of a single immunoglobulin (as is the case with the term "Fc region") or a single antibody chain and includes constant regions or variable regions, as well as more discrete parts or portions of said domains. For example, light chain variable domains include "complementarity determining regions" or "CDRs" interspersed among "framework regions" or "FRs", as defined herein.

Certain regions of an immunoglobulin may be defined as "constant" (C) regions or "variable" (V) regions, based on the relative lack of sequence variation within the regions of various class members in the case of a "constant region", or the significant variation within the regions of various class members in the case of a "variable regions". The terms "constant region" and "variable region" may also be used functionally. In this regard, it will be appreciated that the variable regions of an immunoglobulin or antibody determine antigen recognition and specificity. Conversely, the constant regions of an immunoglobulin or antibody confer important effector functions such as secretion, transplacental mobility, Fc receptor binding, complement binding, and the like. The subunit structures and three dimensional configuration of the constant regions of the various immunoglobulin classes are well known.

The constant and variable regions of immunoglobulin heavy and light chains are folded into domains. The term "domain" refers to an independently folding, globular region of a heavy or light chain polypeptide comprising peptide loops (e.g., comprising 3 to 4 peptide loops) stabilized, for example, by β-pleated sheet and/or intrachain disulfide bond. Constant region domains on the light chain of an immunoglobulin are referred to interchangeably as "light chain constant region domains", "CL regions" or "CL domains". Constant domains on the heavy chain (e.g. hinge, CH1, CH2 or CH3 domains) are referred to interchangeably as "heavy chain constant region domains", "CH" region domains or "CH domains". Variable domains on the light chain are referred to interchangeably as "light chain variable region domains", "VL region domains or "VL domains". Variable domains on the heavy chain are referred to interchangeably as "heavy chain variable region domains", "VH region domains" or "VH domains".

By convention the numbering of the variable and constant region domains increases as they become more distal from the antigen binding moiety or amino-terminus of the immunoglobulin or antibody. The N-terminus of each heavy and light immunoglobulin chain is a variable region and at the C-terminus is a constant region; the CH3 and CL domains actually comprise the carboxy-terminus of the heavy and light chain, respectively. Accordingly, the domains of a light chain immunoglobulin are arranged in a VL-CL orientation, while the domains of the heavy chain are arranged in the VH-CH1-hinge-CH2-CH3 orientation.

Amino acid positions in a heavy chain constant region, including amino acid positions in the CL, CH1, hinge, CH2, and CH3 domains, are numbered herein according to the EU index numbering system (see Kabat et al., in "Sequences of Proteins of Immunological Interest", U.S. Dept. Health and Human Services, $5^{th}$ edition, 1991). (As would be known by one of skill in the art, some portions of immunoglobulin sequences are covered by both the EU index numbering system and the Kabat index numbering system. Some portions of immunoglobulin sequences covered by both numbering systems assign the same residue sequence identification numbers to individual residues, whereas in other portions of the sequence, the residue sequence identification numbers assigned by the two conventions are different.)

As used herein, the term "$V_H$ domain" includes the amino terminal variable domain of an immunoglobulin heavy chain, and the term "$V_L$ domain" includes the amino terminal variable domain of an immunoglobulin light chain.

As used herein, the term "CH1 domain" includes the first (most amino terminal) constant region domain of an immunoglobulin heavy chain that extends, e.g., from about EU positions 118-215. The CH1 domain is adjacent to the $V_H$ domain and amino terminal to the hinge region of an immunoglobulin heavy chain molecule, and does not form a part of the Fc region of an immunoglobulin heavy chain. In one embodiment, an altered polypeptide of the invention comprises a CH1 domain derived from an immunoglobulin heavy chain molecule (e.g., a human IgG1 or IgG4 molecule).

As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al. J. Immunol. 1998, 161:4083).

As used herein, the term "CH2 domain" includes the portion of a heavy chain immunoglobulin molecule that extends, e.g., from about EU positions 231-340. The CH2 domain is unique in that it is not closely paired with another domain. Rather, two N-linked branched carbohydrate chains are interposed between the two CH2 domains of an intact native IgG molecule. In one embodiment, an altered constituent polypeptide of a binding molecule of the invention comprises a CH2 domain derived from an IgG1 molecule (e.g. a human IgG1 molecule). In another embodiment, an altered constituent polypeptide of a binding molecule comprises a CH2 domain derived from an IgG4 molecule (e.g., a human IgG4 molecule). In an exemplary embodiment, an altered constituent polypeptide of a binding molecule comprises a CH2 domain (EU positions 231-340), or a portion thereof.

As used herein, the term "CH3 domain" includes the portion of a heavy chain immunoglobulin molecule that extends approximately 110 residues from C-terminus of the CH2 domain, e.g., from about position 341-447 (EU numbering system). The CH3 domain typically forms the C-terminal portion of the antibody. In some immunoglobulins, however, additional domains may extend from CH3 domain to form the C-terminal portion of the molecule (e.g. the CH4 domain in the μ chain of IgM and the c chain of IgE). In one embodiment, a constituent polypeptide chain of a binding molecule of the invention comprises a CH3 domain derived from an IgG1 molecule (e.g., a human IgG1 molecule). In another embodiment, a constituent polypeptide chain of a binding molecule of the invention comprises a CH3 domain derived from an IgG4 molecule (e.g., a native human IgG4 molecule). In one embodiment, a constituent polypeptide chain of a binding molecule of the invention does not comprise a CH3 domain, e.g., in the case of the C2/D2 pair and the variants of C2/D2 pair in which T cell epitopes have been removed.

As used herein, the term "CL domain" includes the first (most amino terminal) constant region domain of an immunoglobulin light chain that extends, e.g. from about EU position 108-214. The CL domain is adjacent to the $V_L$ domain. In one embodiment, an altered constituent polypeptide of a binding molecule of the invention comprises a CL domain derived from a kappa light chain (e.g., a native human kappa light chain).

As used herein, the term "effector function" refers to the functional ability of the Fc region or portion thereof to bind proteins and/or cells of the immune system and mediate various biological effects. Effector functions may be antigen-dependent or antigen-independent. A decrease in effector function refers to a decrease in one or more effector functions, while maintaining the antigen binding activity of the variable region of the antibody (or fragment thereof). Increase or decreases in effector function, e.g., Fc binding to an Fc receptor or complement protein, can be expressed in terms of fold change (e.g., changed by 1-fold, 2-fold, and the like) and can be calculated based on, e.g., the percent changes in binding activity determined using assays the are well-known in the art.

As used herein, the term "antigen-dependent effector function" refers to an effector function which is normally induced following the binding of an antibody to a corresponding antigen. Typical antigen-dependent effector functions include the ability to bind a complement protein (e.g. C1q). For example, binding of the C1 component of complement to the Fc region can activate the classical complement system leading to the opsonisation and lysis of cell pathogens, a process referred to as complement-dependent cytotoxicity (CDCC). The activation of complement also stimulates the inflammatory response and may also be involved in autoimmune hypersensitivity.

Other antigen-dependent effector functions are mediated by the binding of antibodies, via their Fc region, to certain Fc receptors ("FcRs") on cells. There are a number of Fc receptors which are specific for different classes of antibody, including IgG (gamma receptors, or IgγRs), IgE (epsilon receptors, or IgεRs), IgA (alpha receptors, or IgαRs) and IgM (mu receptors, or IgμRs). Binding of antibody to Fc receptors on cell surfaces triggers a number of important and diverse biological responses including endocytosis of immune complexes, engulfment and destruction of antibody-coated particles or microorganisms (also called antibody-dependent phagocytosis, or ADCP), clearance of immune complexes, lysis of antibody-coated target cells by killer cells (called antibody-dependent cell-mediated cytotoxicity, or ADCC), release of inflammatory mediators, regulation of immune system cell activation, placental transfer and control of immunoglobulin production.

Certain Fc receptors, the Fc gamma receptors (FcγRs), play a critical role in either abrogating or enhancing immune recruitment. FcγRs are expressed on leukocytes and are composed of three related gene families: FcγRI, FcγRII, and FcγRIII (Gessner et al., Ann. Hematol., (1998), 76: 231-48). Furthermore, FcγRIII and FcγRIII are each comprised of two expressed genes, "a" and "b". Structurally, the FcγRs are all members of the immunoglobulin superfamily, having an IgG-binding α-chain with an extracellular portion composed of either two or three Ig-like domains. Human FcγRI (CD64) is an activating receptor expressed on human monocytes, exhibits high affinity binding (Ka=$10^8$-$10^9$ $M^{-1}$) to monomeric IgG1, IgG3, and IgG4. Human FcγRIIa (CD32a) and FcγRIIIa (CD16a) are also activating receptors but have low affinity for IgG1 and IgG3 (Ka<$10^7$ $M^{-1}$), and can bind only complexed or polymeric forms of these IgG isotypes. FcγRIIIa (CD16a) is bound to the surface of NK cells; FcγRIIa (CD32a) and FcγRIIIa (CD16a) are bound to the surface of macrophages and some T cells by a transmembrane domain. FcγRIIIb (CD16b) is selectively bound to cell surface of granulocytes (e.g. neutrophils) via a phosphatidyl inositol glycan (GPI) anchor. FcγRIIb (CD32b) is an inhibitory receptor, bound to cells by a transmembrane domain, is expressed widely on leukocytes and is the sole receptor on B cells, but is not found on NK cells. In mice, there is a closely related, although not exactly homologous, set of activating and inhibitory Fcγ receptors, that sort into the same gene families: FcγRI, FcγRII, and FcγRIII.

As used herein, the term "antigen-independent effector function" refers to an effector function which may be induced by an antibody, regardless of whether it has bound its corresponding antigen. Typical antigen-independent effector functions include cellular transport, circulating half-life and clearance rates of immunoglobulins, and facilitation of purification. A structurally unique Fc receptor, the "neonatal Fc receptor" or "FcRn", also known as the salvage receptor, plays a critical role in regulating half-life and cellular transport. Other Fc receptors purified from microbial cells (e.g. Staphylococcal Protein A or G) are capable of binding to the Fc region with high affinity and can be used to facilitate the purification of a binding molecule with a heteromeric Fc region.

Unlike FcγRs which belong to the Immunoglobulin superfamily, human FcRns structurally resemble polypeptides of Major Histocompatibility Complex (MHC) Class I (Ghetie and Ward, Immunology Today, (1997), 18(12): 592-8). FcRn is typically expressed as a heterodimer consisting of a transmembrane α or heavy chain in complex with a soluble β or light chain (β2 microglobulin). FcRn shares 22-29% sequence identity with Class I MHC molecules and has a non-functional version of the MHC peptide binding groove (Simister and Mostov, Nature, (1989), 337: 184-7 Like MHC, the α chain of FcRn consists of three extracellular domains (α1, α2, α3) and a short cytoplasmic tail anchors the protein to the cell surface. The α1 and α2 domains interact with FcR binding moieties in the Fc region of antibodies (Raghavan et al., Immunity, (1994), 1: 303-15). FcRn is expressed in the maternal placenta or yolk sac of mammals and it is involved in transfer of IgGs from mother to fetus. FcRn is also expressed in the small intestine of rodent neonates, where it is involved in the transfer across the brush border epithelia of maternal IgG from ingested colostrum or milk. FcRn is also expressed in numerous other tissues across numerous species, as well as in various endothelial cell lines. It is also expressed in human adult vascular endothelium, muscle vasculature, and hepatic sinusoids. FcRn is thought to play an additional role in maintaining the circulatory half-life or serum levels of IgG by binding it and recycling it to the serum. The binding of FcRn to IgG molecules is strictly pH-dependent with an optimum binding at a pH of less than 7.0.

As used herein, the term "half-life" refers to a biological half-life of a particular binding molecule in vivo. Half-life may be represented by the time required for half the quantity administered to a subject to be cleared from the circulation and/or other tissues in the animal. When a clearance curve of a given binding molecule is constructed as a function of time, the curve is usually biphasic with a rapid α-phase and longer β-phase. The α-phase typically represents an equilibration of the administered binding molecule between the intra- and extra-vascular space and is, in part, determined by the size of the molecule. The β-phase typically represents the catabolism of the binding molecule in the intravascular space. Therefore, in a preferred embodiment, the term half-life as used herein refers to the half-life of the binding molecule in the β-phase. The typical β phase half-life of a human antibody in humans is 21 days.

As indicated above, the variable regions of an antibody allow it to selectively recognize and specifically bind epitopes on antigens. That is, the $V_L$ domain and $V_H$ domain of an antibody combine to form the variable region (Fv) that defines a three dimensional antigen binding moiety. This quaternary antibody structure forms the antigen binding moiety present at the end of each arm of the Y. More specifically, the antigen binding moiety is defined by three complementary determining regions (CDRs) on each of the heavy and light chain variable regions.

As used herein, the term "antigen binding site" includes a site that specifically binds (immunoreacts with) an antigen such as a cell surface or soluble antigen. In one embodiment, the binding moiety includes an immunoglobulin heavy chain and light chain variable region and the binding moiety formed by these variable regions determines the specificity of the antibody. An antigen binding moiety is formed by variable regions that vary from one polypeptide to another. In one embodiment, a constituent polypeptide chain of a binding molecule of the invention comprises an antigen binding moiety comprising at least one heavy or light chain CDR of an antibody molecule (e.g., the sequence of which is known in the art or described herein). In another embodiment, a constituent polypeptide chain of a binding molecule of the invention comprises an antigen binding moiety comprising at least two CDRs from one or more antibody molecules. In another embodiment, a constituent polypeptide chain of a binding molecule of the invention comprises an antigen binding moiety comprising at least three CDRs from one or more antibody molecules. In another embodiment, a constituent polypeptide chain of a binding molecule of the invention comprises an antigen binding moiety comprising at least four CDRs from one or more antibody molecules. In another embodiment, a constituent polypeptide chain of a binding molecule of the invention comprises an antigen binding moiety comprising at least five CDRs from one or more antibody molecules. In another embodiment, a constituent polypeptide chain of a binding molecule of the invention comprises an antigen binding moiety comprising at least six CDRs from one or more antibody molecules. Exemplary antibody molecules comprising at least one CDR that can be included in the subject constituent polypeptide chains of a binding molecule of the invention are known in the art and exemplary molecules are described herein.

As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat based on sequence comparisons.

| CDR Definitions | | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra The term "framework region" or "FR region" as used herein, includes the amino acid residues that are part of the variable region, but are not part of the CDRs (e.g., using the Kabat definition of CDRs). Therefore, a variable region framework is between about 100-120 amino acids in length but includes only those amino acids outside of the CDRs. For the specific example of a heavy chain variable region and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light chain variable region CDRs. Similarly, using the definition of CDRs by Chothia et al. or McCallum et al. the framework region boundaries are separated by the respective CDR termini as described above. In preferred embodiments, the CDRs are as defined by Kabat.

In naturally occurring antibodies, the six CDRs present on each monomeric antibody are short, non-contiguous sequences of amino acids that are specifically positioned to form the antigen binding moiety as the antibody assumes its three dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding moiety formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

In certain embodiments, the constituent polypeptide chains of binding molecules of the invention comprise at least one antigen binding domain (e.g., at the N- and C-terminus of a single constituent polypeptide chain, or linked to a component constituent polypeptide chain of a heteromeric binding protein of the invention) that provide for the association of the binding molecule with the selected antigen. If the constituent polypeptide chains of binding molecules of the invention comprise more than one antigen binding domain, the antigen binding domains need not be derived from the same immunoglobulin molecule. In this regard, the variable region may or may not be derived from any type of animal that can be induced to mount a humoral response and generate immunoglobulins against the desired antigen. As such, the variable region of the altered antibody may be, for example, of mammalian origin e.g., may be human, murine, non-human primate (such as cynomolgus monkeys, macaques, etc.), lupine, camelid (e.g., from camels, llamas and related species).

The term "antibody variant" includes an antibody which does not occur in nature and which has an amino acid sequence or amino acid side chain chemistry which differs from that of a naturally-derived antibody by at least one amino acid or amino acid modification as described herein. As used herein, the term "antibody variant" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen; heavy chain molecules joined to scFv molecules; single-chain antibodies; diabodies; triabodies; and antibodies with altered effector function and the like.

As used herein the term "scFv molecule" includes binding molecules which consist of one light chain variable domain (VL) or portion thereof, and one heavy chain variable domain (VH) or portion thereof, wherein each variable domain (or portion thereof) is derived from the same or different antibodies. scFv molecules preferably comprise an scFv linker interposed between the VH domain and the VL domain. ScFv molecules are known in the art and are described, e.g., in U.S. Pat. No. 5,892,019, Ho et al. 1989. Gene 77:51; Bird et al. 1988 *Science* 242:423; Pantoliano et al. 1991. *Biochemistry* 30:10117; Milenic et al. 1991. *Cancer Research* 51:6363; Takkinen et al. 1991. *Protein Engineering* 4:837.

A "scFv linker" as used herein refers to a moiety interposed between the VL and VH domains of the scFv. scFv linkers preferably maintain the scFv molecule in a antigen binding conformation. In one embodiment, a scFv linker comprises or consists of an scFv linker peptide. In certain embodiments, a scFv linker peptide comprises or consists of a gly-ser polypeptide linker. In other embodiments, a scFv linker comprises a disulfide bond.

As used herein, the term "gly-ser polypeptide linker" refers to a peptide that consists of glycine and serine residues. An exemplary gly/ser polypeptide linker comprises the amino acid sequence $(Gly_4 Ser)_n$ (SEQ ID NO: 18). In one embodiment, n=1. In one embodiment, n=2. In another embodiment, n=3, i.e., $(Gly_4 Ser)_3$ (SEQ ID NO: 19). In another embodiment, n=4, i.e., $(Gly_4 Ser)_4$ (SEQ ID NO: 20). In another embodiment, n=5. In yet another embodiment, n=6. Another exemplary gly/ser polypeptide linker comprises the amino acid sequence Ser($Gly_4$Ser). (SEQ ID NO: 21). In one embodiment, n=1. In one embodiment, n=2. In a preferred embodiment, n=3. In another embodiment, n=4. In another embodiment, n=5. In yet another embodiment, n=6.

As used herein the term "protein stability" refers to an art-recognized measure of the maintenance of one or more physical properties of a protein in response to an environmental condition (e.g. an elevated or lowered temperature). In one embodiment, the physical property is the maintenance of the covalent structure of the protein (e.g. the absence of proteolytic cleavage, unwanted oxidation or deamidation). In another embodiment, the physical property is the presence of the protein in a properly folded state (e.g. the absence of soluble or insoluble aggregates or precipitates).

The term "glycosylation" refers to the covalent linking of one or more carbohydrates to a polypeptide. Typically, glycosylation is a posttranslational event which can occur within the intracellular milieu of a cell or extract therefrom. The term glycosylation includes, for example, N-linked glycosylation (where one or more sugars are linked to an asparagine residue) and/or O-linked glycosylation (where one or more sugars are linked to an amino acid residue having a hydroxyl group (e.g., serine or threonine).

As used herein, the term "native cysteine" shall refer to a cysteine amino acid that occurs naturally at a particular amino acid position of a polypeptide and which has not been modified, introduced, or altered by the hand of man. The term "engineered cysteine residue or analog thereof" or "engineered cysteine or analog thereof" shall refer to a non-native cysteine residue or a cysteine analog (e.g. thiol-containing analogs such as thiazoline-4-carboxylic acid and thiazolidine-4 carboxylic acid (thioproline, Th)), which is introduced by synthetic means (e.g. by recombinant techniques, in vitro peptide synthesis, by enzymatic or chemical coupling of peptides or some combination of these techniques) into an amino acid position of a polypeptide where the natural protein from which that amino acid sequence was derived does not naturally contain a cysteine residue or analog thereof at that position.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by native disulfide bonds and the two heavy chains are linked by two native disulfide bonds at positions corresponding to 239 and 242 using the Kabat numbering system (position 226 or 229, EU numbering system).

As used herein, the term "bonded cysteine" shall refer to a native or engineered cysteine residue within a polypeptide which forms a disulfide bond or other covalent bond with a second native or engineered cysteine or other residue present within the same or different polypeptide. An "intrachain bonded cysteine" shall refer to a bonded cysteine that is covalently bonded to a second cysteine present within the same polypeptide chain (ie. an intrachain disulfide bond). An "interchain bonded cysteine" shall refer to a bonded cysteine that is covalently bonded to a second cysteine present within a different polypeptide chain (ie. an interchain disulfide bond).

As used herein, the term "free cysteine" refers to a native or engineered cysteine amino acid residue within a polypeptide sequence (and analogs or mimetics thereof, e.g. thiazoline-4-carboxylic acid and thiazolidine-4 carboxylic acid (thioproline, Th)) that exists in a substantially reduced form. Free cysteines are preferably capable of being modified with an effector moiety of the invention.

The term "thiol modification reagent" shall refer to a chemical agent that is capable of selectively reacting with the thiol group of an engineered cysteine residue or analog thereof in a constituent polypeptide chain (e.g., within an polypeptide linker of a binding polypeptide), and thereby providing means for site-specific chemical addition or cross-linking of effector moieties to the constituent polypeptide or binding molecule, thereby forming a modified constituent polypeptide chain or binding molecule. Preferably the thiol modification reagent exploits the thiol or sulfhydryl functional group which is present in a free cysteine residue.

Exemplary thiol modification reagents include maleimides, alkyl and aryl halides, α-haloacyls, and pyridyl disulfides.

The term "functional moiety" includes moieties which, preferably, add a desirable function to the constituent polypeptide chain or the binding molecule. Preferably, the function is added without significantly altering an intrinsic desirable activity of the binding molecule, e.g., the antigen-binding activity of the molecule. A binding molecule of the invention may comprise one or more functional moieties, which may be the same or different. Examples of useful functional moieties include, but are not limited to, an effector moiety, an affinity moiety, and a blocking moiety.

Exemplary blocking moieties include moieties of sufficient steric bulk and/or charge such that reduced glycosylation occurs, for example, by blocking the ability of a glycosidase to glycosylate the polypeptide. The blocking moiety may additionally or alternatively, reduce effector function, for example, by inhibiting the ability of the Fc region to bind a receptor or complement protein. Preferred blocking moieties include cysteine adducts, cystine, mixed disulfide adducts, and PEG moieties. Exemplary detectable moieties include fluorescent moieties, radioisotopic moieties, radiopaque moieties, and the like.

With respect to conjugation of chemical moieties, the term "linking moiety" includes moieties which are capable of linking a functional moiety to the remainder of the constituent polypeptide chain. The linking moiety may be selected such that it is cleavable or non-cleavable. Uncleavable linking moieties generally have high systemic stability, but may also have unfavorable pharmacokinetics.

The term "spacer moiety" may be an optionally substituted chain of 0 to 100 atoms, selected from carbon, oxygen, nitrogen, sulfur, etc. In one embodiment, the spacer moiety is selected such that it is water soluble. In another embodiment, the spacer moiety is polyalkylene glycol, e.g., polyethylene glycol or polypropylene glycol.

The terms "PEGylation moiety" or "PEG moiety" includes a polyalkylene glycol compound or a derivative thereof, with or without coupling agents or derivitization with coupling or activating moieties (e.g., with thiol, triflate, tresylate, azirdine, oxirane, or preferably with a maleimide moiety, e.g., PEG-maleimide). Other appropriate polyalkylene glycol compounds include, maleimido monomethoxy PEG, activated PEG polypropylene glycol, but also charged or neutral polymers of the following types: dextran, colominic acids, or other carbohydrate based polymers, polymers of amino acids, and biotin derivatives.

As used herein, the term "effector moiety" may comprise diagnostic and therapeutic agents (e.g. proteins, nucleic acids, lipids, drug moieties, and fragments thereof) with biological or other functional activity. For example, a modified binding molecule, comprising an effector moiety conjugated to a binding molecule, has at least one additional function or property as compared to the unconjugated binding molecule. For example, the conjugation of a cytotoxic drug moiety (e.g., an effector moiety) to a binding molecule of the invention (e.g., via its polypeptide linker) results in the formation of a modified binding molecule with drug cytotoxicity as second function (i.e. in addition to antigen binding). In another example, the conjugation of an additional polypeptide to a binding molecule may confer additional binding properties to the binding molecule. In another example, the dimerization of a first constituent polypeptide to a second constituent polypeptide and the resultant creation of the heterodimeric Fc region of the binding molecule may confer additional binding properties.

In one aspect, wherein the effector moiety is a genetically encoded therapeutic or diagnostic protein or nucleic acid, the effector moiety may be synthesized or expressed by either peptide synthesis or recombinant DNA methods that are well known in the art. In another aspect, wherein the effector is a non-genetically encoded peptide or a drug moiety, the effector moiety may be synthesized artificially or purified from a natural source.

As used herein, the term "drug moiety" includes anti-inflammatory, anticancer, anti-infective (e.g., anti-fungal, antibacterial, anti-parasitic, anti-viral, etc.), and anesthetic therapeutic agents. In a further embodiment, the drug moiety is an anticancer or cytotoxic agent. Compatible drug moieties may also comprise prodrugs.

As used herein, the term "prodrug" refers to a precursor or derivative form of a pharmaceutically active agent that is less active, reactive or prone to side effects as compared to the parent drug and is capable of being enzymatically activated or otherwise converted into a more active form in vivo. Prodrugs compatible with the invention include, but are not limited to, phosphate-containing prodrugs, amino acid-containing prodrugs, thiophosphate-containing prodrugs, sulfate containing prodrugs, peptide containing prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs that can be converted to the more active cytotoxic free drug. One skilled in the art may make chemical modifications to the desired drug moiety or its prodrug in order to make reactions of that compound more convenient for purposes of preparing modified constituent polypeptides of binding molecules of the invention. The drug moieties also include derivatives, pharmaceutically acceptable salts, esters, amides, and ethers of the drug moieties described herein. Derivatives include modifications to drugs identified herein which may improve or not significantly reduce a particular drug's desired therapeutic activity.

As used herein, the term "anticancer agent" includes agents which are detrimental to the growth and/or proliferation of neoplastic or tumor cells and may act to reduce, inhibit or destroy malignancy. Examples of such agents include, but are not limited to, cytostatic agents, alkylating agents, antibiotics, cytotoxic nucleosides, tubulin binding agents, hormones and hormone antagonists, and the like. Any agent that acts to retard or slow the growth of immunoreactive cells or malignant cells is within the scope of the present invention.

An "affinity tag" or an "affinity moiety" is a chemical moiety that is attached to one or more of the constituent polypeptides, polypeptide linkers, or effector moieties in order to facilitate its separation from other components during a purification procedure. Exemplary affinity domains include the His tag, chitin binding domain, maltose binding domain, biotin, strepII-tags, FLAG-tags and the like.

An "affinity resin" is a chemical surface capable of binding the affinity domain with high affinity to facilitate separation of the protein bound to the affinity domain from the other components of a reaction mixture. Affinity resins can be coated on the surface of a solid support or a portion thereof. Alternatively, the affinity resin can comprise the solid support its. Such solid supports can include a suitably modified chromatography column, microtiter plate, bead, or biochip (e.g. glass wafer). Exemplary affinity resins are comprised of nickel, chitin, amylase, and the like.

The term "vector" or "expression vector" is used herein for the purposes of the specification and claims, to mean vectors used in accordance with the present invention as a vehicle for introducing into and expressing a desired polynucleotide in a cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Exemplary vectors include those described in U.S. Pat. Nos. 6,159,730 and 6,413,777, and U.S. Patent Application No. 2003 0157641 A1, all of which are hereby incorporated by reference. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. In one embodiment, an inducible expression system can be employed. Additional elements may also be needed for optimal synthesis of mRNA. These elements may include signal sequences, splice signals, as well as transcriptional promoters, enhancers, and termination signals. In one embodiment, a secretion signal, e.g., any one of several well characterized bacterial leader peptides (e.g., pelB, phoA, or ompA), can be fused in-frame to the N terminus of a constituent polypeptide chain of the invention to obtain optimal secretion of the binding molecule. (Lei et al. (1988), *Nature*, 331:543; Better et al. (1988) *Science*, 240:1041; Mullinax et al., (1990). *PNAS*, 87:8095).

The term "host cell" refers to a cell that has been transformed with a vector constructed using recombinant DNA techniques and encoding at least one heterologous gene. In descriptions of processes for isolation of proteins from recombinant hosts, the terms "cell" and "cell culture" are used interchangeably to denote the source of protein unless it is clearly specified otherwise. In other words, recovery of protein from the "cells" may mean either from spun down whole cells, or from the cell culture containing both the medium and the suspended cells. The host cell line used for protein expression is most preferably of mammalian origin; those skilled in the art are credited with ability to preferentially determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). CHO cells are particularly preferred. Host cell lines are typically available from commercial services, the American Tissue Culture Collection or from published literature. The polypeptides of the invention can also be expressed in non-mammalian cells such as bacteria or yeast or plant cells. In this regard it will be appreciated that various unicellular non-mammalian microorganisms such as bacteria can also be transformed; i.e. those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the polypeptides typically become part of inclusion bodies. The polypeptides must be isolated, purified and then assembled into functional molecules.

In addition to prokaryotes, eukaryotic microbes may also be used. *Saccharomyces cerevisiae*, or common baker's yeast, is the most commonly used among eukaryotic microorganisms although a number of other strains are commonly available including *Pichia pastoris*. For expression in *Saccharomyces*, the plasmid YRp7, for example, (Stinchcomb et al., (1979), *Nature*, 282:39; Kingsman et al., (1979), *Gene*, 7:141; Tschemper et al., (1980), *Gene*, 10:157) is commonly used. This plasmid already contains the TRP1 gene which provides a selection marker for a mutant strain of yeast lacking the ability to grow in tryptophan, for example ATCC No. 44076 or PEP4-1 (Jones, (1977), *Genetics*, 85:12). The presence of the trp1 lesion as a characteristic of the yeast host cell genome then provides an effective environment for detecting transformation by growth in the absence of tryptophan.

In vitro production allows scale-up to give large amounts of the binding molecules of the invention. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of binding molecules can be purified by the customary chromatography methods, for example gel filtration, ion-exchange chromatography, hydrophobic interaction chromatography (HIC, chromatography over DEAE-cellulose or affinity chromatography.

As used herein, "tumor-associated antigens" means any antigen which is generally associated with tumor cells, i.e., occurring at the same or to a greater extent as compared with normal cells. More generally, tumor associated antigens comprise any antigen that provides for the localization of immunoreactive antibodies at a neoplastic cell irrespective of its expression on non-malignant cells. Such antigens may be relatively tumor specific and limited in their expression to the surface of malignant cells. Alternatively, such antigens may be found on both malignant and non-malignant cells. In certain preferred embodiments, the binding molecules of the present invention preferably bind to tumor-associated antigens. Accordingly, a constituent polypeptide chain or binding molecule of the invention may be derived, generated or fabricated from any one of a number of antibodies that react with tumor associated molecules.

As used herein, the term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas. The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

As used herein, the phrase "subject that would benefit from administration of a binding molecule" includes subjects, such as mammalian subjects, that would benefit from administration of binding molecules used, e.g., for detection of an antigen recognized by a binding molecule of the invention (e.g., for a diagnostic procedure) and/or from treatment with a binding molecule to reduce or eliminate the target recognized by the binding molecule. For example, in one embodiment, the subject may benefit from reduction or elimination of a soluble or particulate molecule from the circulation or serum (e.g., a toxin or pathogen) or from reduction or elimination of a population of cells expressing the target (e.g., tumor cells). As discussed above, the binding molecule can be used in unconjugated form or can be conjugated, e.g., to a drug, prodrug, or an isotope, to form a modified binding molecule for administering to said subject.

II. Binding Molecules Comprising Heterodimeric Fc Regions

Fc regions of binding molecules of the invention comprise two polypeptide chains, each of which comprises at least one Fc moiety (e.g., 1, 2, 3, 4, 5, 6, or more Fc moieties) within a linear constituent polypeptide chain linked to at least one Fab constant region moiety (i.e., CH1 or CL). In a preferred embodiment, the at least one Fab constant region moiety (i.e., CH1 or CL) is fused at its N-terminal end to the C-terminal end of the Fc moiety, or to the C-terminal end of the most C-terminal of the Fc moieties, if there is more than one. Alternatively, the at least one Fab constant region moiety is interposed between two Fc moieties. Preferably, the Fab constant region moiety (i.e., CH1 or CL) and at least one (more preferably all) of the Fc moieties are capable of dimerizing (e.g., intermolecularly pairing) with the corresponding constant region moiety to form at least one functional Fc region. In one embodiment, the Fc region imparts an effector function to the binding molecule. For example, in one preferred embodiment, a binding molecule of the invention is capable of binding to an Fc receptor (e.g. an FcRn, an FcγR receptor (e.g., FcγRIII), or a complement protein (e.g. C1q)) in order to trigger an immune effector function (e.g., antibody-dependent cytotoxicity (ADCC), phagocytosis, or complement-dependent cytotoxicity (CDCC)).

In certain embodiments, at least two of the Fc moieties of a constituent polypeptide chain are directly fused to each other in a contiguous linear sequence of amino acids such that there is no intervening amino acid or peptide between the C-terminus of the first Fc moiety and the N-terminus of the second Fc moiety. In some embodiments, an Fc moiety (or the most C-terminal of all the Fc moieties, if more than one is present) is directly fused at its C-terminal end and in a contiguous linear sequence of amino acids to the N-terminal end of a Fab constant region moiety (i.e., a CH1 or CL moiety). In some embodiments, however, at least two of the Fc moieties (more preferably all) of the Fc region of a constituent polypeptide chain are genetically fused via a polypeptide linker (e.g., a synthetic linker) interposed between at least two Fc moieties. In preferred embodiments, an Fc moiety (or the most C-terminal of all the Fc moieties, if more than one is present) is genetically fused via a polypeptide linker (e.g., a synthetic linker) at its C-terminal end to the N-terminal end of a Fab constant region moiety (i.e., a CH1 or CL moiety). In some embodiments, the polypeptide linker is a glycine-serine linker (gly-ser). In preferred embodiments, the sequence of the polypeptide linker is GS or GGGS (SEQ ID NO: 22).

In certain embodiments, the heterodimeric Fc region of a binding molecule (i.e., formed by the dimerization of two constituent polypeptide chains) is capable of binding to an Fc receptor with a binding affinity of at least $10^{-7}$ M (e.g., at least $10^{-8}$ M, at least M, $10^{-9}$ M, at least $10^{-10}$ M at least $10^{-11}$ M, or at least $10^{-12}$ M).

In some embodiments, binding molecules of the invention may comprise multiple Fc moieties of the same, or substantially the same, sequence composition. In preferred embodiments, the constituent polypeptides of binding molecules of the invention may comprise at least two Fc moieties which are of substantially different sequence composition. In certain embodiments, binding molecules of the invention comprise at least one insertion or amino acid substitution in an Fc moiety as compared to the native immunoglobulin sequence from which the Fc moiety was derived. In one exemplary embodiment, the heterodimeric Fc region of a binding molecule comprises an amino acid substitution (e.g., an amino acid substitution of Asparagine at EU position 297) in a first Fc moiety (i.e. on a first constituent polypeptide chain), but not in a second Fc moiety in a corresponding position within a second polypeptide chain of the heterodimeric binding molecule.

The constituent polypeptide chains of binding molecules of the invention may be assembled together or with other polypeptides to form multimeric binding molecules (also, referred to herein as "multimers"). The multimeric binding molecules of the invention comprise at least two non-identical constituent polypeptides of the invention. Accordingly, the invention is directed without limitation to dimeric as well as multimeric (e.g., trimeric, tetrameric, and hexameric) binding molecules and the like. In preferred embodiments of the invention, at least two constituent polypeptides of the multimeric proteins of the invention are different (ie. heteromeric multimers, e.g. heterodimers, heterotrimers, heterotetramers).

Figure 2:
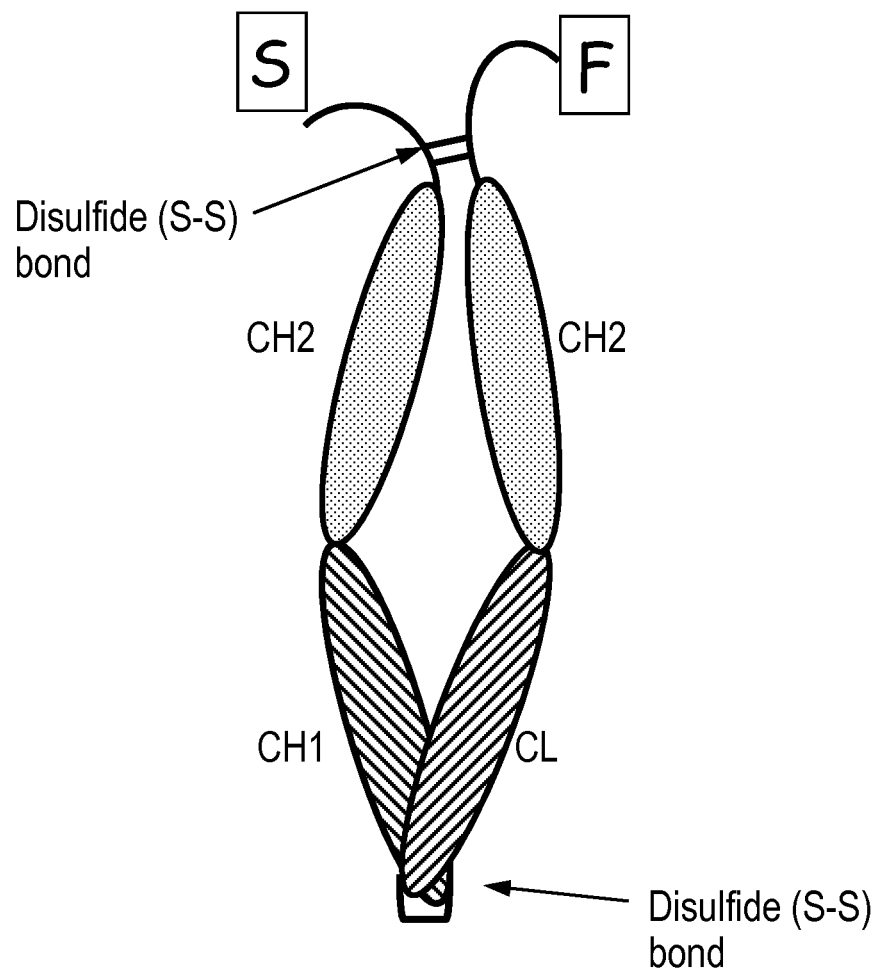
FIG. 2 depicts a close-up view of the anatomy of an exemplary heterodimeric binding molecule of the invention comprising (i) a first polypeptide chain comprising an Fc moiety (a portion of a hinge moiety and a CH2 moiety) interposed between a first binding moiety ("S") and a CH1 moiety and (ii) a second polypeptide chain comprising an Fc moiety (a portion of a hinge moiety and CH2 moiety) interposed between a second binding moiety ("F") and a CL moiety. In certain embodiments, the S and F binding moieties can be selected from an antigen binding moiety (e.g., a variable region, such as a Fab or scFv), a ligand binding portion of a receptor, a receptor binding portion of a ligand, or any combination thereof. In other embodiments, only one of F or S is a binding moiety.

In preferred embodiments, the binding molecules of the invention are stabilized by an interchain disulfide bond at the C-terminal end of the Fc region as well as an interchain disulfide bond between the hinge regions of the two constituent polypeptides (see, for example, FIG. 2). Additional embodiments include binding molecules that do not comprise an interchain disulfide bond between CH1 and CL moieties, binding molecules that do not comprise an interchain disulfide bond between hinge region moieties and binding molecules that do not comprise an interchain sulfide bond between constituent polypeptide chains. Further additional embodiments include binding molecules that do not comprise a cysteine residue in the hinge moiety of a constituent polypeptide chain.

A variety of binding molecules of alternative designs are also within the scope of the invention. For example, one or more binding moieties can be fused to or linked with a binding molecule of the invention, or incorporated within (e.g., veneered onto) a constituent polypeptide chain of a binding molecule of the invention, in multiple orientations. FIGS. 6A-B and 7A-B depict a variety of non-limiting examples of such binding molecules. In one exemplary embodiment, a binding molecule of the invention comprises a binding moiety fused to the N-terminus of a constituent polypeptide chain. In another exemplary embodiment, a binding polypeptide comprises a binding moiety at the C-terminus of a constituent polypeptide chain. The binding molecule of the invention may comprise binding moieties at both the C-terminus and the N-terminus of one or both constituent polypeptide chains of a binding molecule. In yet other embodiments, a binding molecule of the invention may comprise a binding moiety in a linker sequence between Fc moieties or between an Fc moiety and a Fab constant domain moiety (e.g., between a CH2 moiety and CH1 or CL moiety or between CH3 moiety and CH1 or CL moiety. Alternatively, the binding moiety may be incorporated in an interdomain region between the hinge and CH2 moiety of an Fc region.

In still further embodiments, the binding molecule of the invention comprises a binding moiety which is introduced into an Fc moiety of a constituent polypeptide chain. For example, a binding moiety may be veneered into an N-terminal CH2 moiety, a CH3 moiety or a C-terminal CH1 or CL moiety. In one embodiment, the CDR loops of an antibody are veneered into one or both Fc moieties of the constituent polypeptide chains (see, e.g., WO 08/003116, which is incorporated by reference herein).

It is recognized by those skilled in the art that a binding molecule of the invention may comprise two or more binding moieties (e.g., 2, 3, 4, or more binding sites) which are linked or fused into a binding molecule or integrated (e.g., veneered) into a constituent polypeptide chain of a binding molecule of the invention using any combination of the orientations depicted in FIGS. 6A-B or 7A-B.

A. Fc Moieties

Fc moieties useful for producing the constituent polypeptide chains of binding molecules of the present invention may be obtained from a number of different sources. In preferred embodiments, an Fc moiety of the binding molecule is derived from a human immunoglobulin. It is understood, however, that the Fc moiety may be derived from an immunoglobulin of another mammalian species, including for example, a rodent (e.g. a mouse, rat, rabbit, guinea pig) or non-human primate (e.g. chimpanzee, macaque) species. Moreover, the Fc region of a constituent polypeptide chain or portion thereof may be derived from any immunoglobulin class, including IgM, IgG, IgD, IgA and IgE, and any immunoglobulin isotype, including IgG1, IgG2, IgG3 and IgG4. In a preferred embodiment, the human isotype IgG1 or IgG4 is used.

A variety of Fc moiety gene sequences (e.g. human constant region gene sequences) are available in the form of publicly accessible deposits. Constant region domains comprising an Fc moiety sequence can be selected having a particular effector function (or lacking a particular effector function) or with a particular modification to reduce immunogenicity. Many sequences of antibodies and antibody-encoding genes have been published and suitable Fc moiety sequences (e.g. hinge, CH2, and/or CH3 sequences, or portions thereof) can be derived from these sequences using art recognized techniques. The genetic material obtained using any of the foregoing methods may then be altered or synthesized to obtain constituent polypeptide chains of the present invention. It will further be appreciated that the scope of this invention encompasses alleles, variants and mutations of constant region DNA sequences.

Fc moiety sequences can be cloned, e.g., using the polymerase chain reaction and primers which are selected to amplify the particular moiety of interest. To clone an Fc moiety sequence from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. Methods Enzymol. 217:270). PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250). The cloning of antibody sequences is further described in Newman et al., U.S. Pat. No. 5,658,570, filed Jan. 25, 1995, which is incorporated by reference herein.

The constituent polypeptide chains of binding molecules of the invention may comprise one or more Fc moieties (e.g., 1, 2, 3, 4, 5, 6, 7, 8, 9, 10, or more Fc moieties). In one embodiment, the Fc moieties may be of different types. In one embodiment, the constituent polypeptide chains of binding molecules of the invention comprise at least one Fc moiety comprising a hinge domain or portion thereof. In another embodiment, the constituent polypeptide chains of binding molecules of the invention comprise at least one Fc moiety comprising sequence from an immunoglobulin CH2 domain. In another embodiment, the constituent polypeptides of binding molecules of the invention comprise at least one Fc moiety comprising sequence from an immunoglobulin CH3 domain. In another embodiment, the constituent polypeptides of binding molecules of the invention do not comprise an Fc moiety comprising sequence from an immunoglobulin CH3 domain. In another embodiment, the constituent polypeptide chains of binding molecules of the invention comprise at least one Fc moiety comprising sequence from an immunoglobulin CH4 domain. In another embodiment, the constituent polypeptide chains of binding molecules of the invention do not comprise an Fc moiety comprising sequence from an immunoglobulin CH4 domain. In another embodiment, the constituent polypeptide chains of binding molecules of the invention comprise at least one Fc moiety comprising sequence from an immunoglobulin hinge domain and sequence from an immunoglobulin CH2 domain (e.g., in the hinge-CH2 orientation). In another embodiment, the constituent polypeptides of binding molecules of the invention comprise sequence from an immunoglobulin CH2 domain and sequence from an immunoglobulin CH3 domain (e.g., in the CH2-CH3 orientation). In another embodiment, the constituent polypeptides of binding molecules of the invention comprise sequence from an immunoglobulin hinge domain, sequence from an immunoglobulin CH2 domain, and sequence from an immunoglobulin CH3 domain, for example in the orientation hinge-CH2-CH3, hinge-CH3-CH2, or CH2-CH3-hinge.

In certain embodiments, the constituent polypeptide chains comprise the sequence of at least one complete Fc domain from an immunoglobulin heavy chain (i.e., hinge portion, CH2 domain and CH3 domain). In other embodiments, the constituent polypeptide chains comprise at least two complete Fc moieties from an immunoglobulin heavy chain (e.g., the sequences of an immunoglobulin CH2 domain and CH3 domain, but not necessarily in the same position or order as found in a native immunoglobulin heavy chain). In preferred embodiments, a complete Fc moiety is derived from a human IgG immunoglobulin heavy chain (e.g., human IgG1).

In another embodiment, constituent polypeptide chains of the invention comprise at least one Fc moiety comprising a complete CH3 domain (about amino acids 341-438 of an antibody Fc region according to EU numbering). In another embodiment, constituent polypeptide chains of the invention comprise at least one Fc moiety comprising a complete CH2 domain (about amino acids 231-340 of an antibody Fc region according to EU numbering). In another embodiment, constituent polypeptide chains of the invention comprise at least one Fc region sequence comprising at least a CH3 domain, and at least one portion of a hinge region (about amino acids 216-230 of an antibody Fc region according to EU numbering), and a CH2 domain. In one embodiment, a constituent polypeptide chains of the invention comprise at least one Fc region sequence comprising a portion of a hinge region and a CH3 domain. In another embodiment, a constituent polypeptide chains of the invention comprise at least one Fc region sequence comprising a portion of a hinge region, a $CH_2$, and a $CH_3$ domain. In preferred embodiments, the Fc moiety is derived from a human IgG immunoglobulin heavy chain (e.g., human IgG1). Fc moieties may be found in the same order (e.g., from N-terminal to C-terminal) as found in a native immunoglobulin molecule, or may be rearranged into a different order as compared to a native immunoglobulin molecule.

The immunoglobulin constant region sequences or portions thereof making up one or more Fc moieties of a constituent polypeptide chains of binding molecules of the invention may be derived from different immunoglobulin molecules. For example, a constituent polypeptide chain of the invention may comprise a CH2 domain or portion thereof derived from an IgG1 molecule and a CH3 domain or portion thereof derived from an IgG3 molecule. In another example, a constituent polypeptide chain can comprise an Fc region comprising a portion of a hinge domain derived, in part, from an IgG1 molecule and, in part, from an IgG3 molecule. Thus a constituent polypeptide chain of the invention may comprise Fc moieties where individual Fc moieties are derived from immunoglobulins of different genotypes, classes or species. Likewise, a constituent polypeptide chain of the invention may comprise one or more Fc moieties that contain, within a single Fc moiety derived from a particular type of immunoglobulin domain (e.g., a CH2 domain), sequences derived from different genotypes, classes or species. For example, a constituent polypeptide chain of the invention may comprise a CH2 Fc moiety with some sequence from a murine CH2 domain and some sequence from a human CH2 domain. As set forth herein, it will be understood by one of ordinary skill in the art that an Fc moiety may be altered such that it varies in amino acid sequence from a naturally occurring antibody molecule.

In another embodiment, constituent polypeptide chains of binding molecules of the invention dimerize to form a heterodimeric Fc region of the binding molecule which comprises one or more truncated Fc moieties that are nonetheless sufficient to confer Fc receptor (FcR) binding properties to the heteromeric Fc region. For example, the portion of an Fc domain that binds to FcRn (i.e., the FcRn binding portion) comprises from about amino acids 282-438 of IgG1, EU numbering. Thus, an Fc moiety of a constituent polypeptide of the invention may comprise or consist of an FcRn binding portion. FcRn binding portions may be derived from heavy chains of any isotype, including IgG1, IgG2, IgG3 and IgG4. In one embodiment, an FcRn binding portion from an antibody of the human isotype IgG1 is used. In another embodiment, an FcRn binding portion from an antibody of the human isotype IgG4 is used.

In other constructs it may be desirable to provide a peptide spacer between one or more constituent domains of the Fc region (e.g., between an Fc moiety and a Fab constant domain moiety). For example, a peptide spacer may be placed between a hinge region and a CH2 moiety and/or between a CH2 moiety and a CH3 moiety; between a CH2 moiety and a CH1 moiety or between a CH2 moiety and a CL moiety; and/or between a CH3 moiety and a CH1 moiety or between a CH3 moiety and a CL moiety. Such a peptide spacer may be added, for instance, to ensure that the regulatory elements of the Fc region remain free and accessible or that the hinge region remains flexible. Preferably, any linker peptide compatible with the instant invention will be relatively non-immunogenic and not prevent proper dimerization of the heterodimeric Fc region.

B. Variant Fc Moieties

In certain embodiments, an Fc moiety employed in a constituent polypeptide of the invention is a variant Fc moiety. As used herein, the term "variant Fc moiety" refers to an Fc moiety having at least one amino acid substitution relative to the wild-type Fc moiety from which said Fc moiety is derived. For example, wherein the Fc moiety is derived from a human IgG1 antibody, the Fc variant of said human IgG1 Fc moiety comprises at least one amino acid substitution relative to the corresponding sequence from said human IgG1.

The amino acid substitution(s) of an Fc variant may be located at any position (i.e., any EU convention amino acid position) within the Fc moiety. In one embodiment, the Fc variant comprises a substitution at an amino acid position located in a hinge domain or portion thereof. In another embodiment, the Fc variant comprises a substitution at an amino acid position located in a CH2 moiety. In another embodiment, the Fc variant comprises a substitution at an amino acid position located in a CH3 moiety. In another embodiment, the Fc variant comprises a substitution at an amino acid position located in a CH4 moiety.

In certain embodiments, the constituent polypeptide chains of binding molecules of the invention comprise an Fc variant comprising more than one amino acid substitution. Constituent polypeptides of binding molecules of the invention with alterations may comprise, for example, 2, 3, 4, 5, 6, 7, 8, 9, 10 or more amino acid substitutions. Preferably, the amino acid substitutions are spatially positioned from each other by an interval of at least 1 amino acid position or more, for example, at least 2, 3, 4, 5, 6, 7, 8, 9, or 10 amino acid positions or more. More preferably, the engineered amino acids are spatially positioned apart from each other by an interval of at least 5, 10, 15, 20, or 25 amino acid positions or more.

In certain embodiments, the Fc variant confers an improvement in at least one effector function imparted by a heteromeric Fc region that comprises said wild-type Fc moiety (e.g., an improvement in the ability of the Fc region to bind to Fc receptors (e.g. FcγRI, FcγRII, or FcγRIII) or complement proteins (e.g. C1q), or to trigger antibody-dependent cytotoxicity (ADCC), phagocytosis, or complement-dependent cytotoxicity (CDCC)). In other embodiments, the Fc variant provides an engineered cysteine residue.

The binding polypeptides of the invention may employ any art-recognized Fc variant which is known to impart an improvement in effector function and/or FcR binding. Said Fc variants may include, for example, any one of the amino acid substitutions disclosed in International PCT Publications WO88/07089A1, WO96/14339A1, WO098/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO05/070963A1, WO05/077981A2, WO05/092925A2, WO05/123780A2, WO06/019447A1, WO06/047350A2, and WO06/085967A2 or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; and 7,083,784, each of which is incorporated by reference herein.

In certain embodiments, a constituent polypeptide chain of a binding molecule of the invention comprising an Fc variant comprises an amino acid substitution which alters the antigen-independent effector functions of the antibody, in particular the circulating half-life of the antibody. Such binding molecules exhibit either increased or decreased binding to the neonatal Fc receptor (FcRn) when compared to binding molecules lacking these substitutions and, therefore, have an increased or decreased half-life in serum, respectively. Binding molecules comprising Fc variants with improved affinity for FcRn are anticipated to have longer serum half-lives, and such molecules have useful applications in methods of treating mammals where long half-life of the administered binding molecule is desired, e.g., to treat a chronic disease or disorder. In contrast, binding molecules comprising Fc variants with decreased FcRn binding affinity are expected to have shorter half-lives, and such molecules are also useful, for example, for administration to a mammal where a shortened circulation time may be advantageous, e.g. for in vivo diagnostic imaging or in situations where the starting binding molecule has toxic side effects when present in the circulation for prolonged periods. Binding molecules comprising Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization in the brain, kidney, and/or liver is desired. In one exemplary embodiment, the binding molecules of the invention with variant Fc regions exhibit reduced transport across the epithelium of kidney glomeruli from the vasculature. In another embodiment, the binding molecules of the invention with variant Fc regions of the invention exhibit reduced transport across the blood brain barrier (BBB) from the brain into the vascular space. In one embodiment, a binding molecule with altered FcRn binding comprises at least one Fc moiety (e.g., one or two Fc moieties) having one or more amino acid substitutions within the "FcRn binding loop" of an Fc moiety. The FcRn binding loop is comprised of amino acid residues 280-299 (according to EU numbering) of a wild-type, full-length, Fc moiety. In other embodiments, a binding molecule of the invention having altered FcRn binding affinity comprises at least one Fc moiety (e.g., one or two Fc moieties) having one or more amino acid substitutions within the 15 Å FcRn "contact zone." As used herein, the term 15 Å FcRn "contact zone" includes residues at the following positions of a wild-type, full-length Fc moiety: 243-261, 275-280, 282-293, 302-319, 336-348, 367, 369, 372-389, 391, 393, 408, 424, 425-440 (EU numbering). In preferred embodiments, a binding molecule of the invention having altered FcRn binding affinity comprises at least one Fc moiety (e.g., one or two Fc moieties) having one or more amino acid substitutions at any one of the following EU positions: 256, 277-281, 283-288, 303-309, 313, 338, 342, 376, 381, 384, 385, 387, 434, and 438. Exemplary amino acid substitutions which altered FcRn binding activity are disclosed in International PCT Publication No. WO05/047327 which is incorporated by reference herein.

In particular embodiments, key FcRn residues in the CH3 domain of an immunoglobulin can be incorporated into the sequence of an Fc moiety of a constituent polypeptide chain of the invention. One or more amino acid residues in a sequence derived from a constant domain of an immunoglobulin (e.g., a CH2, CH1 or CL moiety) may be changed to a corresponding residue from a CH3 domain. In some embodiments, several residues that are exposed on the surface of a constant domain moiety are changed, i.e. veneered, so that the surface of the resultant binding molecule heteromeric Fc region has activity corresponding to that of an immunoglobulin CH3 domain. Exemplary residues from a CH3 domain that may be veneered onto a CH2, CH1 or CL moiety include: 243 PHE; 244 PRO; 245 PRO; 246 LYS; 247 PRO; 248 LYS; 249 ASP; 250 THR; 251 LEU; 252 MET; 253 ILE; 254 SER; 255 ARG; 256 THR; 257 PRO; 258 GLU; 259 VAL; 260 THR; 261 CYS; 275 PHE; 276 ASN; 277 TRP; 278 TYR; 279 VAL; 280 ASP; 282 VAL; 283 GLU; 284 VAL; 285 HIS; 286 ASN; 287 ALA; 288 LYS; 289 THR; 290 LYS; 291 PRO; 292 ARG; 293 GLU; 302 VAL; 303 VAL; 304 SER; 305 VAL; 306 LEU; 307 THR; 308 VAL; 309 LEU; 310 HIS; 311 GLN; 312 ASP; 313 TRP; 314 LEU; 315 ASN; 316 GLY; 317 LYS; 318 GLU; 319 TYR; 336 ILE; 337 SER; 338 LYS; 339 ALA; 340 LYS; 341 GLY; 342 GLN; 343 PRO; 344 ARG; 345 GLU; 346 PRO; 347 GLN; 348 VAL; 367 CYS; 369 VAL; 372 PHE; 373 TYR; 374 PRO; 375 SER; 376 ASP; 377 ILE; 378 ALA; 379 VAL; 380 GLU; 381 TRP; 382 GLU; 383 SER; 384 ASN; 385 GLY; 386 GLN; 387 PRO; 388 GLU; 389 ASN; 391 TYR; 393 THR; 408 SER; 424 SER; 425 CYS; 426 SER; 427 VAL; 428 MET; 429 HIS; 430 GLU; 431 ALA; 432 LEU; 433 HIS; 434 ASN; 435 HIS; 436 TYR; 437 THR; 438 GLN; 439 LYS; and 440 SER (CH3 domain positions, EU numbering).

In other embodiments, a binding molecule of the invention comprises an Fc variant comprising an amino acid substitution or modification which alters the antigen-dependent effector functions of the antibody, in particular ADCC or complement activation. In exemplary embodiment, said binding molecules exhibit altered binding to an Fc gamma receptor (e.g., CD16). Such binding molecules exhibit either increased or decreased binding to FcR gamma when compared to molecules with wild-type Fc moieties and, therefore, mediate enhanced or reduced effector function, respectively. Fc variants with improved affinity for activating FcγRs are anticipated to enhance effector function, and such molecules have useful applications in methods of treating mammals where target molecule destruction is desired, e.g., in tumor therapy. In contrast, Fc variants with decreased binding affinity towards activating FcγR are expected to reduce effector function, and such molecules are also useful, for example, for treatment of conditions in which target cell destruction is undesirable, e.g., where normal cells may express target molecules, or where chronic administration of the binding molecule might result in unwanted immune system activation. In one embodiment, the binding molecule exhibits at least one altered antigen-dependent effector function selected from the group consisting of opsonization, phagocytosis, complement dependent cytotoxicity, antigen-dependent cellular cytotoxicity (ADCC), or effector cell modulation. In one embodiment the binding molecule exhibits its altered binding to an activating FcγR (e.g. FcγRI, FcγRIIa, or FcγRIIIa). In another embodiment, the binding molecule exhibits altered binding affinity to an inhibitory FcγR (e.g. FcγRIIb). In other embodiments, a binding molecule of the invention having increased FcγR binding affinity (e.g. increased FcγRIIIa binding affinity) comprises at least one Fc moiety (e.g., one or two Fc moieties) having one or more amino acid substitutions at any one of the following positions: 239, 268, 298, 332, 334, and 378 (EU numbering). In other embodiments, a binding molecule of the invention having decreased FcγR binding affinity (e.g. decreased FcγRI, FcγRII, or FcγRIIIa binding affinity) comprises at least one Fc moiety (e.g., one or two Fc moieties) having one or more amino acid substitutions at any one of the following positions: 234, 236, 239, 241, 251, 261, 265, 268, 293, 294, 296, 298, 299, 301, 326, 328, 332, 334, 338, 376, 378, and 435 (EU numbering). In other embodiments, a binding molecule of the invention having increased complement binding affinity (e.g. increased C1q binding affinity) comprises an Fc moiety (e.g., one or two Fc moieties) having one or more amino acid substitutions at any one of the following positions: 251, 334, 378, and 435 (EU numbering). In other embodiments, a binding molecule of the invention having decreased complement binding affinity (e.g. decreased C1q binding affinity) comprises an Fc moiety (e.g, one or two Fc moieties) having one or more amino acid substitutions at any one of the following positions: 239, 294, 296, 301, 328, 333, and 376 (EU numbering). Exemplary amino acid substitutions which altered FcγR or complement binding activity are disclosed in International PCT Publication No. WO05/063815 which is incorporated by reference herein.

A binding molecule of the invention may also comprise a variant Fc moiety comprising an amino acid substitution which alters the glycosylation of the binding molecule. For example, said variant Fc moiety may have reduced glycosylation (e.g., N- or O-linked glycosylation) or may comprise an altered glycoform of the wild-type Fc domain (e.g., a low fucose or fucose-free glycan). In exemplary embodiments, the Fc variant comprises reduced glycosylation of the N-linked glycan normally found at amino acid position 297 (EU numbering). In another exemplary embodiment, the Fc variant comprises a low fucose or fucose free glycan at amino acid position 297 (EU numbering). In another embodiment, the binding polypeptide has an amino acid substitution near or within a glycosylation motif, for example, an N-linked glycosylation motif that contains the amino acid sequence NXT or NXS. In a particular embodiment, the binding polypeptide comprises a variant Fc moiety with an amino acid substitution at amino acid position 299 (EU numbering). Exemplary amino acid substitutions which confer reduce or altered glycosylation are disclosed in International PCT Publication No. WO05/018572 and US Patent Publication No. 2007/0111281, which are incorporated by reference herein.

In other embodiments, a binding molecule of the invention comprises at least one variant Fc moiety having engineered cysteine residue or analog thereof which is located at the solvent-exposed surface of an Fc moiety. Preferably the engineered cysteine residue or analog thereof does not interfere with an effector function conferred by the heteromeric Fc region. More preferably, the alteration does not interfere with the ability of the Fc region to bind to Fc receptors (e.g. FcγRI, FcγRII, or FcγRIII) or complement proteins (e.g. C1q), or to trigger immune effector function (e.g., antibody-dependent cytotoxicity (ADCC), phagocytosis, or complement-dependent cytotoxicity (CDCC)). In preferred embodiments, the binding molecules of the invention comprising an Fc variant comprising at least one engineered free cysteine residue or analog thereof that is substantially free of disulfide bonding with a second cysteine residue. In preferred embodiments, the binding molecules of the invention may comprise an Fc variant having engineered cysteine residues or analogs thereof at any one of the following positions in the CH3 domain: 349-371, 390, 392, 394-423, 441-446, and 446b (EU numbering). In more preferred embodiments, the binding molecules of the invention comprise an Fc variant having engineered cysteine residues or analogs thereof at any one of the following positions: 350, 355, 359, 360, 361, 389, 413, 415, 418, 422, 441, 443, and EU position 446b (EU numbering). Any of the above engineered cysteine residues or analogs thereof may subsequently be conjugated to a functional moiety using art-recognized techniques (e.g., conjugated with a thiol-reactive heterobifunctional linker).

Binding molecules of the invention include molecules that comprise a heterodimeric Fc region (i.e., comprising at least two constituent non-identical polypeptide chains) having two or more of its constituent Fc moieties independently selected from the Fc moieties described in this section. In certain embodiments, at least two of the Fc moieties are the same. In some embodiments, at least two of the Fc moieties are different. For example, the Fc moieties of the constituent polypeptide chains of binding molecules of the invention comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In yet other embodiments, the Fc moieties of the constituent polypeptides chains of binding molecules of the invention may differ in sequence at one or more amino acid positions. For example, at least two of the Fc moieties may differ at about 5 amino acid positions (e.g., 1, 2, 3, 4, or 5 amino acid positions), about 10 positions, about 15 positions, about 20 positions, about 30 positions, about 40 positions, or about 50 positions).

Variant Fc moieties may also be made by veneering amino acid residues which confer desired functionality into an Fc moiety.

Methods of altering proteins to confer or modify catalytic and binding activities are known in the art. As noted above, for example, methods for veneering CDR loops and other binding moieties into immunoglobulin moieties are disclosed in International PCT Publication No. WO 08/003116, which is incorporated by reference herein. Techniques for loop grafting have been used successfully to add functionality to non-immunoglobulin proteins as well (see, for example, Kolmar et al. FEBS Journal (2008) 275: 2684-2690, disclosing the addition of functionality to knottin proteins via loop grafting). In one embodiment, techniques known in the art for three-dimensional modeling of single proteins and protein complexes and for sequence alignment and analysis may be used in veneering and thereby modify the function of heteromeric binding molecules of the invention.

As is known in the art, many proteins have a stable core, formed by specific arrangements of secondary structure elements such as beta sheets or alpha helices. These core secondary structure elements are interconnected by structures such as loops, turns, or random coils that are less crucial for the overall structure of the protein. Individual amino acid residues in these structure elements can often be exchanged without destroying the general fold or core structure of the protein. Often multiple amino acids and stretches of non-native sequence can be added to or used as a replacement for native sequence in a protein without changing the core structure or fold. Naturally occurring examples for this design principle are the CDRs of immunoglobulin-like domains as can be found in antibodies, T-cell receptors and other molecules of the immunoglobulin superfamily. Artificial examples include lipocalins, ankyrins, kunitz domain inhibitor, knottin and other protein scaffolds.

To determine the most suitable locations for modification within the linear amino acid sequence of a protein, three-dimensional modeling techniques can be used to identify structure elements that are not closely involved with protein cores. Stretches of peptide sequence and individual residues that potentially have a larger degree of exposure to the exterior surface of the protein can also be identified. X-ray diffraction is a traditional method for determining the molecular structure of crystalline forms and has been used successfully to determine the structure of crystallizable proteins, including large and complex proteins (see Saphire et al. (2001) Science 293:1155-1159, for a description of the crystallization and structural elucidation of a human IgG1). In addition to mapping the overall three-dimensional structure of a protein and identifying moieties that may be ameniable to modification, techniques that estimate the static accessibility of molecules and atoms within a macromolecule or peptidic chain and analyze the conformational limitations of accessing individual amino acids on the surface of a peptide can also be used to determine which parts of a protein are most suitable for modification (Lee and Richards, J. Mol. Biol. (1971) 55:379-400; Hubbard et al., J. Mol. Biol. (1991) 220:507-530).

Models of the three-dimensional structure of a protein of interest can also be based on the known three-dimensional structure of another protein, if the homology between the two proteins is sufficiently high. Given the alignment of the amino acid sequences of the proteins and the known three-dimensional structure of one of the proteins, a homology-based structure for the other protein can be computed (Sali et al., J. Mol. Biol. (1993) 234:779-815). Information obtained through analysis of three-dimensional protein structures, used in conjunction with standard linear sequence alignment analysis, can indicate where adjustments to a sequence should be made in order for key structural residues to be positioned properly. For example, as discussed in Example 2 below, a gap was added to the sequences of the CH1 and CL domains in order to properly align key residues and create a structure-based sequence alignment (FIG. 9), with which veneering of FcRn-binding moieties onto CH1 and CL domains could be designed.

These and additional techniques known in the art can be used to identify portions of a protein that appear potentially suitable for manipulation without disrupting the protein's core structure. Once these moieties or locations have been identified, genetic engineering techniques can be used to alter the corresponding nucleic acid coding sequence to introduce modifications. For example, sequences from peptidic drugs used as platelet aggregation inhibitors have been added to cysteine-knot microproteins, using loop grafting techniques to add nucleic acid sequence encoding a drug peptide to an exterior loop of the microprotein. The engineered proteins were found to retain the aggregation inhibition features of the peptidic drug and in some cases, the drug effects were more potent than with the original peptide (Kolmar et al. 2008). Genetic changes to the coding sequences of proteins may also be made to increase or ensure the solvent accessibility of protein moieties by adding or eliminating amino acid sequence from non-core structure domains to extend or change the conformation of loops, turns or coils.

Recent innovation in the protein modeling and modification fields has allowed the creation of targeted enzymatic activity de novo. As detailed by Jiang et al. (Science (2008) 319:1387-1391), beginning with a desired chemical reaction to catalyze and potential catabolic mechanisms, a range of suitable protein scaffolds that can accommodate the intermediate and transition states of the protein functional groups involved. Appropriate catalytic side chains in proper orientation are selected by computer and unfavorable candidate protein scaffolds, due to poor catalytic geometry or significant steric clashes, are eliminated from contention. Candidate engineered enzymes can then be expressed in bacteria, purified by standard techniques and tested for activity. With this approach, Jiang et al. were able to create 23 novel artificial enzymes with significant levels of the desired enzymatic activity.

In some embodiments of the invention, protein engineering, modeling and modification techniques as known in the art are used modify properties of heteromeric binding molecules of the invention. As detailed in Example 2 below, CH1 and CL moieties found in the constituent polypeptide chains of heterodimeric binding molecules of the invention can be modified, in order to add short sequences from CH3 moieties and impart FcRn binding function to the CH1 and CL moieties. As will be clear to the skilled artisan, additional modifications of the function of heterodimeric binding molecules of the invention are possible. For example, in some embodiments of the invention, sequences isolated from the complementarity determining regions (CDRs) of antibody variable regions are veneered onto exterior loops of constituent polypeptide chains of the invention to introduce a binding moiety into an Fc moiety of a binding molecule which lacks a CH3 domain.

C. Polypeptide Linkers

In certain embodiments, it is desirable to employ a polypeptide linker to genetically fuse two or more Fc moieties of a constituent peptide of a binding molecule of the invention. In certain preferred aspects, it is desirable to employ a polypeptide linker to genetically fuse an Fc moiety to a Fab constant domain moiety (i.e., a CH1 or CL moiety) of a constituent polypeptide chain of a binding molecule of the invention. Such polypeptide linkers are referred to herein as "Fc connecting polypeptides". In one embodiment, the polypeptide linker is synthetic. As used herein the term "synthetic" with respect to a polypeptide linker includes peptides and polypeptides which comprise an amino acid sequence (which may or may not be naturally occurring) that is linked in a linear sequence of amino acids to a sequence (which may or may not be naturally occurring) (e.g., an Fc moiety sequence) to which it is not naturally linked in nature. For example, said polypeptide linker may comprise non-naturally occurring polypeptides which are modified forms of naturally occurring polypeptides (e.g., comprising a mutation such as an addition, substitution or deletion) or which comprise a first amino acid sequence (which may or may not be naturally occurring). The polypeptide linkers of the invention may be employed, for instance, to ensure that Fc moieties of the heterodimeric Fc region (i.e., Fc moieties comprised by at least two constituent non-identical polypeptides) are juxtaposed to ensure proper folding and formation of a functional heterodimeric Fc region. Preferably, a polypeptide linker compatible with the instant invention will be relatively non-immunogenic and not inhibit any non-covalent association among monomer subunits of a binding molecule.

In certain embodiments, the constitutent polypeptide chains of binding molecules of the invention employ a polypeptide linker to join any two or more Fc moieties in frame in a single polypeptide chain. The two or more Fc moieties may be independently selected from any of the Fc moieties discussed supra. For example, in certain embodiments, a polypeptide linker can be used to fuse identical Fc moieties within a constituent polypeptide chain. In other embodiments, a polypeptide linker can be used to fuse different Fc moieties (e.g. a wild-type Fc moiety and an Fc variant) within a constituent polypeptide. In other embodiments, a polypeptide linker of the invention can be used to genetically fuse the C-terminus of a first Fc moiety (e.g. a hinge region or portion thereof, a CH2 moiety, a CH3 moiety, an FcRn binding portion of a moiety, an FcγR binding portion of a moiety, a complement binding portion of a moiety or variants thereof) to the N-terminus of a second Fc moiety. In other embodiments, a polypeptide linker of the invention can be used to genetically fuse the C-terminus of an Fc moiety (e.g. a hinge domain or portion thereof, a CH2 domain or portion thereof, a complete CH3 domain or portion thereof, an FcRn binding portion, an FcγR binding portion, a complement binding portion, or portion thereof) to the N-terminus of a Fab constant domain moiety (e.g. a CH1 moiety, a CL moiety or variants thereof).

In one embodiment, a synthetic polypeptide linker comprises a portion of an Fc moiety. For example, in one embodiment, a polypeptide linker can comprise an immunoglobulin hinge region or portion thereof from an IgG1, IgG2, IgG3, and/or IgG4 antibody. In another embodiment, a polypeptide linker can comprise CH2 domain sequence of an IgG1, IgG2, IgG3, and/or IgG4 antibody. In other embodiments, a polypeptide linker can comprise CH3 domain sequence of an IgG1, IgG2, IgG3, and/or IgG4 antibody. Other portions of an immunoglobulin (e.g. a human immunoglobulin) can be used as well. For example, a polypeptide linker can comprise sequences from a CH1 domain or portion thereof, a CL domain or portion thereof, a VH domain or portion thereof, or a VL domain or portion thereof. Said portions can be derived from any immunoglobulin, including, for example, an IgG1, IgG2, IgG3, and/or IgG4 antibody. A polypeptide linker may comprise sequences from more than one antibody genotype, class or species of origin.

In exemplary embodiments, a polypeptide linker can comprise at least a portion of an immunoglobulin hinge region. In one embodiment, a polypeptide linker comprises an upper hinge domain (e.g., an IgG1, an IgG2, an IgG3, or IgG4 upper hinge domain). In another embodiment, a polypeptide linker comprises a middle hinge domain (e.g., an IgG1, an IgG2, an IgG3, or an IgG4 middle hinge domain). In another embodiment, a polypeptide linker comprises a lower hinge domain (e.g., an IgG1, an IgG2, an IgG3, or an IgG4 lower hinge domain). Exemplary hinge domain portions are listed in Table 1 below. In addition, any sub-portion of these exemplary hinges may be employed (e.g, the repeat portion of the IgG3 middle region (i.e., EPKSCDTPPP-CPRCP) (SEQ ID NO: 99).

TABLE 1

IgG1, IgG2, IgG3 and IgG4 Hinge Domains

| IgG | Upper Hinge | Middle Hinge | Lower Hinge |
|---|---|---|---|
| IgG1 | EPKSCDKTHT (SEQ ID NO: 1) | CPPCP (SEQ ID NO: 2) | APELLGGP (SEQ ID NO: 3) |

TABLE 1-continued

IgG1, IgG2, IgG3 and IgG4 Hinge Domains

| IgG | Upper Hinge | Middle Hinge | Lower Hinge |
|---|---|---|---|
| IgG2 | ERKCCVE (SEQ ID NO: 4) | CPPCP (SEQ ID NO: 5) | APPVAGP (SEQ ID NO: 6) |
| IgG3 | ELKTPLGDTTHT (SEQ ID NO: 7) | CPRCP (EPKSCD TPPPCPRCP)$_3$ (SEQ ID NO: 8) | APELLGGP (SEQ ID NO: 9) |
| IgG4 | ESKYGPP (SEQ ID NO: 10) | CPSCP (SEQ ID NO: 11) | APEFLGGP (SEQ ID NO: 12) |

In other embodiments, polypeptide linkers can be constructed which combine hinge elements derived from the same or different antibody isotypes. In one embodiment, the polypeptide linker comprises a chimeric hinge comprising at least a portion of an IgG1 hinge region and at least a portion of an IgG2 hinge region. In one embodiment, the polypeptide linker comprises a chimeric hinge comprising at least a portion of an IgG1 hinge region and at least a portion of an IgG3 hinge region. In another embodiment, a polypeptide linker comprises a chimeric hinge comprising at least a portion of an IgG1 hinge region and at least a portion of an IgG4 hinge region. In one embodiment, the polypeptide linker comprises a chimeric hinge comprising at least a portion of an IgG2 hinge region and at least a portion of an IgG3 hinge region. In one embodiment, the polypeptide linker comprises a chimeric hinge comprising at least a portion of an IgG2 hinge region and at least a portion of an IgG4 hinge region. In one embodiment, the polypeptide linker comprises a chimeric hinge comprising at least a portion of an IgG1 hinge region, at least a portion of an IgG2 hinge region, and at least a portion of an IgG4 hinge region. In another embodiment, a polypeptide linker can comprise an IgG1 upper and middle hinge and a single IgG3 middle hinge repeat motif. In another embodiment, a polypeptide linker can comprise an IgG4 upper hinge, an IgG1 middle hinge and a Ig2 lower hinge.

In another embodiment, a polypeptide linker comprises or consists of a gly-ser linker. As used herein, the term "gly-ser linker" refers to a peptide that consists of glycine and serine residues. An exemplary gly/ser linker comprises an amino acid sequence of the formula (Gly$_x$Ser)n, wherein n and x are positive integers (e.g., 1, 2, 3, 4, or 5). A preferred gly/ser linker is (Gly$_4$Ser)$_4$ (SEQ ID NO: 20). Another preferred gly/ser linker is (Gly$_4$Ser)$_3$ (SEQ ID NO: 19). Another exemplary gly-ser linker is GGGSSGGGSG (SEQ ID NO:13). In certain embodiments, said gly-ser linker may be inserted between two other sequences of the polypeptide linker (e.g., any of the polypeptide linker sequences described herein). In other embodiments, a Gly-Ser linker is attached at one or both ends of another sequence of the polypeptide linker (e.g., any of the polypeptide linker sequences described herein). In yet other embodiments, two or more gly-ser linker are incorporated in series in a polypeptide linker. In one embodiment, a polypeptide linker of the invention comprises at least a portion of an upper hinge region (e.g., derived from an IgG1, IgG2, IgG3, or IgG4 molecule), at least a portion of a middle hinge region (e.g., derived from an IgG1, IgG2, IgG3, or IgG4 molecule) and a series of gly/ser amino acid residues (e.g., a gly/ser linker such as (Gly$_x$Ser)n).

In another embodiment, a polypeptide linker comprises an amino acid sequence such as described in WO 02/060955. In another embodiment, a polypeptide linker comprises the amino acid sequence IGKTISKKAK (SEQ ID NO:14). Another exemplary polypeptide linker comprises the sequence (G₄S)₄GGGAS (SEQ ID NO: 15).

A particularly preferred polypeptide linker comprises the amino acid sequence SLSLSPGGGGGSEPKSS (SEQ ID NO: 16). Another preferred polypeptide linker comprises a human IgG1 hinge sequence, e.g., DKTHTCPPCPA-PELLGG (SEQ ID NO: 17). Yet another preferred polypeptide linker comprises both SEQ ID NO: 16 and SEQ ID NO: 17.

In one embodiment, a polypeptide linker of the invention comprises a non-naturally occurring immunoglobulin hinge region domain, e.g., a hinge region domain that is not naturally found in the polypeptide comprising the hinge region domain and/or a hinge region domain that has been altered so that it differs in amino acid sequence from a naturally occurring immunoglobulin hinge region domain. In one embodiment, mutations can be made to hinge region domains to make a polypeptide linker of the invention. In one embodiment, a polypeptide linker of the invention comprises a hinge domain which does not comprise a naturally occurring number of cysteines, i.e., the polypeptide linker comprises either fewer cysteines or a greater number of cysteines than a naturally occurring hinge molecule. In one embodiment of the invention, a polypeptide linker comprises hinge region domain comprising a proline residue at an amino acid position corresponding to amino acid position 230 (EU numbering system). In one embodiment, a polypeptide linker comprises an alanine residue at an amino acid position corresponding to position 231 (EU numbering system). In another embodiment, a polypeptide linker of the invention comprises a proline residue at an amino acid position corresponding to position 232 (EU numbering system)). In one embodiment, a polypeptide linker comprises a cysteine residue at an amino acid position corresponding to position 226 (EU numbering system). In one embodiment, a polypeptide linker comprises a serine residue at an amino acid position corresponding to position 226 (EU numbering system). In one embodiment, a polypeptide linker comprises a cysteine residue at an amino acid position corresponding to position 229 (EU numbering system). In one embodiment, a polypeptide linker comprises a serine residue at an amino acid position corresponding to position 229 (EU numbering system).

In other embodiments, a polypeptide linker of the invention comprises a biologically relevant peptide sequence or a sequence portion thereof. For example, a biologically relevant peptide sequence may include, but is not limited to, sequences derived from an anti-rejection or anti-inflammatory peptide. Said anti-rejection or anti-inflammatory peptides may be selected from the group consisting of a cytokine inhibitory peptide, a cell adhesion inhibitory peptide, a thrombin inhibitory peptide, and a platelet inhibitory peptide. In a one preferred embodiment, a polypeptide linker comprises a peptide sequence selected from the group consisting of an IL-1 inhibitory or antagonist peptide sequence, an erythropoietin (EPO)-mimetic peptide sequence, a thrombopoietin (TPO)-mimetic peptide sequence, G-CSF mimetic peptide sequence, a TNF-antagonist peptide sequence, an integrin-binding peptide sequence, a selectin antagonist peptide sequence, an anti-pathogenic peptide sequence, a vasoactive intestinal peptide (VIP) mimetic peptide sequence, a calmodulin antagonist peptide sequence, a mast cell antagonist, a SH3 antagonist peptide sequence, an urokinase receptor (UKR) antagonist peptide sequence, a somatostatin or cortistatin mimetic peptide sequence, and a macrophage and/or T-cell inhibiting peptide sequence. Exemplary peptide sequences, any one of which may be employed as a polypeptide linker, are disclosed in U.S. Pat. No. 6,660,843, which is incorporated by reference herein.

In other embodiments, a polypeptide linker comprises one or more of any one of the binding moieties described infra (e.g., a Fab, an scFv molecule, a receptor binding portion of ligand, a ligand binding portion of a receptor, etc.).

It will be understood that variant forms of these exemplary polypeptide linkers can be created by introducing one or more nucleotide substitutions, additions or deletions into the nucleotide sequence encoding a polypeptide linker such that one or more amino acid substitutions, additions or deletions are introduced into the polypeptide linker. For example, mutations may be introduced by standard techniques, such as site-directed mutagenesis and PCR-mediated mutagenesis. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Polypeptide linkers of the invention can be of varying lengths. In one embodiment, a polypeptide linker of the invention is from about 1 to about 50 amino acids in length. In another embodiment, a polypeptide linker of the invention is from about 10-20 amino acids in length. In another embodiment, a polypeptide linker of the invention is from about 15 to about 50 amino acids in length. In another embodiment, a polypeptide linker of the invention is from about 20 to about 45 amino acids in length. In another embodiment, a polypeptide linker of the invention is from about 15 to about 25 amino acids in length. In another embodiment, a polypeptide linker of the invention is from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 amino acids in length.

Polypeptide linkers can be introduced into polypeptide sequences using techniques known in the art. Modifications can be confirmed by DNA sequence analysis. Plasmid DNA can be used to transform host cells for stable production of the polypeptides produced.

D. Fab Constant Region Moieties (CH1 and CL moieties)

Figure 1:
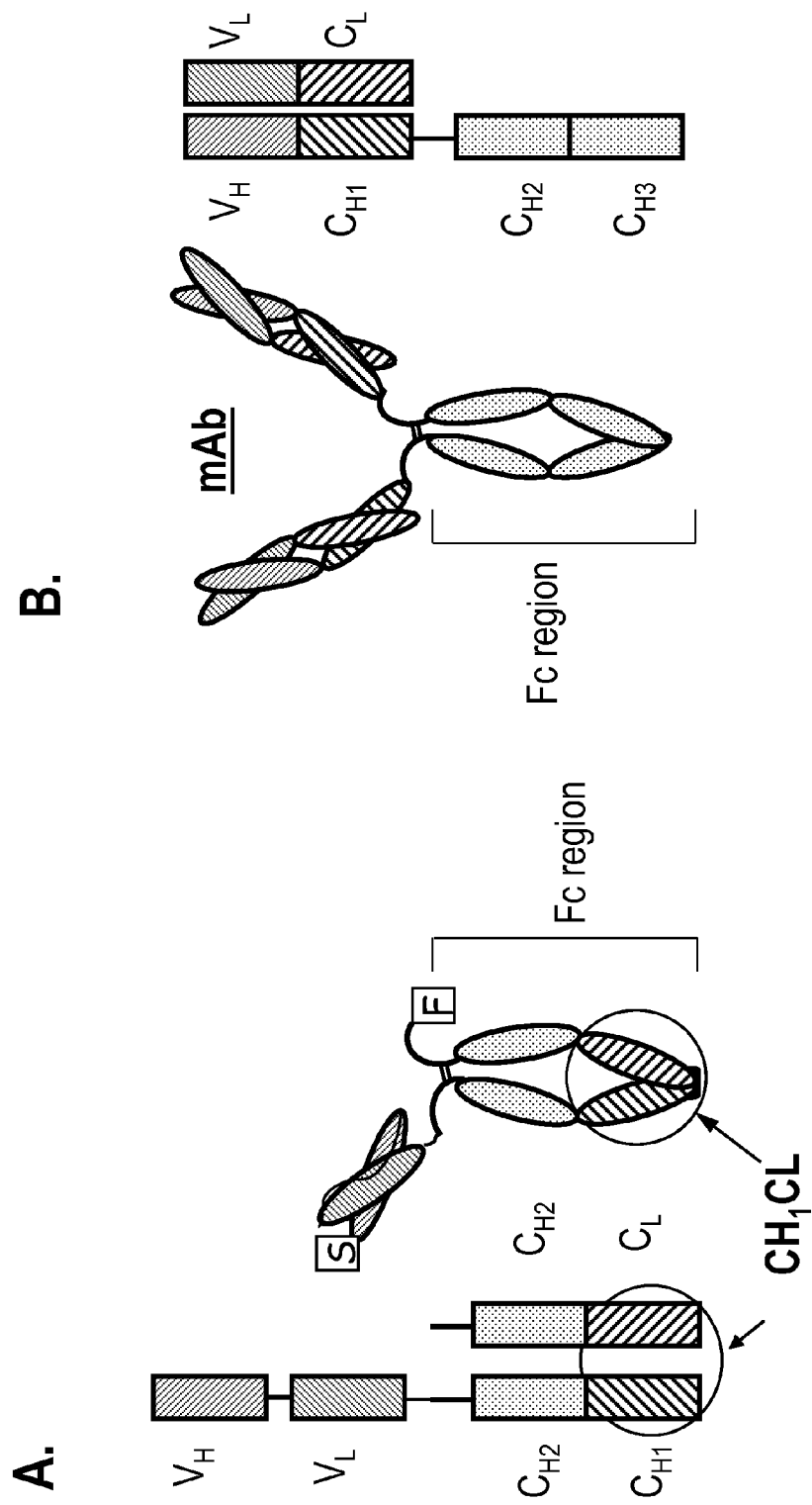
FIGS. 1A-B depict schematic diagrams comparing the structure of an exemplary heterodimeric binding molecule of the invention (FIG. 1A) and a conventional immunoglobulin molecule (FIG. 1B). The heterodimer binding molecule comprises an antigen-binding moiety (e.g., a scFv molecule) linked (e.g., by a human IgG1 hinge) to a heteromeric Fc region comprising a CH1:CL dimer (highlighted circle). In contrast, the conventional immunoglobulin molecule has a homomeric Fc region that lacks a CH1:CL dimer.

The Fab (fragment, antigen binding) portion of an immunoglobulin lies N-terminal to the Fc region of the immunoglobulin and includes the immunoglobulin light chain and the N-terminal portion of the immunoglobulin heavy chain (FIG. 1B). The Fab region includes the VL and CL domains of the light chain and the VH and CH1 domains, as well as part of the hinge sequence, of the heavy chain. Thus, the Fab region contains both variable sequence and constant sequence. The dimerization of the N-terminal region of an immunoglobulin heavy chain with an immunoglobulin light chain is driven by interaction between the CH1 and CL domains.

Embodiments of the invention feature binding molecules that comprise non-identical constituent polypeptide chains that comprise immunoglobulin Fab constant region moieties which mediate the dimerization of the Fc region (i.e., CH1 or CL moieities; see, for example, FIG. 1A). In preferred embodiments, binding molecules of the invention comprise at least one constituent polypeptide chain with at least one CH1 moiety at its C-terminal end and at least one constituent polypeptide with at least one CL moiety at its C-terminal end. Thus, in preferred embodiments, binding molecules of the invention comprise at least two non-identical constituent polypeptide chains that comprise sequence dissimilarities at their C-terminal ends. Embodiments of the invention feature binding molecules formed by the dimerization of two non-identical constituent polypeptide chains that is driven by interaction between one or more CH1 moieties in a first constituent polypeptide and one or more CL moieties in a second constituent polypeptides.

Additional embodiments of the invention feature binding molecules comprised of constituent polypeptide chains that comprise Fc moieties at their C-terminal ends. In these embodiments, a CH1 moiety in a first constituent polypeptide chain and a CL moiety in a second constituent polypeptide chain are fused at their C-terminal ends to an Fc moiety at its N-terminal end. In preferred embodiments, the CH1 and CL moieties of the constituent polypeptide chains are also fused, at their N-terminal ends, to the C-terminal ends of Fc moieties (i.e., the CH1 and CL moieties of the constituent polypeptide chains are found between two or more Fc moieties). FIG. 8B shows an example of this type of alternative binding molecule structure.

Fab constant region moieties useful for producing the constituent polypeptide chains of binding molecules of the present invention may be obtained from a number of different sources. In preferred embodiments, a Fab constant region moiety of the binding polypeptide is derived from a human immunoglobulin. It is understood, however, that the Fab constant region moiety may be derived from an immunoglobulin of another mammalian species, including for example, a rodent (e.g. a mouse, rat, rabbit, guinea pig) or non-human primate (e.g. chimpanzee, macaque) species. In some embodiments, the amino acid sequence of a non-human Fab constant domain moiety may be changed by substituting, adding or eliminating residues from the sequence (e.g., to change functionality of the moiety or reduce the immunogenicity of the resultant binding molecule). Moreover, the constituent polypeptide Fab constant region domain moiety may be derived from any immunoglobulin class, including IgM, IgG, IgD, IgA and IgE, and any immunoglobulin isotype, including IgG1, IgG2, IgG3 and IgG4. In a preferred embodiment, the human isotype IgG1 is used.

A variety of Fab constant region moiety gene sequences (e.g., human constant region gene sequences from the antigen binding fragment of an antibody) are available in the form of publicly accessible deposits. Constant region domains comprising an Fab constant region moiety sequence can be selected having a particular modification to reduce immunogenicity. Many sequences of antibodies and antibody-encoding genes have been published and suitable Fab constant region moiety sequences (e.g. CH1, CL or hinge sequences, or portions thereof) can be derived from these sequences using art recognized techniques. The genetic material obtained using any of the foregoing methods may then be altered or synthesized to obtain constituent polypeptides of the present invention. It will further be appreciated that the scope of this invention encompasses alleles, variants and mutations of constant region DNA sequences.

Fab constant region moiety sequences can be cloned, e.g., using the polymerase chain reaction and primers which are selected to amplify the domain of interest. To clone an Fab constant region moiety sequence from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. Methods Enzymol. 217:270). PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250). The cloning of antibody sequences is further described in Newman et al., U.S. Pat. No. 5,658,570, filed Jan. 25, 1995, which is incorporated by reference herein.

The constituent polypeptide chains of binding molecules of the invention may comprise one or more Fab constant region moieties (e.g., 1, 2, 3, 4, 5, 6, 7, 8, 9, 10, or more Fab constant region moieties). In preferred embodiments, a constituent polypeptide chain comprises a CH1 moiety or a CL moiety. In preferred embodiments, the CH1 moiety or CL moiety is attached at its N-terminal end to the C-terminal end of an Fc moiety or to the C-terminal end of a polypeptide linker, which is itself attached at its N-terminal end to the C-terminal end of an Fc moiety. In one embodiment, the N-terminal end of a Fab constant region moiety (or polypeptide linker—Fab constant region moiety fusion) is attached to the C-terminal end of at least one Fc moiety comprising a hinge domain or portion thereof. In one embodiment, the N-terminal end of a Fab constant region moiety (or polypeptide linker—Fab constant region moiety fusion) is attached to the C-terminal end of at least one Fc moiety comprising at least one CH2 moiety. In another embodiment, the constituent polypeptide chains of binding molecules of the invention comprise, at their C-terminal ends, an Fab constant region moiety (or polypeptide linker—Fab constant region moiety fusion) attached at its N-terminal end to at least one Fc moiety comprising at least one CH3 moiety. In another embodiment, the constituent polypeptide chains of binding molecules of the invention comprise, at their C-terminal ends, an Fab constant region moiety (or polypeptide linker—Fab constant region moiety fusion) attached at its N-terminal end to at least one Fc moiety comprising at least one CH4 moiety. In another embodiment, the constituent polypeptide chains of binding molecules of the invention comprise, at their C-terminal ends, an Fab constant region moiety (or polypeptide linker—Fab constant region moiety fusion) attached at its N-terminal end to at least one Fc moiety comprising at least one hinge domain or portion thereof and at least one CH2 moiety (e.g., in the hinge-CH2 orientation). In another embodiment, the constituent polypeptide chains of binding molecules of the invention comprise, at their C-terminal ends, an Fab constant region moiety (or polypeptide linker—Fab constant region moiety fusion) attached at its N-terminal end to at least one Fc moiety comprising at least one CH2 moiety and at least one CH3 moiety (e.g., in the CH2-CH3 orientation). In another embodiment, the constituent polypeptides of binding molecules of the invention comprise, at their C-terminal ends, an Fab constant region moiety (or polypeptide linker—Fab constant region moiety fusion) attached at its N-terminal end to at least one Fc moiety comprising at least one hinge domain or portion thereof, at least one CH2 moiety, and least one CH3 moiety, for example in the orientation hinge-CH2-CH3, hinge-CH3-CH2, or CH2-CH3-hinge.

In certain embodiments, the constituent polypeptide chains comprise at least one complete Fab constant region moiety derived from an immunoglobulin heavy chain (e.g., including a CH1 domain and a portion of a hinge domain). In certain embodiments, the constituent polypeptide chains comprise at least one complete Fab constant domain moiety derived from an immunoglobulin heavy chain (e.g., a CH1 domain). In certain embodiments, the constituent polypeptide chains comprise at least one complete Fab constant domain moiety derived from an immunoglobulin light chain (e.g., a CL domain). In preferred embodiments, the complete Fab CH1 moiety is derived from a human IgG immunoglobulin heavy chain (e.g., human IgG1).

In another embodiment, constituent polypeptide chains of the invention comprise at least one Fab constant region moiety comprising a complete CH1 domain. In another embodiment, constituent polypeptide chains of the invention comprise at least one Fab constant region moiety comprising a complete CL domain. In another embodiment, constituent polypeptide chains of the invention comprise at least one Fab moiety comprising at least a CH1 domain, and at least one portion of a hinge region, ending near the papain cleavage site (i.e. residue 223 in IgG, taking the first residue of heavy chain constant region to be 118). In one embodiment, the portion of the hinge region comprises the C-terminal end of the polypeptide chain. In some embodiments, the hinge portion may comprise a sequence ending at the serine residue at position 219, the cysteine residue at position 220 or the aspartic acid residue at position 221 of the native IgG1 heavy chain sequence. In some embodiments, the cysteine residue at position 220 in the hinge portion may be replaced with a different amino acid or analogue. In preferred embodiments, the cysteine at position 220 is replaced with a serine. In preferred embodiments, the CH1 moiety is derived from a human IgG immunoglobulin heavy chain (e.g., human IgG1). In another embodiment, constituent polypeptide chains of the invention do not comprise a portion of a hinge region.

For example, as shown in Table 2 a hinge region portion is found at the end of the CH2-CH1 sequence (found in the fourth column), comprising residues 216 (E) to 221 (D) of the IgG sequence. In FIG. 9, the CH1 sequence contains no hinge sequence portion (i.e., end at Valine 215 of the IgG1 sequence). In Example 3, the hinge portion leaves off D221 and ends with the cysteine at 220. In Example 4, there is a cysteine-scrubbed (serine replacement) full length hinge sequence and a CH2-CH1 sequence with a smaller hinge portion (leaving off the C220 and D221 residues).

The Fab constant region domain sequences making up one or more Fab moieties of a constituent polypeptide chains of a binding molecule of the invention may be derived from different immunoglobulin molecules. For example, a constituent polypeptide chain of the invention may comprise a CH1 moiety derived from sequences of an IgG1 molecule and sequences from an IgG3 molecule. As set forth herein, it will be understood by one of ordinary skill in the art that an Fab constant region moiety may be altered such that it varies in amino acid sequence from a naturally occurring antibody molecule.

In a preferred embodiment, constituent polypeptide chains of binding molecules of the invention dimerize to form a heterodimeric Fc region of the binding molecule which comprises one or more non-identical Fab constant region moieties on at least two constituent peptides at their C-terminal ends. The interaction between one or more CH1 moieties on a first constituent polypeptide and one or more CL moieties on a second constituent peptide drive the dimerization of non-identical molecules to form a binding molecule of the invention.

The non-covalent binding of CH1 and CL moieties to each other is mediated by key residues that constitute the core of the human CL-CH1 interface. In the CL domain, core interface residues comprise: F:116, F:118, S:121, E:123, Q:124, S:127, S:131, V:133, L:135, L:136, N:137, N:138, Q:160, S:162, E:165, D:167, S:174, S:176, T:178 and T:180 (numbering according to the EU numbering convention). In the CH1 domain, core interface residues comprise: F:126, L:128, A:129, A:141, L:142, L:145, K:147, H:168, F:170, P:171, V:173, Q:175, L:182, S:183, V:185 and K:213 (numbering according to the EU numbering convention). In some embodiments of the invention, one or more residues in the polypeptide sequences of the CH1 or CL moieties exclusive of these core interface residues may be altered, e.g. by replacement, addition or deletion, with other amino acid residues, e.g., to add an effector function to the binding molecule, e.g., to add a binding moiety to the molecule, or may be excluded from the binding molecule. In some embodiments of the invention, 1, 2, 3, 4, 5, 6, 7, 8, 9, 10, 11, 12, 13, 14, 15 or more residues made be altered. In some embodiments of the invention, the polypeptide sequences of the CH1 or CL moieties of the constituent polypeptide chains consists essentially of immunoglobulin Fab constant domain sequence, including the core interface residues.

Exemplary embodiments of the invention feature constituent polypeptide chains comprising CH1 and CL domain moieties at their C-terminal ends comprising residues that are conserved between murine and human CH1 and CL domains. The alignments between murine and human immunoglobulin CH1 domains (i.e., heavy chain sequence) (SEQ ID NOS: 23 and 24, respectively) and between murine and human immunoglobulin CL domains (i.e., light chain sequence) (SEQ ID NOS: 25 and 26, respectively) is given below.

```
Heavy Chains:
Mouse 1  EVQLQQSGAEVVRSGASVKLSCTASGFNIKDYYIHWVKQRPEKGLEWIGWIDPEIGDTEY    60
         EVQL QSGAEV + GA+VK+SC  SG+   DYY+HWV+Q P KGLEW+G +DPE G+T Y
```

```
                                           -continued
Human  19 EVQLVQSGAEVKKPGATVKISCKVSGYTFTDYYVHWVQQAPGKGLEWMGLVDPEDGETIY          78

Mouse  61 VPKFQGKATMTADTSSNTAYLQLSSLTSEDTAVYYCNAGHDYDR--GRF--PYWGQGTLV          116
          KFQG+ T+TADTS++TAY++LSSL SEDTAVYYC    G      R     R     YWGQGTLV
Human  79 AEKFQGRVTITADTSTDTAYMELSSLRSEDTAVYYCATGVFIRRIAARLGGDYWGQGTLV          138

Mouse 117 TV SAAKTTPPSV YPLAPGSAAQ TNSMVTLGCL VKGYFPEPVT VTWNSGSLSS GVHTFPAV
          TV S+A T  PSV +PLAP S +  +        LGCL VK YFPEPVT V+WNSG+L+S GVHTFPAV
Human 139 TV SSASTKGPSV FPLAPSSKST SGGTAALGCL VKDYFPEPVT VSWNSGALTS GVHTFPAV Mouse 177 LQ SD-LYTLSSSVTVPSSTWPSETVTCNVAHPASSTKVDKKIVPR                        220
          LQ S  LY+LSS  VTVPSS+   ++T  CNV H  S+TKVDKK+ P+
Human 199 LQ SSGLYSLSSV VTVPSSSLGTQTYICNVNHKPSNTKVDKKVEPK                       243

Light Chains:
Mouse   1 DIVMTQSQKFMSTSVGDRVSITCKASQNVGTAVAWYQQKPGQSPKLMIYSASNRYTGVPD          60
          DI MTQS    +S SVGDRVSITC+A+Q++        +WYQQKPG++PK++IY ASN    GVP
Human   1 DIQMTQSPSSLSASVGDRVSITCQANQDINNYLNWYQQKPGKAPKVLIYDASNLEIGVPS          60

Mouse  61 RFTGSGSGTDFTLTISNMQSEDLADYFCQQYSSYPLTFGAGTKLELKRADAAPTVSIFPP         120
          RF+GSGSGTDFT TIS++Q ED+A Y+CQQY + PLTFG GTK+E+KR  AAP+V IFPP
Human  61 RFSGSGSGTDFTFTISSLQPEDIATYYCQQYENLPLTFGGGTKVEIKRTVAAPSVFIFPP         120

Mouse 121 SSEQLTSGGASVVCFLNNFYPKDINVKWKIDGSERQNGVLNSATDQDSKDSTYSMSSTLT         180
          S EQL SG ASVVC LNNFYP++  V+WK+D + +       S T+QDSKDSTYS+SSTLT
Human 121 SDEQLKSGTASVVCLLNNFYPREAKVQWKVDNALQSGNSQESVTEQDSKDSTYSLSSTLT         180

Mouse 181 LTKDEYERHNSYTCEATHKTSTSPIVKSFNRNEC                                   214
          L+K +YE+H  Y CE TH+   +SP+  KSFNR EC
Human 181 LSKADYEKHKVYACEVTHQGLSSPVTKSFNRGEC                                   214
```

Other exemplary embodiments of the invention feature binding molecules with heterodimeric Fc regions comprising constituent polypeptide chains with Fab constant domain moieties (i.e., a CH1 moiety or a CL moiety) attached at their N-terminal ends to the C-terminal end of an Fc moiety, with additional peptidic sequence attached to the C-terminal end of the Fab moiety. In some embodiments, a binding moiety is attached to the C-terminal end of the Fab moiety. In some embodiments, an Fc moiety is attached at its N-terminal end to the C-terminal end of an Fab moiety.

E. FcRn Binding Moieties

In on embodiment, an Fc moiety comprises a variant Fc moiety which has been modified to enable the Fc moiety to bind to FcRn. In one example, CH2-CL amino acid sequences are modified such that they bind to FcRn. The objective was to give the new constructs pH-dependent FcRn-binding behavior like that of native Fc. The pH-dependence of FcRn binding in the native complex depends upon two key histidines (Martin, W L et al. Mol. Cell (2001), 7:867-877), which in the human sequence are His435 and His310. Binding affinity of Fc is completely lost if either of these His residues is mutated to Ala (Shields, R L et al. J. Biol. Chem. (2001) 276: 6591-6604). Charged residues of CH3 contribute to pH-dependence binding of FcRn even if they are not part of the interface. The loop was extended to include residues within 8 Å that change charge between CL and CH3. Therefore the loop consisting of CH3 residues 428-436 was expanded to include Ser426, which is Glu in the CL domain, and Val427, which is conserved between the two domains (located at positions 88 and 89 in FIG. 9, respectively). Since Cys194 in CL (position 87 in FIG. 9) is well-aligned structurally with the conserved Cys425 in CH3 (both form an intradomain disulfide bond), and Val205 in CL (position 99 in FIG. 9) is aligned with Thr437 (0.6 A apart), these residues were chosen as the N- and C-terminal splice sites for the FcRn-binding loop of CH3. Residues 426-436 of CH3 were spliced in place of residues 195-204 from CL in all the CH2-CL constructs.

In addition to the FcRn contacting loop, the residues connecting the CH2 and CH3 domains in a native IgG1 molecule were incorporated into the CH2-CL constructs in order to maintain the correct geometry of the domain linker. Residues 341-345 from CH3 (positions 1-6 of FIG. 9) were incorporated in place of residues 108-112 from CL. Pro113 was retained in CL, since it is conserved as Pro346 in CH3.

The first construct shown below comprises these two substitutions. Additional elements of the CH3 domain were included in constructs 2 and 3 to increase FcRn binding affinity. The substitution in these additional constructs occurred in the region from residues 142-155 of CL, which contacts the main FcRn binding loop described above (residues 195-204) and also forms intramolecular contacts with CH2. The second construct shown in Table 3 has the CH3 residues 375-380 spliced in place of CL residues 142-147. These residues make intramolecular contacts with the CH2 domain, and charged residues such as Glu380 from CH3 or Lys 145 from CL affect the pH dependence of FcRn binding. The mutations assist in keeping the CH2/CL domains oriented as the CH2/CH3 domains are when they bind FcRn.

The third construct includes a larger spliced loop: residues 142-155 of CL are replaced with residues 375-388 of CH3. The first several residues are in the same loop as the residues mutated above for the second construct. The additional residues have a structural role, and therefore they were mutated in the third construct.

When the CH1/CL heterodimers were superimposed on a CH3 homodimer, the CH1 and CL domains had conformations that were twisted relative to one another in a way that was different from the native pair of CH3 domains. The structures indicated that the CL N-terminus in the new constructs is displaced by 6-8 A relative to the native CH3 domain. Therefore, three additional constructs were made to allow the CL domain to move with respect to the CH2 domain. Constructs 4-6 correspond to constructs 1-3 with an additional Gly-Ser linker inserted just after residue 340 of CH2 (i.e., immediately N-terminal to the N-terminal-most CH3/CL sequence replacement, at positions 1-5 of FIG. 9). The Gly-Ser linker allows additional flexibility for the CH1 domain to move relative to the CH2 domain so that CH1 can still form an interface with CL. Similarly, constructs 7-9 correspond to constructs 1-3 with a Gly-Gly-Gly-Ser linker to allow still more flexibility.

Table 3 below shows the sequences of CH2-CL constructs c1-c9, any of which can be included in a binding molecule of the invention. Each of c1-c9 were designed to be paired with any one of the CH2-CH1 constructs d1-d8 in the heterodimeric binding molecules of the invention. The CH2 domains comprise native IgG1 sequence. Constructs c1-c3 have progressively more CH3 sequence spliced into the CL domain. Constructs c4-c6 are identical to constructs c1-c3, respectively, but with the addition of a Gly-Ser linker at the start of the CL domain to provide flexibility for the formation of the three-dimensional structure of the CH2-CL portion of the constituent peptide chain. Likewise, constructs c7-c9 are identical to c1-c3, respectively, but comprise a GGGS (SEQ ID NO: 22) linker. Sequence in the constructs that has been changed from the original CH2-CL construct are shown in bold and the hinge sequence is underlined.

TABLE 4

CH2-CL amino acid sequences:

>c0 hinge-CH2-CL (reference)(SEQ ID NO: 27):
EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC >c1 hinge-CH2-CL (SEQ ID NO: 28)
EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGQPREPSVFIFPPSDEQLKSGTASVVCLLNNEYPREAKVQWKVDNALQSGNS
QESVTEQDSKDSTYSLSSTLTLSKADYEKHKVYACSVMHEALHNHYVTKSFNRGEC >c2 hinge-CH2-CL (SEQ ID NO: 29)
EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGQPREPSVFIFPPSDEQLKSGTASVVCLLNNEYPSDIAVEWKVDNALQSGNS
QESVTEQDSKDSTYSLSSTLTLSKADYEKHKVYACSVMHEALHNHYVTKSFNRGEC >c3 hinge-CH2-CL (SEQ ID NO: 30)
EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGQPREPSVFIFPPSDEQLKSGTASVVCLLNNEYPSDIAVEWESNGQPESGNS
QESVTEQDSKDSTYSLSSTLTLSKADYEKHKVYACSVMHEALHNHYVTKSFNRGEC >c4 hinge-CH2-CL (SEQ ID NO: 31)
EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGSGQPREPSVFIFPPSDEQLKSGTASVVCLLNNEYPREAKVQWKVDNALQSG
NSQESVTEQDSKDSTYSLSSTLTLSKADYEKHKVYACSVMHEALHNHYVTKSFNRGEC >c5 hinge-CH2-CL (SEQ ID NO: 32)
EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGSGQPREPSVFIFPPSDEQLKSGTASVVCLLNNEYPSDIAVEWKVDNALQSG
NSQESVTEQDSKDSTYSLSSTLTLSKADYEKHKVYACSVMHEALHNHYVTKSFNRGEC >c6 hinge-CH2-CL (SEQ ID NO: 33)
EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGSGQPREPSVFIFPPSDEQLKSGTASVVCLLNNEYPSDIAVEWESNGQPESG
NSQESVTEQDSKDSTYSLSSTLTLSKADYEKHKVYACSVMHEALHNHYVTKSFNRGEC >c7 hinge-CH2-CL (SEQ ID NO: 34)
EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGGGSGQPREPSVFIFPPSDEQLKSGTASVVCLLNNEYPREAKVQWKVDNALQ
SGNSQESVTEQDSKDSTYSLSSTLTLSKADYEKHKVYACSVMHEALHNHYVTKSFNRGE
C >c8 hinge-CH2-CL (SEQ ID NO: 35)
EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGGGSGQPREPSVFIFPPSDEQLKSGTASVVCLLNNEYPSDIAVEWKVDNALQ
SGNSQESVTEQDSKDSTYSLSSTLTLSKADYEKHKVYACSVMHEALHNHYVTKSFNRGE
C >c9 hinge-CH2-CL (SEQ ID NO: 36)
EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGGGSGQPREPSVFIFPPSDEQLKSGTASVVCLLNNEYPSDIAVEWESNGQPE
SGNSQESVTEQDSKDSTYSLSSTLTLSKADYEKHKVYACSVMHEALHNHYVTKSFNRGE
C In each of constructs c1-c9 above, amino acids 1-15 (underlined) correspond to the hinge region; amino acids 16-125 correspond to the CH2 domain; and the amino acid sequence starting at position 126 (the first boldened "G") to the end of each sequence ("C") corresponds to the CL moiety.

Addition of FcRn-Binding Elements to CH2-CH1 Domain

In on embodiment, an Fc moiety comprises a variant Fc moiety which has been modified to enable the Fc moiety to bind to FcRn. In one example, CH2-CH1 amino acid sequences are modified such that they bind to FcRn. The overall procedure was similar to that used for the CH2-CL domain. The Fc/FcRn complex structure was searched for CH3 residues within 6 Angstroms of the FcRn subunit. These interface residues are important for FcRn binding, and therefore were incorporated into the CH1 domain to allow the new CH2-CH1 construct to bind FcRn. The CH3 residues at the interface are all in the loop extending from Met428 to Tyr436 (native CH3 domain EU numbering, located at positions 90 and 98, respectively, in the sequence alignment of FIG. 9). Since Val202 in CH1 was well-aligned structurally with the conserved Val427 in CH3 (0.4 Å apart in aligned structures; at position 89 in FIG. 9), and Val211 in CH1 was aligned with Thr437 (0.6 Å apart; position 99 in FIG. 9), these residues were chosen as the N- and C-terminal splice sites for the FcRn-binding loop of CH3. Residues 428-436 of CH3 were spliced in place of residues 203-210 from CH1 (positions 90-98 of FIG. 9 for both sets of residues) in all the CH2-CH1 constructs.

In addition to the FcRn contacting loop, the residues connecting the CH2 and CH3 domains were incorporated into the CH2-CH1 constructs to maintain the correct geometry of the domain linker. Residues 341-345 from CH3 were incorporated in place of residues 118-122 from CH1. Pro123 was retained in CH1, since it is conserved as Pro346 in CH3.

The first construct shown below comprised these two substitutions. Additional elements of the CH3 domain were included in constructs 2-4 to increase FcRn binding. The second construct included the changes made in construct 1 and also replaced residues 150-155 of CH1 with residues 373-378 of CH3. (Residue 154 was retained as Val, since it is buried and does not contribute to FcRn binding or CH2 interactions.) This loop contacts the main FcRn binding loop described above (residues 203-210) and also forms intramolecular contacts with CH2. The mutations are necessary to keep the CH2/CH1 domains oriented as the CH2/CH3 domains are when they bind FcRn.

The third construct expanded the region that is spliced from CH3. In addition to the changes made in the first construct, it has residues 149-159 of CH1 replaced with residues 372-382 of CH3, and residues 201-214 of CH1 replaced with 426-440 of CH3. Both of these changes are in regions more distant from the interface, but they include charged residues from CH3 and remove charges remaining from CH1. The charge state of the protein is important for pH-dependent binding, and an increased number of peripheral residues contribute to the binding in construct 3.

The fourth construct was based on the third construct, expanding to a replacement of the residues 149-167 of CH1 with residues 372-391 from CH3. The residues at the N- and C-termini of the loop were chosen because CH1 and CH3 structure are aligned closely (<0.5 Å deviation) at those points. The conformation of this loop is important for maintaining the structure of the FcRn interface and the required contacts with the CH2 domain. The mutation Q196N was included in the fourth construct because Gln196 of CH1 interferes with the conformation of the loop from CH3.

Finally, four additional constructs were made. Constructs 5-8 correspond to constructs 1-4 with an additional Gly-Ser linker inserted just after residue 340 of CH2 (i.e., immediately N-terminal to the N-terminal-most CH3/CL sequence replacement, at positions 1-5 of FIG. 9). As described above, the CH1/CL heterodimers had different orientations than native CH3 homodimers when their structures were analyzed. The aligned structures show that the CH1 N-terminus in the new constructs is displaced by 3-4 Å relative to the native CH3 domain. The Gly-Ser linker allows additional flexibility for the CH1 domain to move relative to the CH2 domain so that CH1 can still form an interface with CL.

The sequences of CH2-CH1 constructs d1-d8 were designed to be paired with CH2-CL constructs c1-c9 above in the heterodimeric binding molecules of the invention. The heavy chain constant domains comprise native IgG1 heavy chain constant domain sequence. Constructs d1-d4 have progressively more CH3 sequence spliced into the CH1 domain. Constructs d5-d8 are identical to constructs d1-d4, respectively, but with the addition of a Gly-Ser linker at the start of the CH1 domain to provide flexibility for the formation of the three-dimensional structure of the CH2-CH1 portion of the constituent peptide chain. Sequence in the constructs that has been changed from the original CH2-CH1 construct are shown in bold and the hinge sequence is underlined. Each CH1 sequence has the beginning of a hinge at its C-terminus to maintain the CH1 moiety's native structure.

TABLE 5

CH2-CH1 amino acid sequences:

```
>d0 hinge-CH2-CH1 portion (reference) (SEQ ID NO: 37):
EPKSSDKTHTCPPCPAPELLGGPSVFLEPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKKVEPKSC >d1 hinge-CH2-CH1 portion (SEQ ID NO: 38)
EPKSSDKTHTCPPCPAPELLGGPSVFLEPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGQPREPSVFPLAPSSKSTSGGTAALGCLVKDYFPEPVTVSWNSGALTSGVHT
FPAVLQSSGLYSLSSVVTVPSSSLGTQTYICNVMHEALHNHYVDKKVEPKSC >d2 hinge-CH2-CH1 portion (SEQ ID NO: 39)
EPKSSDKTHTCPPCPAPELLGGPSVFLEPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGQPREPSVFPLAPSSKSTSGGTAALGCLVKDYYPSDVAVSWNSGALTSGVHT
FPAVLQSSGLYSLSSVVTVPSSSLGTQTYICNVMHEALHNHYVDKKVEPKSC
```

TABLE 5-continued

CH2-CH1 amino acid sequences:

>d3 hinge-CH2-CH1 portion (SEQ ID NO: 40)
EPKSSDKTHTCPPCPAPELLGGPSVFLEPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGQPREPSVFPLAPSSKSTSGGTAALGCLVKDFYPSDIAVEWESGALTSGVHT
FPAVLQSSGLYSLSSVVTVPSSSLGTQTYICSVMHEALHNHYVQKSVEPKSC >d4 hinge-CH2-CH1 portion (SEQ ID NO: 41)
EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGQPREPSVFPLAPSSKSTSGGTAALGCLVKDFYPSDIAVEWESNGQPENNYH
TFPAVLQSSGLYSLSSVVTVPSSSLGTNTYICSVMHEALHNHYVQKSVEPKSC >d5 hinge-CH2-CH1 portion (SEQ ID NO: 42)
EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGSGQPREPSVFPLAPSSKSTSGGTAALGCLVKDYFPEPVTVSWNSGALTSGV
HTFPAVLQSSGLYSLSSVVTVPSSSLGTQTYICNVMHEALHNHYVDKKVEPKSC >d6 hinge-CH2-CH1 portion (SEQ ID NO: 43)
EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGSGQPREPSVFPLAPSSKSTSGGTAALGCLVKDYYPSDVAVSWNSGALTSGV
HTFPAVLQSSGLYSLSSVVTVPSSSLGTQTYICNVMHEALHNHYVDKKVEPKSC >d7 hinge-CH2-CH1 portion (SEQ ID NO: 44)
EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGSGQPREPSVFPLAPSSKSTSGGTAALGCLVKDFYPSDIAVEWESGALTSGV
HTFPAVLQSSGLYSLSSVVTVPSSSLGTQTYICSVMHEALHNHYVQKSVEPKSC >d8 hinge-CH2-CH1 portion (SEQ ID NO: 45)
EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGSGQPREPSVFPLAPSSKSTSGGTAALGCLVKD**FYPSDIAVEWESNGQPENN
YHTFPAVLQSSGLYSLSSVVTVPSSSLGTNTYICSVMHEALHNHY**VQKSVEPKSC In each of constructs d1-d8 above, amino acids 1-15 (underlined) correspond to the hinge region; amino acids 16-125 correspond to the CH2 domain; the amino acid sequence starting at position 126 (the first boldened "G") to the last valine ("V") corresponds to the CH1 moiety; followed by the first four amino acids of the hinge capped with a C-terminal cysteine.

In one embodiment, a binding molecule of the invention comprises a heterodimer which comprises a c1 sequence in combination with any one of d1, d2, d3, d4, d5, d6, d7, and d8. In another embodiment, a binding molecule of the invention comprises a heterodimer which comprises a c2 sequence in combination with any one of d1, d2, d3, d4, d5, d6, d7, and d8. In another embodiment, a binding molecule of the invention comprises a heterodimer which comprises a c3 sequence in combination with any one of d1, d2, d3, d4, d5, d6, d7, and d8. In another embodiment, a binding molecule of the invention comprises a heterodimer which comprises a c4 sequence in combination with any one of d1, d2, d3, d4, d5, d6, d7, and d8. In another embodiment, a binding molecule of the invention comprises a heterodimer which comprises a c5 sequence in combination with any one of d1, d2, d3, d4, d5, d6, d7, and d8. In another embodiment, a binding molecule of the invention comprises a heterodimer which comprises a c6 sequence in combination with any one of d1, d2, d3, d4, d5, d6, d7, and d8. In another embodiment, a binding molecule of the invention comprises a heterodimer which comprises a c7 sequence in combination with any one of d1, d2, d3, d4, d5, d6, d7, and d8. In another embodiment, a binding molecule of the invention comprises a heterodimer which comprises a c8 sequence in combination with any one of d1, d2, d3, d4, d5, d6, d7, and d8. In another embodiment, a binding molecule of the invention comprises a heterodimer which comprises a c9 sequence in combination with any one of d1, d2, d3, d4, d5, d6, d7, and d8.

In one embodiment, a binding molecule of the invention comprises a heterodimer which comprises a d1 sequence in combination with any one of c1, c2, c3, c4, c5, c6, c7, c8 and c9. In another embodiment, a binding molecule of the invention comprises a heterodimer which comprises a d 2 sequence in combination with any one of c1, c2, c3, c4, c5, c6, c7, c8 and c9. In another embodiment, a binding molecule of the invention comprises a heterodimer which comprises a d 3 sequence in combination with any one of c1, c2, c3, c4, c5, c6, c7, c8 and c9. In another embodiment, a binding molecule of the invention comprises a heterodimer which comprises a d4 sequence in combination with any one of c1, c2, c3, c4, c5, c6, c7, c8 and c9. In another embodiment, a binding molecule of the invention comprises a heterodimer which comprises a d5 sequence in combination with any one of c1, c2, c3, c4, c5, c6, c7, c8 and c9. In another embodiment, a binding molecule of the invention comprises a heterodimer which comprises a d6 sequence in combination with any one of c1, c2, c3, c4, c5, c6, c7, c8 and c9. In another embodiment, a binding molecule of the invention comprises a heterodimer which comprises a d7 sequence in combination with any one of c1, c2, c3, c4, c5, c6, c7, c8 and c9. In another embodiment, a binding molecule of the invention comprises a heterodimer which comprises a d8 sequence in combination with any one of c1, c2, c3, c4, c5, c6, c7, c8 and c9. In one embodiment a binding molecule of the invention comprises a c2 and a d2 amino acid sequence as set forth herein In one embodiment, a c1-c9 or d1-d8 variant Fc moiety is further modified to reduce or eliminate potential T cell epitopes. Exemplary such sequences that can be included in a binding moiety of the invention are set forth below:

```
>c2.2 (V437T/T438Q double mutant)
                                                                (SEQ ID NO: 46)
MDWTWRVFCLLAVAPGAHSDYKDDDDKEPKSSDKTHTCPPCPAPELLGGPSVFLFPPKPKDTLMISRTPEV

TCVVVDVSHEDPEVKFNWYVDGVEVHNAKTKPREEQYNSTYRVVSVLTVLHQDWLNGKEYKCKVSNKALPA

PIEKTISKAKGQPREPSVFIFPPSDEQLKSGTASVVCLLNNFYPSDIAVEWKVDNALQSGNSQESVTEQDS

KDSTYSLSSTLTLSKADYEKHKVYACSVMHEALHNHYTQKSFNRGEC

>d2.2 (Y372F/V377I double mutant)
                                                                (SEQ ID NO: 47)
MDWTWRVFCLLAVAPGAHSWSHPQFEKQVQLVQSGAEVKKPGESVKVSCKASGYTFTTYYLHWVRQAPGQG

LEWMGWIYPGNGHAQYNEKFKGRVTITADKSTSTAYMELSSLRSEDTAVYYCARSWEGFPYWGQGTTVTVS

SGGGGSGGGGSGGGGSGGGGSDIQMTQSPSSLSASVGDRVTITCKASQNVGINVAWYQQKPGKAPKLLISS

ASYRYSGVPSRFSGSGSGTDFTLTISSLQPEDFATYFCQQYDTYPFTFGQGTKVEIKGGGGSGGGGSEPKS

SDKTHTCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAKGQPREPSVFPLAPSSKSTSGG

TAALGCLVKDFYPSDIAVSWNSGALTSGVHTFPAVLQSSGLYSLSSVVTVPSSSLGTQTYICNVMHEALHN

HYTDKKVEPKSC

>d2.3 (Y372F/V377I/V437T triple mutant)
                                                                (SEQ ID NO: 48)
MDWTWRVFCLLAVAPGAHSWSHPQFEKQVQLVQSGAEVKKPGESVKVSCKASGYTFTTYYLHWVRQAPGQG

LEWMGWIYPGNGHAQYNEKFKGRVTITADKSTSTAYMELSSLRSEDTAVYYCARSWEGFPYWGQGTTVTVS

SGGGGSGGGGSGGGGSGGGGSDIQMTQSPSSLSASVGDRVTITCKASQNVGINVAWYQQKPGKAPKLLISS

ASYRYSGVPSRFSGSGSGTDFTLTISSLQPEDFATYFCQQYDTYPFTFGQGTKVEIKGGGGSGGGGSEPKS

SDKTHTCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAKGQPREPSVFPLAPSSKSTSGG

TAALGCLVKDFYPSDIAVSWNSGALTSGVHTFPAVLQSSGLYSLSSVVTVPSSSLGTQTYICNVMHEALHN

HYTDKKVEPKSC

>d2.4 (Y372F/V377I/S380E/V437T quad mutant)
                                                                (SEQ ID NO: 49)
MDWTWRVFCLLAVAPGAHSWSHPQFEKQVQLVQSGAEVKKPGESVKVSCKASGYTFTTYYLHWVRQAPGQG

LEWMGWIYPGNGHAQYNEKFKGRVTITADKSTSTAYMELSSLRSEDTAVYYCARSWEGFPYWGQGTTVTVS

SGGGGSGGGGSGGGGSGGGGSDIQMTQSPSSLSASVGDRVTITCKASQNVGINVAWYQQKPGKAPKLLISS

ASYRYSGVPSRFSGSGSGTDFTLTISSLQPEDFATYFCQQYDTYPFTFGQGTKVEIKGGGGSGGGGSEPKS

SDKTHTCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAKGQPREPSVFPLAPSSKSTSGG

TAALGCLVKDFYPSDIAVEWNSGALTSGVHTFPAVLQSSGLYSLSSVVTVPSSSLGTQTYICNVMHEALHN

HYTDKKVEPKSC
```

In construct c2.2 (SEQ ID NO: 46), amino acids 1-19 corresponds to the humanized 5C8 secretion signal (see, Table 6); amino acids 20-27 correspond to the FLAG tag (see, Table 6), amino acids 28-42 correspond to CL cysteine-scrubbed IgG1 hinge (see, Table 6); amino acids 43-152 to the IgG1 CH2 domain (see, Table 6); and amino acids 153-260 to the CL moiety.

In construct d2.2 (SEQ ID NO: 47), amino acids 1-19 corresponds to the humanized 5C8 secretion signal (see, Table 6); amino acids 20-27 correspond to the strep tag (see, Table 6), amino acids 28-143 correspond to the VH of the BHA10 scFv (see, Table 6); amino acids 144-163 to the Gly-Ser linker (see, Table 6); amino acids 164-270 to the VL of the BHA10 scFv (see, Table 6); amino acids 271-280 to the Gly-Ser linker (see, Table 6); amino acids 281-295 to the hinge sequence; amino acids 296-405 to the IgG1 CH2 domain; amino acids 406-504 to the CH1 moiety; followed by the first four amino acids of the hinge capped with a C-terminal cysteine.

In construct d2.3 (SEQ ID NO: 48), amino acids 1-19 corresponds to the humanized 5C8 secretion signal (see, Table 6); amino acids 20-27 correspond to the strep tag (see, Table 6), amino acids 28-143 correspond to the VH of the BHA10 scFv (see, Table 6); amino acids 144-163 to the Gly-Ser linker (see, Table 6); amino acids 164-270 to the VL of the BHA10 scFv (see, Table 6); amino acids 271-280 to the Gly-Ser linker (see, Table 6); amino acids 281-295 to the hinge sequence; amino acids 296-405 to the IgG1 CH2 domain; amino acids 406-504 to the CH1 moiety; followed by the first four amino acids of the hinge capped with a C-terminal cysteine.

In construct d2.4 (SEQ ID NO: 49), amino acids 1-19 corresponds to the humanized 5C8 secretion signal (see, Table 6); amino acids 20-27 correspond to the strep tag (see, Table 6), amino acids 28-143 correspond to the VH of the BHA10 scFv (see, Table 6); amino acids 144-163 to the Gly-Ser linker (see, Table 6); amino acids 164-270 to the VL of the BHA10 scFv (see, Table 6); amino acids 271-280 to the Gly-Ser linker (see, Table 6); amino acids 281-295 to the hinge sequence; amino acids 296-405 to the IgG1 CH2 domain; amino acids 406-504 to the CH1 moiety; followed by the first four amino acids of the hinge capped with a C-terminal cysteine.

F. Target Binding Moieties

In certain aspects, the binding molecules of the invention comprise at least one binding moiety which binds to a desired target. Accordingly, the binding molecules of the invention typically comprise at least one binding moiety and at least one heterodimeric Fc region (i.e., comprising at least two constituent non-identical polypeptide chains). In one embodiment, the binding moiety is operably linked (e.g., chemically conjugated or genetically fused (e.g., either directly or via a polypeptide linker)) to the N-terminus of a heterodimeric Fc region. In another embodiment, the binding moiety is operably linked (e.g., chemically conjugated or genetically fused (e.g., either directly or via a polypeptide linker)) to the C-terminus of a heterodimeric Fc region. In other embodiments, a binding moiety is operably linked (e.g., chemically conjugated or genetically fused (e.g., either directly or via a polypeptide linker)) via an amino acid side chain of a constituent polypeptide chain. In certain exemplary embodiments, the binding moiety is fused to a heterodimeric Fc region (i.e., comprising at least two constituent non-identical polypeptides) via a human immunoglobulin hinge domain or portion thereof (e.g., a human IgG1 sequence, e.g., DKTHTCPPCPAPELLGG (SEQ ID NO: 17)).

In certain embodiments, the binding molecules of the invention comprise two binding moieties and at least one heterodimeric Fc region. For example, binding moieties may be operably linked to both the N-terminus and C-terminus of a single constituent polypeptide chain; binding moieties on two genetically distinct constituent polypeptide chains may be operably linked by the heterodimeric Fc region.

In other embodiments, two or more binding moieties are linked to each other (e.g., via a polypeptide linker) in series, and the tandem array of binding moieties is operably linked (e.g., chemically conjugated or genetically fused (e.g., either directly or via a polypeptide linker to either the C-terminus or the N-terminus of a constituent polypeptide chain of a binding molecule of the invention)). In other embodiments, the tandem array of binding moieties is operably linked to binding moieties on a separate constituent polypeptide chain via the heterodimeric Fc region.

In other embodiments, a binding molecule of the invention is a trivalent binding molecule comprising three binding sites. An exemplary tri valent binding molecule of the invention is bispecific or trispecific. For example, a trivalent binding molecule may be bivalent (i.e., have two binding sites) for one specificity and monovalent for a second specificity.

In yet other embodiments, a binding molecule of the invention is a tetravalent binding molecule comprising four binding moieties (FIG. 8D). Exemplary tetravalent binding molecules of the invention are monospecific or bispecific. For example, a tetravalent binding molecule may be bivalent (i.e., have two binding sites) for each of two specificities. Tetravalent binding molecules may have four distinct binding moiety that bind with different affinities and/or to different targets.

As mentioned above, in other embodiments, one or more binding moieties may be inserted between two Fc moieties of a constituent polypeptide chain. One or more binding moieties may be inserted between an Fc moiety and a Fab constant region moiety of a constituent polypeptide chain. For example, one or more binding moieties may form all or part of a polypeptide linker of a constituent polypeptide chain of the invention.

Preferred binding molecules of the invention comprise at least one of an antigen binding moiety (e.g., an antigen binding moiety of an antibody, antibody variant, or antibody fragment), a receptor binding portion of ligand, or a ligand binding portion of a receptor.

In other embodiments, the binding molecules of the invention comprise at least one binding moiety comprising one or more of any one of the biologically-relevant peptides discussed supra.

In certain embodiments, the binding molecules of the invention have at least one binding moiety specific for a target molecule which mediates a biological effect. In one embodiment, the binding moiety modulates cellular activation or inhibition (e.g., by binding to a cell surface receptor and resulting in transmission of an activating or inhibitory signal). In one embodiment, the binding moiety is capable of initiating transduction of a signal which results in death of the cell (e.g., by a cell signal induced pathway, by complement fixation or exposure to a payload (e.g., a toxic payload) present on the binding molecule), or which modulates a disease or disorder in a subject (e.g., by mediating or promoting cell killing, by promoting lysis of a fibrin clot or promoting clot formation, or by modulating the amount of a substance which is bioavailable (e.g., by enhancing or reducing the amount of a ligand such as TNFα in the subject)). In another embodiment, the binding molecules of the invention have at least one binding moiety specific for an antigen targeted for reduction or elimination, e.g., a cell surface antigen or a soluble antigen, together with at least one heterodimeric Fc region (i.e., comprising at least two constituent non-identical polypeptide chains).

In another embodiment, binding of the binding molecules of the invention to a target molecule (e.g. antigen) results in the reduction or elimination of the target molecule, e.g., from a tissue or from circulation. In another embodiment, the binding molecule has at least one binding moiety specific for a target molecule that can be used to detect the presence of the target molecule (e.g., to detect a contaminant or diagnose a condition or disorder). In yet another embodiment, a binding molecule of the invention comprises at least one binding moiety that targets the molecule to a specific site in a subject (e.g., to a tumor cell, an immune cell, or blood clot).

In certain embodiments, the binding molecules of the invention may comprise two or more binding sites. In one embodiment, the binding moieties are identical. In another embodiment, the binding moieties are different.

In other embodiments, the constituent polypeptide chains of binding molecules of the invention may be assembled with other polypeptides to form binding proteins having three or more polypeptides ("binding proteins" or "multimers"), wherein at least two constituent polypeptide chains of the multimer form a binding molecule of the invention comprising a heteromeric Fc region. Exemplary multimeric forms include trimeric, tetrameric, and hexameric altered binding proteins and the like.

i. Antigen Binding Sites

In certain embodiments, a binding molecule of the invention comprises at least one antigen binding moiety of an antibody. Binding molecules of the invention may comprise a variable region or portion thereof (e.g. a VL and/or VH domain) derived from any immunoglobulin using art recognized protocols. For example, the variable domain may be derived from immunoglobulin produced in a non-human mammal, e.g., murine, guinea pig, primate, rabbit or rat, by immunizing the mammal with the antigen or a fragment thereof. See Harlow & Lane, supra, incorporated by reference for all purposes. The immunoglobulin may be generated by multiple subcutaneous or intraperitoneal injections of the relevant antigen (e.g., purified tumor associated antigens or cells or cellular extracts comprising such antigens) and an adjuvant. This immunization typically elicits an immune response that comprises production of antigen-reactive antibodies from activated splenocytes or lymphocytes.

While the variable region may be derived from polyclonal antibodies harvested from the serum of an immunized mammal, it is often desirable to isolate individual lymphocytes from the spleen, lymph nodes or peripheral blood to provide homogenous preparations of monoclonal antibodies (MAbs) from which the desired variable region is derived. Rabbits or guinea pigs are typically used for making polyclonal antibodies. Mice are typically used for making monoclonal antibodies. Monoclonal antibodies can be prepared against a fragment by injecting an antigen fragment into a mouse, preparing "hybridomas" and screening the hybridomas for an antibody that specifically binds to the antigen. In this well known process (Kohler et al., (1975), *Nature*, 256:495) the relatively short-lived, or mortal, lymphocytes from the mouse which has been injected with the antigen are fused with an immortal tumor cell line (e.g. a myeloma cell line), thus, producing hybrid cells or "hybridomas" which are both immortal and capable of producing the antibody genetically encoded by the B cell. The resulting hybrids are segregated into single genetic strains by selection, dilution, and regrowth with each individual strain comprising specific genes for the formation of a single antibody. They produce antibodies which are homogeneous against a desired antigen and, in reference to their pure genetic parentage, are termed "monoclonal".

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by immunoprecipitation or by an in vitro assay, such as a radioimmunoassay (RIA) or enzyme-linked immunosorbent assay (ELISA). After hybridoma cells are identified that produce antibodies of the desired specificity, affinity and/or activity, the clones may be subcloned by limiting dilution procedures and grown by standard methods (Goding, *Monoclonal Antibodies: Principles and Practice*, pp 59-103 (Academic Press, 1986)). It will further be appreciated that the monoclonal antibodies secreted by the subclones may be separated from culture medium, ascites fluid or serum by conventional purification procedures such as, for example, affinity chromatography (e.g., protein-A, protein-G, or protein-L affinity chromatography), hydroxylapatite chromatography, gel electrophoresis, or dialysis.

Optionally, antibodies may be screened for binding to a specific region or desired fragment of the antigen without binding to other nonoverlapping fragments of the antigen. The latter screening can be accomplished by determining binding of an antibody to a collection of deletion mutants of the antigen and determining which deletion mutants bind to the antibody. Binding can be assessed, for example, by Western blot or ELISA. The smallest fragment to show specific binding to the antibody defines the epitope of the antibody. Alternatively, epitope specificity can be determined by a competition assay is which a test and reference antibody compete for binding to the antigen. If the test and reference antibodies compete, then they bind to the same epitope or epitopes sufficiently proximal such that binding of one antibody interferes with binding of the other.

DNA encoding the desired monoclonal antibody may be readily isolated and sequenced using any of the conventional procedures described supra for the isolation of constant region domain sequences (e.g., by using oligonucleotide probes that are capable of binding specifically to genes encoding the heavy and light chains of murine antibodies). The isolated and subcloned hybridoma cells serve as a preferred source of such DNA. More particularly, the isolated DNA (which may be synthetic as described herein) may be used to clone the desired variable region sequences for incorporation in the binding polypeptides of the invention.

In other embodiments, the binding moiety is derived from a fully human antibody. Human or substantially human antibodies may be generated in transgenic animals (e.g., mice) that are incapable of endogenous immunoglobulin production (see e.g., U.S. Pat. Nos. 6,075,181, 5,939,598, 5,591,669 and 5,589,369, each of which is incorporated herein by reference). For example, it has been described that the homozygous deletion of the antibody heavy-chain joining region in chimeric and germline mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, *Biotechnology*, 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the VH and VL genes can be amplified using, e.g., RT-PCR. The VH and VL genes can be cloned into an antibody expression vector and transfected into cells (e.g., eukaryotic or prokaryotic cells) for expression.

Alternatively, variable (V) domains can be obtained from libraries of variable gene sequences from an animal of choice. Libraries expressing random combinations of domains, e.g., $V_H$ and $V_L$ domains, can be screened with a desired antigen to identify elements which have desired binding characteristics. Methods of such screening are well known in the art. For example, antibody gene repertoires can be cloned into a λ bacteriophage expression vector (Huse, W D et al. (1989). Science, 2476:1275). In addition, cells (Francisco et al. (1994), PNAS, 90:10444; Georgiou et al. (1997), Nat. Biotech., 15:29; Boder and Wittrup (1997) Nat. Biotechnol. 15:553; Boder et al. (2000), PNAS, 97:10701; Daugtherty, P. et al. (2000) J. Immunol. Methods. 243:211) or viruses (e.g., Hoogenboom, H R. (1998), Immunotechnology 4:1; Winter et al. (1994). Annu. Rev. Immunol. 12:433; Griffiths, A D. (1998). Curr. Opin. Biotechnol. 9:102) expressing antibodies on their surface can be screened.

Those skilled in the art will also appreciate that DNA encoding antibody variable domains may also be derived from antibody phage libraries, e.g., using pd phage or Fd phagemid technology. Exemplary methods are set forth, for example, in EP 368 684 B1; U.S. Pat. No. 5,969,108; Hoogenboom et al., (2000) Immunol. Today 21:371; Nagy et al. (2002) Nat. Med. 8:801; Huie et al. (2001), PNAS, 98:2682; Lui et al. (2002), J. Mol. Biol. 315:1063, each of which is incorporated herein by reference. Several publications (e.g., Marks et al. (1992), Bio/Technology 10:779-783) have described the production of high affinity human antibodies by chain shuffling, as well as combinatorial infection and in vivo recombination as a strategy for constructing large phage libraries. In another embodiment, ribosomal display can be used to replace bacteriophage as the display platform (see, e.g., Hanes, et al. (1998), PNAS 95:14130; Hanes and Pluckthun. (1999), Curr. Top. Microbiol. Immunol. 243:107; He and Taussig. (1997), Nuc. Acids Res., 25:5132; Hanes et al. (2000), Nat. Biotechnol. 18:1287; Wilson et al. (2001), PNAS, 98:3750; or Irving et al. (2001) J. Immunol. Methods 248:31).

Preferred libraries for screening are human variable gene libraries. $V_L$ and $V_H$ domains from a non-human source may also be used. Libraries can be naïve, from immunized subjects, or semi-synthetic (Hoogenboom and Winter. (1992). J. Mol. Biol. 227:381; Griffiths et al. (1995) EMBO J. 13:3245; de Kruif et al. (1995). J. Mol. Biol. 248:97; Barbas et al. (1992), PNAS, 89:4457). In one embodiment, mutations can be made to immunoglobulin domains to create a library of nucleic acid molecules having greater heterogeneity (Thompson et al. (1996), J. Mol. Biol. 256:77; Lamminmaki et al. (1999), J. Mol. Biol. 291:589; Caldwell and Joyce. (1992), PCR Methods Appl. 2:28; Caldwell and Joyce. (1994), PCR Methods Appl. 3:S136). Standard screening procedures can be used to select high affinity variants. In another embodiment, changes to $V_H$ and $V_L$ sequences can be made to increase antibody avidity, e.g., using information obtained from crystal structures using techniques known in the art.

Moreover, variable region sequences useful for producing the binding molecules of the present invention may be obtained from a number of different sources. For example, as discussed above, a variety of human gene sequences are available in the form of publicly accessible deposits. Many sequences of antibodies and antibody-encoding genes have been published and suitable variable region sequences (e.g. VL and VH sequences) can be chemically synthesized from these sequences using art recognized techniques.

In another embodiment, at least one variable region domain of a binding molecule of the invention is catalytic (Shokat and Schultz. (1990). Annu. Rev. Immunol. 8:335). Variable region domains with catalytic binding specificities can be made using art recognized techniques (see, e.g., U.S. Pat. No. 6,590,080, U.S. Pat. No. 5,658,753). Catalytic binding specificities can work by a number of basic mechanisms similar to those identified for enzymes to stabilize the transition state, thereby reducing the free energy of activation. For example, general acid and base residues can be optimally positioned for participation in catalysis within catalytic active sites; covalent enzyme-substrate intermediates can be formed; catalytic antibodies can also be in proper orientation for reaction and increase the effective concentration of reactants by at least seven orders of magnitude (Fersht et al., (1968), J. Am. Chem. Soc. 90:5833) and thereby greatly reduce the entropy of a chemical reaction. Finally, catalytic antibodies can convert the energy obtained upon substrate binding and/or subsequent stabilization of the transition state intermediate to drive the reaction.

Acid or base residues can be brought into the antigen binding moiety by using a complementary charged molecule as an immunogen. This technique has proved successful for elicitation of antibodies with a hapten containing a positively-charged ammonium ion (Shokat, et al., (1988), Chem. Int. Ed. Engl. 27:269-271). In another approach, antibodies can be elicited to stable compounds that resemble the size, shape, and charge of the transition state intermediate of a desired reaction (i.e., transition state analogs). See U.S. Pat. No. 4,792,446 and U.S. Pat. No. 4,963,355 which describe the use of transition state analogs to immunize animals and the production of catalytic antibodies. Both of these patents are hereby incorporated by reference. Such molecules can be administered as part of an immunoconjugate, e.g., with an immunogenic carrier molecule, such as KLH.

In another embodiment, a variable region domain of binding molecule of the invention consists of a $V_H$ domain, e.g., derived from camelids, which is stable in the absence of a $V_L$ chain (Hamers-Casterman et al. (1993). Nature, 363:446; Desmyter et al. (1996). Nat. Struct. Biol. 3: 803; Decanniere et al. (1999). Structure, 7:361; Davies et al. (1996). Protein Eng., 9:531; Kortt et al. (1995). J. Protein Chem., 14:167).

Further, a binding molecule of the invention may comprise a variable domain or CDR or set of CDRs (e.g., all six CDRs) derived from a fully murine, fully human, chimeric, humanized, non-human primate or primatized antibody. Non-human antibodies, or fragments or domains thereof, can be altered to reduce their immunogenicity using art recognized techniques. Humanized antibodies are antibodies derived from non-human antibodies, that have been modified to retain or substantially retain the binding properties of the parent antibody, but which are less immunogenic in humans that the parent, non-human antibodies. In the case of humanized target antibodies, this may be achieved by various methods, including (a) grafting the entire non-human variable domains onto human constant regions to generate chimeric target antibodies; (b) grafting at least a part of one or more of the non-human complementarity determining regions (CDRs) into a human framework and constant regions with or without retention of critical framework residues; (c) transplanting the entire non-human variable domains, but "cloaking" them with a human-like section by replacement of surface residues. Such methods are disclosed in Morrison et al., (1984), *PNAS.* 81: 6851-5; Morrison et al., (1988), *Adv. Immunol.* 44: 65-92; Verhoeyen et al., (1988), *Science* 239: 1534-1536; Padlan, (1991), *Molec. Immun.* 28: 489-498; Padlan, (1994), *Molec. Immun.* 31: 169-217; and U.S. Pat. Nos. 5,585,089, 5,693,761 and 5,693,762 all of which are hereby incorporated by reference in their entirety. In one embodiment, one or more framework amino acid residues from a human acceptor amino acid sequence may be altered, e.g., by backmutation to the corresponding donor amino acid residue at that position, or by changing to another amino acid residue, e.g., a germline amino acid residue.

De-immunization can also be used to decrease the immunogenicity of a binding molecule of the invention. As used herein, the term "de-immunization" includes modification of T cell epitopes (see, e.g., WO9852976A1, WO0034317A2). For example, VH and VL sequences are analyzed and a human T cell epitope "map" from each V region showing the location of epitopes in relation to complementarity-determining regions (CDRs) and other key residues within the sequence is generated. Individual T cell epitopes from the T cell epitope map are analyzed in order to identify alternative amino acid substitutions with a low risk of altering the activity of the final antibody. A range of alternative VH and VL sequences are designed comprising combinations of amino acid substitutions and these sequences are subsequently incorporated into a range of constituent polypeptide chains of the invention that are tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Preferably, the variable domains employed in a binding molecule of the invention are altered by at least partial replacement of one or more CDRs and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. It may not be necessary to replace all of the CDRs with the complete CDRs from the donor variable region to transfer the antigen binding capacity of one variable domain to another. Rather, it may only be necessary to transfer those residues that are necessary to maintain the activity of the binding domain. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antigen binding moiety with reduced immunogenicity.

In one embodiment, a binding molecule of the invention comprises at least one CDR from an antibody that recognizes a desired target. In another embodiment, a binding molecule of the present invention comprises at least two CDRs from an antibody that recognizes a desired target. In another embodiment, a binding molecule of the present invention comprises at least three CDRs from an antibody that recognizes a desired target. In another embodiment, a binding molecule of the present invention comprises at least four CDRs from an antibody that recognizes a desired target. In another embodiment, a binding molecule of the present invention comprises at least five CDRs from an antibody that recognizes a desired target. In another embodiment, a binding molecule of the present invention comprises at least six CDRs (i.e., three light chain CDRs and three heavy chain CDRs) from an antibody that recognizes a desired target.

In other aspects, the binding molecules of the invention may comprise antigen binding sites, or portions thereof, derived from antibody variants. Exemplary antibody variants include, e.g., minibodies, diabodies, triabodies, nanobodies, camelids, Dabs, tetravalent antibodies, intradiabodies (e.g., Jendreyko et al. 2003. J. Biol. Chem. 278:47813), fusion proteins (e.g., antibody cytokine fusion proteins, proteins fused to at least a portion of an Fc receptor), and bispecific antibodies. Other antibody variants are described, for example in U.S. Pat. No. 4,745,055; EP 256,654; Faulkner et al., Nature 298:286 (1982); EP 120,694; EP 125,023; Morrison, J. Immun. 123:793 (1979); Kohler et al., Proc. Natl. Acad. Sci. USA 77:2197 (1980); Raso et al., Cancer Res. 41:2073 (1981); Morrison et al., Ann. Rev. Immunol. 2:239 (1984); Morrison, Science 229:1202 (1985); Morrison et al., Proc. Natl. Acad. Sci. USA 81:6851 (1984); EP 255,694; EP 266,663; and WO 88/03559. Reassorted immunoglobulin chains also are known. See, for example, U.S. Pat. No. 4,444,878; WO 88/03565; and EP 68,763 and references cited therein.

In other embodiments, a binding molecule of the invention may comprise an antigen binding fragment. The term "antigen-binding portion" refers to a polypeptide fragment of an immunoglobulin, antibody, or antibody variant which binds antigen or competes with intact antibody (i.e., with the intact antibody from which they were derived) for antigen binding (i.e., specific binding). For example, said antigen binding fragments can be derived from any of the antibodies or antibody variants described supra. Antigen binding fragments can be produced by recombinant or biochemical methods that are well known in the art. Exemplary antigen-binding fragments include Fv, Fab, Fab', and (Fab')$_2$.

In exemplary embodiments, a binding molecule of the invention comprises at least one antigen binding fragment that is operably linked (e.g., chemically conjugated or genetically-fused (e.g., directly fused or fused via a polypeptide linker)) to the C-terminus and/or N-terminus of a constituent peptide chain that is also part of a heterodimeric Fc region (i.e., comprising at least two constituent non-identical polypeptides). In one exemplary embodiment, a binding molecule of the invention comprises an antigen binding fragment (e.g, a Fab or scFv) which is operably linked to the N-terminus (or C-terminus) of at least one constituent peptide chain of a heterodimeric Fc region via a hinge domain or portion thereof (e.g., an IgG1 hinge or portion thereof, e.g., a human IgG1 hinge). An exemplary hinge domain portion comprises the sequence DKTHTCPPCPAPELLGG (SEQ ID NO: 17).

In certain embodiments, a binding molecule of the invention comprises one or more binding moieties or regions comprising a single chain variable region sequence (scFv). Single chain variable region sequences comprise a single polypeptide having one or more antigen binding sites, e.g., a $V_L$ domain linked by a flexible linker to a $V_H$ domain. The VL and/or VH domains may be derived from any of the antibodies or antibody variants described supra. ScFv molecules can be constructed in a $V_H$-linker-$V_L$ orientation or $V_L$-linker-$V_H$ orientation. The flexible linker that links the $V_L$ and $V_H$ domains that make up the antigen binding moiety preferably comprises from about 10 to about 50 amino acid residues. In one embodiment, the polypeptide linker is a gly-ser polypeptide linker. An exemplary gly/ser polypeptide linker is of the formula (Gly4Ser)n (SEQ ID NO: 18), wherein n is a positive integer (e.g., 1, 2, 3, 4, 5, or 6). Other polypeptide linkers are known in the art. Antibodies having single chain variable region sequences (e.g. single chain Fv antibodies) and methods of making said single chain antibodies are well-known in the art (see e.g., Ho et al. 1989. *Gene* 77:51; Bird et al. 1988 *Science* 242:423; Pantoliano et al. 1991. *Biochemistry* 30:10117; Milenic et al. 1991. *Cancer Research* 51:6363; Takkinen et al. 1991. *Protein Engineering* 4:837).

In certain embodiments, a scFv molecule employed in a binding molecule of the invention is a stabilized scFv molecule. In one embodiment, the stabilized cFv molecule may comprise a scFv linker interposed between a $V_H$ domain and a $V_L$ domain, wherein the $V_H$ and $V_L$ domains are linked by a disulfide bond between an amino acid in the $V_H$ and an amino acid in the $V_L$ domain. In other embodiments, the stabilized scFv molecule may comprise a scFv linker having an optimized length or composition. In yet other embodiments, the stabilized scFv molecule may comprise a $V_H$ or $V_L$ domain having at least one stabilizing amino acid substitution(s). In yet another embodiment, a stabilized scFv molecule may have at least two of the above listed stabilizing features.

Stabilized scFv molecules may have improved protein stability or impart improved protein stability to the binding molecule to which it is operably linked. Preferred scFv linkers of the invention improve the thermal stability of a binding molecule of the invention by at least about 2° C. or 3° C. as compared to a conventional binding polypeptide. Comparisons can be made, for example, between the scFv molecules of the invention. In certain preferred embodiments, the stabilized scFv molecule comprises a $(Gly_4Ser)_4$ (SEQ ID NO: 20) scFv linker and a disulfide bond which links $V_H$ amino acid 44 and $V_L$ amino acid 100. Other exemplary stabilized scFv molecules which may be employed in the binding molecules of the invention are described in U.S. Provisional Patent Application No. 60/873,996, filed on Dec. 8, 2006 or U.S. patent application Ser. No. 11/725,970, filed on Mar. 19, 2007, each of which is incorporated herein by reference in its entirety.

In certain exemplary embodiments, the binding molecules of the invention comprise at least one scFv molecule that is operably linked (e.g., chemically conjugated or genetically-fused (e.g., directly fused or fused via a polypeptide linker) to the C-terminus and/or N-terminus of a constituent polypeptide chain of a heterodimeric Fc region. In one exemplary embodiment, a binding molecule of the invention comprises at least one scFv molecule (e.g, one or more stabilized scFv molecules) which are operably linked to the N-terminus (or C-terminus) of at least one constituent polypeptide chain of a heterodimeric Fc region via a hinge domain or portion thereof (e.g., an IgG1 hinge or portion thereof, e.g., a human IgG1 hinge). An exemplary hinge domain portion comprises the sequence DKTHTCPPCPAPELLGG (SEQ ID NO: 17).

In certain embodiments, a binding molecule of the invention comprises a tetravalent binding moiety or region formed by fusing two or more scFv molecules in series. For example, in one embodiment, scFv molecules are combined such that a first scFv molecule is operably linked at its N-terminus (e.g., via a polypeptide linker (e.g., a gly/ser polypeptide linker)) to at least one additional scFv molecule having the same or different binding specificity. Tandem arrays of scFv molecules are operably linked to the N-terminus and/or C-terminus of at least one constituent polypeptide chain of a heterodimeric Fc region to form a binding polypeptide of the invention.

In another embodiment, a binding molecule of the invention comprises a tetravalent binding moiety or region which is formed by operably linking a scFv molecule (e.g. via a polypeptide linker) to an antigen biding fragment (e.g., a Fab fragment). Said tetravalent binding moiety or region is operably linked to the N-terminus and/or C-terminus of at least one constituent polypeptide chain of a heterodimeric Fc region to form a binding polypeptide of the invention.

In another embodiment, a binding molecule of the invention comprises an antigen binding moiety or region which is a minibody or an antigen binding moiety derived therefrom. Minibodies are dimeric molecules made up of two polypeptide chains each comprising a scFv molecule which is fused to a CH3 moiety via a polypeptide linker. Minibodies can be made by linking a scFv component and polypeptide linker-CH3 component using methods described in the art (see, e.g., U.S. Pat. No. 5,837,821 or WO 94/09817A1). These components can be isolated from separate plasmids as restriction fragments and then ligated and recloned into an appropriate vector (e.g., an expression vector). Appropriate assembly (e.g., of the open reading frame (ORF) encoding the monomeric minibody polypeptide chain) can be verified by restriction digestion and DNA sequence analysis. In one embodiment, a binding molecule of the invention comprises the scFv component of a minibody which is operably linked to at least one constituent polypeptide of a heterodimeric Fc region. In another embodiment, a binding molecule of the invention comprises a tetravalent minibody as a binding moiety or region. Tetravalent minibodies can be constructed in the same manner as minibodies, except that two scFv molecules are linked using a polypeptide linker. The linked scFv-scFv construct is then operably linked to a constituent polypeptide chain of a heterodimeric Fc region to form a binding molecule of the invention.

In another embodiment, a binding molecule of the invention comprises an antigen binding moiety or region which is a diabody or an antigen binding moiety derived therefrom. Diabodies are dimeric, tetravalent molecules each having a polypeptide similar to scFv molecules, but usually having a short (e.g., less than 10 and preferably 1-5) amino acid residue linker connecting both variable domains, such that the $V_L$ and $V_H$ domains on the same polypeptide chain cannot interact. Instead, the $V_L$ and $V_H$ domain of one polypeptide chain interact with the $V_H$ and $V_L$ domain (respectively) on a second polypeptide chain (see, for example, WO 02/02781). In one embodiment, a binding molecule of the invention comprises a diabody which is operably linked to the N-terminus and/or C-terminus of at least one constituent polypeptide chain of a heterodimeric Fc region.

In one embodiment, antigen binding moieties employed in the binding molecules of the present invention may be immunoreactive with one or more tumor-associated antigens. For example, for treating a cancer or neoplasia an antigen binding domain of a binding molecule preferably binds to a selected tumor associated antigen. Given the number of reported antigens associated with neoplasias, and the number of related antibodies, those skilled in the art will appreciate that a binding molecule of the invention may comprise a variable region sequence or portion thereof derived from any one of a number of whole antibodies. More generally, such a variable region sequence may be obtained or derived from any antibody (including those previously reported in the literature) that reacts with an antigen or marker associated with the selected condition. Exemplary tumor-associated antigens bound by the binding molecules of the invention include for example, pan B antigens (e.g. CD20 found on the surface of both malignant and non-malignant B cells such as those in non-Hodgkin's lymphoma) and pan T cell antigens (e.g. CD2, CD3, CD5, CD6, CD7). Other exemplary tumor associated antigens comprise but are not limited to MAGE-1, MAGE-3, MUC-1, HPV 16, HPV E6 & E7, TAG-72, CEA, α-Lewis$^y$, L6-Antigen, CD19, CD22, CD25, CD30, CD33, CD37, CD44, CD52, CD56, mesothelin, PSMA, HLA-DR, EGF Receptor, VEGF, VEGF Receptor, Cripto antigen, and HER2 Receptor.

In other embodiments, the binding molecule of the invention may comprise variable region or CDR sequences from antibodies that have previously been reported to react with tumor-associated antigens. Exemplary antibodies capable of reacting with tumor-associated antigens include: 2B8, Lym 1, Lym 2, LL2, Her2, B1, BR96, MB1, BH3, B4, B72.3, 5E8, B3F6, 5E10, α-CD33, α-CanAg, α-CD56, α-CD44v6, α-Lewis, and α-CD30. More specifically, these exemplary antibodies include, but are not limited to 2B8 and C2B8 (Zevalin® and Rituxan®, Biogen Idec, Cambridge), Lym 1 and Lym 2 (Techniclone), LL2 (Immunomedics Corp., New Jersey), Trastuzumab (Herceptin®, Genentech Inc., South San Francisco), Tositumomab (Bexxar®, Coulter Pharm., San Francisco), Alemtuzumab (Campath®, Millennium Pharmaceuticals, Cambridge), Gemtuzumab ozogamicin (Mylotarg®, Wyeth-Ayerst, Philadelphia), Cetuximab (Erbitux®, Imclone Systems, New York), Bevacizumab (Avastin®, Genentech Inc., South San Francisco), BR96, BL22, LMB9, LMB2, MB1, BH3, B4, B72.3 (Cytogen Corp.), SS1 (NeoPharm), CC49 (National Cancer Institute), Cantuzumab mertansine (ImmunoGen, Cambridge), MNL 2704 (Milleneum Pharmaceuticals, Cambridge), Bivatuzumab mertansine (Boehringer Ingelheim, Germany), Trastuzumab-DM1 (Genentech, South San Francisco), My9-6-DM1 (ImmunoGen, Cabridge), SGN-10, -15, -25, and -35 (Seattle Genetics, Seattle), and 5E10 (University of Iowa). In preferred embodiments, the binding molecules of the present invention will bind to the same tumor-associated antigens as the antibodies enumerated immediately above. In particularly preferred embodiments, the molecules will be derived from or bind the same antigens as Y2B8, C2B8, CC49 and C5E10.

In a first preferred embodiment, the binding molecule will bind to the same tumor-associated antigen as Rituxan®. Rituxan® (also known as, rituximab, IDEC-C2B8 and C2B8) was the first FDA-approved monoclonal antibody for treatment of human B-cell lymphoma (see U.S. Pat. Nos. 5,843,439; 5,776,456 and 5,736,137 each of which is incorporated herein by reference). Y2B8 (90Y labeled 2B8; Zevalin®; ibritumomab tiuxetan) is the murine, parent antibody of C2B8. Rituxan® is a chimeric, anti-CD20 monoclonal antibody which is growth inhibitory and reportedly sensitizes certain lymphoma cell lines for apoptosis by chemotherapeutic agents in vitro. The antibody efficiently binds human complement, has strong FcR binding, and can effectively kill human lymphocytes in vitro via both complement dependent (CDC) and antibody-dependent (ADCC) mechanisms (Reff et al., *Blood* 83: 435-445 (1994)). Those skilled in the art will appreciate that binding molecules of the invention may comprise variable regions or CDRs of C2B8 or 2B8, in order to provide binding molecules that are even more effective in treating patients presenting with CD20+ malignancies.

In other preferred embodiments of the present invention, the binding molecule of the invention will bind to the same tumor-associated antigen as CC49. CC49 binds human tumor-associated antigen TAG-72 which is associated with the surface of certain tumor cells of human origin, specifically the LS 174T tumor cell line. LS 174T is a variant of the LS 180 colon adenocarcinoma line.

Binding molecules of the invention may comprise antigen binding moieties derived from numerous murine monoclonal antibodies that have been developed and which have binding specificity for TAG-72. One of these monoclonal antibodies, designated B72.3, is a murine IgG1 produced by hybridoma B72.3. B72.3 is a first generation monoclonal antibody developed using a human breast carcinoma extract as the immunogen (see Colcher et al., Proc. Natl. Acad. Sci. (USA), 78:3199-3203 (1981); and U.S. Pat. Nos. 4,522,918 and 4,612,282, each of which is incorporated herein by reference). Other monoclonal antibodies directed against TAG-72 are designated "CC" (for colon cancer). As described by Schlom et al. (U.S. Pat. No. 5,512,443 which is incorporated herein by reference) CC monoclonal antibodies are a family of second generation murine monoclonal antibodies that were prepared using TAG-72 purified with B72.3. Because of their relatively good binding affinities to TAG-72, the following CC antibodies are preferred: CC49, CC 83, CC46, CC92, CC30, CC11, and CC15. Schlom et al. have also produced variants of a humanized CC49 antibody as disclosed in PCT/US99/25552 and single chain Fv (scFv) constructs as disclosed in U.S. Pat. No. 5,892,019, each of which is also incorporated herein by reference. Those skilled in the art will appreciate that each of the foregoing antibodies, constructs or recombinants, and variations thereof, may be synthetic and used to provide binding moietiesfor the production of binding molecules in accordance with the present invention.

In addition to the anti-TAG-72 antibodies discussed above, various groups have also reported the construction and partial characterization of domain-deleted CC49 and B72.3 antibodies (e.g., Calvo et al. *Cancer Biotherapy*, 8(1):95-109 (1993), Slavin-Chiorini et al. *Int. J. Cancer* 53:97-103 (1993) and Slavin-Chiorini et al. *Cancer. Res.* 55:5957-5967 (1995). Accordingly, binding polypeptides may comprise antigen binding sites, variable region, or CDRs derived from these antibodies as well.

In one embodiment, a binding molecule of the invention comprises an antigen binding moiety that binds to the CD23 antigen (U.S. Pat. No. 6,011,138). In a preferred embodiment, a binding molecule of the invention binds to the same epitope as the 5E8 antibody. In another embodiment, a binding molecule of the invention comprises at least one CDR from an anti-CD23 antibody, e.g., the 5E8 antibody.

In one embodiment, a binding molecule of the invention binds to the CRIPTO-I antigen (WO02/088170A2 or WO03/083041A2). In a more preferred embodiment, a binding molecule of the invention binds to the same epitope as the B3F6 antibody. In still another embodiment, a binding molecule of the invention comprises at least one CDR or variable region from an anti-CRIPTO-I antibody, e.g., the B3F6 antibody.

In one embodiment, a binding molecule of the invention binds to one or more receptor tyrosine kinases (RTK). In one embodiment, the RTK is c-MET. In one embodiment, the RTK is RON. In a more preferred embodiment, a binding molecule of the invention binds to the same epitope as the 5D5 antibody (Jin et al., Cancer Research 68:4360-68 (2008) and Martens et al., Clin. Cancer Research 12:6144-52 (2006), both of which are hereby incorporated by reference in their entirety). In one embodiment, a binding molecule of the invention binds to the same epitope as the DN30 antibody (Petrelli, A. et al., PNAS 103:5090-5095 (2006), hereby incorporated by reference in its entirety). In one embodiment, a binding molecule of the invention binds to the same epitope as the IMC-41A10 antibody (O'Toole et al., Cancer Research 66:9162-9170 (2006), hereby incorporated by reference in its entirety). In still another embodiment, a binding molecule of the invention comprises at least one CDR or variable region from an anti-RTK antibody, e.g., the 5D5 antibody. In another embodiment, a binding molecule of the invention binds to antigen which is a member of the TNF superfamily of receptors ("TNFRs"). In another embodiment, the binding molecules of the invention bind at least one target that transduces a signal to a cell, e.g., by binding to a cell surface receptor, such as a TNF family receptor. By "transduces a signal" it is meant that by binding to the cell, the binding molecule converts the extracellular influence on the cell surface receptor into a cellular response, e.g., by modulating a signal transduction pathway. The term "TNF receptor" or "TNF receptor family member" refers to any receptor belonging to the Tumor Necrosis Factor ("TNF") superfamily of receptors. Members of the TNF Receptor Superfamily ("TNFRSF") are characterized by an extracellular region with two or more cysteine-rich domains (~40 amino acids each) arranged as cysteine knots (see Dempsey et al., *Cytokine Growth Factor Rev.* (2003). 14(3-4):193-209). Upon binding their cognate TNF ligands, TNF receptors transduce signals by interacting directly or indirectly with cytoplasmic adapter proteins known as TRAFs (TNF receptor associate factors). TRAFs can induce the activation of several kinase cascades that ultimately lead to the activation of signal transduction pathways such as NF-KappaB, JNK, ERK, p38 and PI3K, which in turn regulate cellular processes ranging from immune function and tissue differentiation to apoptosis. The nucleotide and amino acid sequences of several TNF receptors family members are known in the art and include at least 29 human genes: TNFRSF1A (TNFR1, also known as DR1, CD120a, TNF-R-I p55, TNF-R, TNFRI, TNFAR, TNF-R55, p55TNFR, p55R, or TNFR60, GenBank GI No. 4507575; see also U.S. Pat. No. 5,395,760)), TNFRSF1B (CD120b, also known as p'75, TNF-R, TNF-R-II, TNFR80, TNFR2, TNF-R75, TNFBR, or p75TNFR; GenBank GI No. 4507577), TNFRSF3 (Lymphotoxin Beta Receptor (LTI3R), also known as TNFR2-RP, CD18, TNFR-RP, TNFCR, or TNF-R-III; GI Nos. 4505038 and 20072212), TNFRSF4 (OX40, also known as ACT35, TXGP1L, or CD134 antigen; GI Nos. 4507579 and 8926702), TNFRSF5 (CD40, also known as p50 or Bp50; GI Nos. 4507581 and 23312371), TNFRSF6 (FAS, also known as FAS-R, DcR-2, DR2, CD95, APO-1, or APT1; GenBank GI Nos. 4507583, 23510421, 23510423, 23510425, 23510427, 23510429, 23510431, and 23510434)), TNFRSF6B (DcR3, DR3; GenBank GI Nos. 4507569, 23200021, 23200023, 23200025, 23200027, 23200029, 23200031, 23200033, 23200035, 23200037, and 23200039), TNFRSF7 (CD27, also known as Tp55 or S152; GenBank GI No. 4507587), TNFRSF8 (CD30, also known as Ki-1, or D1S166E; GenBank GI Nos. 4507589 and 23510437), TNFRSF9 (4-1-BB, also known as CD137 or ILA; GI Nos. 5730095 and 728738), TNFRSF10A (TRAIL-R1, also known as DR4 or Apo2; GenBank GI No. 21361086), TNFRSF10B (TRAIL-R2, also known as DR5, KILLER, TRICK2A, or TRICKB; GenBank GI Nos. 22547116 and 22547119), TNFRSF10C (TRAIL-R3, also known as DcR1, LIT, or TRID; GenBank GI No. 22547121), TNFRSF10D (TRAIL-R4, also known as DcR2 or TRUNDD), TNFRSF11A (RANK; GenBank GI No. 4507565; see U.S. Pat. Nos. 6,562,948; 6,537,763; 6,528,482; 6,479,635; 6,271,349; 6,017,729), TNFRSF11B (Osteoprotegerin (OPG), also known as OCIF or TR1; GI Nos. 38530116, 22547122 and 33878056), TNFRSF12 (Translocating chain-Association Membrane Protein (TRAMP), also known as DR3, WSL-1, LARD, WSL-LR, DDR3, TR3, APO-3, Fn14, or TWEAKR; GenBank GI No. 7706186; US Patent Application Publication No. 2004/0033225A1), TNFRSF12L (DR3L), TNFRSF13B (TACI; GI No. 6912694), TNFRSF13C (BAFFR; GI No. 16445027), TNFRSF14 (Herpes Virus Entry Mediator (HVEM), also known as ATAR, TR2, LIGHTR, or HVEA; GenBank GI Nos. 23200041, 12803895, and 3878821), TNFRSF16 (Low-Affinity Nerve Growth Factor Receptor (LNGFR), also known as Neurotrophin Receptor or p75(NTR); GenBank GI Nos. 128156 and 4505393), TNFRSF17 (BCM, also known as BCMA; GI No. 23238192), TNFRSF18 (AITR, also known as GITR; GenBank GI Nos. 4759246, 23238194 and 23238197), TNFRSF19 (Troy/Trade, also known as TAJ; GenBank GI Nos. 23238202 and 23238204), TNFRSF20 (RELT, also known as F1114993; GI Nos. 21361873 and 23238200), TNFRSF21 (DR6), TNFRSF22 (SOBa, also known as Tnfrh2 or 2810028K06Rik), and TNFRSF23 (mSOB, also known as Tnfrh1). Other TNF family members include EDAR1 (Ectodysplasin A Receptor, also known as Downless (DL), ED3, ED5, ED1R, EDA3, EDA1R, EDA-A1R; GenBank GI No. 11641231; U.S. Pat. No. 6,355,782), XEDAR (also known as EDA-A2R; GenBank GI No. 11140823); and CD39 (GI Nos. 2135580 and 765256). In another embodiment, a binding molecule of the invention binds to a TNF receptor family member lacking a death domain. In one embodiment, the TNF receptor lacking a death domain is involved in tissue differentiation. In a more specific embodiment, the TNF receptor involved in tissue differentiation is selected from the group consisting of LTβR, RANK, EDAR1, XEDAR, Fn14, Troy/Trade, and NGFR. In another embodiment, the TNF receptor lacking a death domain is involved in immune regulation. In a more specific embodiment, TNF receptor family member involved in immune regulation is selected from the group consisting of TNFR2, HVEM, CD27, CD30, CD40, 4-1BB, OX40, and GITR.

In another embodiment, a binding molecule of the invention binds to a TNF ligand belonging to the TNF ligand superfamily. TNF ligands bind to distinct receptors of the TNF receptor superfamily and exhibit 15-25% amino acid sequence homology with each other (Gaur et al., *Biochem. Pharmacol.* (2003), 66(8):1403-8). The nucleotide and amino acid sequences of several TNF Receptor (Ligand) Superfamily ("TNFSF") members are known in the art and include at least 16 human genes: TNFSF1 (also known as Lymphotoxin-α (LTA), TNFβ or LT, GI No.: 34444 and 6806893), TNFSF2 (also known as TNF, TNFα, or DIF; GI No. 25952111), TNFSF3 (also known as Lymphotoxin-β (LTB), TNFC, or p33), TNFSF4 (also known as OX-40L, gp34, CD134L, or tax-transcriptionally activated glycoprotein 1, 34 kD (TXGP1); GI No. 4507603), TNFSF5 (also known as CD40LG, IMD3, HIGM1, CD40L, hCD40L, TRAP, CD154, or gp39; GI No. 4557433), TNFSF6 (also known as FasL or APT1LG1; GenBank GI No. 4557329), TNFSF7 (also known as CD70, CD27L, or CD27LG; GI No. 4507605), TNFSF8 (also known as CD30LG, CD30L, or CD153; GI No. 4507607), TNFSF9 (also known as 4-1BB-L or ILA ligand; GI No. 4507609), TNFSF10 (also known as TRAIL, Apo-2L, or TL2; GI No. 4507593), TNFSF11 (also known as TRANCE, RANKL, OPGL, or ODF; GI Nos. 4507595 and 14790152), TNFSF12 (also known as Fn14L, TWEAK, DR3LG, or APO3L; GI Nos. 4507597 and 23510441), TNFSF13 (also known as APRIL), TNFSF14 (also known as LIGHT, LTg, or HVEM-L; GI Nos. 25952144 and 25952147), TNFSF15 (also known as TL1 or VEGI), or TNFSF16 (also known as AITRL, TL6, hGITRL, or GITRL; GI No. 4827034). Other TNF ligand family members include EDAR1 & XEDAR ligand (ED1; GI No. 4503449; Monreal et al. (1998) *Am J Hum Genet.* 63:380), Troy/Trade ligand, BAFF (also known as TALL1; GI No. 5730097), and NGF ligands (e.g. NGF-β (GI No. 4505391), NGF-2/NTF3; GI No. 4505469), NTF5 (GI No. 5453808)), BDNF (GI Nos. 25306267, 25306235, 25306253, 25306257, 25306261, 25306264; IFRD1 (GI No. 4504607)).

In a more preferred embodiment, a binding molecule of the invention binds to the same epitope as an anti-LTβR antibody (e.g. a BHA10 or a CBE11 antibody) set forth in WO 02/30986, which is incorporated herein by reference. In still another embodiment, a binding molecule of the invention comprises at least one CDR from an anti-LTβR antibody, e.g., the CBE11 antibody.

In another preferred embodiment, a binding molecule of the invention binds to the same epitope as an anti-TRAIL-R2 antibody (e.g. a 14A2 antibody). In still another embodiment, a binding molecule of the invention comprises at least one CDR from an anti-TRAIL-R2 antibody, e.g., the 14A2 antibody.

Still other embodiments of the present invention comprise binding molecules that are derived from or bind to the same tumor associated antigen as C5E10. As set forth in co-pending application Ser. No. 09/104,717, C5E10 is an antibody that recognizes a glycoprotein determinant of approximately 115 kDa that appears to be specific to prostate tumor cell lines (e.g. DU145, PC3, or ND1). Thus, in conjunction with the present invention, molecules that specifically bind to the same tumor-associated antigen recognized by C5E10 antibodies could be used alone or conjugated with an effector moiety by the methods of the invention, thereby providing a modified molecule that is useful for the improved treatment of neoplastic disorders. In particularly preferred embodiments, a constituent polypeptide chain will be derived or comprise all or part of the antigen binding region of the C5E10 antibody as secreted from the hybridoma cell line having ATCC accession No. PTA-865. The constituent polypeptide chain or the resulting binding molecule could then be conjugated to a therapeutic effector moiety as described below and administered to a patient suffering from prostate cancer in accordance with the methods herein.

In still other embodiments, a binding molecule of the invention binds to a molecule which is useful in treating an autoimmune or inflammatory disease or disorder. For example, a binding molecule may bind to an antigen present on an immune cell (e.g., a B or T cell) or an autoantigen responsible for an autoimmune disease or disorder. As used herein, the term "autoimmune disease or disorder" refers to disorders or conditions in a subject wherein the immune system attacks the body's own cells, causing tissue destruction. Autoimmune diseases include general autoimmune diseases, i.e., in which the autoimmune reaction takes place simultaneously in a number of tissues, or organ specific autoimmune diseases, i.e., in which the autoimmune reaction targets a single organ. Examples of autoimmune diseases that can be diagnosed, prevented or treated by the methods and compositions of the present invention include, but are not limited to, Crohn's disease; Inflammatory bowel disease (IBD); systemic lupus erythematosus; ulcerative colitis; rheumatoid arthritis; Goodpasture's syndrome; Grave's disease; Hashimoto's thyroiditis; *pemphigus vulgaris*; myasthenia gravis; scleroderma; autoimmune hemolytic anemia; autoimmune thrombocytopenic purpura; polymyositis and dermatomyositis; pernicious anemia; Sjögren's syndrome; ankylosing spondylitis; vasculitis; type I diabetes mellitus; neurological disorders, multiple sclerosis, and secondary diseases caused as a result of autoimmune diseases.

In other embodiments, the binding molecules of the invention bind to a target molecule associated with an inflammatory disease or disorder. As used herein the term "inflammatory disease or disorder" includes diseases or disorders which are caused, at least in part, or exacerbated by inflammation, e.g., increased blood flow, edema, activation of immune cells (e.g., proliferation, cytokine production, or enhanced phagocytosis). For example, a binding molecule of the invention may bind to an inflammatory factor (e.g., a matrix metalloproteinase (MMP), TNFα, an interleukin, a plasma protein, a cytokine, a lipid metabolite, a protease, a toxic radical, a mitochondrial protein, an apoptotic protein, an adhesion molecule, etc.) involved or present in an area in aberrant amounts, e.g., in amounts which may be advantageous to alter, e.g., to benefit the subject. The inflammatory process is the response of living tissue to damage. The cause of inflammation may be due to physical damage, chemical substances, microorganisms, tissue necrosis, cancer or other agents. Acute inflammation is short-lasting, e.g., lasting only a few days. If it is longer lasting however, then it may be referred to as chronic inflammation.

Inflammatory disorders include acute inflammatory disorders, chronic inflammatory disorders, and recurrent inflammatory disorders. Acute inflammatory disorders are generally of relatively short duration, and last for from about a few minutes to about one to two days, although they may last several weeks. The main characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or even longer, and are associated histologically with the presence of lymphocytes and macrophages and with proliferation of blood vessels and connective tissue. Recurrent inflammatory disorders include disorders which recur after a period of time or which have periodic episodes. Examples of recurrent inflammatory disorders include asthma and multiple sclerosis. Some disorders may fall within one or more categories. Inflammatory disorders are generally characterized by heat, redness, swelling, pain and loss of function. Examples of causes of inflammatory disorders include, but are not limited to, microbial infections (e.g., bacterial, viral and fungal infections), physical agents (e.g., burns, radiation, and trauma), chemical agents (e.g., toxins and caustic substances), tissue necrosis and various types of immunologic reactions. Examples of inflammatory disorders include, but are not limited to, osteoarthritis, rheumatoid arthritis, acute and chronic infections (bacterial, viral and fungal); acute and chronic bronchitis, sinusitis, and other respiratory infections, including the common cold; acute and chronic gastroenteritis and colitis; acute and chronic cystitis and urethritis; acute respiratory distress syndrome; cystic fibrosis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; and burns (thermal, chemical, and electrical).

In one preferred embodiment, a binding molecule of the invention binds to the same epitope as an anti-CD40L antibody (e.g., a 5C8 antibody). In still another embodiment, a molecule of the invention comprises at least one antigen binding site, one or more CDRs, or one or more variable regions (VH or VL) from an anti-CD40L antibody (e.g. a 5C8 antibody). CD40L (CD154, gp39), a transmembrane protein, is expressed on activated $CD4^+$ T cells, mast cells, basophils, eosinophils, natural killer (NK) cells, and activated platelets. CD40L is important for T-cell-dependent B-cell responses. A prominent function of CD40L, isotype switching, is demonstrated by the hyper-immunoglobulin M (IgM) syndrome in which CD40L is congenitally deficient. The interaction of CD40L-CD40 (on antigen-presenting cells such as dendritic cells) is essential for T-cell priming and the T-cell-dependent humoral immune response. Therefore, interruption of the CD40-CD40L interaction with an anti-CD40L monoclonal antibody (mAb) has been considered to be a possible therapeutic strategy in human autoimmune disease, based upon the above information and on studies in animals. Exemplary anti-CD40L antibodies from which the binding molecules of the invention may be derived include the mouse antibody 5C8, disclosed in U.S. Pat. No. 5,474,771, which is incorporated by reference herein, as well as humanized versions thereof, e.g., the IgG1 Hu5C8 antibody disclosed in the Examples. Other anti-CD40L antibodies are known in the art (see e.g., U.S. Pat. No. 5,961,974 and International Publication No. WO 96/23071).

ii. Binding Portions of Receptors and Ligands

In other aspects, the binding molecules of the invention comprise a ligand binding moiety of a receptor and/or a receptor binding portion of a ligand which is operably linked to at least one constituent polypeptide chain of a heterodimeric Fc region.

In certain embodiments, the binding molecule is a fusion of a ligand binding portion of a receptor and/or a receptor binding portion of a ligand with a constituent polypeptide chain of a heterodimeric Fc region. Any transmembrane regions or lipid or phospholipid anchor recognition sequences of the ligand binding receptor can be inactivated or deleted prior to fusion. DNA encoding the ligand or ligand binding partner is cleaved by a restriction enzyme at or proximal to the 5' and 3'ends of the DNA encoding the desired ORF segment. The resultant DNA fragment is then readily inserted (e.g., ligated in-frame) into DNA encoding a constituent polypeptide chain of a heterodimeric Fc region. The precise site at which the fusion is made may be selected empirically to optimize the dimerization and/or secretion characteristics of the constituent polypeptide chain, or binding characteristics of the resultant binding molecule of the invention. DNA encoding the constituent polypeptide chain is then subcloned into an appropriate expression vector than can be transfected into a host cell for expression.

In one embodiment, a binding molecule of the invention combines the binding site(s) of the ligand or receptor (e.g. the extracellular domain (ECD) of a receptor) with at least one constituent polypeptide chain of a heterodimeric Fc region. In one embodiment, the binding domain of the ligand or receptor domain will be operably linked (e.g. fused via a polypeptide linker) to the C-terminus of a constituent polypeptide chain of a heterodimeric Fc region. N-terminal fusions are also possible. In exemplary embodiments, fusions are made to the C-terminus of the constituent polypeptide chain of a heterodimeric Fc region, or immediately N-terminal to the hinge domain of a constituent polypeptide chain of a heterodimeric Fc region.

In certain embodiments, the binding moiety or domain of the ligand-binding portion of a receptor may be derived from a receptor bound by an antibody or antibody variant described supra. In other embodiments, the ligand binding portion of a receptor is derived from a receptor selected from the group consisting of a receptor of the Immunoglobulin (Ig) superfamily, a receptor of the TNF receptor superfamily described supra, a receptor of the G-protein coupled receptor (GPCR) superfamily, a receptor of the Tyrosine Kinase (TK) receptor superfamily, a receptor of the Ligand-Gated (LG) superfamily, a receptor of the chemokine receptor superfamily, IL-1/Toll-like Receptor (TLR) superfamily, and a cytokine receptor superfamily.

In other embodiments, the binding moiety or domain of the receptor-binding portion of a ligand may be derived from a ligand bound by an antibody or antibody variant described supra. For example, the ligand may bind a receptor selected from the group consisting of a receptor of the Immunoglobulin (Ig) superfamily, a receptor of the TNF receptor superfamily, a receptor of the G-protein coupled receptor (GPCR) superfamily, a receptor of the Tyrosine Kinase (TK) receptor superfamily, a receptor of the Ligand-Gated (LG) superfamily, a receptor of the chemokine receptor superfamily, IL-1/Toll-like Receptor (TLR) superfamily, and a cytokine receptor superfamily. In one exemplary embodiment, the binding moiety of the receptor-binding portion of a ligand is derived from a ligand belonging to the TNF ligand superfamily described supra (e.g., CD40L).

In other exemplary embodiments, a binding molecule of the invention may comprise one or more ligand binding domains or receptor binding domains derived from one of the following proteins:

a. Cytokines and Cytokine Receptors

Cytokines have pleiotropic effects on the proliferation, differentiation, and functional activation of lymphocytes. Various cytokines, or receptor binding portions thereof, can be utilized in the binding molecules of the invention. Exemplary cytokines include the interleukins (e.g. IL-1, IL-2, IL-3, IL-4, IL-5, IL-6, IL-7, IL-8, IL-10, IL-11, IL-12, IL-13, and IL-18), the colony stimulating factors (CSFs) (e.g. granulocyte CSF (G-CSF), granulocyte-macrophage CSF (GM-CSF), and monocyte macrophage CSF (M-CSF)), tumor necrosis factor (TNF) alpha and beta, cytotoxic T lymphocyte antigen 4 (CTLA-4), and interferons such as interferon-$\alpha$, $\beta$, or $\gamma$ (U.S. Pat. Nos. 4,925,793 and 4,929,554).

Cytokine receptors typically consist of a ligand-specific alpha chain and a common beta chain. Exemplary cytokine receptors include those for GM-CSF, IL-3 (U.S. Pat. No. 5,639,605), IL-4 (U.S. Pat. No. 5,599,905), IL-5 (U.S. Pat. No. 5,453,491), IL10 receptor, IFN$\gamma$ (EP0240975), and the TNF family of receptors (e.g., TNF$\alpha$ (e.g. TNFR-1 (EP 417,563), TNFR-2 (EP 417,014) lymphotoxin beta receptor).

b. Adhesion Proteins

Adhesion molecules are membrane-bound proteins that allow cells to interact with one another. Various adhesion proteins, including leukocyte homing receptors and cellular adhesion molecules, or receptor binding portions thereof, can be incorporated in a binding molecule of the invention. Leucocyte homing receptors are expressed on leucocyte cell surfaces during inflammation and include the $\beta$-1 integrins (e.g. VLA-1, 2, 3, 4, 5, and 6) which mediate binding to extracellular matrix components, and the β2-integrins (e.g. LFA-1, LPAM-1, CR3, and CR4) which bind cellular adhesion molecules (CAMs) on vascular endothelium. Exemplary CAMs include ICAM-1, ICAM-2, VCAM-1, and MAdCAM-1. Other CAMs include those of the selectin family including E-selectin, L-selectin, and P-selectin.

c. Chemokines

Chemokines, chemotactic proteins which stimulate the migration of leucocytes towards a site of infection, can also be incorporated into a binding molecule of the invention. Exemplary chemokines include Macrophage inflammatory proteins (MIP-1-α and MIP-1-β), neutrophil chemotactic factor, and RANTES (regulated on activation normally T-cell expressed and secreted).

d. Growth Factors and Growth Factor Receptors

Growth factors or their receptors (or receptor binding or ligand binding portions thereof) may be incorporated in the binding molecules of the invention. Exemplary growth factors include Vascular Endothelial Growth Factor (VEGF) and its isoforms (U.S. Pat. No. 5,194,596); Fibroblastic Growth Factors (FGF), including αFGF and bFGF; atrial natriuretic factor (ANF); hepatic growth factors (HGFs; U.S. Pat. Nos. 5,227,158 and 6,099,841), neurotrophic factors such as bone-derived neurotrophic factor (BDNF), neurotrophin-3, -4, -5, or -6 (NT-3, NT-4, NT-5, or NT-6), or a nerve growth factor such as NGF-β platelet-derived growth factor (PDGF) (U.S. Pat. Nos. 4,889,919, 4,845,075, 5,910,574, and 5,877,016); transforming growth factors (TGF) such as TGF-alpha and TGF-beta (WO 90/14359), osteoinductive factors including bone morphogenetic protein (BMP); insulin-like growth factors-I and -II (IGF-I and IGF-II; U.S. Pat. Nos. 6,403,764 and 6,506,874); Erythropoietin (EPO); Thrombopoeitin (TPO; stem-cell factor (SCF), thrombopoietin (TPO, c-Mpl ligand), and the Wnt polypeptides (U.S. Pat. No. 6,159,462).

Exemplary growth factor receptors which may be used as targeting receptor domains of the invention include EGF receptors; VEGF receptors (e.g. Flt1 or Flk1/KDR), PDGF receptors (WO 90/14425); HGF receptors (U.S. Pat. Nos. 5,648,273, and 5,686,292), and neurotrophic receptors including the low affinity receptor (LNGFR), also termed as p75$^{NTR}$ or p75, which binds NGF, BDNF, and NT-3, and high affinity receptors that are members of the trk family of the receptor tyrosine kinases (e.g. trkA, trkB (EP 455,460), trkC (EP 522,530)).

e. Hormones

Exemplary growth hormones for use as targeting agents in the binding molecules of the invention include renin, human growth hormone (HGH; U.S. Pat. No. 5,834,598), N-methionyl human growth hormone; bovine growth hormone; growth hormone releasing factor; parathyroid hormone (PTH); thyroid stimulating hormone (TSH); thyroxine; pro-insulin and insulin (U.S. Pat. Nos. 5,157,021 and 6,576,608); follicle stimulating hormone (FSH); calcitonin, luteinizing hormone (LH), leptin, glucagons; bombesin; somatropin; mullerian-inhibiting substance; relaxin and pro-relaxin; gonadotropin-associated peptide; prolactin; placental lactogen; OB protein; or mullerian-inhibiting substance.

f. Clotting Factors

Exemplary blood coagulation factors for use as targeting agents in the binding molecules of the invention include the clotting factors (e.g., factors V, VII, VIII, IX, X, XI, XII and XIII, von Willebrand factor); tissue factor (U.S. Pat. Nos. 5,346,991, 5,349,991, 5,726,147, and 6,596,84); thrombin and prothrombin; fibrin and fibrinogen; plasmin and plasminogen; plasminogen activators, such as urokinase or human urine or tissue-type plasminogen activator (t-PA).

III. Multispecific Binding Polypeptides

In certain particular aspects, a binding molecule of the invention is multispecific, i.e., has at least one binding moiety that binds to a first molecule or epitope of a molecule and at least one second binding moiety that binds to a second molecule or to a second epitope of the first molecule.

In one embodiment, a binding molecule of the invention is bispecific. Bispecific binding molecules can bind to two different target sites, e.g., on the same target molecule or on different target molecules. For example, in the case of the binding molecules of the invention, a bispecific variant thereof can bind to two different epitopes, e.g., on the same antigen or on two different antigens. Bispecific binding molecules can be used, e.g., in diagnostic and therapeutic applications. For example, they can be used to immobilize enzymes for use in immunoassays. They can also be used in diagnosis and treatment of cancer, e.g., by binding both to a tumor associated molecule and a detectable marker (e.g., a chelator which tightly binds a radionuclide). Bispecific binding molecules can also be used for human therapy, e.g., by directing cytotoxicity to a specific target (for example by binding to a pathogen or tumor cell and to a cytotoxic trigger molecule, such as the T cell receptor or the Fcγ receptor). Bispecific binding molecules can also be used, e.g., as fibrinolytic agents or vaccine adjuvants.

Examples of bispecific binding molecules include those with at least two binding moieties directed against different tumor cell antigens; bispecific binding molecules with at least one binding moiety directed against a tumor cell antigen and at least one binding moiety directed against a cytotoxic trigger molecule (such as anti-Fc.gamma.RI/anti-CD15, anti-p185.sup.HER2/Fc.gamma.RIII (CD16), anti-CD3/anti-malignant B-cell (1D10), anti-CD3/anti-p185.sup.HER2, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3); bispecific binding molecules with at least one binding moiety which binds specifically to a tumor antigen and at least one binding moiety which binds to a toxin (such as anti-saporin/anti-Id-1, anti-CD22/anti-saporin, anti-CD7/anti-saporin, anti-CD38/anti-saporin, anti-CEA/anti-ricin A chain, anti-interferon-.alpha.(IFN-.alpha.)/anti-hybridoma idiotype, anti-CEA/anti-vinca alkaloid); bispecific binding molecules for converting enzyme activated prodrugs (such as anti-CD30/anti-alkaline phosphatase (which catalyzes conversion of mitomycin phosphate prodrug to mitomycin alcohol)); bispecific binding molecules which can be used as fibrinolytic agents (such as anti-fibrin/anti-tissue plasminogen activator (tPA), anti-fibrin/anti-urokinase-type plasminogen activator (uPA)); bispecific binding molecules for targeting immune complexes to cell surface receptors (such as anti-low density lipoprotein (LDL)/anti-Fc receptor (e.g. Fc.gamma.RI, Fc.gamma.RII or Fc.gamma.RIII)); bispecific binding molecules for use in therapy of infectious diseases (such as anti-CD3/anti-herpes simplex virus (HSV), anti-T-cell receptor:CD3 complex/anti-influenza, anti-Fc.gamma.R/anti-HIV; bispecific binding molecules for tumor detection in vitro or in vivo such as anti-CEA/anti-EO- TUBE, anti-CEA/anti-DPTA, anti-p185HER2/anti-hapten); bispecific binding molecules as vaccine adjuvants (see Fanger et al., supra); and bispecific binding molecules as diagnostic tools (such as anti-rabbit IgG/anti-ferritin, anti-horse radish peroxidase (HRP)/anti-hormone, anti-somatostatin/anti-substance P, anti-HRP/anti-FITC, anti-CEA/anti-.beta.-galactosidase (see Nolan et al., supra)). Examples of trispecific molecules include anti-CD3/anti-CD4/anti-CD37, anti-CD3/anti-CD5/anti-CD37 and anti-CD3/anti-CD8/anti-CD37.

In an exemplary embodiment, a bispecific binding molecule of the invention has one binding moiety which binds to CRIPTO-I. In another preferred embodiment, a bispecific binding molecule of the invention has one binding moiety which binds to LTβR. In another preferred embodiment, a bispecific binding molecule of the invention has one binding moiety which binds to TRAIL-R2. In another preferred embodiment, a bispecific binding molecule of the invention has one binding moiety which binds to LTβR and one binding moiety which binds to TRAIL-R2.

Multispecific binding molecules of the invention may be monovalent for each specificity or be multivalent for each specificity. For example, binding molecules of the invention may comprise one binding moiety that reacts with a first target molecule and one binding moiety that reacts with a second target molecule or it may comprise two binding moieties that react with a first target molecule and two binding moieties that react with a second target molecule.

Binding molecules of the invention may have at least two binding specificities from two or more binding domains of a ligand or receptor). They can be assembled as heterodimers, heterotrimers or heterotetramers, essentially as disclosed in WO 89/02922 (published Apr. 6, 1989), in EP 314,317 (published May 3, 1989), and in U.S. Pat. No. 5,116,964 issued May 2, 1992. Examples include CD4-IgG/TNF receptor-IgG and CD4-IgG/L-selectin-IgG. The last mentioned molecule combines the lymph node binding function of the lymphocyte homing receptor (LHR, L-selectin), and the HIV binding function of CD4, and finds potential application in the prevention or treatment of HIV infection, related conditions, or as a diagnostic.

IV. Preparation of Binding Molecules

Having designed a binding molecule, a variety of methods are available for producing it. Because of the degeneracy of the code, a variety of nucleic acid sequences will encode the amino acid sequence of the constituent polypeptide chains of the binding molecule. The desired polynucleotide can be produced by de novo solid-phase DNA synthesis or by PCR mutagenesis or other means known in the art of modifying an earlier prepared polynucleotide.

Oligonucleotide-mediated mutagenesis is one method for preparing a substitution, in-frame insertion, or alteration (e.g., altered codon) to introduce a codon encoding an amino acid substitution (e.g., an Fc variant). For example, the starting polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer. In one embodiment, genetic engineering, e.g., primer-based PCR mutagenesis, is sufficient to incorporate an alteration, as defined herein, for producing a polynucleotide encoding a constituent polypeptide of the invention.

Polynucleotide sequence encoding the constituent polypeptide chain can then be inserted in a suitable expression vector and transfected into prokaryotic or eukaryotic host cells such as E. coli cells, simian COS cells, Chinese Hamster Ovary (CHO) cells or myeloma cells that do not otherwise produce said proteins, for recombinant expression.

In preferred embodiments, polynucleotides sequences for two non-identical constituent polypeptide chains are transfected into host cells in a single transfection procedure (i.e., a mixture of polynucleotides is transfected into host cells). Host cells that express both constituent polypeptide chains, which dimerize during post-translational processing, can produce and secrete binding molecules of the invention.

For the purposes of this invention, numerous expression vector systems may be employed. These expression vectors are typically replicable in the host organisms either as episomes or as an integral part of the host chromosomal DNA. Expression vectors may include expression control sequences including, but not limited to, promoters (e.g., naturally-associated or heterologous promoters), enhancers, signal sequences, splice signals, enhancer elements, and transcription termination sequences. Preferably, the expression control sequences are eukaryotic promoter systems in vectors capable of transforming or transfecting eukaryotic host cells. Expression vectors may also utilize DNA elements which are derived from animal viruses such as bovine papilloma virus, polyoma virus, adenovirus, vaccinia virus, baculovirus, retroviruses (RSV, MMTV or MOMLV), cytomegalovirus (CMV), or SV40 virus. Others involve the use of polycistronic systems with internal ribosome binding sites.

Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362). Cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation.

A preferred expression vector is NEOSPLA (U.S. Pat. No. 6,159,730, hereby incorporated by reference in its entirety). This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in CHO cells, followed by selection in G418 containing medium and methotrexate amplification. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777, hereby incorporated by reference in its entirety.

Where the binding molecule of the invention comprises the antigen binding moiety of an antibody, polynucleotides encoding additional light and heavy chain variable regions, optionally linked to a constituent polypeptide chain of a heterodimeric Fc region, may be inserted into the same or different expression vector. The DNA segments encoding immunoglobulin chains are operably linked to control sequences in the expression vector(s) that ensure the expression of immunoglobulin polypeptides.

In other preferred embodiments the binding molecules of the invention of the instant invention may be expressed using polycistronic constructs. In these expression systems, multiple gene products of interest, such as multiple constituent polypeptide chains of a binding protein of the invention, may be produced from a single polycistronic construct. These systems advantageously use an internal ribosome entry site (IRES) to provide relatively high levels of constituent polypeptide chains of the invention in eukaryotic host cells. Compatible IRES sequences are disclosed in U.S. Pat. No. 6,193,980 which is also incorporated herein by reference. Those skilled in the art will appreciate that such expression systems may be used to effectively produce the full range of constituent polypeptide chains disclosed in the instant application.

More generally, once the vectors or DNA sequences encoding constituent polypeptide chains have been prepared, the expression vectors may be introduced into an appropriate host cell. That is, the host cells may be transformed. Introduction of plasmids into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the constituent polypeptide chains, and assayed for binding molecule synthesis and secretion. Exemplary assay techniques include enzyme-linked immunosorbent assay (ELISA), radioimmunoassay (RIA), or fluorescence-activated cell sorter analysis (FACS), immunohistochemistry and the like.

As used herein, the term "transformation" shall be used in a broad sense to refer to the introduction of DNA into a recipient host cell that changes the genotype and consequently results in a change in the recipient cell.

Along those same lines, "host cells" refers to cells that have been transformed with vectors constructed using recombinant DNA techniques and encoding at least one heterologous gene. In descriptions of processes for isolation of binding molecules from recombinant hosts, the terms "cell" and "cell culture" are used interchangeably to denote the source of binding molecules unless it is clearly specified otherwise. In other words, recovery of molecules from the "cells" may mean either from spun down whole cells, or from the cell culture containing both the medium and the suspended cells.

The host cell line used for protein expression is most preferably of mammalian origin; those skilled in the art are credited with ability to preferentially determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/0 (mouse myeloma), P3.times.63-Ag3.653 (mouse myeloma), BFA-1c1BPT (bovine endothelial cells), RAJI (human lymphocyte) and 293 (human kidney). CHO cells are particularly preferred. Host cell lines are typically available from commercial services, the American Tissue Culture Collection or from published literature.

Genes encoding the constituent polypeptide chains of the invention can also be expressed in non-mammalian cells such as bacteria or yeast or plant cells. In this regard it will be appreciated that various unicellular non-mammalian microorganisms such as bacteria can also be transformed; i.e., those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis*; *Pneumococcus*; *Streptococcus*, and *Haemophilus influenzae*. It will further be appreciated that, when expressed in bacteria, the constituent polypeptide chains typically become part of inclusion bodies. The polypeptide chains or binding proteins must be isolated and purified and may need to be assembled into functional molecules.

In addition to prokaryates, eukaryotic microbes may also be used. *Saccharomyces cerevisiae*, or common baker's yeast, is the most commonly used among eukaryotic microorganisms although a number of other strains are commonly available. For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trp1 lesion as a characteristic of the yeast host cell genome then provides an effective environment for detecting transformation by growth in the absence of tryptophan. Other yeast hosts such *Pichia* may also be employed. Yeast expression vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for methanol, maltose, and galactose utilization.

Alternatively, constituent polypeptide chain-encoding nucleotide sequences can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for constituent polypeptide chains in operable linkage with a promoter and enhancer from a mammary gland specific gene, such as casein or beta lactoglobulin.

In vitro production allows scale-up to give large amounts of the desired binding molecules. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of binding molecules can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein. An affinity tag sequence (e.g. a His(6) tag) may optionally be attached or included within one or more constituent polypeptide chain sequences to facilitate downstream purification.

Heterodimeric binding proteins of the invention, comprising two or more non-identical constituent polypeptide chains, can be expressed using a single vector or two vectors. When the constituent polypeptide chains are cloned on separate expression vectors, the vectors are co-transfected to obtain expression and assembly of intact whole heterodimeric molecules. Once expressed, heterodimeric binding molecules can be purified according to standard procedures of the art, including ammonium sulfate precipitation, affinity column chromatography, HPLC purification, gel electrophoresis and the like (see generally Scopes, Protein Purification (Springer-Verlag, N.Y., (1982)). Substantially pure binding molecules of at least about 90 to 95% homogeneity are preferred, and 98 to 99% or more homogeneity most preferred, for pharmaceutical uses.

V. Purification of Binding Molecules

In one embodiment, the invention pertains to a method of purification of binding molecules of the invention which are expressed as double-chain (i.e., heterodimeric, comprising two non-identical polypeptide chains) binding molecules comprising heterodimeric Fc regions away from single-chain (i.e., monomeric, unmultimerized) constituent polypeptide chains. In other embodiments, the invention provides methods of purifying double-chain heterodimeric Fc binding molecules away from binding molecules comprising multimer combinations of constituent polypeptides greater than two.

In one embodiment, a population comprising both single-chain constituent polypeptide chains and heterodimeric binding molecules may be purified by size-exclusion chromatography. For example, single-chain constituent polypeptide chains may be separated from aggregates and heterodimeric binding molecules, e.g., using a Superdex 200 gel filtration column. Gel filtration fractions may be analyzed, e.g., by reducing and non-reducing SDS-PAGE and appropriate fractions combined to obtain homogeneous pools of the single-chain constituent polypeptide chains and/or heterodimeric binding molecule populations, as desired. These pools may be further characterized to determine homogeneity and molecular mass of the molecules, e.g., by analytical SEC (TSK-Gel G3000 SW$_{XL}$ column) with on-line light scattering analysis. The invention also pertains to purified populations of binding molecules comprising heterodimeric Fc regions comprising genetically-fused Fc and Fab constant domain moieties (i.e., heterodimeric Fc binding molecules) as well as purified populations of single-chain constituent polypeptides comprising genetically fused Fc and Fab constant domain moieties (i.e., monomeric polypeptides capable of forming heterodimers).

VI. Labeling or Conjugation of Binding Molecules

The binding molecules of the present invention may be used in non-conjugated form or may be conjugated to at least one of a variety of functional moieties, e.g., to facilitate target detection or for imaging or therapy of the patient. The constituent polypeptide chains or binding molecules of the invention can be labeled or conjugated either before or after purification, when purification is performed. In particular, the constituent polypeptide chains or binding molecules of the present invention may be conjugated (e.g., via an engineered cysteine residue) to a functional moiety. Functional moieties are preferably attached to a portion of the binding molecules other than a binding moiety (e.g., a polypeptide linker or an Fc moiety of a heterodimeric Fc region).

Exemplary functional moieties include affinity moieties, and effector moieties. Exemplary effector moieties include cytotoxins (such as radioisotopes, cytotoxic drugs, or toxins) therapeutic agents, cytostatic agents, biological toxins, pro-drugs, peptides, proteins, enzymes, viruses, lipids, biological response modifiers, pharmaceutical agents, immunologically active ligands (e.g., lymphokines or other antibodies wherein the resulting molecule binds to both the neoplastic cell and an effector cell such as a T cell), PEG, or detectable molecules useful in imaging. In another embodiment, a binding molecule of the invention can be conjugated to a molecule that decreases vascularization of tumors. In other embodiments, the disclosed compositions may comprise binding molecules of the invention coupled to drugs or prodrugs. Still other embodiments of the present invention comprise the use of binding molecules of the invention conjugated to specific biotoxins or their cytotoxic fragments such as ricin, gelonin, *Pseudomonas* exotoxin or diphtheria toxin. The selection of which conjugated or unconjugated binding molecule to use will depend on the type and stage of cancer, use of adjunct treatment (e.g., chemotherapy or external radiation) and patient condition. It will be appreciated that one skilled in the art could readily make such a selection in view of the teachings herein.

It will be appreciated that, in previous studies, anti-tumor antibodies labeled with isotopes have been used successfully to destroy cells in solid tumors as well as lymphomas/leukemias in animal models, and in some cases in humans. Exemplary radioisotopes include: $^{90}$Y, $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re and $^{188}$Re. The radionuclides act by producing ionizing radiation which causes multiple strand breaks in nuclear DNA, leading to cell death. The isotopes used to produce therapeutic conjugates typically produce high energy α- or β-particles which have a short path length. Such radionuclides kill cells to which they are in close proximity, for example neoplastic cells to which the conjugate has attached or has entered. They have little or no effect on non-localized cells. Radionuclides are essentially non-immunogenic.

With respect to the use of radiolabeled conjugates in conjunction with the present invention, binding molecules of the invention may be directly labeled (such as through iodination) or may be labeled indirectly through the use of a chelating agent. As used herein, the phrases "indirect labeling" and "indirect labeling approach" both mean that a chelating agent is covalently attached to a binding molecule and at least one radionuclide is associated with the chelating agent. Such chelating agents are typically referred to as bifunctional chelating agents as they bind both the molecule and the radioisotope. Particularly preferred chelating agents comprise 1-isothiocycmatobenzyl-3-methyldiothelene triaminepentaacetic acid ("MX-DTPA") and cyclohexyl diethylenetriamine pentaacetic acid ("CHX-DTPA") derivatives. Other chelating agents comprise P-DOTA and EDTA derivatives. Particularly preferred radionuclides for indirect labeling include $^{111}$In and $^{90}$Y.

As used herein, the phrases "direct labeling" and "direct labeling approach" both mean that a radionuclide is covalently attached directly to a molecule (typically via an amino acid residue). More specifically, these linking technologies include random labeling and site-directed labeling. In the latter case, the labeling is directed at specific sites on the molecule, such as the N-linked sugar residues present only in an Fc domain of the molecule. Further, various direct labeling techniques and protocols are compatible with the instant invention. For example, Technetium-99m labeled polypeptides may be prepared by ligand exchange processes, by reducing pertechnate ($TcO_4^-$) with stannous ion solution, chelating the reduced technetium onto a Sephadex column and applying the polypeptides to this column, or by batch labeling techniques, e.g. by incubating pertechnate, a reducing agent such as $SnCl_2$, a buffer solution such as a sodium-potassium phthalate-solution, and the antibodies. In any event, preferred radionuclides for directly labeling antibodies are well known in the art and a particularly preferred radionuclide for direct labeling is $^{131}I$ covalently attached via tyrosine residues. Binding molecules according to the invention may be derived, for example, with radioactive sodium or potassium iodide and a chemical oxidizing agent, such as sodium hypochlorite, chloramine T or the like, or an enzymatic oxidizing agent, such as lactoperoxidase, glucose oxidase and glucose. However, for the purposes of the present invention, the indirect labeling approach is particularly preferred.

Patents relating to chelators and chelator conjugates are known in the art. For instance, U.S. Pat. No. 4,831,175 of Gansow (hereby incorporated by reference in its entirety) is directed to polysubstituted diethylenetriaminepentaacetic acid chelates and protein conjugates containing the same, and methods for their preparation. U.S. Pat. Nos. 5,099,069, 5,246,692, 5,286,850, 5,434,287 and 5,124,471 of Gansow also relate to polysubstituted DTPA chelates. These patents are incorporated herein in their entirety. Other examples of compatible metal chelators are ethylenediaminetetraacetic acid (EDTA), diethylenetriaminepentaacetic acid (DPTA), 1,4,8,11-tetraazatetradecane, 1,4,8,11-tetraazatetradecane-1,4,8,11-tetraacetic acid, 1-oxa-4,7,12,15-tetraazaheptadecane-4,7,12,15-tetraacetic acid, or the like. Cyclohexyl-DTPA or CHX-DTPA is particularly preferred and is exemplified extensively below. Still other compatible chelators, including those yet to be discovered, may easily be discerned by a skilled artisan and are clearly within the scope of the present invention.

Compatible chelators, including the specific bifunctional chelator used to facilitate chelation in U.S. Pat. Nos. 5,843,439; 6,399,061; and 6,682,734 (hereby incorporated by reference in their entirety), are preferably selected to provide high affinity for trivalent metals, exhibit increased tumor-to-non-tumor ratios and decreased bone uptake as well as greater in vivo retention of radionuclide at target sites, i.e., B-cell lymphoma tumor sites. However, other bifunctional chelators that may or may not possess all of these characteristics are known in the art and may also be beneficial in tumor therapy.

It will also be appreciated that, in accordance with the teachings herein, binding molecules may be conjugated to different radiolabels for diagnostic and therapeutic purposes. To this end the aforementioned co-pending applications, herein incorporated by reference in their entirety, disclose radiolabeled therapeutic conjugates for diagnostic "imaging" of tumors before administration of therapeutic antibody. "In2B8" conjugate comprises a murine monoclonal antibody, 2B8, specific to human CD20 antigen, that is attached to $^{111}In$ via a bifunctional chelator, i.e., MX-DTPA (diethylenetriaminepentaacetic acid), which comprises a 1:1 mixture of 1-isothiocyanatobenzyl-3-methyl-DTPA and 1-methyl-3-isothiocyanatobenzyl-DTPA. $^{111}In$ is particularly preferred as a diagnostic radionuclide because between about 1 to about 10 mCi can be safely administered without detectable toxicity; and the imaging data is generally predictive of subsequent $^{90}Y$-labeled antibody distribution. Most imaging studies utilize 5 mCi $^{111}In$-labeled antibody, because this dose is both safe and has increased imaging efficiency compared with lower doses, with optimal imaging occurring at three to six days after antibody administration. See, for example, Murray, *J. Nuc. Med.* 26: 3328 (1985) and Carraguillo et al., *J. Nuc. Med.* 26: 67 (1985).

As indicated above, a variety of radionuclides are applicable to the present invention and those skilled in the art can readily determine which radionuclide is most appropriate under various circumstances. For example, $^{131}I$ is a well known radionuclide used for targeted immunotherapy. However, the clinical usefulness of $^{131}I$ can be limited by several factors including: eight-day physical half-life; dehalogenation of iodinated antibody both in the blood and at tumor sites; and emission characteristics (e.g., large gamma component) which can be suboptimal for localized dose deposition in tumor. With the advent of superior chelating agents, the opportunity for attaching metal chelating groups to proteins has increased the opportunities to utilize other radionuclides such as $^{111}In$ and $^{90}Y$. $^{90}Y$ provides several benefits for utilization in radioimmunotherapeutic applications: the 64 hour half-life of $^{90}Y$ is long enough to allow antibody accumulation by tumor and, unlike e.g., $^{131}I$, $^{90}Y$ is a pure beta emitter of high energy with no accompanying gamma irradiation in its decay, with a range in tissue of 100 to 1,000 cell diameters. Furthermore, the minimal amount of penetrating radiation allows for outpatient administration of $^{90}Y$-labeled antibodies. Additionally, internalization of labeled antibody is not required for cell killing, and the local emission of ionizing radiation should be lethal for adjacent tumor cells lacking the target molecule.

Those skilled in the art will appreciate that these non-radioactive conjugates may also be assembled using a variety of techniques depending on the selected agent to be conjugated. For example, conjugates with biotin are prepared e.g. by reacting the polypeptides with an activated ester of biotin such as the biotin N-hydroxysuccinimide ester. Similarly, conjugates with a fluorescent marker may be prepared in the presence of a coupling agent, e.g. those listed above, or by reaction with an isothiocyanate, preferably fluorescein-isothiocyanate. Conjugates of the binding molecules of the invention with cytostatic/cytotoxic substances and metal chelates are prepared in an analogous manner.

Many functional moieties lack suitable functional groups to which binding molecules can be linked. In one embodiment, an effector molecule, e.g., a drug or prodrug is attached to the binding molecule through a linking molecule. In one embodiment, the linking molecule contains a chemical bond that allows for the activation of cytotoxicity at a particular site. Suitable chemical bonds are well known in the art and include disulfide bonds, acid labile bonds, photolabile bonds, peptidase labile bonds, thioether bonds formed between sulfhydryl and maleimide groups, and esterase labile bonds. Most preferably, the linking molecule comprises a disulfide bond or a thioether bond. In accordance with the invention, the linking molecule preferably comprises a reactive chemical group. Particularly preferred reactive chemical groups are N-succinimidyl esters and N-sulfosuccinimidyl esters. In a preferred embodiment, the reactive chemical group can be covalently bound to the effector via disulfide bonding between thiol groups. In one embodiment an effector molecule is modified to comprise a thiol group. One of ordinary skill in the art will appreciate that a thiol group contains a sulfur atom bonded to a hydrogen atom and is typically also referred to in the art as a sulfhydryl group, which can be denoted as "--SH" or "RSH."

In one embodiment, a linking molecule may be used to join an effector molecule with a binding molecule of the invention. The linking molecule may be cleavable or non-cleavable. In one embodiment, the cleavable linking molecule is a redox-cleavable linking molecule, such that the linking molecule is cleavable in environments with a lower redox potential, such as the cytoplasm and other regions with higher concentrations of molecules with free sulfhydryl groups. In another embodiment, a linking molecule may be a polypeptide linker. Examples of linking molecules that may be cleaved due to a change in redox potential include those containing disulfides. The cleaving stimulus can be provided upon intracellular uptake of the binding molecule of the invention where the lower redox potential of the cytoplasm facilitates cleavage of the linking molecule. In another embodiment, a decrease in pH triggers the release of the maytansinoid cargo into the target cell. The decrease in pH is implicated in many physiological and pathological processes, such as endosome trafficking, tumor growth, inflammation, and myocardial ischemia. The pH drops from a physiological 7.4 to 5-6 in endosomes or 4-5 in lysosomes. Examples of acid sensitive linking molecules which may be used to target lysosomes or endosomes of cancer cells, include those with acid-cleavable bonds such as those found in acetals, ketals, orthoesters, hydrazones, tritylsulfurals, cis-aconityls, or thiocarbamoyls (see for example, Willner et al., (1993), *Bioconj. Chem.*, 4: 521-7; U.S. Pat. Nos. 4,569,789, 4,631,190, 5,306,809, and 5,665,358; all of which are hereby incorporated by reference in their entirety. Other exemplary acid-sensitive linking molecules comprise dipeptide sequences Phe-Lys and Val-Lys (King et al., (2002), *J. Med. Chem.*, 45: 4336-43, hereby incorporated by reference in its entirety). The cleaving stimulus can be provided upon intracellular uptake trafficking to low pH endosomal compartments (e.g. lysosomes). Other exemplary acid-cleavable linking molecules are the molecules that contain two or more acid cleavable bonds for attachment of two or more maytansinoids (King et al., (1999), *Bioconj. Chem.*, 10: 279-88 and WO 98/19705, hereby incorporated by reference in their entirety).

Cleavable linking molecules may be sensitive to biologically supplied cleaving agents that are associated with a particular target cell, for example, lysosomal or tumor-associated enzymes. Examples of linking molecules that can be cleaved enzymatically include, but are not limited to, peptides and esters. Exemplary enzyme cleavable linking molecules include those that are sensitive to tumor-associated proteases such as Cathepsin B or plasmin (Dubowchik et al., (1999), *Pharm. Ther.*, 83: 67-123; Dubowchik et al., (1998), *Bioorg. Med. Chem. Lett.*, 8: 3341-52; de Groot et al., (2000), *J. Med. Chem.*, 43: 3093-102; de Groot et al., (1999)m 42: 5277-83; hereby incorporated by reference in their entirety). Cathepsin B-cleavable sites include the dipeptide sequences valine-citrulline and phenylalanine-lysine (Doronina et al., (2003), *Nat. Biotech.*, 21(7): 778-84); Dubowchik et al., (2002), *Bioconjug. Chem.*, 13: 855-69; hereby incorporated by reference in their entirety). Other exemplary enzyme-cleavable sites include those formed by oligopeptide sequences of 4 to 16 amino acids (e.g., Suc-β-Ala-Leu-Ala-Leu) which recognized by trouse proteases such as Thimet Oliogopeptidase (TOP), an enzyme that is preferentially released by neutrophils, macrophages, and other granulocytes.

In a further embodiment, a binding molecule of the invention is reacted with a linking molecule of the formula:

wherein:
X is an attachment molecule;
Y is a spacer molecule; and
Z is a effector attachment moiety.

The term "attachment molecule" includes molecules which allow for the covalent attachment of the linking molecule to a binding molecule of the invention. The attachment molecule may comprise, for example, a covalent chain of 1-60 carbon, oxygen, nitrogen, sulfur atoms, optionally substituted with hydrogen atoms and other substituents which allow the binding molecule to perform its intended function. The attachment molecule may comprise peptide, ester, alkyl, alkenyl, alkynyl, aryl, ether, thioether, etc. functional groups. Preferably, the attachment molecule is selected such that it is capable of reacting with a reactive functional group on a constituent polypeptide chain of a binding molecule comprising at least one antigen binding site, to form a binding molecule of the invention. Examples of attachment molecules include, for example, amino-, carboxylate, and thiol attachment molecules.

Amino attachment molecules include molecules which react with amino groups on a constituent polypeptide chain of a binding molecule, such that a modified binding molecule is formed. Amino attachment molecules are known in the art. Examples of amino attachment molecules include, activated carbamides (e.g., which may react with an amino group on a binding molecule to form a linking molecule which comprises urea group), aldehydes (e.g., which may react with amino groups on a binding molecule), and activated isocyanates (which may react with an amino group on a binding molecule to form a linking molecule which comprises a urea group). Examples of amino attachment molecules include, but are not limited to, N-succinimidyl, N-sulfosuccinimidyl, N-phthalimidyl, N-sulfophthalimidyl, 2-nitrophenyl, 4-nitrophenyl, 2,4-dinitrophenyl, 3-sulfonyl-4-nitrophenyl, or 3-carboxy-4-nitrophenyl molecule.

Carboxylate attachment molecules include molecules which react with carboxylate groups on a binding molecule, such that a modified binding molecule of the invention is formed. Carboxylate attachment molecules are known in the art. Examples of carboxylate attachment molecules include, but are not limited to activated ester intermediates and activated carbonyl intermediates, which may react with a COOH group on a binding molecule to form a linking molecule which comprises a ester, thioester, or amide group.

Thiol attachment molecules include molecules which react with thiol groups present on a constituent polypeptide chain, such that a binding molecule of the invention is formed. Thiol attachment molecules are known in the art. Examples of thiol attachment molecules include activated acyl groups (which may react with a sulfhydryl on a binding molecule to form a linking molecule which comprises a thioester), activated alkyl groups (which may react with a sulfhydryl on a binding molecule to form a linking molecule which comprises a thioester molecule), Michael acceptors such as maleimide or acrylic groups (which may react with a sulfhydryl on a binding molecule to form a Michael-type addition product), groups which react with sulfhydryl groups via redox reactions, activated di-sulfide groups (which may react with a sulfhydryl group on a binding molecule to form, for example, a linking molecule which comprises a disulfide molecule). Other thiol attachment molecules include acrylamides, alpha-iodoacetamides, and cyclopropan-1,1-dicarbonyl compounds. In addition, the thiol attachment molecule may comprise a molecule which modifies a thiol on the binding molecule to form another reactive species to which the linking molecule can be attached to form a binding molecule of the invention.

The spacer molecule, Y, is a covalent bond or a covalent chain of atoms which may contain one or more amino acid residues. It may also comprise 0-60 carbon, oxygen, sulfur or nitrogen atoms optionally substituted with hydrogen or other substituents which allow the resulting binding molecule to perform its intended function. In one embodiment, Y comprises an alkyl, alkenyl, alkynyl, ester, ether, carbonyl, or amide molecule.

In another embodiment, a thiol group on the binding molecule is converted into a reactive group, such as a reactive carbonyl group, such as a ketone or aldehyde. The attachment molecule is then reacted with the ketone or aldehyde to form a modified binding molecule. Examples of carbonyl reactive attachment molecules include, but are not limited to, hydrazines, hydrazides, O-substituted hydroxylamines, alpha-beta-unsaturated ketones, and $H_2C=CH-CO-NH-NH_2$. Other examples of attachment molecules and methods for modifying thiol molecules which can be used to form modified binding molecules are described Pratt, M. L. et al. J Am Chem Soc. 2003 May 21; 125(20): 6149-59; and Saxon, E. Science. 2000 Mar. 17; 287(5460): 2007-10, which are hereby incorporated by reference in their entirety.

The linking molecule may be a molecule which is capable of reacting with an effector molecule or a derivative thereof to form a binding molecule of the invention. For example, the effector molecule may be linked to the remaining portions of the molecule through a disulfide bond. In such cases, the linking molecule is selected such that it is capable of reacting with an appropriate effector moiety derivative such that the effector molecule is attached to the binding molecule of the invention.

Preferred cytotoxic effector molecules for use in the present invention are cytotoxic drugs, particularly those which are used for cancer therapy. As used herein, "a cytotoxin or cytotoxic agent" means any agent that is detrimental to the growth and proliferation of cells and may act to reduce, inhibit or destroy a cell or malignancy. Exemplary cytotoxins include, but are not limited to, radionuclides, biotoxins, enzymatically active toxins, cytostatic or cytotoxic therapeutic agents, prodrugs, immunologically active ligands and biological response modifiers such as cytokines. Any cytotoxin that acts to retard or slow the growth of immunoreactive cells or malignant cells is within the scope of the present invention.

Exemplary cytotoxins include, in general, cytostatic agents, alkylating agents, antimetabolites, anti-proliferative agents, tubulin binding agents, hormones and hormone antagonists, and the like. Exemplary cytostatics that are compatible with the present invention include alkylating substances, such as mechlorethamine, triethylenephosphoramide, cyclophosphamide, ifosfamide, chlorambucil, busulfan, melphalan or triaziquone, also nitrosourea compounds, such as carmustine, lomustine, or semustine.

Exemplary molecules for conjugation are maytansinoids. Maytansinoids were originally isolated from the east African shrub belonging to the genus *Maytenus*, but were subsequently also discovered to be metabolites of soil bacteria, such as Actinosynnema pretiosum (see, e.g., U.S. Pat. No. 3,896,111). Maytansinoids are known in the art to include maytansine, maytansinol, C-3 esters of maytansinol, and other maytansinol analogues and derivatives (see, e.g., U.S. Pat. Nos. 5,208,020 and 6,441,163). C-3 esters of maytansinol can be naturally occurring or synthetically derived. Moreover, both naturally occurring and synthetic C-3 maytansinol esters can be classified as a C-3 ester with simple carboxylic acids, or a C-3 ester with derivatives of N-methyl-L-alanine, the latter being more cytotoxic than the former. Synthetic maytansinoid analogues also are known in the art and described in, for example, Kupchan et al., J. Med. Chem., 21, 31-37 (1978). Methods for generating maytansinol and analogues and derivatives thereof are described in, for example, U.S. Pat. No. 4,151,042. The Kupchan reference (J. Med. Chem., 21, 31-37 (1978)) and U.S. Pat. Nos. 3,896,111; 5,208,020; 6,441,163 and 4,151,042 are hereby incorporated by reference in their entirety.

Suitable maytansinoids for use as conjugates can be isolated from natural sources, synthetically produced, or semi-synthetically produced using methods known in the art. Moreover, the maytansinoid can be modified in any suitable manner, so long as sufficient cytotoxicity is preserved in the ultimate conjugate molecule.

Particularly preferred maytansinoids comprising a linking molecule that contains a reactive chemical group are C-3 esters of maytansinol and its analogs where the linking molecule contains a disulfide bond and the attachment molecule comprises a N-succinimidyl or N-sulfosuccinimidyl ester. Many positions on maytansinoids can serve as the position to chemically link the linking molecule, e.g., through an effector attachment molecule. For example, the C-3 position having a hydroxyl group, the C-14 position modified with hydroxymethyl, the C-15 position modified with hydroxy and the C-20 position having a hydroxy group are all useful. The linking molecule most preferably is linked to the C-3 position of maytansinol. Most preferably, the maytansinoid used in connection with the inventive composition is $N^{2'}$-deacetyl-$N^{2'}$-(-3-mercapto-1-oxopropyl)-maytansine (DM1) or $N^{2'}$-deacetyl-$N^{2'}$-(4-mercapto-4-methyl-1-oxopentyl)-maytansine (DM4).

Linking molecules with other chemical bonds also can be used in the context of the invention, as can other maytansinoids. Specific examples of other chemical bonds which may be incorporated in the linking molecules include those described above, such as, for example acid labile bonds, thioether bonds, photolabile bonds, peptidase labile bonds and esterase labile bonds. Methods for producing maytansinoids with linking molecules and/or effector attachment molecules are described in, for example, U.S. Pat. Nos. 5,208,020, 5,416,064, and 6,333,410, hereby incorporated by reference in their entirety.

The linking molecule (and/or the effector attachment molecule) of a maytansinoid typically and preferably is part of a larger peptide molecule that is used to join the binding molecule to the maytansinoid. Any suitable peptide molecule can be used in connection with the invention, so long as the linking molecule provides for retention of the cytotoxicity and targeting characteristics of the maytansinoid and the binding molecule, respectively. The linking molecule joins the maytansinoid to the binding molecule through chemical bonds (as described above), such that the maytansinoid and the binding molecule are chemically coupled (e.g., covalently bonded) to each other. Desirably, the linking molecule chemically couples the maytansinoid to the binding molecule through disulfide bonds or thioether bonds. Most preferably, the binding molecule is chemically coupled to the maytansinoid via disulfide bonds.

Other preferred classes of cytotoxic agents include, for example, the anthracycline family of drugs, the vinca drugs, the mitomycins, the bleomycins, the cytotoxic nucleosides, the pteridine family of drugs, diynenes, and the podophyllotoxins. Particularly useful members of those classes include, for example, adriamycin, carminomycin, daunorubicin (daunomycin), doxorubicin, aminopterin, methotrexate, methopterin, mithramycin, streptonigrin, dichloromethotrexate, mitomycin C, actinomycin-D, porfiromycin, 5-fluorouracil, floxuridine, ftorafur, 6-mercaptopurine, cytarabine, cytosine arabinoside, podophyllotoxin, or podophyllotoxin derivatives such as etoposide or etoposide phosphate, melphalan, vinblastine, vincristine, leurosidine, vindesine, leurosine and the like. Still other cytotoxins that are compatible with the teachings herein include taxol, taxane, cytochalasin B, gramicidin D, ethidium bromide, emetine, tenoposide, colchicin, dihydroxy anthracin dione, mitoxantrone, procaine, tetracaine, lidocaine, propranolol, and puromycin and analogs or homologs thereof. Hormones and hormone antagonists, such as corticosteroids, e.g. prednisone, progestins, e.g. hydroxyprogesterone or medroprogesterone, estrogens, e.g. diethylstilbestrol, antiestrogens, e.g. tamoxifen, androgens, e.g. testosterone, and aromatase inhibitors, e.g. aminogluthetimide are also compatible with the teachings herein. As noted previously, one skilled in the art may make chemical modifications to the desired compound in order to make reactions of that compound more convenient for purposes of preparing binding molecule conjugates of the invention.

Other exemplary cytotoxins comprise members or derivatives of the enediyne family of anti-tumor antibiotics, including calicheamicin, esperamicins or dynemicins. These toxins are extremely potent and act by cleaving nuclear DNA, leading to cell death. Unlike protein toxins which can be cleaved in vivo to give many inactive but immunogenic polypeptide fragments, toxins such as calicheamicin, esperamicins and other enediynes are small molecules which are essentially non-immunogenic. These non-peptide toxins are chemically-linked to the dimers or tetramers by techniques which have been previously used to label monoclonal antibodies and other molecules. These linking technologies include site-specific linkage via the N-linked sugar residues present within the heterodimeric Fc region of a binding molecule of the invention. Such site-directed linking methods have the advantage of reducing the possible effects of linkage on the binding properties of the constructs.

Among other cytotoxins, it will be appreciated that molecules can also be associated with a biotoxin such as ricin subunit A, abrin, diptheria toxin, botulinum, cyanginosins, saxitoxin, shigatoxin, tetanus, tetrodotoxin, trichothecene, verrucologen or a toxic enzyme. Preferably, such constructs will be made using genetic engineering techniques that allow for direct expression of the constituent polypeptide chain-toxin construct. Other biological response modifiers that may be associated with the binding molecules of the invention include cytokines such as lymphokines and interferons. In view of the instant disclosure it is submitted that one skilled in the art could readily form such constructs using conventional techniques.

Another class of compatible cytotoxins that may be used in conjunction with the disclosed binding molecules are radiosensitizing drugs that may be effectively directed to tumor or immunoreactive cells. Such drugs enhance the sensitivity to ionizing radiation, thereby increasing the efficacy of radiotherapy. A binding molecule conjugate internalized by the tumor cell would deliver the radiosensitizer nearer the nucleus where radiosensitization would be maximal. The unbound radiosensitizer-linked binding molecules of the invention would be cleared quickly from the blood, localizing the remaining radiosensitization agent in the target tumor and providing minimal uptake in normal tissues. After rapid clearance from the blood, adjunct radiotherapy would be administered in one of three ways: 1) external beam radiation directed specifically to the tumor, 2) radioactivity directly implanted in the tumor or 3) systemic radioimmunotherapy with the same targeting binding molecule. A potentially attractive variation of this approach would be the attachment of a therapeutic radioisotope to the radiosensitized immunoconjugate, thereby providing the convenience of administering to the patient a single drug.

In one embodiment, a molecule that enhances the stability or efficacy of the binding molecule can be conjugated. For example, in one embodiment, PEG can be conjugated to the binding molecules of the invention to increase their half-life in vivo. See Leong, S. R., et al. 2001. Cytokine 16:106; 2002; Adv. in Drug Deliv. Rev. 54:531; or Weir et al. 2002. Biochem. Soc. Transactions 30:512, all of which are hereby incorporated by reference in their entirety.

As previously alluded to, compatible cytotoxins may comprise a prodrug. As used herein, the term "prodrug" refers to a precursor or derivative form of a pharmaceutically active substance that is less cytotoxic to tumor cells compared to the parent drug and is capable of being enzymatically activated or converted into the more active parent form. Prodrugs compatible with the invention include, but are not limited to, phosphate-containing prodrugs, thiophosphate-containing prodrugs, sulfate containing prodrugs, peptide containing prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs that can be converted to the more active cytotoxic free drug. In one embodiment, a cytotoxic agent, such as a maytansinoid, is administered as a prodrug which is released by the hydrolysis of disulfide bonds. Further examples of cytotoxic drugs that can be derivatized into a prodrug form for use in the present invention comprise those chemotherapeutic agents described above.

VII. Methods of Use of the Binding Molecules of the Invention

The binding molecules of the invention can be used in a number of applications, for example in diagnostic or therapeutic purposes. Preferred embodiments of the present invention provide kits and methods for the diagnosis and/or treatment of disorders, e.g., neoplastic disorders in a mammalian subject in need of such treatment. Preferably, the subject is a human.

As will be understood by one of ordinary skill in the art, the methods of use of subject binding molecules will depend on the binding site(s) present in the molecule. For example, if one or more binding moieties are included in the molecule that bind to tumor cell antigen(s), the binding molecule will be useful in imaging and/or inhibiting proliferation of the tumor. Accordingly, upon reading the instant application, one of ordinary skill in the art will understand that the heterodimeric scaffold platform can be used to improve the expression/alter the functionality of a wide range of binding moieties and that the binding molecules constructed using the scaffold will be useful in the same applications as the binding moieties employed therein. Exemplary applications are set forth below.

A. Anti-Tumor Therapy

The binding molecules of the instant invention will be useful in a number of different applications. For example, in one embodiment, the subject binding molecules should be useful for reducing or eliminating cells bearing an epitope recognized by the binding molecule. In another embodiment, the subject binding molecules are effective in reducing the concentration of or eliminating soluble antigen in the circulation.

In one embodiment, the binding molecules of the invention which recognize tumor-associated antigens may reduce tumor size, inhibit tumor growth and/or prolong the survival time of tumor-bearing animals. Accordingly, this invention also relates to a method of treating tumors in a human or other animal by administering to such human or animal an effective, non-toxic amount of said binding molecules. One skilled in the art would be able, by routine experimentation, to determine what an effective, non-toxic amount of modified binding molecule would be for the purpose of treating malignancies. For example, a therapeutically active amount of a binding molecule may vary according to factors such as the disease stage (e.g., stage I versus stage IV), age, sex, medical complications (e.g., immunosuppressed conditions or diseases) and weight of the subject, and the ability of the binding molecule to elicit a desired response in the subject. The dosage regimen may be adjusted to provide the optimum therapeutic response. For example, several divided doses may be administered daily, or the dose may be proportionally reduced as indicated by the exigencies of the therapeutic situation. Generally, however, an effective dosage is expected to be in the range of about 0.05 to 100 milligrams per kilogram body weight per day and more preferably from about 0.5 to 10, milligrams per kilogram body weight per day.

In general, the binding molecules of the invention may be used to prophylactically or therapeutically treat neoplasia comprising an antigenic marker that allows for the targeting of the cancerous cells by the modified antibody. Exemplary cancers that may be treated include, but are not limited to, prostate, gastric carcinomas such as colon, skin, breast, ovarian, lung and pancreatic. More particularly, the binding molecules of the instant invention may be used to treat Kaposi's sarcoma, CNS neoplasias (capillary hemangioblastomas, meningiomas and cerebral metastases), melanoma, gastrointestinal and renal sarcomas, rhabdomyosarcoma, glioblastoma (preferably glioblastoma multiforme), leiomyosarcoma, retinoblastoma, papillary cystadenocarcinoma of the ovary, Wilm's tumor or small cell lung carcinoma. It will be appreciated that appropriate target-binding molecules may be derived for tumor associated antigens related to each of the forgoing neoplasias without undue experimentation in view of the instant disclosure.

Exemplary hematologic malignancies that are amenable to treatment with the disclosed invention include Hodgkins and non-Hodgkins lymphoma as well as leukemias, including ALL-L3 (Burkitt's type leukemia), chronic lymphocytic leukemia (CLL) and monocytic cell leukemias. It will be appreciated that the compounds and methods of the present invention are particularly effective in treating a variety of B-cell lymphomas, including low grade/follicular non-Hodgkin's lymphoma (NHL), cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL and Waldenstrom's Macroglobulinemia. It should be clear to those of skill in the art that these lymphomas will often have different names due to changing systems of classification, and that patients having lymphomas classified under different names may also benefit from the combined therapeutic regimens of the present invention. In addition to the aforementioned neoplastic disorders, it will be appreciated that the molecules of the invention may advantageously be used to treat additional malignancies bearing compatible tumor associated antigens.

B. Immune Disorder Therapies

Besides neoplastic disorders, the binding molecules of the instant invention are particularly effective in the treatment of autoimmune disorders or abnormal immune responses. In this regard, it will be appreciated that the binding molecules of the present invention may be used to control, suppress, modulate or eliminate unwanted immune responses to both external and autoantigens. For example, in one embodiment, the antigen is an autoantigen. In another embodiment, the antigen is an allergen. In yet other embodiments, the antigen is an alloantigen or xenoantigen. Use of the binding molecules of the invention to reduce an immune response to alloantigens and xenoantigens is of particular use in transplantation, for example to inhibit rejection by a transplant recipient of a donor graft, e.g. a tissue or organ graft or bone marrow transplant. Additionally, suppression or elimination of donor T cells within a bone marrow graft is useful for inhibiting graft versus host disease.

In yet other embodiments the binding molecules of the present invention may be used to treat immune disorders that include, but are not limited to, allergic bronchopulmonary aspergillosis; Allergic rhinitis Autoimmune hemolytic anemia; Acanthosis nigricans; Allergic contact dermatitis; Addison's disease; Atopic dermatitis; Alopecia areata; Alopecia universalis; Amyloidosis; Anaphylactoid purpura; Anaphylactoid reaction; Aplastic anemia; Angio\edema, hereditary; Angioedema, idiopathic; Ankylosing spondylitis; Arteritis, cranial; Arteritis, giant cell; Arteritis, Takayasu's; Arteritis, temporal; Asthma; Ataxia-telangiectasia; Autoimmune oophoritis; Autoimmune orchitis; Autoimmune polyendocrine failure; Behcet's disease; Berger's disease; Buerger's disease; bronchitis; Bullous pemphigus; Candidiasis, chronic mucocutaneous; Caplan's syndrome; Post-myocardial infarction syndrome; Post-pericardiotomy syndrome; Carditis; Celiac sprue; Chagas's disease; Chediak-Higashi syndrome; Churg-Strauss disease; Cogan's syndrome; Cold agglutinin disease; CREST syndrome; Crohn's disease; Cryoglobulinemia; Cryptogenic fibrosing alveolitis; Dermatitis herpetifomis; Dermatomyositis; Diabetes mellitus; Diamond-Blackfan syndrome; DiGeorge syndrome; Discoid lupus erythematosus; Eosinophilic fasciitis; Episcleritis; Drythema elevatum diutinum; Erythema marginatum; Erythema multiforme; Erythema nodosum; Familial Mediterranean fever; Felty's syndrome; Fibrosis pulmonary; Glomerulonephritis, anaphylactoid; Glomerulonephritis, autoimmune; Glomerulonephritis, post-streptococcal; Glomerulonephritis, post-transplantation; Glomerulopathy, membranous; Goodpasture's syndrome; Granulocytopenia, immune-mediated; Granuloma annulare; Granulomatosis, allergic; Granulomatous myositis; Grave's disease; Hashimoto's thyroiditis; Hemolytic disease of the newborn; Hemochromatosis, idiopathic; Henoch-Schoenlein purpura; Hepatitis, chronic active and chronic progressive; Histiocytosis X; Hypereosinophilic syndrome; Idiopathic thrombocytopenic purpura; Job's syndrome; Juvenile dermatomyositis; Juvenile rheumatoid arthritis (Juvenile chronic arthritis); Kawasaki's disease; Keratitis; Keratoconjunctivitis sicca; Landry-Guillain-Barre-Strohl syndrome; Leprosy, lepromatous; Loeffler's syndrome; lupus; Lyell's syndrome; Lyme disease; Lymphomatoid granulomatosis; Mastocytosis, systemic; Mixed connective tissue disease; Mononeuritis multiplex; Muckle-Wells syndrome; Mucocutaneous lymph node syndrome; Mucocutaneous lymph node syndrome; Multicentric reticulohistiocytosis; Multiple sclerosis; Myasthenia gravis; Mycosis fungoides; Necrotizing vasculitis, systemic; Nephrotic syndrome; Overlap syndrome; Panniculitis; Paroxysmal cold hemoglobinuria; Paroxysmal nocturnal hemoglobinuria; Pemphigoid; Pemphigus; Pemphigus erythematosus; Pemphigus foliaceus; Pemphigus vulgaris; Pigeon breeder's disease; Pneumonitis, hypersensitivity; Polyarteritis nodosa; Polymyalgia rheumatic; Polymyositis; Polyneuritis, idiopathic; Portuguese familial polyneuropathies; Pre-eclampsia/eclampsia; Primary biliary cirrhosis; Progressive systemic sclerosis (Scleroderma); Psoriasis; Psoriatic arthritis; Pulmonary alveolar proteinosis; Pulmonary fibrosis, Raynaud's phenomenon/syndrome; Reidel's thyroiditis; Reiter's syndrome, Relapsing polychrondritis; Rheumatic fever; Rheumatoid arthritis; Sarcoidosis; Scleritis; Sclerosing cholangitis; Serum sickness; Sezary syndrome; Sjogren's syndrome; Stevens-Johnson syndrome; Still's disease; Sub-acute sclerosing panencephalitis; Sympathetic ophthalmia; Systemic lupus erythematosus; Transplant rejection; Ulcerative colitis; Undifferentiated connective tissue disease; Urticaria, chronic; Urticaria, cold; Uveitis; Vitiligo; Weber-Christian disease; Wegener's granulomatosis and Wiskott-Aldrich syndrome.

C. Anti-inflammatory Therapy

In yet other embodiments, the binding molecules of the present invention may be used to treat inflammatory disorders that are caused, at least in part, or exacerbated by inflammation, e.g., increased blood flow, edema, activation of immune cells (e.g., proliferation, cytokine production, or enhanced phagocytosis). Exemplary inflammatory disorders include those in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, mitochondria, apoptosis, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, microorganisms, tissue necrosis, cancer or other agents. Acute inflammation is short-lasting, lasting only a few days. If it is longer lasting however, then it may be referred to as chronic inflammation.

Inflammatory disorders include acute inflammatory disorders, chronic inflammatory disorders, and recurrent inflammatory disorders. Acute inflammatory disorders are generally of relatively short duration, and last for from about a few minutes to about one to two days, although they may last several weeks. The main characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or even longer, and are associated histologically with the presence of lymphocytes and macrophages and with proliferation of blood vessels and connective tissue. Recurrent inflammatory disorders include disorders which recur after a period of time or which have periodic episodes. Examples of recurrent inflammatory disorders include asthma and multiple sclerosis. Some disorders may fall within one or more categories.

Inflammatory disorders are generally characterized by heat, redness, swelling, pain and loss of function. Examples of causes of inflammatory disorders include, but are not limited to, microbial infections (e.g., bacterial, viral and fungal infections), physical agents (e.g., burns, radiation, and trauma), chemical agents (e.g., toxins and caustic substances), tissue necrosis and various types of immunologic reactions. Examples of inflammatory disorders include, but are not limited to, osteoarthritis, rheumatoid arthritis, acute and chronic infections (bacterial, viral and fungal); acute and chronic bronchitis, sinusitis, and other respiratory infections, including the common cold; acute and chronic gastroenteritis and colitis; acute and chronic cystitis and urethritis; acute respiratory distress syndrome; cystic fibrosis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; and burns (thermal, chemical, and electrical).

VIII. Methods of Administering Binding Molecules of the Invention

Methods of preparing and administering binding molecules of the invention to a subject are well known to or are readily determined by those skilled in the art. The route of administration of the binding molecules of the invention may be oral, parenteral, by inhalation or topical. The term parenteral, as used herein, includes intravenous, intraarterial, intraperitoneal, intramuscular, subcutaneous, rectal or vaginal administration. The intravenous, intraarterial, subcutaneous and intramuscular forms of parenteral administration are generally preferred. While all these forms of administration are clearly contemplated as being within the scope of the invention, a preferred form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, the binding molecules can be delivered directly to the site of the adverse cellular population thereby increasing the exposure of the diseased tissue to the therapeutic agent.

Preparations for parenteral administration include sterile aqueous or non-aqueous solutions, suspensions and emulsions. Examples of non-aqueous solvents are propylene glycol, polyethylene glycol, vegetable oils such as olive oil and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's solution or fixed oils. Intravenous vehicles include fluid and nutrient replenishers, electrolyte replenishers, such as those based on Ringer's dextrose, and the like. Preservatives and other additives may also be present such as, for example, antimicrobials, antioxidants, chelating agents, inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption such as, for example, aluminum monostearate and gelatin.

In any case, sterile injectable solutions can be prepared by incorporating an active compound (e.g., a binding molecule by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in co-pending U.S. Ser. No. 09/259,337 and U.S. Ser. No. 09/259,338, each of which is incorporated herein by reference. Such articles of manufacture will preferably have labels or package inserts indicating that the associated compositions are useful for treating a subject suffering from, or predisposed to autoimmune or neoplastic disorders.

Effective doses of the compositions of the present invention for the treatment of the above described conditions vary depending upon many different factors, including means of administration, target site, physiological state of the patient, whether the patient is human or an animal, other medications administered and whether treatment is prophylactic or therapeutic. Usually, the patient is a human but non-human mammals including transgenic mammals can also be treated. Treatment dosages may be titrated using routine methods known to those of skill in the art to optimize safety and efficacy.

For passive immunization with a binding molecule, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example, dosages can be 1 mg/kg body weight, 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more binding molecules with different binding specificities are administered simultaneously, in which case the dosage of each binding molecule administered falls within the ranges indicated.

Binding molecules of the invention can be administered on multiple occasions. Intervals between single dosages can be weekly, monthly or yearly. Intervals can also be irregular as indicated by measuring blood levels of the binding molecule or antigen in the patient. In some methods, dosage is adjusted to achieve a plasma binding molecule concentration of 1-1000 µg/ml and in some methods 25-300 µg/ml. Alternatively, molecules can be administered as a sustained release formulation, in which case less frequent administration is required. Dosage and frequency vary depending on the half-life of the molecule in the patient.

The dosage and frequency of administration can vary depending on whether the treatment is prophylactic or therapeutic. In prophylactic applications, compositions containing the binding molecules of the invention or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In therapeutic applications, a relatively high dosage (e.g., from about 1 to 400 mg/kg of binding molecule per dose, with dosages of from 5 to 25 mg being more commonly used for radioimmunoconjugates and higher doses for cytotoxin-drug modified binding molecules) at relatively short intervals is sometimes required until progression of the disease is reduced or terminated, and preferably until the patient shows partial or complete amelioration of symptoms of disease. Thereafter, the patient can be administered a prophylactic regime.

Binding molecules of the invention can optionally be administered in combination with other agents that are effective in treating the disorder or condition in need of treatment (e.g., prophylactic or therapeutic).

Effective single treatment dosages (i.e., therapeutically effective amounts) of $^{90}$Y-labeled modified binding molecules of the invention range from between about 5 and about 75 mCi, more preferably between about 10 and about 40 mCi. Effective single treatment non-marrow ablative dosages of $^{131}$I-modified binding molecules range from between about 5 and about 70 mCi, more preferably between about 5 and about 40 mCi and more preferably less than about 30 mCi. Effective single treatment ablative dosages (i.e., may require autologous bone marrow transplantation) of $^{131}$I-labeled binding molecules range from between about 30 and about 600 mCi, more preferably between about 50 and less than about 500 mCi. Imaging criteria for, e.g., the $^{111}$In label, are typically less than about 5 mCi.

While the binding molecules of the invention may be administered as described immediately above, it must be emphasized that, in other embodiments, binding molecules may be administered to otherwise healthy patients as a first line therapy. In such embodiments, the binding molecules may be administered to patients having normal or average red marrow reserves and/or to patients that have not, and are not, undergoing other therapy. As used herein, the administration of binding molecules of the invention in conjunction or combination with an adjunct therapy means the sequential, simultaneous, coextensive, concurrent, concomitant or contemporaneous administration or application of the therapy and the disclosed binding molecules. Those skilled in the art will appreciate that the administration or application of the various components of the combined therapeutic regimen may be timed to enhance the overall effectiveness of the treatment. For example, chemotherapeutic agents could be administered in standard, well known courses of treatment followed within a few weeks by radioimmunoconjugates of the binding molecules of the present invention. Conversely, cytotoxin-associated modified binding molecules could be administered intravenously followed by tumor localized external beam radiation. In yet other embodiments, the molecule may be administered concurrently with one or more selected chemotherapeutic agents in a single office visit. A skilled artisan (e.g. an experienced oncologist) would be readily be able to discern effective combined therapeutic regimens without undue experimentation based on the selected adjunct therapy and the teachings of the instant specification.

In this regard, it will be appreciated that the combination of the binding molecule and the chemotherapeutic agent may be administered in any order and within any time frame that provides a therapeutic benefit to the patient. That is, the chemotherapeutic agent and binding molecule may be administered in any order or concurrently. In selected embodiments, the binding molecules of the present invention will be administered to patients that have previously undergone chemotherapy. In yet other embodiments, the binding molecules and the chemotherapeutic treatment will be administered substantially simultaneously or concurrently. For example, the patient may be given the binding molecule while undergoing a course of chemotherapy. In preferred embodiments, the binding molecule will be administered within 1 year of any chemotherapeutic agent or treatment. In other preferred embodiments, the binding molecule will be administered within 10, 8, 6, 4, or 2 months of any chemotherapeutic agent or treatment. In still other preferred embodiments, the binding molecule will be administered within 4, 3, 2 or 1 week(s) of any chemotherapeutic agent or treatment. In yet other embodiments, the binding molecule will be administered within 5, 4, 3, 2 or 1 day(s) of the selected chemotherapeutic agent or treatment. It will further be appreciated that the two agents or treatments may be administered to the patient within a matter of hours or minutes (i.e., substantially simultaneously).

It will further be appreciated that the binding molecules of the instant invention may be used in conjunction or combination with any chemotherapeutic agent or agents (e.g., to provide a combined therapeutic regimen) that eliminates, reduces, inhibits or controls the growth of neoplastic cells in vivo. Exemplary chemotherapeutic agents that are compatible with the instant invention include alkylating agents, vinca alkaloids (e.g., vincristine and vinblastine), procarbazine, methotrexate and prednisone. The four-drug combination MOPP (mechlethamine (nitrogen mustard), vincristine (Oncovin), procarbazine and prednisone) is very effective in treating various types of lymphoma and comprises a preferred embodiment of the present invention. In MOPP-resistant patients, ABVD (e.g., adriamycin, bleomycin, vinblastine and dacarbazine), Ch1VPP (chlorambucil, vinblastine, procarbazine and prednisone), CABS (lomustine, doxorubicin, bleomycin and streptozotocin), MOPP plus ABVD, MOPP plus ABV (doxorubicin, bleomycin and vinblastine) or BCVPP (carmustine, cyclophosphamide, vinblastine, procarbazine and prednisone) combinations can be used. (See Arnold S. Freedman and Lee M. Nadler, *Malignant Lymphomas*, in HARRISON'S PRINCIPLES OF INTERNAL MEDICINE 1774-1788 (Kurt J. Isselbacher et al., eds., 13$^{th}$ ed. 1994) and V. T. DeVita et al., (1997) and the references cited therein for standard dosing and scheduling.) These therapies can be used unchanged, or altered as needed for a particular patient, in combination with one or more binding molecules of the invention as described herein.

Additional regimens that are useful in the context of the present invention include use of single alkylating agents such as cyclophosphamide or chlorambucil, or combinations such as CVP (cyclophosphamide, vincristine and prednisone), CHOP (CVP and doxorubicin), C-MOPP (cyclophosphamide, vincristine, prednisone and procarbazine), CAP-BOP (CHOP plus procarbazine and bleomycin), m-BACOD (CHOP plus methotrexate, bleomycin and leucovorin), ProMACE-MOPP (prednisone, methotrexate, doxorubicin, cyclophosphamide, etoposide and leucovorin plus standard MOPP), ProMACE-CytaBOM (prednisone, doxorubicin, cyclophosphamide, etoposide, cytarabine, bleomycin, vincristine, methotrexate and leucovorin) and MACOP-B (methotrexate, doxorubicin, cyclophosphamide, vincristine, fixed dose prednisone, bleomycin and leucovorin). Those skilled in the art will readily be able to determine standard dosages and scheduling for each of these regimens. CHOP has also been combined with bleomycin, methotrexate, procarbazine, nitrogen mustard, cytosine arabinoside and etoposide. Other compatible chemotherapeutic agents include, but are not limited to, 2-chlorodeoxyadenosine (2-CDA), 2'-deoxycoformycin and fludarabine.

For patients with intermediate- and high-grade NHL, who fail to achieve remission or relapse, salvage therapy is used. Salvage therapies employ drugs such as cytosine arabinoside, carboplatin, cisplatin, etoposide and ifosfamide given alone or in combination. In relapsed or aggressive forms of certain neoplastic disorders, the following protocols are often used: IMVP-16 (ifosfamide, methotrexate and etoposide), MIME (methyl-gag, ifosfamide, methotrexate and etoposide), DHAP (dexamethasone, high dose cytarabine and cisplatin), ESHAP (etoposide, methylpredisolone, HD cytarabine, cisplatin), CEPP(B) (cyclophosphamide, etoposide, procarbazine, prednisone and bleomycin) and CAMP (lomustine, mitoxantrone, cytarabine and prednisone) each with well known dosing rates and schedules.

The amount of chemotherapeutic agent to be used in combination with the binding molecules of the instant invention may vary by subject or may be administered according to what is known in the art. See, for example, Bruce A Chabner et al., *Antineoplastic Agents*, in GOODMAN & GILMAN'S THE PHARMACOLOGICAL BASIS OF THERAPEUTICS 1233-1287 ((Joel G. Hardman et al., eds., 9$^{th}$ ed. 1996).

As previously discussed, the binding molecules of the present invention, may be administered in a pharmaceutically effective amount for the in vivo treatment of mammalian disorders. In this regard, it will be appreciated that the binding molecules of the invention can be formulated to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like.

For the purposes of the instant application, a pharmaceutically effective amount of a binding molecule of the invention, conjugated or unconjugated to a therapeutic agent, shall be held to mean an amount sufficient to achieve effective binding to an antigen and to achieve a benefit, e.g., to ameliorate symptoms of a disease or disorder or to detect a substance or a cell. In the case of tumor cells, the binding molecule will be preferably be capable of interacting with selected immunoreactive antigens on neoplastic or immunoreactive cells and provide for an increase in the death of those cells. Of course, the pharmaceutical compositions of the present invention may be administered in single or multiple doses to provide for a pharmaceutically effective amount of the polypeptide.

In keeping with the scope of the present disclosure, the binding molecules of the invention may be administered to a human or other animal in accordance with the aforementioned methods of treatment in an amount sufficient to produce a therapeutic or prophylactic effect. A binding molecule of the invention can be administered to such human or other animal in a conventional dosage form prepared by combining the binding molecule with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of molecules of the invention may prove to be particularly effective.

This invention is further illustrated by the following examples which should not be construed as limiting. The contents of all references, patents and published patent applications cited throughout this application are incorporated herein by reference.

EXAMPLES

Throughout the examples, the following materials and methods were used unless otherwise stated.

General Materials and Methods

In general, the practice of the present invention employs, unless otherwise indicated, conventional techniques of chemistry, biophysics, molecular biology, recombinant DNA technology, immunology (especially, e.g., antibody technology), and standard techniques in electrophoresis. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C.S.H.L. Press, Pub. (1999); and Current Protocols in Molecular Biology, eds. Ausubel et al., John Wiley & Sons (1992).

Constituent polypeptides comprising CH2-CH3, CH2-CH1 and CH2-CL constant domains were constructed with Fc regions having the sequences shown in Table 2:

TABLE 2

Fc region sequences of constituent polypeptides

| Numbering Schemes Kabat numbering of CH2-CH1 construct | Kabat numbering of CH2-CL construct | Kabat numbering of CH2-CH3 construct | Sequential numbering of the constructs | Basic Constructs Amino acid present in a given position in CH2_CH1 construct | Amino acid present in a given position in CH2_CL construct | Amino acid present in a given position in CH2_CH3 construct |
|---|---|---|---|---|---|---|
| 237 | 237 | 237 | 1 | G | G | G |
| 238 | 238 | 238 | 2 | P | P | P |
| 239 | 239 | 239 | 3 | S | S | S |
| 240 | 240 | 240 | 4 | V | V | V |
| 241 | 241 | 241 | 5 | F | F | F |
| 242 | 242 | 242 | 6 | L | L | L |
| 243 | 243 | 243 | 7 | F | F | F |
| 244 | 244 | 244 | 8 | P | P | P |
| 245 | 245 | 245 | 9 | P | P | P |
| 246 | 246 | 246 | 10 | K | K | K |
| 247 | 247 | 247 | 11 | P | P | P |
| 248 | 248 | 248 | 12 | K | K | K |
| 249 | 249 | 249 | 13 | D | D | D |
| 250 | 250 | 250 | 14 | T | T | T |
| 251 | 251 | 251 | 15 | L | L | L |
| 252 | 252 | 252 | 16 | M | M | M |
| 253 | 253 | 253 | 17 | I | I | I |
| 254 | 254 | 254 | 18 | S | S | S |
| 255 | 255 | 255 | 19 | R | R | R |
| 256 | 256 | 256 | 20 | T | T | T |
| 257 | 257 | 257 | 21 | P | P | P |
| 258 | 258 | 258 | 22 | E | E | E |
| 259 | 259 | 259 | 23 | V | V | V |
| 260 | 260 | 260 | 24 | T | T | T |
| 261 | 261 | 261 | 25 | C | C | C |
| 262 | 262 | 262 | 26 | V | V | V |
| 263 | 263 | 263 | 27 | V | V | V |
| 264 | 264 | 264 | 28 | V | V | V |
| 265 | 265 | 265 | 29 | D | D | D |
| 266 | 266 | 266 | 30 | V | V | V |
| 267 | 267 | 267 | 31 | S | S | S |
| 268 | 268 | 268 | 32 | H | H | H |
| 269 | 269 | 269 | 33 | E | E | E |

TABLE 2-continued

Fc region sequences of constituent polypeptides

| Numbering Schemes Kabat numbering of CH2-CH1 construct | Kabat numbering of CH2-CL construct | Kabat numbering of CH2-CH3 construct | Sequential numbering of the constructs | Basic Constructs Amino acid present in a given position in CH2_CH1 construct | Amino acid present in a given position in CH2_CL construct | Amino acid present in a given position in CH2_CH3 construct |
|---|---|---|---|---|---|---|
| 270 | 270 | 270 | 34 | D | D | D |
| 271 | 271 | 271 | 35 | P | P | P |
| 272 | 272 | 272 | 36 | E | E | E |
| 273 | 273 | 273 | 37 | V | V | V |
| 274 | 274 | 274 | 38 | K | K | K |
| 275 | 275 | 275 | 39 | F | F | F |
| 276 | 276 | 276 | 40 | N | N | N |
| 277 | 277 | 277 | 41 | W | W | W |
| 278 | 278 | 278 | 42 | Y | Y | Y |
| 279 | 279 | 279 | 43 | V | V | V |
| 280 | 280 | 280 | 44 | D | D | D |
| 281 | 281 | 281 | 45 | G | G | G |
| 282 | 282 | 282 | 46 | V | V | V |
| 283 | 283 | 283 | 47 | E | E | E |
| 284 | 284 | 284 | 48 | V | V | V |
| 285 | 285 | 285 | 49 | H | H | H |
| 286 | 286 | 286 | 50 | N | N | N |
| 287 | 287 | 287 | 51 | A | A | A |
| 288 | 288 | 288 | 52 | K | K | K |
| 289 | 289 | 289 | 53 | T | T | T |
| 290 | 290 | 290 | 54 | K | K | K |
| 291 | 291 | 291 | 55 | P | P | P |
| 292 | 292 | 292 | 56 | R | R | R |
| 293 | 293 | 293 | 57 | E | E | E |
| 294 | 294 | 294 | 58 | E | E | E |
| 295 | 295 | 295 | 59 | Q | Q | Q |
| 296 | 296 | 296 | 60 | Y | Y | Y |
| 297 | 297 | 297 | 61 | N | N | N |
| 298 | 298 | 298 | 62 | S | S | S |
| 299 | 299 | 299 | 63 | T | T | T |
| 300 | 300 | 300 | 64 | Y | Y | Y |
| 301 | 301 | 301 | 65 | R | R | R |
| 302 | 302 | 302 | 66 | V | V | V |
| 303 | 303 | 303 | 67 | V | V | V |
| 304 | 304 | 304 | 68 | S | S | S |
| 305 | 305 | 305 | 69 | V | V | V |
| 306 | 306 | 306 | 70 | L | L | L |
| 307 | 307 | 307 | 71 | T | T | T |
| 308 | 308 | 308 | 72 | V | V | V |
| 309 | 309 | 309 | 73 | L | L | L |
| 310 | 310 | 310 | 74 | H | H | H |
| 311 | 311 | 311 | 75 | Q | Q | Q |
| 312 | 312 | 312 | 76 | D | D | D |
| 313 | 313 | 313 | 77 | W | W | W |
| 314 | 314 | 314 | 78 | L | L | L |
| 315 | 315 | 315 | 79 | N | N | N |
| 316 | 316 | 316 | 80 | G | G | G |
| 317 | 317 | 317 | 81 | K | K | K |
| 318 | 318 | 318 | 82 | E | E | E |
| 319 | 319 | 319 | 83 | Y | Y | Y |
| 320 | 320 | 320 | 84 | K | K | K |
| 321 | 321 | 321 | 85 | C | C | C |
| 322 | 322 | 322 | 86 | K | K | K |
| 323 | 323 | 323 | 87 | V | V | V |
| 324 | 324 | 324 | 88 | S | S | S |
| 325 | 325 | 325 | 89 | N | N | N |
| 326 | 326 | 326 | 90 | K | K | K |
| 327 | 327 | 327 | 91 | A | A | A |
| 328 | 328 | 328 | 92 | L | L | L |
| 329 | 329 | 329 | 93 | P | P | P |
| 330 | 330 | 330 | 94 | A | A | A |
| 331 | 331 | 331 | 95 | P | P | P |
| 332 | 332 | 332 | 96 | I | I | I |
| 333 | 333 | 333 | 97 | E | E | E |
| 334 | 334 | 334 | 98 | K | K | K |
| 335 | 335 | 335 | 99 | T | T | T |
| 336 | 336 | 336 | 100 | I | I | I |
| 337 | 337 | 337 | 101 | S | S | S |
| 338 | 338 | 338 | 102 | K | K | K |
| 339 | 339 | 339 | 103 | A | A | A |
| 340 | 340 | 340 | 104 | K | K | K |

TABLE 2-continued

Fc region sequences of constituent polypeptides

| Numbering Schemes Kabat numbering of CH2-CH1 construct | Kabat numbering of CH2-CL construct | Kabat numbering of CH2-CH3 construct | Sequential numbering of the constructs | Basic Constructs Amino acid present in a given position in CH2_CH1 construct | Amino acid present in a given position in CH2_CL construct | Amino acid present in a given position in CH2_CH3 construct |
|---|---|---|---|---|---|---|
| 118 | 108 | 341 | 105 | A | R | G |
| 119 | 109 | 342 | 106 | S | T | Q |
| 120 | 110 | 343 | 107 | T | V | P |
| 121 | 111 | 344 | 108 | K | A | R |
| 122 | 112 | 345 | 109 | G | A | E |
| 123 | 113 | 346 | 110 | P | P | P |
| 124 | 114 | 347 | 111 | S | S | Q |
| 125 | 115 | 348 | 112 | V | V | V |
| 126 | 116 | 349 | 113 | F | F | Y |
| 127 | 117 | 350 | 114 | P | I | T |
| 128 | 118 | 351 | 115 | L | F | L |
| 129 | 119 | 352 | 116 | A | P | P |
| 130 | 120 | 353 | 117 | P | P | P |
| 131 | 121 | 354 | 118 | S | S | S |
| 132 | 122 | 355 | 119 | S | D | R |
| 133 | 123 | 356 | 120 | K | E | D |
| 134 | 124 | 357 | 121 | S | Q | E |
| 135 | 125 | 358 | 122 | T | L | L |
| 136 | 126 | 359 | 123 | S | K | T |
| 137 | 127 | 360 | 124 | G | S | K |
| 138 | 128 | 361 | 125 | G | G | N |
| 139 | 129 | 362 | 126 | T | T | Q |
| 140 | 130 | 363 | 127 | A | A | V |
| 141 | 131 | 364 | 128 | A | S | S |
| 142 | 132 | 365 | 129 | L | V | L |
| 143 | 133 | 366 | 130 | G | V | T |
| 144 | 134 | 367 | 131 | C | C | C |
| 145 | 135 | 368 | 132 | L | L | L |
| 146 | 136 | 369 | 133 | V | L | V |
| 147 | 137 | 370 | 134 | K | N | K |
| 148 | 138 | 371 | 135 | D | N | G |
| 149 | 139 | 372 | 136 | Y | F | F |
| 150 | 140 | 373 | 137 | F | Y | Y |
| 151 | 141 | 374 | 138 | P | P | P |
| 152 | 142 | 375 | 139 | E | R | S |
| 153 | 143 | 376 | 140 | P | E | D |
| 154 | 144 | 377 | 141 | V | A | I |
| 155 | 145 | 378 | 142 | T | K | A |
| 156 | 146 | 379 | 143 | V | V | V |
| 157 | 147 | 380 | 144 | S | Q | E |
| 158 | 148 | 381 | 145 | W | W | W |
| 159 | 149 | 382 | 146 | N | K | E |
| 160 | 150 | 383 | 147 | S | V | S |
| 161 | 151 | 384 | 148 | G | D | N |
| 162 | 152 | 385 | 149 | A | N | G |
| 163 | 153 | 386 | 150 | L | A | Q |
| 164 | 154 | 387 | 151 | T | L | P |
| 165 | 155 | 388 | 152 | S | Q | E |
| 166 | 156 | 389 | 153 | G | S | N |
| 167 | 157 | 390 | 154 | V | G | N |
| 168 | 158 | 391 | 155 | H | N | Y |
| 169 | 159 | 392 | 156 | T | S | K |
| 170 | 160 | 393 | 157 | F | Q | T |
| 171 | 161 | 394 | 158 | P | E | T |
| 172 | 162 | 395 | 159 | A | S | P |
| 173 | 163 | 396 | 160 | V | V | P |
| 174 | 164 | 397 | 161 | L | T | V |
| 175 | 165 | 398 | 162 | Q | E | L |
| 176 | 166 | 399 | 163 | S | Q | D |
| 177 | 167 | 400 | 164 | S | D | S |
| 178 | 168 | 401 | 165 | G | S | D |
| 179 | 169 | 402 | 166 | L | K | G |
| 180 | 170 | 403 | 167 | Y | D | S |
| 181 | 171 | 404 | 168 | S | S | F |
| 182 | 172 | 405 | 169 | L | T | F |
| 183 | 173 | 406 | 170 | S | Y | L |
| 184 | 174 | 407 | 171 | S | S | Y |
| 185 | 175 | 408 | 172 | V | L | S |
| 186 | 176 | 409 | 173 | V | S | K |
| 187 | 177 | 410 | 174 | T | S | L |
| 188 | 178 | 411 | 175 | V | T | T |

TABLE 2-continued

Fc region sequences of constituent polypeptides

| Numbering Schemes Kabat numbering of CH2-CH1 construct | Kabat numbering of CH2-CL construct | Kabat numbering of CH2-CH3 construct | Sequential numbering of the constructs | Basic Constructs Amino acid present in a given position in CH2_CH1 construct | Amino acid present in a given position in CH2_CL construct | Amino acid present in a given position in CH2_CH3 construct |
|---|---|---|---|---|---|---|
| 189 | 179 | 412 | 176 | P | L | V |
| 190 | 180 | 413 | 177 | S | T | D |
| 191 | 181 | 414 | 178 | S | L | K |
| 192 | 182 | 415 | 179 | S | S | S |
| 193 | 183 | 416 | 180 | L | K | R |
| 194 | 184 | 417 | 181 | G | A | W |
| 195 | 185 | 418 | 182 | T | D | Q |
| 196 | 186 | 419 | 183 | Q | Y | Q |
| 197 | 187 | 420 | 184 | T | E | G |
| 198 | 188 | 421 | 185 | Y | K | N |
| 199 | 189 | 422 | 186 | I | H | V |
| 200 | 190 | 423 | 187 | C | K | F |
| 201 | 191 | 424 | 188 | N | V | S |
| 202 | 192 | 425 | 189 | V | Y | C |
| 203 | 193 | 426 | 190 | N | A | S |
| 204 | 194 | 427 | 191 | H | C | V |
| 205 | 195 | 428 | 192 | K | E | M |
| 206 | 196 | 429 | 193 | P | V | H |
| 207 | 197 | 430 | 194 | S | T | E |
| 208 | 198 | 431 | 195 | N | H | A |
| 209 | 199 | 432 | 196 | T | Q | L |
| 210 | 200 | 433 | 197 | K | G | H |
| 211 | 201 | 434 | 198 | V | L | N |
| 212 | 202 | 435 | 199 | D | S | H |
| 213 | 203 | 436 | 200 | K | S | Y |
| 214 | 204 | 437 | 201 | K | P | T |
| 215 | 205 | 438 | 202 | V | V | Q |
| 216 | 206 | 439 | 203 | E | T | K |
| 217 | 207 | 440 | 204 | P | K | S |
| 218 | 208 | 441 | 205 | K | S | L |
| 219 | 209 | 442 | 206 | S | F | S |
| 220 | 210 | 443 | 207 | C | N | L |
| 221 | 211 | | 208 | D | R | |
| | 212 | | 209 | | G | |
| | 213 | | 210 | | E | |
| | 214 | | 211 | | C | |

Example 1. Expression and Purification of Binding Molecules with Dimeric Fc Domains The following experiment tested the production of dimeric binding molecules with homodimeric (CH2-CH3) and heterodimer (CH2-CH1 and CH2-CL) Fc domains. The sequences of the Fc regions of the constituent peptides of these molecules can be found in Table 3 below.

TABLE 3

Heterodimeric and homodimeric Fc sequences.

```
>homodimeric Fc chain H (strep-BHA10 scFv-CH2-CH3) (SEQ ID NO: 50)
METDTLLLWVLLLWVPGSTGDVWSHPQFEKQVQLVQSGAEVKKPGSSVKVSCKASGYTFT
TYYLHWVRQAPGQCLEWMGWIYPGNVHAQYNEKFKGRVTITADKSTSTAYMELSSLRSED
TAVYYCARSWEGFPYWGQGTTVTVSSGGGGSGGGGSGGGGSDIQMTQSPSSLSASVGDRV
TITCKASQNVGINVAWYQQKPGKAPKSLISSASYRYSGVPSRFSGSGSGTDFTLTISSLQ
PEDFATYFCQQYDTYPFTFGCGTKVEIKGGGGSGGGGSEPKSCDKTHTCPPCPAPELLGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDE
LTKNQVSLTCLVKGFYPSDIAVEWESNGQPENNYKTTPPVLDSDGSFFLYSKLTVDKSRW
QQGNVFSCSVMHEALHNHYTQKSLSLSPG >homodimeric Fc chain L (flag-CH2-CH3) (SEQ ID NO: 51)
METDTLLLWVLLLWVPGSTGDVDYKDDDDKEPKSCDKTHTCPPCPAPELLGGPSVFLFPP
KPKDTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSC
SVMHEALHNHYTQKSLSLSPG >heterodimeric (CH1CL) Fc chain H (strep-BHA10 scFv-CH2-CH1)
(SEQ ID NO: 52)
METDTLLLWVLLLWVPGSTGDVWSHPQFEKQVQLVQSGAEVKKPGSSVKVSCKASGYTFT
TYYLHWVRQAPGQCLEWMGWIYPGNVHAQYNEKFKGRVTITADKSTSTAYMELSSLRSED
```

TABLE 3-continued

Heterodimeric and homodimeric Fc sequences.

```
TAVYYCARSWEGFPYWGQGTTVTVSSGGGGSGGGGSGGGGSDIQMTQSPSSLSASVGDRV
TITCKASQNVGINVAWYQQKPGKAPKSLISSASYRYSGVPSRFSGSGSGTDFTLTISSLQ
PEDFATYFCQQYDTYPFTFGCGTKVEIKGGGGSGGGGSEPKSCDKTHTCPPCPAPELLGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAASTKGPSVFPLAPSSKST
SGGTAALGCLVKDYFPEPVTVSWNSGALTSGVHTFPAVLQSSGLYSLSSVVTVPSSSLGT
QTYICNVNHKPSNTKVDKKVEPKSC

>heterodimeric Fc chain L (flag-CH2-CL) (SEQ ID NO: 53)
METDTLLLWVLLLWVPGSTGDVDYKDDDDKEPKSCDKTHTCPPCPAPELLGGPSVFLFPP
KPKDTLMISRTPEVTCVVVDVSHEDPEVKFNWYVDGVEVHNAKTKPREEQYNSTYRVVSV
LTVLHQDWLNGKEYKCKVSNKALPAPIEKTISKARTVAAPSVFIFPPSDEQLKSGTASVV
CLLNNFYPREAKVQWKVDNALQSGNSQESVTEQDSKDSTYSLSSTLTLSKADYEKHKVYA
CEVTHQGLSSPVTKSFNRGEC
```

FIG. 3A illustrates the constituent polypeptide chains for a bispecific homodimeric Fc domain binding molecule ("Fc"). The larger chain H includes a strep tag and a scFv fragment of the antibody BHA10 at its N-terminus, followed by hinge, CH2, and CH3 regions of a wild-type IgG1 Fc. The smaller chain L consists of a flag tag followed by the same hinge, CH2, and CH3 regions of the IgG1 Fc. The dimerization of these two molecules is mediated primarily by the hinge and CH3 regions. Since the Fc regions of the two chains are identical, dimeric molecules are expected to be a mixture of HH, HL, and LL pairs.

FIG. 3B shows the constituent polypeptide chains for a bispecific heterodimeric Fc domain binding molecule ("CH1CL") The larger chain H includes the same strep tag and scFv as in "Fc" chain H, but it has a CH1 domain in place of the CH3 domain. The smaller chain L of the CH1CL mixture consists of the same flag tag and CH2 domain as "Fc" chain L, but it has a CL domain in place of the CH3 domain. Dimerization of these two chains is expected to be mediated by the pairing of the CH1 and CL domains. Therefore, we expect that dimeric "CH1CL" molecules will consist of a higher proportion of HL heterodimers (and correspondingly fewer HH and LL pairs) than would be seen if the two chains paired at random.

These two molecules ("Fc" and "CH1CL", each of which consists of the two chains described above) were expressed in DG44 CHO cells according to previously described methods. To affinity purify the Fc and CHCL binding molecules that resulted (see FIG. 3), the CHO cell fermentation medium (1 L) was adjusted to pH 7.0 and the proteins were affinity captured on a ProteinG columns that had been previously equilibrated in binding buffer (100 mM NaPO$_4$, pH 7, 150 mM NaCl). The columns were washed in binding buffer until the A280 trace reached baseline and the bound molecules were eluted in 25 mM glycine pH 2.8, 100 mM sodium chloride. Fractions were immediately neutralized by addition of 0.1 volumes 1M Tris buffer, pH 8. Protein in A280 absorbing fractions were analyzed by reducing and non-reducing SDS-PAGE, pooled and concentrated for further purification by size-exclusion chromatography. Single-chain (i.e., monomeric constituent peptides) molecules were separated from double-chain (i.e., dimeric) binding molecules on a Superdex 200 gel filtration column in PBS, pH7.

Figure 4B:
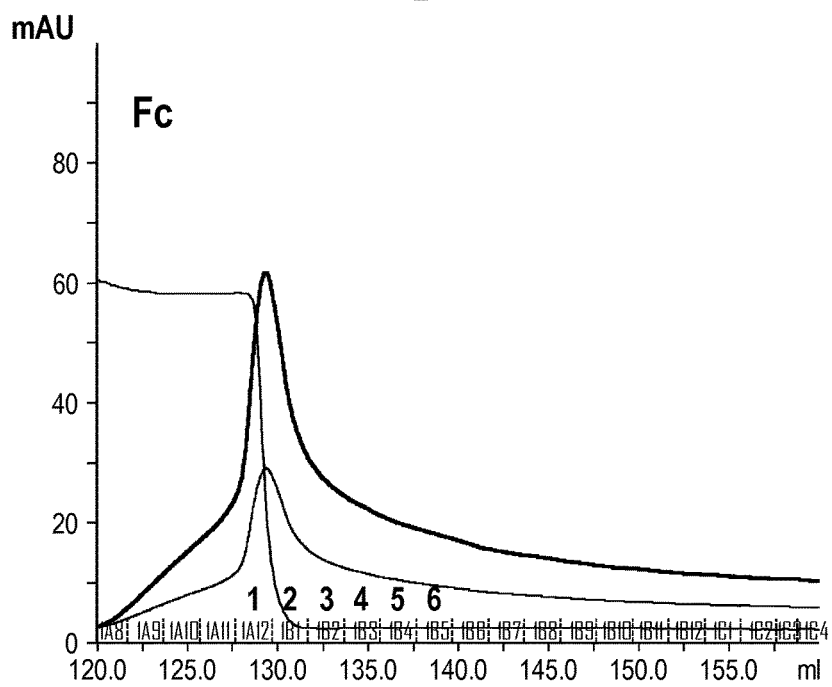

FIG. 4 A-D show the results of the purification process for separating monomeric (e.g., non-dimerized, single chain constituent polypeptides) molecules from dimeric molecules. The purification process employed affinity chromatography followed by gel filtration chromatography. FIGS. 4A and 4B show the absorbance profile of column fractions eluted at low pH from the ProteinG affinity column for the CH1CL pair and the Fc pair, respectively. FIGS. 4C and 4D show the corresponding SD-PAGE analysis of those eluted fractions which contain dimeric (HH, HL and LL) and monomeric (H and L) forms of the Fc and CHCL binding molecules. Both the monomeric and dimeric forms eluted essentially as a single peak from the protein G column. FIG. 4C shows that in the case of the CH1CL heterodimer, there is a significantly higher proportion of heterodimeric HL molecules than the homodimeric HH molecules. The homodimeric LL molecules, if present, would not be captured by Protein G since they do not contain the CH1 or CH3 Protein G binding sites. FIG. 4D, by contrast, shows that chains 1 and 2 pair essentially at random, yielding significant quantities of HH, HL, and LL pairs.

Figure 5B:
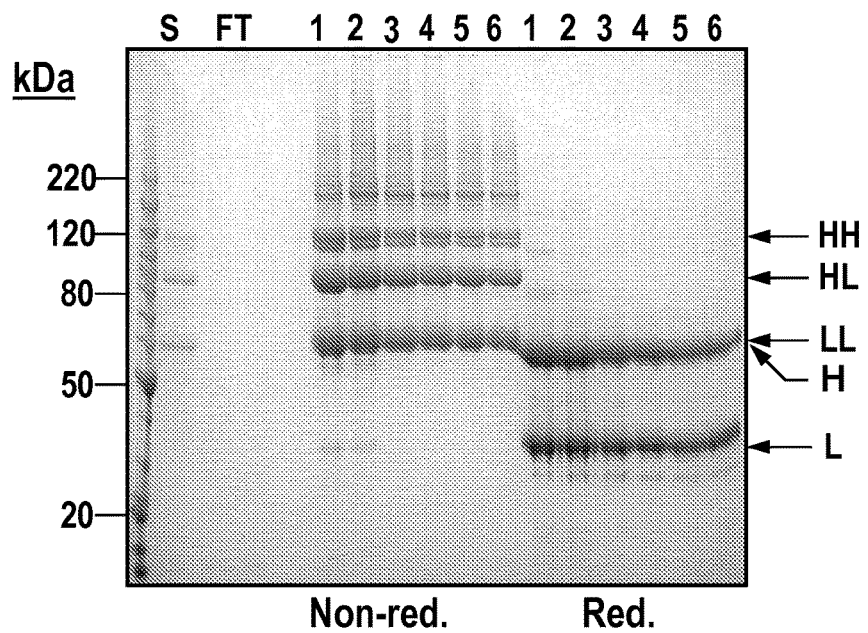

FIGS. 5 A-D show the results of size fractionation analysis with Superdex 200 gel filtration columns on dimer binding molecule pools. FIG. 5A shows the elution fraction peaks and FIGS. 5C and 5D show corresponding SDS-PAGE analysis of the gel filtration eluates. As in the protein G eluates, the CH1CL molecule shows significant enrichment of the heterodimeric HL over the possible HH homodimers. As expected, the "Fc" molecule shows a mixture of HH, HL, and LL dimers without significant enrichment of heterodimers over homodimers.

Example 2. Modeling and Design of FcRn-Binding Heterodimeric Binding Molecules

Functionality of heterodimeric binding molecules can be added to binding molecules of the invention by making alterations to the sequences of the constituent polypeptide chains of a binding molecule, e.g., by altering solvent accessible residues found on or close to the surface of the three dimensional constituent polypeptide chain structure. The following experiment describes methods for adding FcRn-binding functionality to the CH1 and CL domains of a heterodimeric binding molecule.

CH2-CH1/CH2-CL Heterodimeric Fc Constructs

The Fc portion of a native IgG molecule comprises a homodimer whose interface consists of a CH2 domain and a CH3 domain. As shown in Example 1 above, the initial constructs used as the starting material for FcRn-binding heterodimeric binding molecules were (1) the CH2-CH1 construct, which comprises an Fc chain where the CH3 domain (residues 341-445 in EU numbering for IgG1) is replaced by the CH1 domain residues 118-221 of IgG1 in EU numbering; and (2) the CH2-CL construct, which also replaces CH3 domain (residues 341-445) with a kappa chain constant domain CL, residues 108-214. (In this example, residue numbers in these constructs refer to the CH1 or CL domains from which the residues originally came. Thus, in the CH2-CH1 construct, residues 118-221 of CH1 are found C-terminal to residues 216-340 of CH2 (i.e., the residue numbering from N-term to C-term begins with 216-340, which is immediately followed by residues 118-221)).

Fc/FcRn Complex Structure

As a first step in the design of the FcRn-binding heterodimeric binding molecule, a homology model of the human Fc/FcRn receptor complex was built using the program MODELLER (Sali, A, Blundell T L. J Mol Biol (1993) 234, 779-815) with the rat Fc/FcRn complex crystal structure of Martin et al. (*Mol. Cell* (2001), 7, 867-877) as a template (PDB ID 1I1A). This template structure comprises one FcRn-binding Fc chain and a second Fc polypeptide chain that had been altered so that it did not bind FcRn (in order to avoid crosslinking and facilitate crystallization). Only the FcRn-binding chain was carried forward to analyze the Fc/FcRn interface of human IgG.

Sequence alignments of rat Fc/FcRn with their human orthologs were performed with the program CLUSTALW.

Structural alignment of CH1 and CL domains

As noted above, the two CH3 domains in separate chains of Fc had been replaced with one CH1 and one CL domain to generate the Fc region of the heterodimeric molecule. For the design process described below, the sequences of CH1 and CL were aligned with the CH3 sequence using the program CLUSTALW, while the three-dimensional CH1 and CL domain crystal structures were obtained from the intact IgG1 structure of Saphire et al. (Science (2001) 293:1155-1159) (pdb code 1hzh).

The CH1 domain of IgG1 was superimposed on the CH3 domain from the FcRn complex structure using a least-square fit of the backbone $C_\alpha$'s. The amino acid sequence alignment for the CH1 and CH3 domains was then reexamined alongside the three-dimensional structures in order to make sure that matched residues in the alignment were actually matched in the structures. In particular, as seen in FIG. 9, the structure-based sequence alignment was edited in the CH1 loop between Val202 and Lys210 (EU numbering for the native CH1 domain, located at positions 89 and 98, respectively, of the figure's sequence alignment numbering). In the structures, Val202 of CH1 is aligned with Val427 (position 89) of CH3 in one β-strand, and Lys210 of CH1 is aligned with Tyr436 (position 98) at the beginning of a subsequent β-strand. A gap was inserted into the original sequence alignment for CH1 (opposite CH3 His435, at position 97) so that both these residue pairs were aligned correctly.

The CL domain was similarly superimposed on the same CH3 domain from the FcRn complex structure. The sequence alignment of CL and CH3 was also modified to obtain a structure-based sequence alignment. As in the CH1/CH3 comparison, most of the CL/CH3 sequence alignment was unchanged except for the loop between CH3 residues Val427 and Thr437 (positions 89 and 98 in FIG. 9, respectively). In the structure, these two residues were aligned with CL residues Val196 and Val205, respectively. A gap was inserted into the sequence alignment for CL opposite CH3 His435 so that both these residue pairs were aligned Addition of FcRn-Binding Elements to CH2-CL Domain The human Fc/FcRn complex structure model was searched for CH3 residues within 6 Angstroms of the FcRn subunit. These interface residues are important for FcRn binding, and therefore were incorporated into the CL domain to allow the new CH2-CL construct to bind FcRn. The CH3 residues at the interface are all in the loop extending from Met428 to Tyr436 (native CH3 domain EU numbering, located at positions 90 and 98, respectively, in the sequence alignment of FIG. 9). The objective was to give the new constructs pH-dependent FcRn-binding behavior like that of native Fc. The pH-dependence of FcRn binding in the native complex depends upon two key histidines (Martin, W L et al. Mol. Cell (2001), 7:867-877), which in the human sequence are His435 and His310. Binding affinity of Fc is completely lost if either of these His residues is mutated to Ala (Shields, R L et al. J. Biol. Chem. (2001) 276: 6591-6604). Charged residues of CH3 contribute to pH-dependence binding of FcRn even if they are not part of the interface. The loop was extended to include residues within 8 Å that change charge between CL and CH3. Therefore the loop consisting of CH3 residues 428-436 was expanded to include Ser426, which is Glu in the CL domain, and Val427, which is conserved between the two domains (located at positions 88 and 89 in FIG. 9, respectively). Since Cys194 in CL (position 87 in FIG. 9) is well-aligned structurally with the conserved Cys425 in CH3 (both form an intradomain disulfide bond), and Val205 in CL (position 99 in FIG. 9) is aligned with Thr437 (0.6 A apart), these residues were chosen as the N- and C-terminal splice sites for the FcRn-binding loop of CH3. Residues 426-436 of CH3 were spliced in place of residues 195-204 from CL in all the CH2-CL constructs.

In addition to the FcRn contacting loop, the residues connecting the CH2 and CH3 domains in a native IgG1 molecule were incorporated into the CH2-CL constructs in order to maintain the correct geometry of the domain linker. Residues 341-345 from CH3 (positions 1-6 of FIG. 9) were incorporated in place of residues 108-112 from CL. Pro113 was retained in CL, since it is conserved as Pro346 in CH3.

The first construct shown in Table 3 (below) comprises these two substitutions. Additional elements of the CH3 domain were included in constructs 2 and 3 to increase FcRn binding affinity. The substitution in these additional constructs occurred in the region from residues 142-155 of CL, which contacts the main FcRn binding loop described above (residues 195-204) and also forms intramolecular contacts with CH2. The second construct shown in Table 3 has the CH3 residues 375-380 spliced in place of CL residues 142-147. These residues make intramolecular contacts with the CH2 domain, and charged residues such as Glu380 from CH3 or Lys 145 from CL affect the pH dependence of FcRn binding. The mutations assist in keeping the CH2/CL domains oriented as the CH2/CH3 domains are when they bind FcRn.

The third construct includes a larger spliced loop: residues 142-155 of CL are replaced with residues 375-388 of CH3. The first several residues are in the same loop as the residues mutated above for the second construct. The additional residues have a structural role, and therefore they were mutated in the third construct.

When the CH1/CL heterodimers were superimposed on a CH3 homodimer, the CH1 and CL domains had conformations that were twisted relative to one another in a way that was different from the native pair of CH3 domains. The structures indicated that the CL N-terminus in the new constructs is displaced by 6-8 A relative to the native CH3 domain. Therefore, three additional constructs were made to allow the CL domain to move with respect to the CH2 domain. Constructs 4-6 correspond to constructs 1-3 with an additional Gly-Ser linker inserted just after residue 340 of CH2 (i.e., immediately N-terminal to the N-terminal-most CH3/CL sequence replacement, at positions 1-5 of FIG. 9). The Gly-Ser linker allows additional flexibility for the CH1 domain to move relative to the CH2 domain so that CH1 can still form an interface with CL. Similarly, constructs 7-9 correspond to constructs 1-3 with a Gly-Gly-Gly-Ser linker to allow still more flexibility.

Table 3 below shows the sequences of CH2-CL constructs c1-c9, each of which were designed to be paired with any one of the CH2-CH1 constructs d1-d8 of Table 4 in the heterodimeric binding molecules of the invention. The CH2 domains comprise native IgG1 sequence. Constructs c1-c3 have progressively more CH3 sequence spliced into the CL domain. Constructs c4-c6 are identical to constructs c1-c3, respectively, but with the addition of a Gly-Ser linker at the start of the CL domain to provide flexibility for the formation of the three-dimensional structure of the CH2-CL portion of the constituent peptide chain. Likewise, constructs c7-c9 are identical to c1-c3, respectively, but comprise a GGGS (SEQ ID NO: 22) linker. Sequence in the constructs that has been changed from the original CH2-CL construct are shown in bold and the hinge sequence is underlined.

TABLE 4

CH2-CL amino acid sequences:

>c0 hinge-CH2-CL (reference)(SEQ ID NO: 27):
<u>EPKSSDKTHTCPPCP</u>APELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC >c1 hinge-CH2-CL (SEQ ID NO: 28)
<u>EPKSSDKTHTCPPCP</u>APELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGQPREPSVFIFPPSDEQLKSGTASVVCLLNNEYPREAKVQWKVDNALQSGNS
QESVTEQDSKDSTYSLSSTLTLSKADYEKHKVYACSVMHEALHNHYVTKSFNRGEC >c2 hinge-CH2-CL (SEQ ID NO: 29)
<u>EPKSSDKTHTCPPCP</u>APELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGQPREPSVFIFPPSDEQLKSGTASVVCLLNNEYPSDIAVEWKVDNALQSGNS
QESVTEQDSKDSTYSLSSTLTLSKADYEKHKVYACSVMHEALHNHYVTKSFNRGEC >c3 hinge-CH2-CL (SEQ ID NO: 30)
<u>EPKSSDKTHTCPPCP</u>APELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGQPREPSVFIFPPSDEQLKSGTASVVCLLNNEYPSDIAVEWESNGQPESGNS
QESVTEQDSKDSTYSLSSTLTLSKADYEKHKVYACSVMHEALHNHYVTKSFNRGEC >c4 hinge-CH2-CL (SEQ ID NO: 31)
<u>EPKSSDKTHTCPPCP</u>APELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGSGQPREPSVFIFPPSDEQLKSGTASVVCLLNNEYPREAKVQWKVDNALQSG
NSQESVTEQDSKDSTYSLSSTLTLSKADYEKHKVYACSVMHEALHNHYVTKSFNRGEC >c5 hinge-CH2-CL (SEQ ID NO: 32)
<u>EPKSSDKTHTCPPCP</u>APELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGSGQPREPSVFIFPPSDEQLKSGTASVVCLLNNEYPSDIAVEWKVDNALQSG
NSQESVTEQDSKDSTYSLSSTLTLSKADYEKHKVYACSVMHEALHNHYVTKSFNRGEC >c6 hinge-CH2-CL (SEQ ID NO: 33)
<u>EPKSSDKTHTCPPCP</u>APELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGSGQPREPSVFIFPPSDEQLKSGTASVVCLLNNEYPSDIAVEWESNGQPESG
NSQESVTEQDSKDSTYSLSSTLTLSKADYEKHKVYACSVMHEALHNHYVTKSFNRGEC >c7 hinge-CH2-CL (SEQ ID NO: 34)
<u>EPKSSDKTHTCPPCP</u>APELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGGGSGQPREPSVFIFPPSDEQLKSGTASVVCLLNNEYPREAKVQWKVDNALQ
SGNSQESVTEQDSKDSTYSLSSTLTLSKADYEKHKVYACSVMHEALHNHYVTKSFNRGE
C >c8 hinge-CH2-CL (SEQ ID NO: 35)
<u>EPKSSDKTHTCPPCP</u>APELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGGGSGQPREPSVFIFPPSDEQLKSGTASVVCLLNNEYPSDIAVEWKVDNALQ
SGNSQESVTEQDSKDSTYSLSSTLTLSKADYEKHKVYACSVMHEALHNHYVTKSFNRGE
C >c9 hinge-CH2-CL (SEQ ID NO: 36)
<u>EPKSSDKTHTCPPCP</u>APELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGGGSGQPREPSVFIFPPSDEQLKSGTASVVCLLNNEYPSDIAVEWESNGQPE
SGNSQESVTEQDSKDSTYSLSSTLTLSKADYEKHKVYACSVMHEALHNHYVTKSFNRGE
C Addition of FcRn-Binding Elements to CH2-CH1 Domain The overall procedure was similar to that used for the CH2-CL domain. The Fc/FcRn complex structure was sear TABLE 5-continued CH2-CH1 amino acid sequences:

>d4 hinge-CH2-CH1 portion (SEQ ID NO: 41)
EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGQPREPSVFPLAPSSKSTSGGTAALGCLVKDFYPSDIAVEWESNGQPENNYH
TFPAVLQSSGLYSLSSVVTVPSSSLGTNTYICSVMHEALHNHYVQKSVEPKSC >d5 hinge-CH2-CH1 portion (SEQ ID NO: 42)
EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGSGQPREPSVFPLAPSSKSTSGGTAALGCLVKDYFPEPVTVSWNSGALTSGV
HTFPAVLQSSGLYSLSSVVTVPSSSLGTQTYICNVMHEALHNHYVDKKVEPKSC >d6 hinge-CH2-CH1 portion (SEQ ID NO: 43)
EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGSGQPREPSVFPLAPSSKSTSGGTAALGCLVKDYYPSDVAVSWNSGALTSGV
HTFPAVLQSSGLYSLSSVVTVPSSSLGTQTYICNVMHEALHNHYVDKKVEPKSC >d7 hinge-CH2-CH1 portion (SEQ ID NO: 44)
EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGSGQPREPSVFPLAPSSKSTSGGTAALGCLVKDFYPSDIAVEWESGALTSGV
HTFPAVLQSSGLYSLSSVVTVPSSSLGTQTYICSVMHEALHNHYVQKSVEPKSC >d8 hinge-CH2-CH1 portion (SEQ ID NO: 45)
EPKSSDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIE
KTISKAKGSGQPREPSVFPLAPSSKSTSGGTAALGCLVKD**FYPSDIAVEWESNGQPENN
YHTFPAVLQSSGLYSLSSVVTVPSSSLGTNTYICSVMHEALHNHY**VQKSVEPKSC

Example 3. Addition of Functionality to FcRn Optimized Heterodimeric Molecules Additional sequences, such as a secretion signal or a peptide tag, may be added to the sequences provided in Example 2 to construct heterodimeric binding molecules with additional functionalities. The following designs feature CL constant domain constituent polypeptide chains as disclosed above, further comprising a humanized 5C8 secretion signal and a FLAG peptide tag, as well as $CH_1$ constant domain constitutent polypeptide chains as disclosed above, further comprising a humanized 5C8 secretion signal, a STREP-tag II peptide tag, and a BHA10 scFv antibody fragment that binds LTβR.

Table 6 presents ten sequences that are used as part of the sequence of a constituent polypeptide chain of the binding molecules of the invention whose designs are presented below in Table 7. A person with skill in the art will appreciate that these sequences do not need to appear in the exact order given in the following three designs in order to create binding molecules of the invention.

TABLE 6

Sequence Modules used in Exemplary $CH_2$-$CH_1$ / $CH_2$-CL Heterodimeric Binding Molecules

| Description | Sequence |
| --- | --- |
| Humanized 5C8 secretion signal | MDWTWRVFCLLAVAPGAHS (SEQ ID NO: 54) |
| STREP-TAG II (IBA) | WSHPQFEK (SEQ ID NO: 55) |
| Linker and S16E, V55G stabilized BHA10 SCFV $V_H$ | QVQLVQSGAEVKKPGESVKVSCKA SGYTFTTYYLHWVRQAPGQGLEW MGWIYPGNGHAQYNEKFKGRVTI TADKSTSTAYMELSSLRSEDTAVY YCARSWEGFPYWGQGTTVTVSS (SEQ ID NO: 56) |
| $G_4$S linker (one unit shown; may be repeated) | GGGGS (SEQ ID NO: 57) |
| Linker and S46L stabilized BHA10 scFv $V_L$ | DIQMTQSPSSLSASVGDRVTITCKA SQNVGINVAWYQQKPGKAPKLLIS SASYRYSGVPSRFSGSGSGTDFTLT ISSLQPEDFATYFCQQYDTYPFTFG QGTKVEIK (SEQ ID NO: 58) |
| CL cysteine-scrubbed IgG$_1$ hinge IgG$_1$ CH$_2$ | EPKSSDKTHTCPPCP (SEQ ID NO: 59) APELLGGPSVFLFPPKPKDTLMISR TPEVTCVVVDVSHEDPEVKFNWY VDGVEVHNAKTKPREEQYNSTYR |

TABLE 6-continued

Sequence Modules used in Exemplary CH₂-CH₁ / CH₂-CL Heterodimeric Binding Molecules

| Description | Sequence |
|---|---|
| | VVSVLTVLHQDWLNGKEYKCKV SNKALPAPIEKTISKAK (SEQ ID NO: 60) |
| IgG₁ C_L with terminal cysteine (original sequence presented here; additional mutations are indicated within constituent polypeptide chain designs) | RTVAAPSVFIFPPSDEQLKSGTAS VVCLLNNFYPREAKVQWKVDNA LQSGNSQESVTEQDSKDSTYSLSS TLTLSKADYEKHKVYACEVTHQ GLSSPVTKSFNRGEC (SEQ ID NO: 61) |
| FLAG tag | *DYKDDDDK* (SEQ ID NO: 62) |
| IgG₁ C_H1 with terminal cysteine (original sequence presented here; additional mutations are indicated within constituent polypeptide chain designs) | ASTKGPSVFPLAPSSKSTSGGTAA LGCLVKDYFPEPVTVSWNSGALT SGVHTFPAVLQSSGLYSLSSVVTV PSSSLGTQTYICNVNHKPSNTKVD KKVEPKSC (SEQ ID NO: 63) |

In Table 7 below, constituent polypeptide chains for exemplary binding molecules are presented. The polypeptide chains of the first group, c0-c9 (Flag-IgG1 Hinge+CH2+CL constructs), each contain a CL moiety and the polypeptide chains of the second group, d0-d8 (IBA-scFv BHA10-IgG1Hinge+CH2+CH1 constructs), each contain a CH₁ moiety. As in Example 2 above, the first polypeptide chain of each group, i.e. c0 and d0, contain CL and CH₁ moieties, respectively, that lack any of the modifications detailed in Example 2. Subsequent polypeptide chains contain modifications to the CL and CH₁ sequences as described supra (modifications to the sequences are underlined).

One constituent polypeptide chain from each group, i.e. one from the c group and one from the d group, may be expressed in a host cell to generate exemplary binding molecules of the invention. The individual modular sequences within each chain are indicated through alternating font changes (i.e., first sequence second sequence third sequence fourth sequence, etc.).

TABLE 7

Exemplary sequences

```
>c0 (reference) (SEQ ID NO: 80)
MDWTWRVFCLLAVAPGAHSDYKDDDDKEPKSSDKTHTCPPCPAPELLGGPSVF
LFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKRTVAAPSVFIF
PPSDEQLKSGTASVVCLLNNFYPREAKVQWKVDNALQSGNSQESVTEQDSKDST
YSLSSTLTLSKADYEKHKVYACEVTHQGLSSPVTKSFNRGEC >c1 (SEQ ID NO: 81)
MDWTWRVFCLLAVAPGAHSDYKDDDDKEPKSSDKTHTCPPCPAPELLGGPSVF
LFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPSVFIF
PPSDEQLKSGTASVVCLLNNFYPREAKVQWKVDNALQSGNSQESVTEQDSKDST
YSLSSTLTLSKADYEKHKVYACSVMHEALHNHYVTKSFNRGEC >c2 (SEQ ID NO: 82)
MDWTWRVFCLLAVAPGAHSDYKDDDDKEPKSSDKTHTCPPCPAPELLGGPSVF
LFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPSVFIF
PPSDEQLKSGTASVVCLLNNFYPSDIAVEWKVDNALQSGNSQESVTEQDSKDST
YSLSSTLTLSKADYEKHKVYACSVMHEALHNHYVTKSFNRGEC >c3 (SEQ ID NO: 83)
MDWTWRVFCLLAVAPGAHSDYKDDDDKEPKSSDKTHTCPPCPAPELLGGPSVF
LFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPSVFIF
PPSDEQLKSGTASVVCLLNNFYPSDIAVEWESNGQPESGNSQESVTEQDSKDSTY
SLSSTLTLSKADYEKHKVYACSVMHEALHNHYVTKSFNRGEC >c4 (SEQ ID NO: 84)
MDWTWRVFCLLAVAPGAHSDYKDDDDKEPKSSDKTHTCPPCPAPELLGGPSVF
LFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGSGQPREPSVF
IFPPSDEQLKSGTASVVCLLNNFYPREAKVQWKVDNALQSGNSQESVTEQDSKD
STYSLSSTLTLSKADYEKHKVYACSVMHEALHNHYVTKSFNRGEC >c5 (SEQ ID NO: 85)
MDWTWRVFCLLAVAPGAHSDYKDDDDKEPKSSDKTHTCPPCPAPELLGGPSVF
LFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGSGQPREPSVF
```

TABLE 7-continued

Exemplary sequences

IFPPSDEQLKSGTASVVCLLNNFYPSDIAVEWKVDNALQSGNSQESVTEQDSKDS
TYSLSSTLTLSKADYEKHKVYACSVMHEALHNHYVTKSFNRGEC

>c6 (SEQ ID NO: 86)
MDWTWRVFCLLAVAPGAHS*DYKDDDDK*EPKSSDKTHTCPPCP***APELLGGPSVF
LFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAK***GSGQPREPSVF
IFPPSDEQLKSGTASVVCLLNNFYPSDIAVEWESNGQPESGNSQESVTEQDSKDST
YSLSSTLTLSKADYEKHKVYACSVMHEALHNHYVTKSFNRGEC

>c7 (SEQ ID NO: 87)
MDWTWRVFCLLAVAPGAHS*DYKDDDDK*EPKSSDKTHTCPPCP***APELLGGPSVF
LFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAK***GGGSGQPREP
SVFIFPPSDEQLKSGTASVVCLLNNFYPREAKVQWKVDNALQSGNSQESVTEQD
SKDSTYSLSSTLTLSKADYEKHKVYACSVMHEALHNHYVTKSFNRGEC

>c8 (SEQ ID NO: 88)
MDWTWRVFCLLAVAPGAHS*DYKDDDDK*EPKSSDKTHTCPPCP***APELLGGPSVF
LFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAK***GGGSGQPREP
SVFIFPPSDEQLKSGTASVVCLLNNFYPSDIAVEWKVDNALQSGNSQESVTEQDS
KDSTYSLSSTLTLSKADYEKHKVYACSVMHEALHNHYVTKSFNRGEC

>c9 (SEQ ID NO: 89)
MDWTWRVFCLLAVAPGAHS*DYKDDDDK*EPKSSDKTHTCPPCP***APELLGGPSVF
LFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAK***GGGSGQPREP
SVFIFPPSDEQLKSGTASVVCLLNNFYPSDIAVEWESNGQPESGNSQESVTEQDSK
DSTYSLSSTLTLSKADYEKHKVYACSVMHEALHNHYVTKSFNRGEC

>d0(reference) (SEQ ID NO: 90)
MDWTWRVFCLLAVAPGAHS*WSHPQFEK*QVQLVQSGAEVKKPGESVKVSCKAS
GYTFTTYYLHWVRQAPGQGLEWMGWIYPGNGHAQYNEKFKGRVTITADKSTST
AYMELSSLRSEDTAVYYCARSWEGFPYWGQGTTVTVSS***GGGGSGGGGSGGGGS
GGGGS***DIQMTQSPSSLSASVGDRVTITCKASQNVGINVAWYQQKPGKAPKLLISS
ASYRYSGVPSRFSGSGSGTDFTLTISSLQPEDFATYFCQQYDTYPFTFGQGTKVEI
K*GGGGSGGGGS*EPKSSDKTHTCPPCP***APELLGGPSVFLFPPKPKDTLMISRTPEV
TCVVVDVSHEDPEVKFNWYVDGVEVHNAKTKPREEQYNSTYRVVSVLTVLHQD
WLNGKEYKCKVSNKALPAPIEKTISKAK***ASTKGPSVFPLAPSSKSTSGGTAALGCL
VKDYFPEPVTVSWNSGALTSGVHTFPAVLQSSGLYSLSSVVTVPSSSLGTQTYIC
NVNHKPSNTKVDKKVEPKSC >d1 (SEQ ID NO: 91)
MDWTWRVFCLLAVAPGAHS*WSHPQFEK*QVQLVQSGAEVKKPGESVKVSCKAS
GYTFTTYYLHWVRQAPGQGLEWMGWIYPGNGHAQYNEKFKGRVTITADKSTST
AYMELSSLRSEDTAVYYCARSWEGFPYWGQGTTVTVSS***GGGGSGGGGSGGGGS
GGGGS***DIQMTQSPSSLSASVGDRVTITCKASQNVGINVAWYQQKPGKAPKLLISS
ASYRYSGVPSRFSGSGSGTDFTLTISSLQPEDFATYFCQQYDTYPFTFGQGTKVEI
K*GGGGSGGGGS*EPKSSDKTHTCPPCP***APELLGGPSVFLFPPKPKDTLMISRTPEV
TCVVVDVSHEDPEVKFNWYVDGVEVHNAKTKPREEQYNSTYRVVSVLTVLHQD
WLNGKEYKCKVSNKALPAPIEKTISKAK***GQPREPSVFPLAPSSKSTSGGTAALGCL
VKDYFPEPVTVSWNSGALTSGVHTFPAVLQSSGLYSLSSVVTVPSSSLGTQTYIC
NVMHEALHNHYVDKKVEPKSC >d2 (SEQ ID NO: 92)
MDWTWRVFCLLAVAPGAHS*WSHPQFEK*QVQLVQSGAEVKKPGESVKVSCKAS
GYTFTTYYLHWVRQAPGQGLEWMGWIYPGNGHAQYNEKFKGRVTITADKSTST
AYMELSSLRSEDTAVYYCARSWEGFPYWGQGTTVTVSS***GGGGSGGGGSGGGGS
GGGGS***DIQMTQSPSSLSASVGDRVTITCKASQNVGINVAWYQQKPGKAPKLLISS
ASYRYSGVPSRFSGSGSGTDFTLTISSLQPEDFATYFCQQYDTYPFTFGQGTKVEI
K*GGGGSGGGGS*EPKSSDKTHTCPPCP***APELLGGPSVFLFPPKPKDTLMISRTPEV
TCVVVDVSHEDPEVKFNWYVDGVEVHNAKTKPREEQYNSTYRVVSVLTVLHQD
WLNGKEYKCKVSNKALPAPIEKTISKAK***GQPREPSVFPLAPSSKSTSGGTAALGCL
VKDYYPSDVAVSWNSGALTSGVHTFPAVLQSSGLYSLSSVVTVPSS SLGTQTYIC
NVMHEALHNHYVDKKVEPKSC >d3 (SEQ ID NO: 93)
MDWTWRVFCLLAVAPGAHS*WSHPQFEK*QVQLVQSGAEVKKPGESVKVSCKAS
GYTFTTYYLHWVRQAPGQGLEWMGWIYPGNGHAQYNEKFKGRVTITADKSTST
AYMELSSLRSEDTAVYYCARSWEGFPYWGQGTTVTVSS***GGGGSGGGGSGGGGS
GGGGS***DIQMTQSPSSLSASVGDRVTITCKASQNVGINVAWYQQKPGKAPKLLISS
ASYRYSGVPSRFSGSGSGTDFTLTISSLQPEDFATYFCQQYDTYPFTFGQGTKVEI
K*GGGGSGGGGS*EPKSSDKTHTCPPCP***APELLGGPSVFLFPPKPKDTLMISRTPEV
TCVVVDVSHEDPEVKFNWYVDGVEVHNAKTKPREEQYNSTYRVVSVLTVLHQD
WLNGKEYKCKVSNKALPAPIEKTISKAK***GQPREPSVFPLAPSSKSTSGGTAALGCL
VKDFYPSDIAVEWESGALTSGVHTFPAVLQSSGLYSLSSVVTVPSSSLGTQTYICS
VMHEALHNHYVQKSVEPKSC TABLE 7-continued Exemplary sequences

```
>d4 (SEQ ID NO: 94)
MDWTWRVFCLLAVAPGAHSWSHPQFEKQVQLVQSGAEVKKPGESVKVSCKAS
GYTFTTYYLHWVRQAPGQGLEWMGWIYPGNGHAQYNEKFKGRVTITADKSTST
AYMELSSLRSEDTAVYYCARSWEGFPYWGQGTTVTVSSGGGGSGGGGSGGGGS
GGGGSDIQMTQSPSSLSASVGDRVTITCKASQNVGINVAWYQQKPGKAPKLLISS
ASYRYSGVPSRFSGSGSGTDFTLTISSLQPEDFATYFCQQYDTYPFTFGQGTKVEI
KGGGGSGGGGSEPKSSDKTHTCPPCPAPELLGGPSVFLFPPKPKDTLMISRTPEV
TCVVVDVSHEDPEVKFNWYVDGVEVHNAKTKPREEQYNSTYRVVSVLTVLHQD
WLNGKEYKCKVSNKALPAPIEKTISKAKGQPREPSVFPLAPSSKSTSGGTAALGCL
VKDFYPSDIAVEWESNGQPENNYHTFPAVLQSSGLYSLSSVVTVPSS SLGTNTYIC
SVMHEALHNHYVQKSVEPKSC

>d5 (SEQ ID NO: 95)
MDWTWRVFCLLAVAPGAHSWSHPQFEKQVQLVQSGAEVKKPGESVKVSCKAS
GYTFTTYYLHWVRQAPGQGLEWMGWIYPGNGHAQYNEKFKGRVTITADKSTST
AYMELSSLRSEDTAVYYCARSWEGFPYWGQGTTVTVSSGGGGSGGGGSGGGGS
GGGGSDIQMTQSPSSLSASVGDRVTITCKASQNVGINVAWYQQKPGKAPKLLISS
ASYRYSGVPSRFSGSGSGTDFTLTISSLQPEDFATYFCQQYDTYPFTFGQGTKVEI
KGGGGSGGGGSEPKSSDKTHTCPPCPAPELLGGPSVFLFPPKPKDTLMISRTPEV
TCVVVDVSHEDPEVKFNWYVDGVEVHNAKTKPREEQYNSTYRVVSVLTVLHQD
WLNGKEYKCKVSNKALPAPIEKTISKAKGSGQPREPSVFPLAPSSKSTSGGTAALG
CLVKDYFPEPVTVSWNSGALTSGVHTFPAVLQSSGLYSLSSVVTVPSS SLGTQTYI
CNVMHEALHNHYVDKKVEPKSC

>d6 (SEQ ID NO: 96)
MDWTWRVFCLLAVAPGAHSWSHPQFEKQVQLVQSGAEVKKPGESVKVSCKAS
GYTFTTYYLHWVRQAPGQGLEWMGWIYPGNGHAQYNEKFKGRVTITADKSTST
AYMELSSLRSEDTAVYYCARSWEGFPYWGQGTTVTVSSGGGGSGGGGSGGGGS
GGGGSDIQMTQSPSSLSASVGDRVTITCKASQNVGINVAWYQQKPGKAPKLLISS
ASYRYSGVPSRFSGSGSGTDFTLTISSLQPEDFATYFCQQYDTYPFTFGQGTKVEI
KGGGGSGGGGSEPKSSDKTHTCPPCPAPELLGGPSVFLFPPKPKDTLMISRTPEV
TCVVVDVSHEDPEVKFNWYVDGVEVHNAKTKPREEQYNSTYRVVSVLTVLHQD
WLNGKEYKCKVSNKALPAPIEKTISKAKGSGQPREPSVFPLAPSSKSTSGGTAALG
CLVKDYPSDVAVSWNSGALTSGVHTFPAVLQSSGLYSLSSVVTVPSSSLGTQT
YICNVMHEALHNHYVDKKVEPKSC

>d7 (SEQ ID NO: 97)
MDWTWRVFCLLAVAPGAHSWSHPQFEKQVQLVQSGAEVKKPGESVKVSCKAS
GYTFTTYYLHWVRQAPGQGLEWMGWIYPGNGHAQYNEKFKGRVTITADKSTST
AYMELSSLRSEDTAVYYCARSWEGFPYWGQGTTVTVSSGGGGSGGGGSGGGGS
GGGGSDIQMTQSPSSLSASVGDRVTITCKASQNVGINVAWYQQKPGKAPKLLISS
ASYRYSGVPSRFSGSGSGTDFTLTISSLQPEDFATYFCQQYDTYPFTFGQGTKVEI
KGGGGSGGGGSEPKSSDKTHTCPPCPAPELLGGPSVFLFPPKPKDTLMISRTPEV
TCVVVDVSHEDPEVKFNWYVDGVEVHNAKTKPREEQYNSTYRVVSVLTVLHQD
WLNGKEYKCKVSNKALPAPIEKTISKAKGSGQPREPSVFPLAPSSKSTSGGTAALG
CLVKDFYPSDIAVEWESGALTSGVHTFPAVLQSSGLYSLSSVVTVPSSSLGTQTYI
CSVMHEALHNHYVQKSVEPKSC

>d8 (SEQ ID NO: 98)
MDWTWRVFCLLAVAPGAHSWSHPQFEKQVQLVQSGAEVKKPGESVKVSCKAS
GYTFTTYYLHWVRQAPGQGLEWMGWIYPGNGHAQYNEKFKGRVTITADKSTST
AYMELSSLRSEDTAVYYCARSWEGFPYWGQGTTVTVSSGGGGSGGGGSGGGGS
GGGGSDIQMTQSPSSLSASVGDRVTITCKASQNVGINVAWYQQKPGKAPKLLISS
ASYRYSGVPSRFSGSGSGTDFTLTISSLQPEDFATYFCQQYDTYPFTFGQGTKVEI
KGGGGSGGGGSEPKSSDKTHTCPPCPAPELLGGPSVFLFPPKPKDTLMISRTPEV
TCVVVDVSHEDPEVKFNWYVDGVEVHNAKTKPREEQYNSTYRVVSVLTVLHQD
WLNGKEYKCKVSNKALPAPIEKTISKAKGSGQPREPSVFPLAPSSKSTSGGTAALG
CLVKDFYPSDIAVEWESNGQPENNYHTFPAVLQSSGLYSLSSVVTVPSSSLGTNT
YICSVMHEALHNHYVQKSVEPKSC
```

In each of the above c0 to c9 sequences, the underlined sequence corresponds to the humanized 5C8 secretion signal; the sequence in bold and italics corresponds to a FLAG tag; the sequence following the Flag tag corresponds to the hinge; the italicized, boldened, and double underlined sequence that follows is the CH2 domain; finally followed by the CL moiety.

In each of the above d0 to d8 sequences, the italicized sequence corresponds to strep tag; followed by the BHA10 scFv sequence (wherein the VH is linked to the VL by a Gly-Ser linker); followed by a second Gly-Ser linker; followed by the hinge; the italicized, boldened, and double underlined sequence that follows is the CH2 domain; followed by the CH1 moiety, followed by four amino acids of the hinge and capped with a C-terminal cysteine.

Example 4. Modeling and Design of $CH_3$ Moiety-Containing Heterodimeric Binding Molecules Heterodimeric binding molecules of the invention may be designed to comprise $CH_3$ domain moieties. The following designs feature constituent polypeptide chains comprising a $CH_3$ constant domain moiety inserted between a $CH_2$ moiety and a $CH_1$ or CL constant chain moiety (e.g., $CH_2$—$CH_3$—$CH_1$ or $CH_2$—$CH_3$—CL).

Table 8 presents thirteen sequences that may be used as part of the sequence of a constituent polypeptide chain of a binding molecule of the invention. Each of the sequences is used in one or more of the following $CH_3$ heteromeric binding molecule designs; some of the sequences are used in all three designs. A person with skill in the art will appreciate that these sequences do not need to appear in the exact order given in the following three designs in order to create binding molecules of the invention.

In Table 9 below, three exemplary designs of $CH_2$—$CH_3$—$CH_1$/$CH_2$—$CH_3$—CL heterodimeric binding molecules are provided. The individual modular sequences within each chain are indicated through alternating font changes (i.e., first sequence second sequence third sequence fourth sequence, etc.). Design 2 has the same module order as Design 1 but contains extra linker units.

TABLE 8

Sequence Modules used in Exemplary $CH_2$-$CH_3$-$CH_1$ / $CH_2$-$CH_3$-CL Heterodimeric Binding Molecules

| Description | Sequence |
|---|---|
| Humanized 5C8 secretion signal | MDWTWRVFCLLAVAPGAHS (SEQ ID NO: 54) |
| STREP-TAG II (IBA) | WSHPQFEK (SEQ ID NO: 55) |
| Linker and S16E, V55G stabilized BHA10 scFv $V_H$ | QVQLVQSGAEVKKPGESVKVSCKA SGYTFTTYYLHWVRQAPGQGLEWM GWIYPGNGHAQYNEKFKGRVTITA DKSTSTAYMELSSLRSEDTAVYYC ARSWEGFPYWGQGTTVTVSS (SEQ ID NO: 56) |
| $G_4S$ linker (one unit shown; may be repeated) | GGGGS (SEQ ID NO: 57) |
| Linker and S46L stabilized BHA10 scFv $V_L$ | DIQMTQSPSSLSASVGDRVTITCK ASQNVGINVAWYQQKPGKAPKLLI SSASYRYSGVPSRFSGSGSGTDFT LTISSLQPEDFATYFCQQYDTYPF TFGQGTKVEIK (SEQ ID NO: 58) |
| $IgG_4$ hinge | ESKYGPPCPSCP (SEQ ID NO: 64) |
| $C_L$ cysteine-scrubbed $IgG_1$ hinge | EPKSSDKTHTCPPCP (SEQ ID NO: 59) |
| $IgG_4$ $CH_2$ | APEFLGGPSVFLFPPKPKDTLMIS RTPEVTCVVVDVSQEDPEVQFNWY VDGVEVHNAKTKPREEQFNSTYRV VSVLTVLHQDWLNGKEYKCKVSNK GLPSSIEKTISKAK (SEQ ID NO: 65) |
| $IgG_1$ $CH_2$ (differences between $G_1$ and $G_4$ are indicated) | APELLGGPSVFLFPPKPKDTLMIS RTPEVTCVVVDVSHEDPEVKFNWY VDGVEVHNAKTKPREEQYNSTYRV VSVLTVLHQDWLNGKEYKCKVSNK ALPAPIEKTISKAK (SEQ ID NO: 60) |
| $IgG_4$ $CH_3$ | GQPREPQVYTLPPSQEEMTKNQVS LTCLVKGFYPSDIAVEWESNGQPE NNYKTTPPVLDSDGSFFLYSRLTV DKSRWQEGNVFSCSVMHEALHNHY TQKSLSLSLG (SEQ ID NO: 66) |
| IgG1 $C_L$ without terminal cysteine | RTVAAPSVFIFPPSDEQLKSGTAS VVCLLNNFYPREAKVQWKVDNALQ SGNSQESVTEQDSKDSTYSLSSTL TLSKADYEKHKVYACEVTHQGLSS PVTKSFNRGE (SEQ ID NO: 67) |
| FLAG tag | DYKDDDDK (SEQ ID NO: 62) |
| IgG1 $C_{H1}$ without terminal cysteine | ASTKGPSVFPLAPSSKSTSGGTAA LGCLVKDYFPEPVTVSWNSGALTS GVHTFPAVLQSSGLYSLSSVVTVP SSSLGTQTYICNVNHKPSNTKVDK KVEPKS (SEQ ID NO: 68) |

TABLE 9

Exemplary CH$_2$-CH$_3$-CH$_1$ / CH$_2$-CH$_3$-CL Heterodimeric Binding Molecules Design 1: Flag-IgG$_4$ Hinge + CH$_2$ + CH$_3$-IgG$_1$ C$_L$ (Chain A1) and
         IBA-scFv BHA10-IgG$_4$ Hinge + CH2 + CH3-IgG$_1$ C$_{H1}$ (Chain B1)
Chain A1: (SEQ ID NO: 69)
MDTWRVFCLLAVAPGAHS*DYKDDDDK*ESKYGPPCPSCPAPEFLGGPSVFLFP
PKPKDTLMISRTPEVTCVVVDVSQEDPEVQFNWYVDGVEVHNAKTKPREEQFNS
TYRVVSVLTVLHQDWLNGKEYKCKVSNKGLPSSIEKTISKAKGQPREPQVYTLPPS
QEEMTKNQVSLTCLVKGFYPSDIAVEWESNGQPENNYKTTPPVLDSDGSFFLYS
RLTVDKSRWQEGNVFSCSVMHEALHNHYTQKSLSLSLG*GGGGS*RTVAAPSVFIF
PPSDEQLKSGTASVVCLLNNFYPREAKVQWKVDNALQSGNSQESVTEQDSKDST
YSLSSTLTLSKADYEKHKVYACEVTHQGLSSPVTKSFNRGE Chain B1: (SEQ ID NO: 70)
MDTWRVFCLLAVAPGAHS*WSHPQFEK*QVQLVQSGAEVKKPGESVKVSCKAS
GYTFTTYYLHWVRQAPGQGLEWMGWIYPGNGHAQYNEKFKGRVTITADKSTST
AYMELSSLRSEDTAVYYCARSWEGFPYWGQGTTVTVSS*GGGGSGGGGSGGGGS*
*GGGGS*DIQMTQSPSSLSASVGDRVTITCKASQNVGINVAWYQQKPGKAPKLLISS
ASYRYSGVPSRFSGSGSGTDFTLTISSLQPEDFATYFCQQYDTYPFTFGQGTKVEI
K*GGGGSGGGGS*ESKYGPPCPSCPAPEFLGGPSVFLFPPKPKDTLMISRTPEVTCV
VVDVSQEDPEVQFNWYVDGVEVHNAKTKPREEQFNSTYRVVSVLTVLHQDWLN
GKEYKCKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEGNVFS
CSVMHEALHNHYTQKSLSLSLG*GGGGS*ASTKGPSVFPLAPSSKSTSGGTAALGCL
VKDYFPEPVTVSWNSGALTSGVHTFPAVLQSSGLYSLSSVVTVPSSSLGTQTYIC
NVNHKPSNTKVDKKVEP Design 2: Flag-IgG$_4$ Hinge + CH$_2$ + CH$_3$-IgG$_1$ C$_L$ (Chain A2)
         IBA-scFv BHA10-IgG$_4$ Hinge + CH2 + CH3-IgG$_1$ C$_{H1}$ (Chain B2)
Chain A2: (SEQ ID NO: 71)
MDTWRVFCLLAVAPGAHS*DYKDDDDK*ESKYGPPCPSCPAPEFLGGPSVFLFP
PKPKDTLMISRTPEVTCVVVDVSQEDPEVQFNWYVDGVEVHNAKTKPREEQFNS
TYRVVSVLTVLHQDWLNGKEYKCKVSNKGLPSSIEKTISKAKGQPREPQVYTLPPS
QEEMTKNQVSLTCLVKGFYPSDIAVEWESNGQPENNYKTTPPVLDSDGSFFLYS
RLTVDKSRWQEGNVFSCSVMHEALHNHYTQKSLSLSL*GGGGSGGGGS*RTVAA
PSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGE Chain B2: (SEQ ID NO: 72)
MDTWRVFCLLAVAPGAHS*WSHPQFEK*QVQLVQSGAEVKKPGESVKVSCKAS
GYTFTTYYLHWVRQAPGQGLEWMGWIYPGNGHAQYNEKFKGRVTITADKSTST
AYMELSSLRSEDTAVYYCARSWEGFPYWGQGTTVTVSS*GGGGSGGGGSGGGGS*
*GGGGS*DIQMTQSPSSLSASVGDRVTITCKASQNVGINVAWYQQKPGKAPKLLISS
ASYRYSGVPSRFSGSGSGTDFTLTISSLQPEDFATYFCQQYDTYPFTFGQGTKVEI
K*GGGGSGGGGS*ESKYGPPCPSCPAPEFLGGPSVFLFPPKPKDTLMISRTPEVTCV
VVDVSQEDPEVQFNWYVDGVEVHNAKTKPREEQFNSTYRVVSVLTVLHQDWLN
GKEYKCKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEGNVFS
CSVMHEALHNHYTQKSLSLSLG*GGGGSGGGGS*ASTKGPSVFPLAPSSKSTSGGT
AALGCLVKDYFPEPVTVSWNSGALTSGVHTFPAVLQSSGLYSLSSVVTVPSSSLG
TQTYICNVNHKPSNTKVDKKVEP Design 3: Flag-IgG$_1$ Hinge + CH$_2$-IgG$_4$ CH$_3$-IgG$_1$ C$_L$(Chain A3)
         IBA-scFv BHA10-IgG$_1$ Hinge + CH$_2$-IgG$_4$CH$_3$-IgG$_1$ C$_{H1}$(Chain B3)
Chain A3: (SEQ ID NO: 73)
MDTWRVFCLLAVAPGAHS*DYKDDDDK*EPKSSDKTHTCPPCPAPELLGGPSVF
LFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYT
LPPSQEEMTKNQVSLTCLVKGFYPSDIAVEWESNGQPENNYKTTPPVLDSDGSFF
LYSRLTVDKSRWQEGNVFSCSVMHEALHNHYTQKSLSLSLG*GGGGS*RTVAAPS
VFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGE Chain B3: (SEQ ID NO: 74)
MDTWRVFCLLAVAPGAHS*WSHPQFEK*QVQLVQSGAEVKKPGESVKVSCKAS
GYTFTTYYLHWVRQAPGQGLEWMGWIYPGNGHAQYNEKFKGRVTITADKSTST
AYMELSSLRSEDTAVYYCARSWEGFPYWGQGTTVTVSS*GGGGSGGGGSGGGGS*
*GGGGS*DIQMTQSPSSLSASVGDRVTITCKASQNVGINVAWYQQKPGKAPKLLISS
ASYRYSGVPSRFSGSGSGTDFTLTISSLQPEDFATYFCQQYDTYPFTFGQGTKVEI
K*GGGGSGGGGS*EPKSSDKTHTCPPCPAPELLGGPSVFLFPPKPKDTLMISRTPEV
TCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSQEEMTKNQVSLTC
LVKGFYPSDIAVEWESNGQPENNYKTTPPVLDSDGSFFLYSRLTVDKSRWQEGN
VFSCSVMHEALHNHYTQKSLSLSLG*GGGGS*ASTKGPSVFPLAPSSKSTSGGTAAL
GCLVKDYFPEPVTVSWNSGALTSGVHTFPAVLQSSGLYSLSSVVTVPSSSLGTQT
YICNVNHKPSNTKVDKKVEP Taking Design 1 as an example, in Chain A1 (SEQ ID NO:69), amino acids 1-19 correspond the humanized 5C8 secretion signal; amino acids 20-27 to the Flag tag; amino acids 28-39 to the hinge sequence; amino acids 40-149 to the CH2 domain; amino acids 150-255 to the CH3 domain; amino acids 256-260 to a Gly-Ser linker; amino acids 261-366 to the CL domain. Thus, amino acids 40-366 of SEQ ID NO:69 correspond to the CH2-CH3-CL region.

In Chain B1 (SEQ ID NO:70), amino acids 1-19 correspond the humanized 5C8 secretion signal; amino acids 20-27 to the strep tag; amino acids 28-143 correspond to the VH of the BHA10 scFv; amino acids 144-163 to Gly-Ser linker; amino acids 164-270 to the VL of the BHA10 scFv; amino acids 271-280 to Gly-Ser linker; amino acids 281-292 to the hinge region; amino acids 293-402 to the CH2 domain; amino acids 403-508 to the CH3 domain; amino acids 509-513 to a Gly-Ser linker; amino acids 514-613 to the CH1 domain. Thus, amino acids 293-613 of SEQ ID NO:70 correspond to the CH2-CH3-CH1 region.

Example 5. Comparison of Heterodimer Formation by Fc Domains Comprised of CH1/CL Domain Pairs, with and without CH3 Domains The following experiment compared the heterodimerization of CH2-CH1 and CH2-CL Fc domains, similar to those described in Example 1 (the C0 and D0 reference sequences listed in Table 7, with two pairs of Fc's that include IgG4 CH3 domains (CH2-CH3-CH1 and CH2-CH3-CL) (Designs 2 and 3 in Table 9).

The pairs of constructs were expressed transiently in CHO cells in two different media to produce two supernatants of the C0/D0 construct lacking the CH3 domains, and two supernatants of design 3 with the CH3 domains. Design 2 with the CH3 domains was expressed in duplicate in each medium to produce four supernatants. Heterodimer formation was analyzed by running a portion of each supernatant on reducing and non-reducing SDS-PAGE and detecting by immunoblot using an anti-human IgG (H+L). Since one member of each pair has a ~25 kDa single-chain Fv at the N-terminus and the other does not, the two chains are of different molecular weight and the CL-CL, CL-CH1, and CH1-CH1 pairings can be readily distinguished by electrophoretic mobility. This method circumvents the difficulty of capturing the CL-CL homodimeric pair on Protein G, described in Example 1. Figure FT1 shows the immunoblot results from a reducing gel, which provides information about relative expression levels of the two chains, irrespective of heterodimer pairing. For the CH3-containing constructs the larger of the two chains containing the CH1 domain gave a much fainter band than its smaller partner. This was either due to poorer expression, transfer, or detection compared to the smaller CL containing domain. The C0/D0 pair seemed somewhat more evenly detected but gave less intense signal compared the constructs with the CH3 domain. Figure FT2 shows the immunoblot results from a non-reducing gel, which provides information on the degree of heterodimer pairing. For the CH3-containing constructs all three pairings are visible (ie CL-C, CL-CH1, and CH1-CH1). The ratio is skewed toward the CL-CL and CL-CH1 pairings as expected if pairing were random and the CL-containing construct were expressed at much higher levels than the CH1-containing constructs. For the constructs not containing CH3 domains the CL-CH1 heterodimer is clearly favored over the other two pairings, demonstrating that the CL-CH1 interaction is favorable enough to drive the desired heterodimerization.

Example 6. Restoring FcRn and Protein a Binding to CL-CH1 Heterodimers

FcRn and Protein A both bind to the IgG Fc at the CH2-CH3 interface. Although the CL and CH1 domains are structurally homologous to the CH3 domain, they lack the specific surface amino acid residues required for binding to the FcRn and Protein A ligands. To restore binding several peptide segments from the CH3 domain were substituted into the CL and CH1 domains in a stepwise fashion to determine the minimum chimerization required. The sequences of these designs are shown in Table 7, [except that the D3, D6, and C4 designs were not made]. All possible combinations of the C and D series designs were expressed together in CHO transient transfections and the supernatants tested for expression by Western blot and for binding to FcRn and Protein A. A representative Western blot shows several different patterns of expression. Under reducing conditions (FIG. 12) it was apparent that most of the construct combinations expressed at the same level although there was an occasional exception such as seen in lane #31. On the non-reducing gel (FIG. 13) most supernatants showed a predominance of the CL-CH1 heterodimer although in lanes 3, 57, and 62 the CL-CL form appears a bit more prominent and in lane 31 a considerable degree of high molecular weight aggregate is evident.

The FcRn binding assay was carried out on a Fortbio Octet instrument with biotin-labeled FcRn-Fc fusion protein bound to streptavidin tips. The cell supernatants from the transient transfection were adjusted to pH 5.8 to measure the on-rate, and the off-rate was measured at pH 5.8 or pH 7, with a final elution at pH 8.6. The parental CL-CH1 construct (C0/D0) did not show binding to the FcRn loaded Octet tips, nor did constructs with the first segment of the CH3 domain incorporated into each chain (C1/D1). If one chain had two segments, while the second chain had only one segment (C2/D1 or C1D2), intermediate binding was found. Full binding to FcRn was restored when two segments were present on both chains (for example C2/D2). MAbs with more than two segments in both chains also bound well to FcRn. (Examples shown in FIG. 14)

Protein A binding was also carried out on a Fortbio Octet instrument using Protein A tips provided by the vendor. In this case binding of the CL-CH1 constructs in the cell supernatants was monitored at pH 7. The Protein A binding results were similar to the FcRn binding with two CH3 segments on each chain providing the optimum binding interactions. (Examples shown in FIG. 15)

The top two constructs for FcRn and Protein A binding were purified from the supernatants by Protein A and size exclusion chromatography and retested for binding to FcRn (FIG. 16). The extra purification steps removed contaminants that contributed to background binding, such that the binding curves were now very similar to the wild type IgG1 mAb control.

Example 7. Variation of CH1/CH3 and CL/CH3 Junction Sites

In example 6 it was demonstrated that FcRn and Protein A binding could be restored to the CH1-CL heterodimer by substituting short surface segments of the CH3 domain into the CL and CH1 domains, and that one of the better FcRn binding variants was the c2/d2 pair. We used an in silico prediction method to investigate whether new T cell epitopes are introduced into the protein sequence by creating these hybrid molecules and potential new T cell epitopes were identified. Using the same prediction method, changes in the c2 and d2 sequences were identified that eliminated these potential epitopes and they were incorporated into new designs as follows.

In silico T cell epitope prediction was run on the c2 sequence (Table 7). Two T cell epitopes were predicted: the peptide LHNHYVTKS (SEQ ID NO: 75), in the last splice site, and VYACSVMHE, (SEQ ID NO: 76) also near the last splice site. The double mutant V437T/T438Q changes the highest scoring peptide to LHNHYTQKS (SEQ ID NO: 77), a fragment that is entirely from the native IgG1 CH3 domain. The double mutant does not introduce any new predicted T cell epitopes, and is not expected to affect FcRn binding. Alterations to the splice site of the second low-scoring peptide were also considered. However, any changes to move either end of the CH3 splice site upstream or downstream resulted in higher scoring T cell epitopes.

The in silico T cell epitope prediction was also run on the d2 sequence (Table 7). Two epitopes were predicted: the peptide YYPSDVAVS (SEQ ID NO: 78), around the middle splice site, and YVDKKVEPK (SEQ ID NO: 79), at the last splice site. The double mutant Y372F/V377I (which introduces CH3 residues into these positions) reduces the score of the T cell epitope with a minimal predicted affect on stability. The additional mutation S380E removes the high scoring T cell epitope by making this region entirely a fragment of the CH3 domain without introducing a new predicted epitope. The V437T mutation removes the second T cell epitope.

The sequences of the new designs, which include one variant of c2 and three variants of d2 (Table 7), are shown in Table 10. These alternative proteins were expressed and purified by Protein A and size exclusion chromatography and shown to form the desired heterodimers (Fig FT8) and to bind FcRn similarly to a normal human IgG1 antibody (FT9).

TABLE 10

Sequences of c2/d2 variants.

```
>c2.2 (V437T/T438Q double mutant) (SEQ ID NO: 46)
MDWTWRVFCLLAVAPGAHSDYKDDDDKEPKSSDKTHTCPPCPAPELLGGPSVFLFPPKPKDTLMISRTPEV
TCVVVDVSHEDPEVKFNWYVDGVEVHNAKTKPREEQYNSTYRVVSVLTVLHQDWLNGKEYKCKVSNKALPA
PIEKTISKAKGQPREPSVFIFPPSDEQLKSGTASVVCLLNNFYPSDIAVEWKVDNALQSGNSQESVTEQDS
KDSTYSLSSTLTLSKADYEKHKVYACSVMHEALHNHYTQKSFNRGEC >d2.2 (Y372F/V377I double mutant) (SEQ ID NO: 47)
MDWTWRVFCLLAVAPGAHSWSHPQFEKQVQLVQSGAEVKKPGESVKVSCKASGYTFTTYYLHWVRQAPGQG
LEWMGWIYPGNGHAQYNEKFKGRVTITADKSTSTAYMELSSLRSEDTAVYYCARSWEGFPYWGQGTTVTVS
SGGGGSGGGGSGGGGSGGGGSDIQMTQSPSSLSASVGDRVTITCKASQNVGINVAWYQQKPGKAPKLLISS
ASYRYSGVPSRFSGSGSGTDFTLTISSLQPEDFATYFCQQYDTYPFTFGQGTKVEIKGGGGSGGGGSEPKS
SDKTHTCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPSVFPLAPSSKSTSGG
TAALGCLVKDFYPSDIAVSWNSGALTSGVHTFPAVLQSSGLYSLSSVVTVPSSSLGTQTYICNVMHEALHN
HYVDKKVEPKSC >d2.3 (Y372F/V377I/V437T triple mutant) (SEQ ID NO: 48)
MDWTWRVFCLLAVAPGAHSWSHPQFEKQVQLVQSGAEVKKPGESVKVSCKASGYTFTTYYLHWVRQAPGQG
LEWMGWIYPGNGHAQYNEKFKGRVTITADKSTSTAYMELSSLRSEDTAVYYCARSWEGFPYWGQGTTVTVS
SGGGGSGGGGSGGGGSGGGGSDIQMTQSPSSLSASVGDRVTITCKASQNVGINVAWYQQKPGKAPKLLISS
ASYRYSGVPSRFSGSGSGTDFTLTISSLQPEDFATYFCQQYDTYPFTFGQGTKVEIKGGGGSGGGGSEPKS
SDKTHTCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPSVFPLAPSSKSTSGG
TAALGCLVKDFYPSDIAVSWNSGALTSGVHTFPAVLQSSGLYSLSSVVTVPSSSLGTQTYICNVMHEALHN
HYTDKKVEPKSC >d2.4 (Y372F/V377I/S380E/V437T quad mutant) (SEQ ID NO: 49)
MDWTWRVFCLLAVAPGAHSWSHPQFEKQVQLVQSGAEVKKPGESVKVSCKASGYTFTTYYLHWVRQAPGQG
LEWMGWIYPGNGHAQYNEKFKGRVTITADKSTSTAYMELSSLRSEDTAVYYCARSWEGFPYWGQGTTVTVS
SGGGGSGGGGSGGGGSGGGGSDIQMTQSPSSLSASVGDRVTITCKASQNVGINVAWYQQKPGKAPKLLISS
ASYRYSGVPSRFSGSGSGTDFTLTISSLQPEDFATYFCQQYDTYPFTFGQGTKVEIKGGGGSGGGGSEPKS
SDKTHTCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPSVFPLAPSSKSTSGG
TAALGCLVKDFYPSDIAVEWNSGALTSGVHTFPAVLQSSGLYSLSSVVTVPSSSLGTQTYICNVMHEALHN
HYTDKKVEPKSC
```

The residue numbers in the sequence above refer to EU numbering in human IgG1.

What is claimed is:

1. A binding molecule comprising:
(i) a binding moiety, wherein the binding moiety comprises an immunoglobulin heavy chain variable domain (VH) and an immunoglobulin light chain variable domain (VL),
(ii) a first Fc polypeptide chain comprising a first CH2 domain operably linked to the N-terminus of a CL moiety (CH2-CL), and
(iii) a second Fc polypeptide chain comprising a second CH2 domain operably linked to the N-terminus of a CH1 moiety (CH2-CH1),
wherein the binding moiety is linked to one or both of the first and second Fc polypeptide chains,
wherein said first and second Fc polypeptide chains form a heterodimeric Fc region via CL moiety:CH1 moiety heterodimerization,
wherein the CL moiety comprises an amino acid sequence selected from the group consisting of amino acids:
126-233 of SEQ ID NO:28,
126-233 of SEQ ID NO:29,
126-233 of SEQ ID NO:30,
126-235 of SEQ ID NO:31,
126-235 of SEQ ID NO:32,
126-235 of SEQ ID NO:33,
126-237 of SEQ ID NO:34,
126-237 of SEQ ID NO:35,
126-237 of SEQ ID NO:36, and
153-260 of SEQ ID NO:46, and
wherein the CH1 moiety comprises an amino acid sequence selected from the group consisting of amino acids:
126-228 of SEQ ID NO:37,
126-224 of SEQ ID NO:38,
126-224 of SEQ ID NO:39,
126-224 of SEQ ID NO:40,
126-225 of SEQ ID NO:41,
126-226 of SEQ ID NO:42,
126-226 of SEQ ID NO:43,
126-226 of SEQ ID NO:44,
126-227 of SEQ ID NO:45,
406-504 of SEQ ID NO:47,
406-504 of SEQ ID NO:48, and
406-504 of SEQ ID NO:49.

2. The binding molecule of claim 1, wherein said first Fc polypeptide chain further comprises an Fc moiety operably linked to the C-terminus of the CL moiety (CH2-CL-Fc) and said second Fc polypeptide chain further comprises an Fc moiety operably linked to the C-terminus of the CH1 moiety (CH2-CH1-Fc).

3. The binding molecule of claim 1, wherein the CH1 moiety comprises an amino acid sequence selected from the group consisting of amino acids 406-504 of SEQ ID NO:47, amino acids 406-504 of SEQ ID NO:48, and amino acids 406-504 of SEQ ID NO:49, and wherein the CL moiety comprises the amino acid sequence of amino acids 153-260 of SEQ ID NO:46.

4. The binding molecule of claim 1, wherein both the first and second Fc polypeptide chains are aglycosylated.

5. The binding molecule of claim 1, wherein said binding moiety is selected from the group consisting of an scFv, an Fab, and a diabody.

6. The binding molecule of claim 1, wherein the binding moiety specifically binds an antigen selected from the group consisting of CD20, CD2, CD3, CD5, CD6, CD7, MAGE-1, MAGE-3, MUC-1, HPV16, HPV E6, HPV E7, TAG-72, CEA, α-Lewis$^y$, L6-Antigen, CD19, CD22, CD23, CD25, CD30, CD33, CD37, CD44, CD52, CD56, mesothelin, PSMA, HLA-DR, EGF receptor, VEGF, VEGF receptor, Cripto antigen, HER2 receptor, c-MET, RON, TNFR2, HVEM, CD27, CD40, 4-1BB, OX40, and GITR.

7. A multivalent binding molecule comprising:
(i) a first binding moiety comprising a first immunoglobulin heavy chain variable domain (VH) and a first immunoglobulin light chain variable domain (VL), the first binding moiety operably linked or fused to a first Fc polypeptide chain comprising a first CH2 domain operably linked to the N-terminus of a CL moiety (CH2-CL), and
(ii) a second binding moiety comprising a second immunoglobulin heavy chain variable domain (VH) and a second immunoglobulin light chain variable domain (VL), the second binding moiety operably linked or fused to a second Fc polypeptide chain comprising a second CH2 domain operably linked to the N-terminus of a CH1 moiety (CH2-CH1),
wherein said first and second Fc polypeptide chains form a heterodimeric Fc region via CL moiety:CH1 moiety heterodimerization.

8. The binding molecule of claim 7, wherein heterodimerization is stabilized by one or more interchain disulfide bonds between said CH2-CL and said CH2-CH1.

9. The binding molecule of claim 7, wherein said first Fc polypeptide chain further comprises a hinge region.

10. The binding molecule of claim 7, wherein said second Fc polypeptide chain further comprises a hinge region.

11. The binding molecule of claim 7, wherein said first and second CH2 domains are of the IgG1 isotype.

12. A composition comprising a population of the binding molecule of claim 7, wherein at least 90% of binding molecules in the population are in heterodimeric form.

13. A pharmaceutical composition comprising the binding molecule of claim 7, and a pharmaceutically acceptable carrier.

14. The binding molecule of claim 1, wherein the CH2-CL comprises amino acids 43-260 of SEQ ID NO:46 and the CH2-CH1 comprises amino acids 296-504 of SEQ ID NO:47.

15. The binding molecule of claim 1, wherein the CH2-CL comprises amino acids 43-260 of SEQ ID NO:46 and the CH2-CH1 comprises amino acids 296-504 of SEQ ID NO:48.

16. The binding molecule of claim 1, wherein the CH2-CL comprises amino acids 43-260 of SEQ ID NO:46 and the CH2-CH1 comprises amino acids 296-504 of SEQ ID NO:49.

17. The binding molecule of claim 1, wherein the first and second CH2 domains have the same amino acid sequence.

18. The binding molecule of claim 1, wherein the first and second CH2 domains are either an IgG1 CH2 domain or an IgG4 CH2 domain.

19. The binding molecule of claim 1, wherein the CH2-CL comprises an amino acid sequence selected from the group consisting of:
16-233 of SEQ ID NO:28,
16-233 of SEQ ID NO:29,
16-233 of SEQ ID NO:30,
16-235 of SEQ ID NO:31,
16-235 of SEQ ID NO:32,
16-235 of SEQ ID NO:33,
16-237 of SEQ ID NO:34,
16-237 of SEQ ID NO:35,
16-237 of SEQ ID NO:36, and
43-260 of SEQ ID NO:46.

20. The binding molecule of claim 1, wherein the CH2-CH1 comprises an amino acid sequence selected from the group consisting of:
16-228 of SEQ ID NO:37,
16-224 of SEQ ID NO:38,
16-224 of SEQ ID NO:39,
16-224 of SEQ ID NO:40,
16-225 of SEQ ID NO:41,
16-226 of SEQ ID NO:42,
16-226 of SEQ ID NO:43,
16-226 of SEQ ID NO:44,
16-227 of SEQ ID NO:45,
296-509 of SEQ ID NO:47,
296-509 of SEQ ID NO:48, and
296-509 of SEQ ID NO:49.

21. The binding molecule of claim 1, wherein the first and second Fc polypeptide chains each further comprise a hinge sequence set forth in SEQ ID NO:59 or SEQ ID NO:64.

22. The binding molecule of claim 17, wherein the first and second Fc polypeptide chains each further comprise a hinge sequence set forth in SEQ ID NO:59 or SEQ ID NO:64.

23. The binding molecule of claim 1, comprising two binding moieties.

24. A binding molecule comprising:
(i) a binding moiety, wherein the binding moiety is an scFv,
(ii) a first Fc polypeptide chain comprising a first CH2 domain operably linked to the N-terminus of a CL moiety (CH2-CL), and
(iii) a second Fc polypeptide chain comprising a second CH2 domain operably linked to the N-terminus of a CH1 moiety ((CH2-CH1),
wherein the binding moiety is linked to one of the first and second Fc polypeptide chains,
wherein the first and second Fc polypeptide chains form a heterodimeric Fc region via CL moiety:CH1 moiety heterodimerization,
wherein the CL moiety comprises an amino acid sequence selected from the group consisting of amino acids:
126-233 of SEQ ID NO:28,
126-233 of SEQ ID NO:29,
126-233 of SEQ ID NO:30,
126-235 of SEQ ID NO:31,
126-235 of SEQ ID NO:32,
126-235 of SEQ ID NO:33,
126-237 of SEQ ID NO:34,
126-237 of SEQ ID NO:35,
126-237 of SEQ ID NO:36, and 153-260 of SEQ ID NO:46, and
wherein the CH1 moiety comprises an amino acid sequence selected from the group consisting of amino acids:
126-228 of SEQ ID NO:37,
126-224 of SEQ ID NO:38,
126-224 of SEQ ID NO:39,
126-224 of SEQ ID NO:40,
126-225 of SEQ ID NO:41,
126-226 of SEQ ID NO:42,
126-226 of SEQ ID NO:43,
126-226 of SEQ ID NO:44,
126-227 of SEQ ID NO:45,
406-504 of SEQ ID NO:47,
406-504 of SEQ ID NO:48, and
406-504 of SEQ ID NO:49.

25. The binding molecule of claim 24, wherein the CL moiety comprises the amino acid sequence of amino acids 153-260 of SEQ ID NO:46 and the CH1 moiety comprises the amino acid sequence of amino acids 406-504 of SEQ ID NO:47.

26. The binding molecule of claim 24, wherein the CL moiety comprises the amino acid sequence of amino acids 153-260 of SEQ ID NO:46 and the CH1 moiety comprises the amino acid sequence of amino acids 406-504 of SEQ ID NO:48.

27. The binding molecule of claim 24, wherein the CL moiety comprises the amino acid sequence of amino acids 153-260 of SEQ ID NO:46 and the CH1 moiety comprises the amino acid sequence of amino acids 406-504 of SEQ ID NO:49.

28. The binding molecule of claim 24, wherein the first and second CH2 domains are each either an IgG1 CH2 domain or an IgG4 CH2 domain.

29. A binding molecule comprising:
(i) a binding moiety, wherein the binding moiety comprises an immunoglobulin heavy chain variable domain (VH) and an immunoglobulin light chain variable domain (VL),
(ii) a first Fc polypeptide chain comprising a first CH3 domain operably linked to the N-terminus of a CL moiety (CH3-CL), and
(iii) a second Fc polypeptide chain comprising a second CH3 domain operably linked to the N-terminus of a CH1 moiety (CH3-CH1),
wherein the binding moiety is linked to one or both of the first and second Fc polypeptide chains,
wherein said first and second Fc polypeptide chains form a heterodimeric Fc region via CL moiety:CH1 moiety heterodimerization,
wherein the CL moiety comprises an amino acid sequence selected from the group consisting of amino acids:
126-233 of SEQ ID NO:28,
126-233 of SEQ ID NO:29,
126-233 of SEQ ID NO:30,
126-235 of SEQ ID NO:31,
126-235 of SEQ ID NO:32,
126-235 of SEQ ID NO:33,
126-237 of SEQ ID NO:34,
126-237 of SEQ ID NO:35,
126-237 of SEQ ID NO:36, and
153-260 of SEQ ID NO:46, and
wherein the CH1 moiety comprises an amino acid sequence selected from the group consisting of amino acids:
126-228 of SEQ ID NO:37,
126-224 of SEQ ID NO:38,
126-224 of SEQ ID NO:39,
126-224 of SEQ ID NO:40,
126-225 of SEQ ID NO:41,
126-226 of SEQ ID NO:42,
126-226 of SEQ ID NO:43,
126-226 of SEQ ID NO:44,
126-227 of SEQ ID NO:45,
406-504 of SEQ ID NO:47,
406-504 of SEQ ID NO:48, and
406-504 of SEQ ID NO:49.

30. The binding molecule of claim 29, wherein the first and second Fc polypeptide chains further comprise a first CH2 domain [CH2-CH3-CL] and second CH2 domain [CH2-CH3-CH1], respectively.

31. The binding molecule of claim 29, wherein the first and second CH3 domains are each an IgG4 CH3 domain.

32. The binding molecule of claim 30, wherein the CH2-CH3-CL comprises an amino acid sequence selected from the group consisting of:
40-366 of SEQ ID NO:69,
40-371 of SEQ ID NO:71, and
43-369 of SEQ ID NO:73.

33. The binding molecule of claim 30, wherein the CH2-CH3-CH1 comprises an amino acid sequence selected from the group consisting of:
293-613 of SEQ ID NO:70,
293-618 of SEQ ID NO:72, and
296-616 of SEQ ID NO:74.

* * * * *

UNITED STATES PATENT AND TRADEMARK OFFICE
CERTIFICATE OF CORRECTION

| | | |
|---|---|---|
| PATENT NO. | : 9,738,707 B2 | Page 1 of 1 |
| APPLICATION NO. | : 14/232868 | |
| DATED | : August 22, 2017 | |
| INVENTOR(S) | : Frederick R. Taylor et al. | |

It is certified that error appears in the above-identified patent and that said Letters Patent is hereby corrected as shown below:

In the Claims

<u>Column 265</u>
In Claim 11, Line 49, delete "IgG1sotype." and insert -- IgG1 isotype. --.

<u>Column 266</u>
In Claim 24, Line 51, delete "((CH2-CH1)," and insert -- (CH2-CH1), --.

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 101

<210> SEQ ID NO 1
<211> LENGTH: 10
<212> TYPE: PRT
<213> ORGANISM: Homo sapiens
<220> FEATURE:

```
<221> NAME/KEY: misc_feature
<222> LOCATION: (1)..(10)
<223> OTHER INFORMATION: IgG1 upper hinge

<400> SEQUENCE: 1

Glu Pro Lys Ser Cys Asp Lys Thr His Thr
1               5                   10

<210> SEQ ID NO 2
<211> LENGTH: 5
<212> TYPE: PRT
<213> ORGANISM: Homo sapiens
<220> FEATURE:
<221> NAME/KEY: misc_feature
<222> LOCATION: (1)..(5)
<223> OTHER INFORMATION: IgG1 middle hinge

<400> SEQUENCE: 2

Cys Pro Pro Cys Pro
1               5

<210> SEQ ID NO 3
<211> LENGTH: 8
<212> TYPE: PRT
<213> ORGANISM: Homo sapiens
<220> FEATURE:
<221> NAME/KEY: misc_feature
<222> LOCATION: (1)..(8)
<223> OTHER INFORMATION: IgG1 lower hinge

<400> SEQUENCE: 3

Ala Pro Glu Leu Leu Gly Gly Pro
1               5

<210> SEQ ID NO 4
<211> LENGTH: 7
<212> TYPE: PRT
<213> ORGANISM: Homo sapiens
<220> FEATURE:
<221> NAME/KEY: misc_feature
<222> LOCATION: (1)..(7)
<223> OTHER INFORMATION: IgG2 upper hinge

<400> SEQUENCE: 4

Glu Arg Lys Cys Cys Val Glu
1               5

<210> SEQ ID NO 5
<211> LENGTH: 5
<212> TYPE: PRT
<213> ORGANISM: Homo sapiens
<220> FEATURE:
<221> NAME/KEY: misc_feature
<222> LOCATION: (1)..(5)
<223> OTHER INFORMATION: IgG2 middle hinge

<400> SEQUENCE: 5

Cys Pro Pro Cys Pro
1               5

<210> SEQ ID NO 6
<211> LENGTH: 7
<212> TYPE: PRT
<213> ORGANISM: Homo sapiens
<220> FEATURE:
<221> NAME/KEY: misc_feature
<222> LOCATION: (1)..(7)
<223> OTHER INFORMATION: IgG2 lower hinge
```

```
<400> SEQUENCE: 6

Ala Pro Pro Val Ala Gly Pro
1               5

<210> SEQ ID NO 7
<211> LENGTH: 12
<212> TYPE: PRT
<213> ORGANISM: Homo sapiens
<220> FEATURE:
<221> NAME/KEY: misc_feature
<222> LOCATION: (1)..(12)
<223> OTHER INFORMATION: IgG3 upper hinge

<400> SEQUENCE: 7

Glu Leu Lys Thr Pro Leu Gly Asp Thr Thr His Thr
1               5                   10

<210> SEQ ID NO 8
<211> LENGTH: 50
<212> TYPE: PRT
<213> ORGANISM: Homo sapiens
<220> FEATURE:
<221> NAME/KEY: misc_feature
<222> LOCATION: (1)..(50)
<223> OTHER INFORMATION: IgG3 middle hinge

<400> SEQUENCE: 8

Cys Pro Arg Cys Pro Glu Pro Lys Ser Cys Asp Thr Pro Pro Pro Cys
1               5                   10                  15

Pro Arg Cys Pro Glu Pro Lys Ser Cys Asp Thr Pro Pro Pro Cys Pro
            20                  25                  30

Arg Cys Pro Glu Pro Lys Ser Cys Asp Thr Pro Pro Pro Cys Pro Arg
        35                  40                  45

Cys Pro
    50

<210> SEQ ID NO 9
<211> LENGTH: 8
<212> TYPE: PRT
<213> ORGANISM: Homo sapiens
<220> FEATURE:
<221> NAME/KEY: misc_feature
<222> LOCATION: (1)..(8)
<223> OTHER INFORMATION: IgG3 lower hinge

<400> SEQUENCE: 9

Ala Pro Glu Leu Leu Gly Gly Pro
1               5

<210> SEQ ID NO 10
<211> LENGTH: 7
<212> TYPE: PRT
<213> ORGANISM: Homo sapiens
<220> FEATURE:
<221> NAME/KEY: misc_feature
<222> LOCATION: (1)..(7)
<223> OTHER INFORMATION: IgG4 upper hinge

<400> SEQUENCE: 10

Glu Ser Lys Tyr Gly Pro Pro
1               5

<210> SEQ ID NO 11
<211> LENGTH: 5
<212> TYPE: PRT
<213> ORGANISM: Homo sapiens
```

-continued

```
<220> FEATURE:
<221> NAME/KEY: misc_feature
<222> LOCATION: (1)..(5)
<223> OTHER INFORMATION: IgG4 middle hinge

<400> SEQUENCE: 11

Cys Pro Ser Cys Pro
1               5

<210> SEQ ID NO 12
<211> LENGTH: 8
<212> TYPE: PRT
<213> ORGANISM: Homo sapiens
<220> FEATURE:
<221> NAME/KEY: misc_feature
<222> LOCATION: (1)..(8)
<223> OTHER INFORMATION: IgG4 lower hinge

<400> SEQUENCE: 12

Ala Pro Glu Phe Leu Gly Gly Pro
1               5

<210> SEQ ID NO 13
<211> LENGTH: 10
<212> TYPE: PRT
<213> ORGANISM: Artificial Sequence
<220> FEATURE:
<223> OTHER INFORMATION: Synthetic peptide

<400> SEQUENCE: 13

Gly Gly Gly Ser Ser Gly Gly Gly Ser Gly
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic peptide

<400> SEQUENCE: 14

Ile Gly Lys Thr Ile Ser Lys Lys Ala Lys
1               5                   10

<210> SEQ ID NO 15
<211> LENGTH: 25
<212> TYPE: PRT
<213> ORGANISM: Artificial Sequence
<220> FEATURE:
<223> OTHER INFORMATION: Synthetic peptide

<400> SEQUENCE: 15

Gly Gly Gly Gly Ser Gly Gly Gly Ser Gly Gly Gly Ser Gly
1               5                   10                  15

Gly Gly Gly Ser Gly Gly Gly Ala Ser
            20                  25

<210> SEQ ID NO 16
<211> LENGTH: 17
<212> TYPE: PRT
<213> ORGANISM: Artificial Sequence
<220> FEATURE:
<223> OTHER INFORMATION: Synthetic peptide: Polypeptide linker

<400> SEQUENCE: 16

Ser Leu Ser Leu Ser Pro Gly Gly Gly Gly Ser Glu Pro Lys Ser
1               5                   10                  15
```

Ser

<210> SEQ ID NO 17
<211> LENGTH: 17
<212> TYPE: PRT
<213> ORGANISM: Homo sapiens
<220> FEATURE:
<221> NAME/KEY: misc_feature
<222> LOCATION: (1)..(17)
<223> OTHER INFORMATION: Human IgG1 hinge sequence

<400> SEQUENCE: 17

Asp Lys Thr His Thr Cys Pro Pro Cys Pro Ala Pro Glu Leu Leu Gly
1               5                   10                  15

Gly

<210> SEQ ID NO 18
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (6)..(30)
<223> OTHER INFORMATION: "Gly Gly Gly Gly Ser" may be present or absent

<400> SEQUENCE: 18

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser
                20                  25                  30

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide

<400> SEQUENCE: 19

Gly Gly Gly Gly Ser Gly Gly Gly Gly Ser Gly Gly Gly Gly Ser
1               5                   10                  15

<210> SEQ ID NO 20
<211> LENGTH: 20
<212> TYPE: PRT
<213> ORGANISM: Artificial Sequence
<220> FEATURE:
<223> OTHER INFORMATION: Synthetic peptide

<400> SEQUENCE: 20

Gly Gly Gly Gly Ser Gly Gly Gly Ser Gly Gly Gly Gly Ser Gly
1               5                   10                  15

Gly Gly Gly Ser
            20

<210> SEQ ID NO 21
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (7)..(31)

```
<223> OTHER INFORMATION: "Gly Gly Gly Gly Ser" may be present or absent

<400> SEQUENCE: 21

Ser Gly Gly Gly Gly Ser Gly Gly Gly Ser Gly Gly Gly Gly Ser
1               5                   10                  15

Gly Gly Gly Gly Ser Gly Gly Gly Ser Gly Gly Gly Gly Ser
            20                  25                  30

<210> SEQ ID NO 22
<211> LENGTH: 4
<212> TYPE: PRT
<213> ORGANISM: Artificial Sequence
<220> FEATURE:
<223> OTHER INFORMATION: Synthetic peptide: linker sequence

<400> SEQUENCE: 22

Gly Gly Gly Ser
1

<210> SEQ ID NO 23
<211> LENGTH: 220
<212> TYPE: PRT
<213> ORGANISM: Mouse sp.
<220> FEATURE:
<221> NAME/KEY: misc_feature
<222> LOCATION: (1)..(220)
<223> OTHER INFORMATION: Mouse CH1 domain

<400> SEQUENCE: 23

Glu Val Gln Leu Gln Gln Ser Gly Ala Glu Val Val Arg Ser Gly Ala
1               5                   10                  15

Ser Val Lys Leu Ser Cys Thr Ala Ser Gly Phe Asn Ile Lys Asp Tyr
            20                  25                  30

Tyr Ile His Trp Val Lys Gln Arg Pro Glu Lys Gly Leu Glu Trp Ile
        35                  40                  45

Gly Trp Ile Asp Pro Glu Ile Gly Asp Thr Glu Tyr Val Pro Lys Phe
    50                  55                  60

Gln Gly Lys Ala Thr Met Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Gly His Asp Tyr Asp Arg Gly Arg Phe Pro Tyr Trp Gly Gln
            100                 105                 110

Gly Thr Leu Val Thr Val Ser Ala Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg
    210                 215                 220

<210> SEQ ID NO 24
```

```
<211> LENGTH: 225
<212> TYPE: PRT
<213> ORGANISM: Homo sapiens
<220> FEATURE:
<221> NAME/KEY: misc_feature
<222> LOCATION: (1)..(225)
<223> OTHER INFORMATION: Human CH1 domain

<400> SEQUENCE: 24

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Val His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Val Phe Ile Arg Arg Ile Ala Ala Arg Leu Gly Gly Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Val Glu Pro
    210                 215                 220

Lys
225

<210> SEQ ID NO 25
<211> LENGTH: 214
<212> TYPE: PRT
<213> ORGANISM: Mouse sp.
<220> FEATURE:
<221> NAME/KEY: misc_feature
<222> LOCATION: (1)..(214)
<223> OTHER INFORMATION: Mouse CL domain

<400> SEQUENCE: 25

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Lys Leu Met Ile
        35                  40                  45

Tyr Ser Ala Ser Asn Arg Tyr Thr Gly Val Pro Asp Arg Phe Thr Gly
    50                  55                  60
```

-continued

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Ala Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 26
<211> LENGTH: 214
<212> TYPE: PRT
<213> ORGANISM: Homo sapiens
<220> FEATURE:
<221> NAME/KEY: misc_feature
<222> LOCATION: (1)..(214)
<223> OTHER INFORMATION: Human CL domain

<400> SEQUENCE: 26

Asp Ile Gln Met Thr Gln Ser Pro Ser Ser Leu Ser Ala Ser Val Gly
1               5                   10                  15

Asp Arg Val Ser Ile Thr Cys Gln Ala Asn Gln Asp Ile Asn Asn Tyr
            20                  25                  30

Leu Asn Trp Tyr Gln Gln Lys Pro Gly Lys Ala Pro Lys Val Leu Ile
        35                  40                  45

Tyr Asp Ala Ser Asn Leu Glu Ile Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Glu Asn Leu Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser

```
              195                 200                 205

Phe Asn Arg Gly Glu Cys
    210

<210> SEQ ID NO 27
<211> LENGTH: 232
<212> TYPE: PRT
<213> ORGANISM: Artificial Sequence
<220> FEATURE:
<223> OTHER INFORMATION: Synthetic peptide: c0 hinge-CH2-CL (reference)

<400> SEQUENCE: 27

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 28
<211> LENGTH: 233
<212> TYPE: PRT
<213> ORGANISM: Artificial Sequence
<220> FEATURE:
<223> OTHER INFORMATION: Synthetic peptide: c1 hinge-CH2-CL

<400> SEQUENCE: 28

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45
```

```
Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Ser Val Phe Ile Phe Pro Pro Ser Asp Glu Gln Leu Lys
130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
            195                 200                 205

Val Tyr Ala Cys Ser Val Met His Glu Ala Leu His Asn His Tyr Val
            210                 215                 220

Thr Lys Ser Phe Asn Arg Gly Glu Cys
225                 230

<210> SEQ ID NO 29
<211> LENGTH: 233
<212> TYPE: PRT
<213> ORGANISM: Artificial Sequence
<220> FEATURE:
<223> OTHER INFORMATION: Synthetic peptide: c2 hinge-CH2-CL

<400> SEQUENCE: 29

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Ser Val Phe Ile Phe Pro Pro Ser Asp Glu Gln Leu Lys
130                 135                 140

Ser Gly Thr Ala Ser Val Val Cys Leu Leu Asn Asn Phe Tyr Pro Ser
145                 150                 155                 160

Asp Ile Ala Val Glu Trp Lys Val Asp Asn Ala Leu Gln Ser Gly Asn
                165                 170                 175
```

```
Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Ser Val Met His Glu Ala Leu His Asn His Tyr Val
    210                 215                 220

Thr Lys Ser Phe Asn Arg Gly Glu Cys
225                 230

<210> SEQ ID NO 30
<211> LENGTH: 233
<212> TYPE: PRT
<213> ORGANISM: Artificial Sequence
<220> FEATURE:
<223> OTHER INFORMATION: Synthetic peptide: c3 hinge-CH2-CL

<400> SEQUENCE: 30

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Ser
145                 150                 155                 160

Asp Ile Ala Val Glu Trp Glu Ser Asn Gly Gln Pro Glu Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Ser Val Met His Glu Ala Leu His Asn His Tyr Val
    210                 215                 220

Thr Lys Ser Phe Asn Arg Gly Glu Cys
225                 230

<210> SEQ ID NO 31
<211> LENGTH: 235
<212> TYPE: PRT
<213> ORGANISM: Artificial Sequence
<220> FEATURE:
<223> OTHER INFORMATION: Synthetic peptide: c4 hinge-CH2-CL

<400> SEQUENCE: 31

Glu Pro Lys Ser Ser Asp Lys Thr His Thr Cys Pro Pro Cys Pro Ala
1               5                   10                  15
```

-continued

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Ser Gly
            115                 120                 125

Gln Pro Arg Glu Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
            165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Ser Val Met His Glu Ala Leu His Asn His
            210                 215                 220

Tyr Val Thr Lys Ser Phe Asn Arg Gly Glu Cys
225                 230                 235

<210> SEQ ID NO 32
<211> LENGTH: 235
<212> TYPE: PRT
<213> ORGANISM: Artificial Sequence
<220> FEATURE:
<223> OTHER INFORMATION: Synthetic peptide: c5 hinge-CH2-CL

<400> SEQUENCE: 32

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Ser Gly
            115                 120                 125

Gln Pro Arg Glu Pro Ser Val Phe Ile Phe Pro Pro Ser Asp Glu Gln
130                 135                 140

```
Leu Lys Ser Gly Thr Ala Ser Val Val Cys Leu Leu Asn Asn Phe Tyr
145                 150                 155                 160

Pro Ser Asp Ile Ala Val Glu Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Ser Val Met His Glu Ala Leu His Asn His
    210                 215                 220

Tyr Val Thr Lys Ser Phe Asn Arg Gly Glu Cys
225                 230                 235

<210> SEQ ID NO 33
<211> LENGTH: 235
<212> TYPE: PRT
<213> ORGANISM: Artificial Sequence
<220> FEATURE:
<223> OTHER INFORMATION: Synthetic peptide: c6 hinge-CH2-CL

<400> SEQUENCE: 33

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Ser Gly
        115                 120                 125

Gln Pro Arg Glu Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Ser Asp Ile Ala Val Glu Trp Glu Ser Asn Gly Gln Pro Glu Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Ser Val Met His Glu Ala Leu His Asn His
    210                 215                 220

Tyr Val Thr Lys Ser Phe Asn Arg Gly Glu Cys
225                 230                 235

<210> SEQ ID NO 34
<211> LENGTH: 237
<212> TYPE: PRT
<213> ORGANISM: Artificial Sequence
```

<220> FEATURE:
<223> OTHER INFORMATION: Synthetic peptide: c7 hinge-CH2-CL

<400> SEQUENCE: 34

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gly Gly
        115                 120                 125

Ser Gly Gln Pro Arg Glu Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Ser Val Met His Glu Ala Leu His
210                 215                 220

Asn His Tyr Val Thr Lys Ser Phe Asn Arg Gly Glu Cys
225                 230                 235

<210> SEQ ID NO 35
<211> LENGTH: 237
<212> TYPE: PRT
<213> ORGANISM: Artificial Sequence
<220> FEATURE:
<223> OTHER INFORMATION: Synthetic peptide: c8 hinge-CH2-CL

<400> SEQUENCE: 35

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala

```
              100                 105                 110
Leu Pro Ala Pro Ile Glu Lys Thr Ile Ser Lys Ala Lys Gly Gly Gly
            115                 120                 125

Ser Gly Gln Pro Arg Glu Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Ser Asp Ile Ala Val Glu Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Ser Val Met His Glu Ala Leu His
    210                 215                 220

Asn His Tyr Val Thr Lys Ser Phe Asn Arg Gly Glu Cys
225                 230                 235

<210> SEQ ID NO 36
<211> LENGTH: 237
<212> TYPE: PRT
<213> ORGANISM: Artificial Sequence
<220> FEATURE:
<223> OTHER INFORMATION: Synthetic peptide: c9 hinge-CH2-CL

<400> SEQUENCE: 36

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gly Gly
        115                 120                 125

Ser Gly Gln Pro Arg Glu Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Ser Asp Ile Ala Val Glu Trp Glu Ser Asn Gly Gln Pro
                165                 170                 175

Glu Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Ser Val Met His Glu Ala Leu His
    210                 215                 220

Asn His Tyr Val Thr Lys Ser Phe Asn Arg Gly Glu Cys
```

<210> SEQ ID NO 37
<211> LENGTH: 228
<212> TYPE: PRT
<213> ORGANISM: Artificial Sequence
<220> FEATURE:
<223> OTHER INFORMATION: Synthetic peptide: d0 hinge-CH2-CH1 portion (reference)

<400> SEQUENCE: 37

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys
225

<210> SEQ ID NO 38
<211> LENGTH: 229
<212> TYPE: PRT
<213> ORGANISM: Artificial Sequence
<220> FEATURE:
<223> OTHER INFORMATION: Synthetic peptide: d1 hinge-CH2-CH1 portion

<400> SEQUENCE: 38

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Met His Glu Ala Leu His Asn His Tyr Val Asp Lys Lys Val
    210                 215                 220

Glu Pro Lys Ser Cys
225

<210> SEQ ID NO 39
<211> LENGTH: 229
<212> TYPE: PRT
<213> ORGANISM: Artificial Sequence
<220> FEATURE:
<223> OTHER INFORMATION: Synthetic peptide: d2 hinge-CH2-CH1 portion

<400> SEQUENCE: 39

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Tyr Pro Ser
145                 150                 155                 160

Asp Val Ala Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Met His Glu Ala Leu His Asn His Tyr Val Asp Lys Lys Val
    210                 215                 220

Glu Pro Lys Ser Cys
225

<210> SEQ ID NO 40
<211> LENGTH: 229
<212> TYPE: PRT
<213> ORGANISM: Artificial Sequence
<220> FEATURE:
<223> OTHER INFORMATION: Synthetic peptide: d3 hinge-CH2-CH1 portion

<400> SEQUENCE: 40

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Ser Val Phe Pro Leu Ala Pro Ser Ser Lys Ser Thr Ser
    130                 135                 140

Gly Gly Thr Ala Ala Leu Gly Cys Leu Val Lys Asp Phe Tyr Pro Ser
145                 150                 155                 160

Asp Ile Ala Val Glu Trp Glu Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Ser Val Met His Glu Ala Leu His Asn His Tyr Val Gln Lys Ser Val
    210                 215                 220

Glu Pro Lys Ser Cys
225

<210> SEQ ID NO 41
<211> LENGTH: 230
<212> TYPE: PRT
<213> ORGANISM: Artificial Sequence
<220> FEATURE:
<223> OTHER INFORMATION: Synthetic peptide: d4 hinge-CH2-CH1 portion

<400> SEQUENCE: 41

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro

```
            20                  25                  30
Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Ser Val Phe Pro Leu Ala Pro Ser Ser Lys Ser Thr Ser
    130                 135                 140

Gly Gly Thr Ala Ala Leu Gly Cys Leu Val Lys Asp Phe Tyr Pro Ser
145                 150                 155                 160

Asp Ile Ala Val Glu Trp Glu Ser Asn Gly Gln Pro Glu Asn Asn Tyr
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Asn Thr Tyr Ile
        195                 200                 205

Cys Ser Val Met His Glu Ala Leu His Asn His Tyr Val Gln Lys Ser
    210                 215                 220

Val Glu Pro Lys Ser Cys
225                 230

<210> SEQ ID NO 42
<211> LENGTH: 231
<212> TYPE: PRT
<213> ORGANISM: Artificial Sequence
<220> FEATURE:
<223> OTHER INFORMATION: Synthetic peptide: d5 hinge-CH2-CH1 portion

<400> SEQUENCE: 42

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Ser Gly
        115                 120                 125

Gln Pro Arg Glu Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
```

```
145                 150                 155                 160
Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
                180                 185                 190

Ser Ser Val Val Thr Val Pro Ser Ser Ser Leu Gly Thr Gln Thr Tyr
                195                 200                 205

Ile Cys Asn Val Met His Glu Ala Leu His Asn His Tyr Val Asp Lys
                210                 215                 220

Lys Val Glu Pro Lys Ser Cys
225                 230

<210> SEQ ID NO 43
<211> LENGTH: 231
<212> TYPE: PRT
<213> ORGANISM: Artificial Sequence
<220> FEATURE:
<223> OTHER INFORMATION: Synthetic peptide: d6 hinge-CH2-CH1 portion

<400> SEQUENCE: 43

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
                35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Ser Gly
                115                 120                 125

Gln Pro Arg Glu Pro Ser Val Phe Pro Leu Ala Pro Ser Ser Lys Ser
                130                 135                 140

Thr Ser Gly Gly Thr Ala Ala Leu Gly Cys Leu Val Lys Asp Tyr Tyr
145                 150                 155                 160

Pro Ser Asp Val Ala Val Ser Trp Asn Ser Gly Ala Leu Thr Ser Gly
                165                 170                 175

Val His Thr Phe Pro Ala Val Leu Gln Ser Ser Gly Leu Tyr Ser Leu
                180                 185                 190

Ser Ser Val Val Thr Val Pro Ser Ser Ser Leu Gly Thr Gln Thr Tyr
                195                 200                 205

Ile Cys Asn Val Met His Glu Ala Leu His Asn His Tyr Val Asp Lys
                210                 215                 220

Lys Val Glu Pro Lys Ser Cys
225                 230

<210> SEQ ID NO 44
<211> LENGTH: 231
<212> TYPE: PRT
<213> ORGANISM: Artificial Sequence
<220> FEATURE:
<223> OTHER INFORMATION: Synthetic peptide: d7 hinge-CH2-CH1 portion
```

```
<400> SEQUENCE: 44

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Ser Gly
        115                 120                 125

Gln Pro Arg Glu Pro Ser Val Phe Pro Leu Ala Pro Ser Ser Lys Ser
130                 135                 140

Thr Ser Gly Gly Thr Ala Ala Leu Gly Cys Leu Val Lys Asp Phe Tyr
145                 150                 155                 160

Pro Ser Asp Ile Ala Val Glu Trp Glu Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Ser Val Met His Glu Ala Leu His Asn His Tyr Val Gln Lys
210                 215                 220

Ser Val Glu Pro Lys Ser Cys
225                 230

<210> SEQ ID NO 45
<211> LENGTH: 232
<212> TYPE: PRT
<213> ORGANISM: Artificial Sequence
<220> FEATURE:
<223> OTHER INFORMATION: Synthetic peptide: d8 hinge-CH2-CH1 portion

<400> SEQUENCE: 45

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110
```

```
Leu Pro Ala Pro Ile Glu Lys Thr Ile Ser Lys Ala Lys Gly Ser Gly
            115                 120                 125

Gln Pro Arg Glu Pro Ser Val Phe Pro Leu Ala Pro Ser Ser Lys Ser
        130                 135                 140

Thr Ser Gly Gly Thr Ala Ala Leu Gly Cys Leu Val Lys Asp Phe Tyr
145                 150                 155                 160

Pro Ser Asp Ile Ala Val Glu Trp Glu Ser Asn Gly Gln Pro Glu Asn
                165                 170                 175

Asn Tyr His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Asn Thr
        195                 200                 205

Tyr Ile Cys Ser Val Met His Glu Ala Leu His Asn His Tyr Val Gln
210                 215                 220

Lys Ser Val Glu Pro Lys Ser Cys
225                 230

<210> SEQ ID NO 46
<211> LENGTH: 260
<212> TYPE: PRT
<213> ORGANISM: Artificial Sequence
<220> FEATURE:
<223> OTHER INFORMATION: Synthetic peptide: c2.2 (V437T/T438Q double
      mutant)

<400> SEQUENCE: 46

Met Asp Trp Thr Trp Arg Val Phe Cys Leu Leu Ala Val Ala Pro Gly
1               5                   10                  15

Ala His Ser Asp Tyr Lys Asp Asp Asp Lys Glu Pro Lys Ser Ser
            20                  25                  30

Asp Lys Thr His Thr Cys Pro Pro Cys Pro Ala Pro Glu Leu Leu Gly
        35                  40                  45

Gly Pro Ser Val Phe Leu Phe Pro Pro Lys Pro Lys Asp Thr Leu Met
    50                  55                  60

Ile Ser Arg Thr Pro Glu Val Thr Cys Val Val Val Asp Val Ser His
65                  70                  75                  80

Glu Asp Pro Glu Val Lys Phe Asn Trp Tyr Val Asp Gly Val Glu Val
                85                  90                  95

His Asn Ala Lys Thr Lys Pro Arg Glu Glu Gln Tyr Asn Ser Thr Tyr
            100                 105                 110

Arg Val Val Ser Val Leu Thr Val Leu His Gln Asp Trp Leu Asn Gly
        115                 120                 125

Lys Glu Tyr Lys Cys Lys Val Ser Asn Lys Ala Leu Pro Ala Pro Ile
    130                 135                 140

Glu Lys Thr Ile Ser Lys Ala Lys Gly Gln Pro Arg Glu Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Ser Asp Ile Ala Val Glu
            180                 185                 190

Trp Lys Val Asp Asn Ala Leu Gln Ser Gly Asn Ser Gln Glu Ser Val
        195                 200                 205

Thr Glu Gln Asp Ser Lys Asp Ser Thr Tyr Ser Leu Ser Ser Thr Leu
    210                 215                 220

Thr Leu Ser Lys Ala Asp Tyr Glu Lys His Lys Val Tyr Ala Cys Ser
225                 230                 235                 240
```

```
Val Met His Glu Ala Leu His Asn His Tyr Thr Gln Lys Ser Phe Asn
            245                 250                 255

Arg Gly Glu Cys
            260

<210> SEQ ID NO 47
<211> LENGTH: 509
<212> TYPE: PRT
<213> ORGANISM: Artificial Sequence
<220> FEATURE:
<223> OTHER INFORMATION: Synthetic peptide: d2.2 (Y372F/V377I double
      mutant)

<400> SEQUENCE: 47

Met Asp Trp Thr Trp Arg Val Phe Cys Leu Leu Ala Val Ala Pro Gly
1               5                   10                  15

Ala His Ser Trp Ser His Pro Gln Phe Glu Lys Gln Val Gln Leu Val
                20                  25                  30

Gln Ser Gly Ala Glu Val Lys Lys Pro Gly Glu Ser Val Lys Val Ser
            35                  40                  45

Cys Lys Ala Ser Gly Tyr Thr Phe Thr Thr Tyr Tyr Leu His Trp Val
        50                  55                  60

Arg Gln Ala Pro Gly Gln Gly Leu Glu Trp Met Gly Trp Ile Tyr Pro
65                  70                  75                  80

Gly Asn Gly His Ala Gln Tyr Asn Glu Lys Phe Lys Gly Arg Val Thr
                85                  90                  95

Ile Thr Ala Asp Lys Ser Thr Ser Thr Ala Tyr Met Glu Leu Ser Ser
            100                 105                 110

Leu Arg Ser Glu Asp Thr Ala Val Tyr Tyr Cys Ala Arg Ser Trp Glu
        115                 120                 125

Gly Phe Pro Tyr Trp Gly Gln Gly Thr Thr Val Thr Val Ser Ser Gly
    130                 135                 140

Gly Gly Gly Ser Gly Gly Gly Gly Ser Gly Gly Gly Gly Ser Gly Gly
145                 150                 155                 160

Gly Gly Ser Asp Ile Gln Met Thr Gln Ser Pro Ser Ser Leu Ser Ala
                165                 170                 175

Ser Val Gly Asp Arg Val Thr Ile Thr Cys Lys Ala Ser Gln Asn Val
            180                 185                 190

Gly Ile Asn Val Ala Trp Tyr Gln Gln Lys Pro Gly Lys Ala Pro Lys
        195                 200                 205

Leu Leu Ile Ser Ser Ala Ser Tyr Arg Tyr Ser Gly Val Pro Ser Arg
    210                 215                 220

Phe Ser Gly Ser Gly Ser Gly Thr Asp Phe Thr Leu Thr Ile Ser Ser
225                 230                 235                 240

Leu Gln Pro Glu Asp Phe Ala Thr Tyr Phe Cys Gln Gln Tyr Asp Thr
                245                 250                 255

Tyr Pro Phe Thr Phe Gly Gln Gly Thr Lys Val Glu Ile Lys Gly Gly
            260                 265                 270

Gly Gly Ser Gly Gly Gly Gly Ser Glu Pro Lys Ser Ser Asp Lys Thr
        275                 280                 285

His Thr Cys Pro Pro Cys Pro Ala Pro Glu Leu Leu Gly Gly Pro Ser
    290                 295                 300

Val Phe Leu Phe Pro Pro Lys Pro Lys Asp Thr Leu Met Ile Ser Arg
305                 310                 315                 320

Thr Pro Glu Val Thr Cys Val Val Val Asp Val Ser His Glu Asp Pro
```

```
                    325                 330                 335
Glu Val Lys Phe Asn Trp Tyr Val Asp Gly Val Glu Val His Asn Ala
                340                 345                 350
Lys Thr Lys Pro Arg Glu Glu Gln Tyr Asn Ser Thr Tyr Arg Val Val
            355                 360                 365
Ser Val Leu Thr Val Leu His Gln Asp Trp Leu Asn Gly Lys Glu Tyr
        370                 375                 380
Lys Cys Lys Val Ser Asn Lys Ala Leu Pro Ala Pro Ile Glu Lys Thr
385                 390                 395                 400
Ile Ser Lys Ala Lys Gly Gln Pro Arg Glu Pro Ser Val Phe Pro Leu
                405                 410                 415
Ala Pro Ser Ser Lys Ser Thr Ser Gly Gly Thr Ala Ala Leu Gly Cys
                420                 425                 430
Leu Val Lys Asp Phe Tyr Pro Ser Asp Ile Ala Val Ser Trp Asn Ser
            435                 440                 445
Gly Ala Leu Thr Ser Gly Val His Thr Phe Pro Ala Val Leu Gln Ser
        450                 455                 460
Ser Gly Leu Tyr Ser Leu Ser Ser Val Val Thr Val Pro Ser Ser Ser
465                 470                 475                 480
Leu Gly Thr Gln Thr Tyr Ile Cys Asn Val Met His Glu Ala Leu His
                485                 490                 495
Asn His Tyr Val Asp Lys Lys Val Glu Pro Lys Ser Cys
                500                 505

<210> SEQ ID NO 48
<211> LENGTH: 509
<212> TYPE: PRT
<213> ORGANISM: Artificial Sequence
<220> FEATURE:
<223> OTHER INFORMATION: Synthetic peptide: d2.3 (Y372F/V377I/V437T
      triple mutant)

<400> SEQUENCE: 48

Met Asp Trp Thr Trp Arg Val Phe Cys Leu Leu Ala Val Ala Pro Gly
1               5                   10                  15
Ala His Ser Trp Ser His Pro Gln Phe Glu Lys Gln Val Gln Leu Val
                20                  25                  30
Gln Ser Gly Ala Glu Val Lys Lys Pro Gly Glu Ser Val Lys Val Ser
            35                  40                  45
Cys Lys Ala Ser Gly Tyr Thr Phe Thr Thr Tyr Tyr Leu His Trp Val
        50                  55                  60
Arg Gln Ala Pro Gly Gln Gly Leu Glu Trp Met Gly Trp Ile Tyr Pro
65                  70                  75                  80
Gly Asn Gly His Ala Gln Tyr Asn Glu Lys Phe Lys Gly Arg Val Thr
                85                  90                  95
Ile Thr Ala Asp Lys Ser Thr Ser Thr Ala Tyr Met Glu Leu Ser Ser
                100                 105                 110
Leu Arg Ser Glu Asp Thr Ala Val Tyr Tyr Cys Ala Arg Ser Trp Glu
            115                 120                 125
Gly Phe Pro Tyr Trp Gly Gln Gly Thr Thr Val Thr Val Ser Ser Gly
        130                 135                 140
Gly Gly Gly Ser Gly Gly Gly Gly Ser Gly Gly Gly Gly Ser Gly Gly
145                 150                 155                 160
Gly Gly Ser Asp Ile Gln Met Thr Gln Ser Pro Ser Ser Leu Ser Ala
                165                 170                 175
```

-continued

```
Ser Val Gly Asp Arg Val Thr Ile Thr Cys Lys Ala Ser Gln Asn Val
            180                 185                 190

Gly Ile Asn Val Ala Trp Tyr Gln Gln Lys Pro Gly Lys Ala Pro Lys
        195                 200                 205

Leu Leu Ile Ser Ser Ala Ser Tyr Arg Tyr Ser Gly Val Pro Ser Arg
    210                 215                 220

Phe Ser Gly Ser Gly Ser Gly Thr Asp Phe Thr Leu Thr Ile Ser Ser
225                 230                 235                 240

Leu Gln Pro Glu Asp Phe Ala Thr Tyr Phe Cys Gln Gln Tyr Asp Thr
                245                 250                 255

Tyr Pro Phe Thr Phe Gly Gln Gly Thr Lys Val Glu Ile Lys Gly Gly
            260                 265                 270

Gly Gly Ser Gly Gly Gly Gly Ser Glu Pro Lys Ser Ser Asp Lys Thr
        275                 280                 285

His Thr Cys Pro Pro Cys Pro Ala Pro Glu Leu Leu Gly Gly Pro Ser
    290                 295                 300

Val Phe Leu Phe Pro Pro Lys Pro Lys Asp Thr Leu Met Ile Ser Arg
305                 310                 315                 320

Thr Pro Glu Val Thr Cys Val Val Val Asp Val Ser His Glu Asp Pro
                325                 330                 335

Glu Val Lys Phe Asn Trp Tyr Val Asp Gly Val Glu Val His Asn Ala
            340                 345                 350

Lys Thr Lys Pro Arg Glu Glu Gln Tyr Asn Ser Thr Tyr Arg Val Val
        355                 360                 365

Ser Val Leu Thr Val Leu His Gln Asp Trp Leu Asn Gly Lys Glu Tyr
    370                 375                 380

Lys Cys Lys Val Ser Asn Lys Ala Leu Pro Ala Pro Ile Glu Lys Thr
385                 390                 395                 400

Ile Ser Lys Ala Lys Gly Gln Pro Arg Glu Pro Ser Val Phe Pro Leu
                405                 410                 415

Ala Pro Ser Ser Lys Ser Thr Ser Gly Gly Thr Ala Ala Leu Gly Cys
            420                 425                 430

Leu Val Lys Asp Phe Tyr Pro Ser Asp Ile Ala Val Ser Trp Asn Ser
        435                 440                 445

Gly Ala Leu Thr Ser Gly Val His Thr Phe Pro Ala Val Leu Gln Ser
    450                 455                 460

Ser Gly Leu Tyr Ser Leu Ser Ser Val Val Thr Val Pro Ser Ser Ser
465                 470                 475                 480

Leu Gly Thr Gln Thr Tyr Ile Cys Asn Val Met His Glu Ala Leu His
                485                 490                 495

Asn His Tyr Thr Asp Lys Lys Val Glu Pro Lys Ser Cys
            500                 505

<210> SEQ ID NO 49
<211> LENGTH: 509
<212> TYPE: PRT
<213> ORGANISM: Artificial Sequence
<220> FEATURE:
<223> OTHER INFORMATION: Synthetic peptide: d2.4
      (Y372F/V377I/S380E/V437T quad mutant)

<400> SEQUENCE: 49

Met Asp Trp Thr Trp Arg Val Phe Cys Leu Leu Ala Val Ala Pro Gly
1               5                   10                  15

Ala His Ser Trp Ser His Pro Gln Phe Glu Lys Gln Val Gln Leu Val
            20                  25                  30
```

```
Gln Ser Gly Ala Glu Val Lys Lys Pro Gly Glu Ser Val Lys Val Ser
        35                  40                  45
Cys Lys Ala Ser Gly Tyr Thr Phe Thr Thr Tyr Leu His Trp Val
 50                  55                  60
Arg Gln Ala Pro Gly Gln Gly Leu Glu Trp Met Gly Trp Ile Tyr Pro
 65                  70                  75                  80
Gly Asn Gly His Ala Gln Tyr Asn Glu Lys Phe Lys Gly Arg Val Thr
                85                  90                  95
Ile Thr Ala Asp Lys Ser Thr Ser Thr Ala Tyr Met Glu Leu Ser Ser
            100                 105                 110
Leu Arg Ser Glu Asp Thr Ala Val Tyr Tyr Cys Ala Arg Ser Trp Glu
            115                 120                 125
Gly Phe Pro Tyr Trp Gly Gln Gly Thr Thr Val Thr Val Ser Ser Gly
            130                 135                 140
Gly Gly Gly Ser Gly Gly Gly Gly Ser Gly Gly Gly Gly Ser Gly Gly
145                 150                 155                 160
Gly Gly Ser Asp Ile Gln Met Thr Gln Ser Pro Ser Ser Leu Ser Ala
                165                 170                 175
Ser Val Gly Asp Arg Val Thr Ile Thr Cys Lys Ala Ser Gln Asn Val
            180                 185                 190
Gly Ile Asn Val Ala Trp Tyr Gln Gln Lys Pro Gly Lys Ala Pro Lys
            195                 200                 205
Leu Leu Ile Ser Ser Ala Ser Tyr Arg Tyr Ser Gly Val Pro Ser Arg
            210                 215                 220
Phe Ser Gly Ser Gly Ser Gly Thr Asp Phe Thr Leu Thr Ile Ser Ser
225                 230                 235                 240
Leu Gln Pro Glu Asp Phe Ala Thr Tyr Phe Cys Gln Gln Tyr Asp Thr
            245                 250                 255
Tyr Pro Phe Thr Phe Gly Gln Gly Thr Lys Val Glu Ile Lys Gly Gly
            260                 265                 270
Gly Gly Ser Gly Gly Gly Gly Ser Glu Pro Lys Ser Ser Asp Lys Thr
            275                 280                 285
His Thr Cys Pro Pro Cys Pro Ala Pro Glu Leu Leu Gly Gly Pro Ser
            290                 295                 300
Val Phe Leu Phe Pro Pro Lys Pro Lys Asp Thr Leu Met Ile Ser Arg
305                 310                 315                 320
Thr Pro Glu Val Thr Cys Val Val Asp Val Ser His Glu Asp Pro
            325                 330                 335
Glu Val Lys Phe Asn Trp Tyr Val Asp Gly Val Glu Val His Asn Ala
            340                 345                 350
Lys Thr Lys Pro Arg Glu Glu Gln Tyr Asn Ser Thr Tyr Arg Val Val
            355                 360                 365
Ser Val Leu Thr Val Leu His Gln Asp Trp Leu Asn Gly Lys Glu Tyr
            370                 375                 380
Lys Cys Lys Val Ser Asn Lys Ala Leu Pro Ala Pro Ile Glu Lys Thr
385                 390                 395                 400
Ile Ser Lys Ala Lys Gly Gln Pro Arg Glu Pro Ser Val Phe Pro Leu
            405                 410                 415
Ala Pro Ser Ser Lys Ser Thr Ser Gly Gly Thr Ala Ala Leu Gly Cys
            420                 425                 430
Leu Val Lys Asp Phe Tyr Pro Ser Asp Ile Ala Val Glu Trp Asn Ser
            435                 440                 445
```

```
Gly Ala Leu Thr Ser Gly Val His Thr Phe Pro Ala Val Leu Gln Ser
            450                 455                 460

Ser Gly Leu Tyr Ser Leu Ser Ser Val Val Thr Val Pro Ser Ser Ser
465                 470                 475                 480

Leu Gly Thr Gln Thr Tyr Ile Cys Asn Val Met His Glu Ala Leu His
                485                 490                 495

Asn His Tyr Thr Asp Lys Lys Val Glu Pro Lys Ser Cys
            500                 505

<210> SEQ ID NO 50
<211> LENGTH: 509
<212> TYPE: PRT
<213> ORGANISM: Artificial Sequence
<220> FEATURE:
<223> OTHER INFORMATION: Synthetic peptide: homodimeric Fc chain
      H (strep-BHA10 scFv-CH2-CH3)

<400> SEQUENCE: 50

Met Glu Thr Asp Thr Leu Leu Leu Trp Val Leu Leu Leu Trp Val Pro
1               5                   10                  15

Gly Ser Thr Gly Asp Val Trp Ser His Pro Gln Phe Glu Lys Gln Val
            20                  25                  30

Gln Leu Val Gln Ser Gly Ala Glu Val Lys Lys Pro Gly Ser Ser Val
        35                  40                  45

Lys Val Ser Cys Lys Ala Ser Gly Tyr Thr Phe Thr Thr Tyr Tyr Leu
50                  55                  60

His Trp Val Arg Gln Ala Pro Gly Gln Cys Leu Glu Trp Met Gly Trp
65                  70                  75                  80

Ile Tyr Pro Gly Asn Val His Ala Gln Tyr Asn Glu Lys Phe Lys Gly
                85                  90                  95

Arg Val Thr Ile Thr Ala Asp Lys Ser Thr Ser Thr Ala Tyr Met Glu
            100                 105                 110

Leu Ser Ser Leu Arg Ser Glu Asp Thr Ala Val Tyr Tyr Cys Ala Arg
        115                 120                 125

Ser Trp Glu Gly Phe Pro Tyr Trp Gly Gln Gly Thr Thr Val Thr Val
130                 135                 140

Ser Ser Gly Gly Gly Gly Ser Gly Gly Gly Gly Ser Gly Gly Gly Gly
145                 150                 155                 160

Ser Asp Ile Gln Met Thr Gln Ser Pro Ser Ser Leu Ser Ala Ser Val
                165                 170                 175

Gly Asp Arg Val Thr Ile Thr Cys Lys Ala Ser Gln Asn Val Gly Ile
            180                 185                 190

Asn Val Ala Trp Tyr Gln Gln Lys Pro Gly Lys Ala Pro Lys Ser Leu
        195                 200                 205

Ile Ser Ser Ala Ser Tyr Arg Tyr Ser Gly Val Pro Ser Arg Phe Ser
210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Phe Cys Gln Gln Tyr Asp Thr Tyr Pro
                245                 250                 255

Phe Thr Phe Gly Cys Gly Thr Lys Val Glu Ile Lys Gly Gly Gly Gly
            260                 265                 270

Ser Gly Gly Gly Gly Ser Glu Pro Lys Ser Cys Asp Lys Thr His Thr
        275                 280                 285

Cys Pro Pro Cys Pro Ala Pro Glu Leu Leu Gly Gly Pro Ser Val Phe
290                 295                 300
```

```
Leu Phe Pro Pro Lys Pro Lys Asp Thr Leu Met Ile Ser Arg Thr Pro
305                 310                 315                 320

Glu Val Thr Cys Val Val Asp Val Ser His Glu Asp Pro Glu Val
            325                 330                 335

Lys Phe Asn Trp Tyr Val Asp Gly Val Glu Val His Asn Ala Lys Thr
                340                 345                 350

Lys Pro Arg Glu Glu Gln Tyr Asn Ser Thr Tyr Arg Val Val Ser Val
            355                 360                 365

Leu Thr Val Leu His Gln Asp Trp Leu Asn Gly Lys Glu Tyr Lys Cys
370                 375                 380

Lys Val Ser Asn Lys Ala Leu Pro Ala Pro Ile Glu Lys Thr Ile Ser
385                 390                 395                 400

Lys Ala Lys Gly Gln Pro Arg Glu Pro Gln Val Tyr Thr Leu Pro Pro
            405                 410                 415

Ser Arg Asp Glu Leu Thr Lys Asn Gln Val Ser Leu Thr Cys Leu Val
            420                 425                 430

Lys Gly Phe Tyr Pro Ser Asp Ile Ala Val Glu Trp Glu Ser Asn Gly
            435                 440                 445

Gln Pro Glu Asn Asn Tyr Lys Thr Thr Pro Pro Val Leu Asp Ser Asp
    450                 455                 460

Gly Ser Phe Phe Leu Tyr Ser Lys Leu Thr Val Asp Lys Ser Arg Trp
465                 470                 475                 480

Gln Gln Gly Asn Val Phe Ser Cys Ser Val Met His Glu Ala Leu His
                485                 490                 495

Asn His Tyr Thr Gln Lys Ser Leu Ser Leu Ser Pro Gly
            500                 505

<210> SEQ ID NO 51
<211> LENGTH: 261
<212> TYPE: PRT
<213> ORGANISM: Artificial Sequence
<220> FEATURE:
<223> OTHER INFORMATION: Synthetic peptide: homodimeric Fc chain
      L (flag-CH2-CH3)

<400> SEQUENCE: 51

Met Glu Thr Asp Thr Leu Leu Leu Trp Val Leu Leu Leu Trp Val Pro
1               5                   10                  15

Gly Ser Thr Gly Asp Val Asp Tyr Lys Asp Asp Asp Asp Lys Glu Pro
            20                  25                  30

Lys Ser Cys Asp Lys Thr His Thr Cys Pro Pro Cys Pro Ala Pro Glu
        35                  40                  45

Leu Leu Gly Gly Pro Ser Val Phe Leu Phe Pro Pro Lys Pro Lys Asp
    50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
                85                  90                  95

Val Glu Val His Asn Ala Lys Thr Lys Pro Arg Glu Glu Gln Tyr Asn
            100                 105                 110

Ser Thr Tyr Arg Val Val Ser Val Leu Thr Val Leu His Gln Asp Trp
        115                 120                 125

Leu Asn Gly Lys Glu Tyr Lys Cys Lys Val Ser Asn Lys Ala Leu Pro
    130                 135                 140

Ala Pro Ile Glu Lys Thr Ile Ser Lys Ala Lys Gly Gln Pro Arg Glu
```

```
                145                 150                 155                 160
Pro Gln Val Tyr Thr Leu Pro Pro Ser Arg Asp Glu Leu Thr Lys Asn
                    165                 170                 175

Gln Val Ser Leu Thr Cys Leu Val Lys Gly Phe Tyr Pro Ser Asp Ile
                180                 185                 190

Ala Val Glu Trp Glu Ser Asn Gly Gln Pro Glu Asn Asn Tyr Lys Thr
            195                 200                 205

Thr Pro Pro Val Leu Asp Ser Asp Gly Ser Phe Phe Leu Tyr Ser Lys
        210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
                245                 250                 255

Ser Leu Ser Pro Gly
                260

<210> SEQ ID NO 52
<211> LENGTH: 505
<212> TYPE: PRT
<213> ORGANISM: Artificial Sequence
<220> FEATURE:
<223> OTHER INFORMATION: Synthetic peptide: heterodimeric (CH1CL) Fc
      chain H (strep-BHA10 scFv-CH2-CH1)

<400> SEQUENCE: 52

Met Glu Thr Asp Thr Leu Leu Leu Trp Val Leu Leu Leu Trp Val Pro
1               5                   10                  15

Gly Ser Thr Gly Asp Val Trp Ser His Pro Gln Phe Glu Lys Gln Val
                20                  25                  30

Gln Leu Val Gln Ser Gly Ala Glu Val Lys Lys Pro Gly Ser Ser Val
            35                  40                  45

Lys Val Ser Cys Lys Ala Ser Gly Tyr Thr Phe Thr Thr Tyr Tyr Leu
        50                  55                  60

His Trp Val Arg Gln Ala Pro Gly Gln Cys Leu Glu Trp Met Gly Trp
65                  70                  75                  80

Ile Tyr Pro Gly Asn Val His Ala Gln Tyr Asn Glu Lys Phe Lys Gly
                85                  90                  95

Arg Val Thr Ile Thr Ala Asp Lys Ser Thr Ser Thr Ala Tyr Met Glu
                100                 105                 110

Leu Ser Ser Leu Arg Ser Glu Asp Thr Ala Val Tyr Tyr Cys Ala Arg
            115                 120                 125

Ser Trp Glu Gly Phe Pro Tyr Trp Gly Gln Gly Thr Thr Val Thr Val
        130                 135                 140

Ser Ser Gly Gly Gly Gly Ser Gly Gly Gly Gly Ser Gly Gly Gly Gly
145                 150                 155                 160

Ser Asp Ile Gln Met Thr Gln Ser Pro Ser Ser Leu Ser Ala Ser Val
                165                 170                 175

Gly Asp Arg Val Thr Ile Thr Cys Lys Ala Ser Gln Asn Val Gly Ile
            180                 185                 190

Asn Val Ala Trp Tyr Gln Gln Lys Pro Gly Lys Ala Pro Lys Ser Leu
        195                 200                 205

Ile Ser Ser Ala Ser Tyr Arg Tyr Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240
```

```
Pro Glu Asp Phe Ala Thr Tyr Phe Cys Gln Gln Tyr Asp Thr Tyr Pro
                245                 250                 255

Phe Thr Phe Gly Cys Gly Thr Lys Val Glu Ile Lys Gly Gly Gly Gly
            260                 265                 270

Ser Gly Gly Gly Gly Ser Glu Pro Lys Ser Cys Asp Lys Thr His Thr
        275                 280                 285

Cys Pro Pro Cys Pro Ala Pro Glu Leu Leu Gly Gly Pro Ser Val Phe
    290                 295                 300

Leu Phe Pro Pro Lys Pro Lys Asp Thr Leu Met Ile Ser Arg Thr Pro
305                 310                 315                 320

Glu Val Thr Cys Val Val Val Asp Val Ser His Glu Asp Pro Glu Val
                325                 330                 335

Lys Phe Asn Trp Tyr Val Asp Gly Val Glu Val His Asn Ala Lys Thr
            340                 345                 350

Lys Pro Arg Glu Glu Gln Tyr Asn Ser Thr Tyr Arg Val Val Ser Val
        355                 360                 365

Leu Thr Val Leu His Gln Asp Trp Leu Asn Gly Lys Glu Tyr Lys Cys
    370                 375                 380

Lys Val Ser Asn Lys Ala Leu Pro Ala Pro Ile Glu Lys Thr Ile Ser
385                 390                 395                 400

Lys Ala Ala Ser Thr Lys Gly Pro Ser Val Phe Pro Leu Ala Pro Ser
                405                 410                 415

Ser Lys Ser Thr Ser Gly Gly Thr Ala Ala Leu Gly Cys Leu Val Lys
            420                 425                 430

Asp Tyr Phe Pro Glu Pro Val Thr Val Ser Trp Asn Ser Gly Ala Leu
        435                 440                 445

Thr Ser Gly Val His Thr Phe Pro Ala Val Leu Gln Ser Ser Gly Leu
    450                 455                 460

Tyr Ser Leu Ser Ser Val Val Thr Val Pro Ser Ser Ser Leu Gly Thr
465                 470                 475                 480

Gln Thr Tyr Ile Cys Asn Val Asn His Lys Pro Ser Asn Thr Lys Val
                485                 490                 495

Asp Lys Lys Val Glu Pro Lys Ser Cys
            500                 505

<210> SEQ ID NO 53
<211> LENGTH: 261
<212> TYPE: PRT
<213> ORGANISM: Artificial Sequence
<220> FEATURE:
<223> OTHER INFORMATION: Synthetic peptide: heterodimeric Fc chain L
      (flag-CH2-CL)

<400> SEQUENCE: 53

Met Glu Thr Asp Thr Leu Leu Leu Trp Val Leu Leu Leu Trp Val Pro
1               5                   10                  15

Gly Ser Thr Gly Asp Val Asp Tyr Lys Asp Asp Asp Asp Lys Glu Pro
            20                  25                  30

Lys Ser Cys Asp Lys Thr His Thr Cys Pro Pro Cys Pro Ala Pro Glu
        35                  40                  45

Leu Leu Gly Gly Pro Ser Val Phe Leu Phe Pro Pro Lys Pro Lys Asp
    50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
                85                  90                  95
```

```
Val Glu Val His Asn Ala Lys Thr Lys Pro Arg Glu Gln Tyr Asn
            100                 105                 110

Ser Thr Tyr Arg Val Val Ser Val Leu Thr Val Leu His Gln Asp Trp
        115                 120                 125

Leu Asn Gly Lys Glu Tyr Lys Cys Lys Val Ser Asn Lys Ala Leu Pro
    130                 135                 140

Ala Pro Ile Glu Lys Thr Ile Ser Lys Ala Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260

<210> SEQ ID NO 54
<211> LENGTH: 19
<212> TYPE: PRT
<213> ORGANISM: Artificial Sequence
<220> FEATURE:
<223> OTHER INFORMATION: Synthetic peptide: Humanized 5C8 secretion
      signal

<400> SEQUENCE: 54

Met Asp Trp Thr Trp Arg Val Phe Cys Leu Leu Ala Val Ala Pro Gly
1               5                   10                  15

Ala His Ser

<210> SEQ ID NO 55
<211> LENGTH: 8
<212> TYPE: PRT
<213> ORGANISM: Artificial Sequence
<220> FEATURE:
<223> OTHER INFORMATION: Synthetic peptide: STREP-TAG II (IBA)

<400> SEQUENCE: 55

Trp Ser His Pro Gln Phe Glu Lys
1               5

<210> SEQ ID NO 56
<211> LENGTH: 116
<212> TYPE: PRT
<213> ORGANISM: Artificial Sequence
<220> FEATURE:
<223> OTHER INFORMATION: Synthetic peptide: Linker and S16E, V55G
      stabilized BHA10 scFv VH

<400> SEQUENCE: 56

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Thr Tyr
            20                  25                  30
```

Tyr Leu His Trp Val Arg Gln Ala Pro Gly Gln Gly Leu Glu Trp Met
         35                  40                  45

Gly Trp Ile Tyr Pro Gly Asn Gly His Ala Gln Tyr Asn Glu Lys Phe
     50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
             85                  90                  95

Ala Arg Ser Trp Glu Gly Phe Pro Tyr Trp Gly Gln Gly Thr Thr Val
            100                 105                 110

Thr Val Ser Ser
        115

<210> SEQ ID NO 57
<211> LENGTH: 5
<212> TYPE: PRT
<213> ORGANISM: Artificial Sequence
<220> FEATURE:
<223> OTHER INFORMATION: Synthetic peptide: G4S linker

<400> SEQUENCE: 57

Gly Gly Gly Gly Ser
1               5

<210> SEQ ID NO 58
<211> LENGTH: 107
<212> TYPE: PRT
<213> ORGANISM: Artificial Sequence
<220> FEATURE:
<223> OTHER INFORMATION: Synthetic peptide: Linker and S46L stabilized
      BHA10 scFv VL

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Ile Asn
            20                  25                  30

Val Ala Trp Tyr Gln Gln Lys Pro Gly Lys Ala Pro Lys Leu Leu Ile
        35                  40                  45

Ser Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asp Thr Tyr Pro Phe
             85                  90                  95

Thr Phe Gly Gln Gly Thr Lys Val Glu Ile Lys
            100                 105

<210> SEQ ID NO 59
<211> LENGTH: 15
<212> TYPE: PRT
<213> ORGANISM: Artificial Sequence
<220> FEATURE:
<223> OTHER INFORMATION: Synthetic peptide: CL cysteine-scrubbed IgG1
      hinge

<400> SEQUENCE: 59

Glu Pro Lys Ser Ser Asp Lys Thr His Thr Cys Pro Pro Cys Pro
1               5                   10                  15

<210> SEQ ID NO 60
<211> LENGTH: 110
<212> TYPE: PRT
<213> ORGANISM: Artificial Sequence
<220> FEATURE:
<223> OTHER INFORMATION: Synthetic peptide: IgG1 CH2

<400> SEQUENCE: 60

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

<210> SEQ ID NO 61
<211> LENGTH: 107
<212> TYPE: PRT
<213> ORGANISM: Artificial Sequence
<220> FEATURE:
<223> OTHER INFORMATION: Synthetic peptide: IgG1 CL with terminal cysteine

<400> SEQUENCE: 61

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 62
<211> LENGTH: 8
<212> TYPE: PRT
<213> ORGANISM: Artificial Sequence
<220> FEATURE:
<223> OTHER INFORMATION: Synthetic peptide: FLAG tag

<400> SEQUENCE: 62

```
Asp Tyr Lys Asp Asp Asp Asp Lys
1               5
```

<210> SEQ ID NO 63
<211> LENGTH: 103
<212> TYPE: PRT

<213> ORGANISM: Artificial Sequence
<220> FEATURE:
<223> OTHER INFORMATION: Synthetic peptide: IgG1 CH1 with terminal cysteine

<400> SEQUENCE: 63

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys
            100
```

<210> SEQ ID NO 64
<211> LENGTH: 12
<212> TYPE: PRT
<213> ORGANISM: Artificial Sequence
<220> FEATURE:
<223> OTHER INFORMATION: Synthetic peptide: IgG4 hinge

<400> SEQUENCE: 64

```
Glu Ser Lys Tyr Gly Pro Pro Cys Pro Ser Cys Pro
1               5                   10
```

<210> SEQ ID NO 65
<211> LENGTH: 110
<212> TYPE: PRT
<213> ORGANISM: Artificial Sequence
<220> FEATURE:
<223> OTHER INFORMATION: Synthetic peptide: IgG4 CH2

<400> SEQUENCE: 65

```
Ala Pro Glu Phe Leu Gly Gly Pro Ser Val Phe Leu Phe Pro Pro Lys
1               5                   10                  15
Pro Lys Asp Thr Leu Met Ile Ser Arg Thr Pro Glu Val Thr Cys Val
            20                  25                  30
Val Val Asp Val Ser Gln Glu Asp Pro Glu Val Gln Phe Asn Trp Tyr
        35                  40                  45
Val Asp Gly Val Glu Val His Asn Ala Lys Thr Lys Pro Arg Glu Glu
    50                  55                  60
Gln Phe Asn Ser Thr Tyr Arg Val Val Ser Val Leu Thr Val Leu His
65                  70                  75                  80
Gln Asp Trp Leu Asn Gly Lys Glu Tyr Lys Cys Lys Val Ser Asn Lys
                85                  90                  95
Gly Leu Pro Ser Ser Ile Glu Lys Thr Ile Ser Lys Ala Lys
            100                 105                 110
```

<210> SEQ ID NO 66
<211> LENGTH: 106
<212> TYPE: PRT
<213> ORGANISM: Artificial Sequence
<220> FEATURE:
<223> OTHER INFORMATION: Synthetic peptide: IgG4 CH3

<400> SEQUENCE: 66

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly
            100                 105

<210> SEQ ID NO 67
<211> LENGTH: 106
<212> TYPE: PRT
<213> ORGANISM: Artificial Sequence
<220> FEATURE:
<223> OTHER INFORMATION: Synthetic peptide: IgG1 CL without terminal
      cysteine

<400> SEQUENCE: 67

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu
            100                 105

<210> SEQ ID NO 68
<211> LENGTH: 102
<212> TYPE: PRT
<213> ORGANISM: Artificial Sequence
<220> FEATURE:
<223> OTHER INFORMATION: Synthetic peptide: IgG1 CH1 without terminal
      cysteine

<400> SEQUENCE: 68

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

```
Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser
            100
```

<210> SEQ ID NO 69
<211> LENGTH: 366
<212> TYPE: PRT
<213> ORGANISM: Artificial Sequence
<220> FEATURE:
<223> OTHER INFORMATION: Synthetic peptide: Chain A1:

<400> SEQUENCE: 69

```
Met Asp Trp Thr Trp Arg Val Phe Cys Leu Leu Ala Val Ala Pro Gly
1               5                   10                  15

Ala His Ser Asp Tyr Lys Asp Asp Asp Lys Glu Ser Lys Tyr Gly
            20                  25                  30

Pro Pro Cys Pro Ser Cys Pro Ala Pro Glu Phe Leu Gly Gly Pro Ser
            35                  40                  45

Val Phe Leu Phe Pro Pro Lys Pro Lys Asp Thr Leu Met Ile Ser Arg
    50                  55                  60

Thr Pro Glu Val Thr Cys Val Val Asp Val Ser Gln Glu Asp Pro
65                  70                  75                  80

Glu Val Gln Phe Asn Trp Tyr Val Asp Gly Val Glu Val His Asn Ala
                85                  90                  95

Lys Thr Lys Pro Arg Glu Glu Gln Phe Asn Ser Thr Tyr Arg Val Val
            100                 105                 110

Ser Val Leu Thr Val Leu His Gln Asp Trp Leu Asn Gly Lys Glu Tyr
        115                 120                 125

Lys Cys Lys Val Ser Asn Lys Gly Leu Pro Ser Ser Ile Glu Lys Thr
    130                 135                 140

Ile Ser Lys Ala Lys Gly Gln Pro Arg Glu Pro Gln Val Tyr Thr Leu
145                 150                 155                 160

Pro Pro Ser Gln Glu Glu Met Thr Lys Asn Gln Val Ser Leu Thr Cys
                165                 170                 175

Leu Val Lys Gly Phe Tyr Pro Ser Asp Ile Ala Val Glu Trp Glu Ser
            180                 185                 190

Asn Gly Gln Pro Glu Asn Asn Tyr Lys Thr Thr Pro Pro Val Leu Asp
        195                 200                 205

Ser Asp Gly Ser Phe Phe Leu Tyr Ser Arg Leu Thr Val Asp Lys Ser
    210                 215                 220

Arg Trp Gln Glu Gly Asn Val Phe Ser Cys Ser Val Met His Glu Ala
225                 230                 235                 240

Leu His Asn His Tyr Thr Gln Lys Ser Leu Ser Leu Ser Leu Gly Gly
                245                 250                 255

Gly Gly Gly Ser Arg Thr Val Ala Ala Pro Ser Val Phe Ile Phe Pro
            260                 265                 270

Pro Ser Asp Glu Gln Leu Lys Ser Gly Thr Ala Ser Val Val Cys Leu
        275                 280                 285

Leu Asn Asn Phe Tyr Pro Arg Glu Ala Lys Val Gln Trp Lys Val Asp
    290                 295                 300

Asn Ala Leu Gln Ser Gly Asn Ser Gln Glu Ser Val Thr Glu Gln Asp
305                 310                 315                 320
```

Ser Lys Asp Ser Thr Tyr Ser Leu Ser Ser Thr Leu Thr Leu Ser Lys
            325                 330                 335

Ala Asp Tyr Glu Lys His Lys Val Tyr Ala Cys Glu Val Thr His Gln
            340                 345                 350

Gly Leu Ser Ser Pro Val Thr Lys Ser Phe Asn Arg Gly Glu
            355                 360                 365

<210> SEQ ID NO 70
<211> LENGTH: 613
<212> TYPE: PRT
<213> ORGANISM: Artificial Sequence
<220> FEATURE:
<223> OTHER INFORMATION: Synthetic peptide: Chain B1

<400> SEQUENCE: 70

Met Asp Trp Thr Trp Arg Val Phe Cys Leu Leu Ala Val Ala Pro Gly
1               5                   10                  15

Ala His Ser Trp Ser His Pro Gln Phe Glu Lys Gln Val Gln Leu Val
            20                  25                  30

Gln Ser Gly Ala Glu Val Lys Lys Pro Gly Glu Ser Val Lys Val Ser
        35                  40                  45

Cys Lys Ala Ser Gly Tyr Thr Phe Thr Thr Tyr Leu His Trp Val
    50                  55                  60

Arg Gln Ala Pro Gly Gln Gly Leu Glu Trp Met Gly Trp Ile Tyr Pro
65                  70                  75                  80

Gly Asn Gly His Ala Gln Tyr Asn Glu Lys Phe Lys Gly Arg Val Thr
                85                  90                  95

Ile Thr Ala Asp Lys Ser Thr Ser Thr Ala Tyr Met Glu Leu Ser Ser
            100                 105                 110

Leu Arg Ser Glu Asp Thr Ala Val Tyr Tyr Cys Ala Arg Ser Trp Glu
        115                 120                 125

Gly Phe Pro Tyr Trp Gly Gln Gly Thr Thr Val Thr Val Ser Ser Gly
    130                 135                 140

Gly Gly Gly Ser Gly Gly Gly Gly Ser Gly Gly Gly Gly Ser Gly Gly
145                 150                 155                 160

Gly Gly Ser Asp Ile Gln Met Thr Gln Ser Pro Ser Ser Leu Ser Ala
                165                 170                 175

Ser Val Gly Asp Arg Val Thr Ile Thr Cys Lys Ala Ser Gln Asn Val
            180                 185                 190

Gly Ile Asn Val Ala Trp Tyr Gln Gln Lys Pro Gly Lys Ala Pro Lys
        195                 200                 205

Leu Leu Ile Ser Ser Ala Ser Tyr Arg Tyr Ser Gly Val Pro Ser Arg
    210                 215                 220

Phe Ser Gly Ser Gly Ser Gly Thr Asp Phe Thr Leu Thr Ile Ser Ser
225                 230                 235                 240

Leu Gln Pro Glu Asp Phe Ala Thr Tyr Phe Cys Gln Gln Tyr Asp Thr
                245                 250                 255

Tyr Pro Phe Thr Phe Gly Gln Gly Thr Lys Val Glu Ile Lys Gly Gly
            260                 265                 270

Gly Gly Ser Gly Gly Gly Gly Ser Glu Ser Lys Tyr Gly Pro Pro Cys
        275                 280                 285

Pro Ser Cys Pro Ala Pro Glu Phe Leu Gly Gly Pro Ser Val Phe Leu
    290                 295                 300

Phe Pro Pro Lys Pro Lys Asp Thr Leu Met Ile Ser Arg Thr Pro Glu
305                 310                 315                 320

-continued

```
Val Thr Cys Val Val Asp Val Ser Gln Glu Asp Pro Glu Val Gln
            325                 330                 335

Phe Asn Trp Tyr Val Asp Gly Val Glu Val His Asn Ala Lys Thr Lys
            340                 345                 350

Pro Arg Glu Glu Gln Phe Asn Ser Thr Tyr Arg Val Val Ser Val Leu
            355                 360                 365

Thr Val Leu His Gln Asp Trp Leu Asn Gly Lys Glu Tyr Lys Cys Lys
    370                 375                 380

Val Ser Asn Lys Gly Leu Pro Ser Ser Ile Glu Lys Thr Ile Ser Lys
385                 390                 395                 400

Ala Lys Gly Gln Pro Arg Glu Pro Gln Val Tyr Thr Leu Pro Pro Ser
                405                 410                 415

Gln Glu Glu Met Thr Lys Asn Gln Val Ser Leu Thr Cys Leu Val Lys
            420                 425                 430

Gly Phe Tyr Pro Ser Asp Ile Ala Val Glu Trp Glu Ser Asn Gly Gln
        435                 440                 445

Pro Glu Asn Asn Tyr Lys Thr Thr Pro Pro Val Leu Asp Ser Asp Gly
    450                 455                 460

Ser Phe Phe Leu Tyr Ser Arg Leu Thr Val Asp Lys Ser Arg Trp Gln
465                 470                 475                 480

Glu Gly Asn Val Phe Ser Cys Ser Val Met His Glu Ala Leu His Asn
                485                 490                 495

His Tyr Thr Gln Lys Ser Leu Ser Leu Ser Leu Gly Gly Gly Gly Gly
            500                 505                 510

Ser Ala Ser Thr Lys Gly Pro Ser Val Phe Pro Leu Ala Pro Ser Ser
        515                 520                 525

Lys Ser Thr Ser Gly Gly Thr Ala Ala Leu Gly Cys Leu Val Lys Asp
    530                 535                 540

Tyr Phe Pro Glu Pro Val Thr Val Ser Trp Asn Ser Gly Ala Leu Thr
545                 550                 555                 560

Ser Gly Val His Thr Phe Pro Ala Val Leu Gln Ser Ser Gly Leu Tyr
                565                 570                 575

Ser Leu Ser Ser Val Val Thr Val Pro Ser Ser Ser Leu Gly Thr Gln
            580                 585                 590

Thr Tyr Ile Cys Asn Val Asn His Lys Pro Ser Asn Thr Lys Val Asp
        595                 600                 605

Lys Lys Val Glu Pro
    610

<210> SEQ ID NO 71
<211> LENGTH: 371
<212> TYPE: PRT
<213> ORGANISM: Artificial Sequence
<220> FEATURE:
<223> OTHER INFORMATION: Synthetic peptide: Chain A2

<400> SEQUENCE: 71

Met Asp Trp Thr Trp Arg Val Phe Cys Leu Leu Ala Val Ala Pro Gly
1               5                   10                  15

Ala His Ser Asp Tyr Lys Asp Asp Asp Asp Lys Glu Ser Lys Tyr Gly
            20                  25                  30

Pro Pro Cys Pro Ser Cys Pro Ala Pro Glu Phe Leu Gly Gly Pro Ser
        35                  40                  45

Val Phe Leu Phe Pro Pro Lys Pro Lys Asp Thr Leu Met Ile Ser Arg
    50                  55                  60
```

```
Thr Pro Glu Val Thr Cys Val Val Asp Val Ser Gln Glu Asp Pro
 65                  70                  75                  80

Glu Val Gln Phe Asn Trp Tyr Val Asp Gly Val Glu Val His Asn Ala
             85                  90                  95

Lys Thr Lys Pro Arg Glu Glu Gln Phe Asn Ser Thr Tyr Arg Val Val
            100                 105                 110

Ser Val Leu Thr Val Leu His Gln Asp Trp Leu Asn Gly Lys Glu Tyr
            115                 120                 125

Lys Cys Lys Val Ser Asn Lys Gly Leu Pro Ser Ser Ile Glu Lys Thr
            130                 135                 140

Ile Ser Lys Ala Lys Gly Gln Pro Arg Glu Pro Gln Val Tyr Thr Leu
145                 150                 155                 160

Pro Pro Ser Gln Glu Glu Met Thr Lys Asn Gln Val Ser Leu Thr Cys
                165                 170                 175

Leu Val Lys Gly Phe Tyr Pro Ser Asp Ile Ala Val Glu Trp Glu Ser
            180                 185                 190

Asn Gly Gln Pro Glu Asn Asn Tyr Lys Thr Thr Pro Pro Val Leu Asp
            195                 200                 205

Ser Asp Gly Ser Phe Phe Leu Tyr Ser Arg Leu Thr Val Asp Lys Ser
210                 215                 220

Arg Trp Gln Glu Gly Asn Val Phe Ser Cys Ser Val Met His Glu Ala
225                 230                 235                 240

Leu His Asn His Tyr Thr Gln Lys Ser Leu Ser Leu Ser Leu Gly Gly
                245                 250                 255

Gly Gly Gly Ser Gly Gly Gly Ser Arg Thr Val Ala Ala Pro Ser
            260                 265                 270

Val Phe Ile Phe Pro Pro Ser Asp Glu Gln Leu Lys Ser Gly Thr Ala
            275                 280                 285

Ser Val Val Cys Leu Leu Asn Asn Phe Tyr Pro Arg Glu Ala Lys Val
            290                 295                 300

Gln Trp Lys Val Asp Asn Ala Leu Gln Ser Gly Asn Ser Gln Glu Ser
305                 310                 315                 320

Val Thr Glu Gln Asp Ser Lys Asp Ser Thr Tyr Ser Leu Ser Ser Thr
                325                 330                 335

Leu Thr Leu Ser Lys Ala Asp Tyr Glu Lys His Lys Val Tyr Ala Cys
            340                 345                 350

Glu Val Thr His Gln Gly Leu Ser Ser Pro Val Thr Lys Ser Phe Asn
            355                 360                 365

Arg Gly Glu
370
```

<210> SEQ ID NO 72
<211> LENGTH: 618
<212> TYPE: PRT
<213> ORGANISM: Artificial Sequence
<220> FEATURE:
<223> OTHER INFORMATION: Synthetic peptide: Chain B2

<400> SEQUENCE: 72

```
Met Asp Trp Thr Trp Arg Val Phe Cys Leu Leu Ala Val Ala Pro Gly
1                   5                  10                  15

Ala His Ser Trp Ser His Pro Gln Phe Glu Lys Gln Val Gln Leu Val
             20                  25                  30

Gln Ser Gly Ala Glu Val Lys Lys Pro Gly Glu Ser Val Lys Val Ser
         35                  40                  45
```

-continued

```
Cys Lys Ala Ser Gly Tyr Thr Phe Thr Thr Tyr Tyr Leu His Trp Val
    50              55                  60
Arg Gln Ala Pro Gly Gln Gly Leu Glu Trp Met Gly Trp Ile Tyr Pro
65              70                  75                  80
Gly Asn Gly His Ala Gln Tyr Asn Glu Lys Phe Lys Gly Arg Val Thr
                85                  90                  95
Ile Thr Ala Asp Lys Ser Thr Ser Thr Ala Tyr Met Glu Leu Ser Ser
                100                 105                 110
Leu Arg Ser Glu Asp Thr Ala Val Tyr Tyr Cys Ala Arg Ser Trp Glu
            115                 120                 125
Gly Phe Pro Tyr Trp Gly Gln Gly Thr Val Thr Val Ser Ser Gly
    130                 135                 140
Gly Gly Gly Ser Gly Gly Gly Ser Gly Gly Gly Ser Gly Gly
145                 150                 155                 160
Gly Gly Ser Asp Ile Gln Met Thr Gln Ser Pro Ser Ser Leu Ser Ala
                165                 170                 175
Ser Val Gly Asp Arg Val Thr Ile Thr Cys Lys Ala Ser Gln Asn Val
            180                 185                 190
Gly Ile Asn Val Ala Trp Tyr Gln Gln Lys Pro Gly Lys Ala Pro Lys
        195                 200                 205
Leu Leu Ile Ser Ser Ala Ser Tyr Arg Tyr Ser Gly Val Pro Ser Arg
    210                 215                 220
Phe Ser Gly Ser Gly Ser Gly Thr Asp Phe Thr Leu Thr Ile Ser Ser
225                 230                 235                 240
Leu Gln Pro Glu Asp Phe Ala Thr Tyr Phe Cys Gln Gln Tyr Asp Thr
            245                 250                 255
Tyr Pro Phe Thr Phe Gly Gln Gly Thr Lys Val Glu Ile Lys Gly Gly
        260                 265                 270
Gly Gly Ser Gly Gly Gly Ser Glu Ser Lys Tyr Gly Pro Pro Cys
    275                 280                 285
Pro Ser Cys Pro Ala Pro Glu Phe Leu Gly Gly Pro Ser Val Phe Leu
    290                 295                 300
Phe Pro Pro Lys Pro Lys Asp Thr Leu Met Ile Ser Arg Thr Pro Glu
305                 310                 315                 320
Val Thr Cys Val Val Val Asp Val Ser Gln Glu Asp Pro Glu Val Gln
            325                 330                 335
Phe Asn Trp Tyr Val Asp Gly Val Glu Val His Asn Ala Lys Thr Lys
        340                 345                 350
Pro Arg Glu Glu Gln Phe Asn Ser Thr Tyr Arg Val Val Ser Val Leu
    355                 360                 365
Thr Val Leu His Gln Asp Trp Leu Asn Gly Lys Glu Tyr Lys Cys Lys
    370                 375                 380
Val Ser Asn Lys Gly Leu Pro Ser Ser Ile Glu Lys Thr Ile Ser Lys
385                 390                 395                 400
Ala Lys Gly Gln Pro Arg Glu Pro Gln Val Tyr Thr Leu Pro Pro Ser
            405                 410                 415
Gln Glu Glu Met Thr Lys Asn Gln Val Ser Leu Thr Cys Leu Val Lys
        420                 425                 430
Gly Phe Tyr Pro Ser Asp Ile Ala Val Glu Trp Glu Ser Asn Gly Gln
    435                 440                 445
Pro Glu Asn Asn Tyr Lys Thr Thr Pro Pro Val Leu Asp Ser Asp Gly
450                 455                 460
Ser Phe Phe Leu Tyr Ser Arg Leu Thr Val Asp Lys Ser Arg Trp Gln
```

```
                465                 470                 475                 480
Glu Gly Asn Val Phe Ser Cys Ser Val Met His Glu Ala Leu His Asn
                    485                 490                 495

His Tyr Thr Gln Lys Ser Leu Ser Leu Ser Leu Gly Gly Gly Gly Gly
                500                 505                 510

Ser Gly Gly Gly Gly Ser Ala Ser Thr Lys Gly Pro Ser Val Phe Pro
            515                 520                 525

Leu Ala Pro Ser Ser Lys Ser Thr Ser Gly Gly Thr Ala Ala Leu Gly
        530                 535                 540

Cys Leu Val Lys Asp Tyr Phe Pro Glu Pro Val Thr Val Ser Trp Asn
545                 550                 555                 560

Ser Gly Ala Leu Thr Ser Gly Val His Thr Phe Pro Ala Val Leu Gln
                565                 570                 575

Ser Ser Gly Leu Tyr Ser Leu Ser Ser Val Val Thr Val Pro Ser Ser
            580                 585                 590

Ser Leu Gly Thr Gln Thr Tyr Ile Cys Asn Val Asn His Lys Pro Ser
        595                 600                 605

Asn Thr Lys Val Asp Lys Lys Val Glu Pro
    610                 615

<210> SEQ ID NO 73
<211> LENGTH: 369
<212> TYPE: PRT
<213> ORGANISM: Artificial Sequence
<220> FEATURE:
<223> OTHER INFORMATION: Synthetic peptide: Chain A3

<400> SEQUENCE: 73

Met Asp Trp Thr Trp Arg Val Phe Cys Leu Leu Ala Val Ala Pro Gly
1               5                   10                  15

Ala His Ser Asp Tyr Lys Asp Asp Asp Lys Glu Pro Lys Ser Ser
                20                  25                  30

Asp Lys Thr His Thr Cys Pro Pro Cys Pro Ala Pro Glu Leu Leu Gly
            35                  40                  45

Gly Pro Ser Val Phe Leu Phe Pro Pro Lys Pro Lys Asp Thr Leu Met
        50                  55                  60

Ile Ser Arg Thr Pro Glu Val Thr Cys Val Val Val Asp Val Ser His
65                  70                  75                  80

Glu Asp Pro Glu Val Lys Phe Asn Trp Tyr Val Asp Gly Val Glu Val
                85                  90                  95

His Asn Ala Lys Thr Lys Pro Arg Glu Glu Gln Tyr Asn Ser Thr Tyr
                100                 105                 110

Arg Val Val Ser Val Leu Thr Val Leu His Gln Asp Trp Leu Asn Gly
            115                 120                 125

Lys Glu Tyr Lys Cys Lys Val Ser Asn Lys Ala Leu Pro Ala Pro Ile
        130                 135                 140

Glu Lys Thr Ile Ser Lys Ala Lys Gly Gln Pro Arg Glu Pro Gln Val
145                 150                 155                 160

Tyr Thr Leu Pro Pro Ser Gln Glu Glu Met Thr Lys Asn Gln Val Ser
                165                 170                 175

Leu Thr Cys Leu Val Lys Gly Phe Tyr Pro Ser Asp Ile Ala Val Glu
            180                 185                 190

Trp Glu Ser Asn Gly Gln Pro Glu Asn Asn Tyr Lys Thr Thr Pro Pro
        195                 200                 205

Val Leu Asp Ser Asp Gly Ser Phe Phe Leu Tyr Ser Arg Leu Thr Val
```

```
            210                 215                 220
Asp Lys Ser Arg Trp Gln Glu Gly Asn Val Phe Ser Cys Ser Val Met
225                 230                 235                 240

His Glu Ala Leu His Asn His Tyr Thr Gln Lys Ser Leu Ser Leu Ser
                245                 250                 255

Leu Gly Gly Gly Gly Ser Arg Thr Val Ala Ala Pro Ser Val Phe
            260                 265                 270

Ile Phe Pro Pro Ser Asp Glu Gln Leu Lys Ser Gly Thr Ala Ser Val
        275                 280                 285

Val Cys Leu Leu Asn Asn Phe Tyr Pro Arg Glu Ala Lys Val Gln Trp
        290                 295                 300

Lys Val Asp Asn Ala Leu Gln Ser Gly Asn Ser Gln Glu Ser Val Thr
305                 310                 315                 320

Glu Gln Asp Ser Lys Asp Ser Thr Tyr Ser Leu Ser Ser Thr Leu Thr
                325                 330                 335

Leu Ser Lys Ala Asp Tyr Glu Lys His Lys Val Tyr Ala Cys Glu Val
            340                 345                 350

Thr His Gln Gly Leu Ser Ser Pro Val Thr Lys Ser Phe Asn Arg Gly
        355                 360                 365

Glu

<210> SEQ ID NO 74
<211> LENGTH: 616
<212> TYPE: PRT
<213> ORGANISM: Artificial Sequence
<220> FEATURE:
<223> OTHER INFORMATION: Synthetic peptide: Chain B3

<400> SEQUENCE: 74

Met Asp Trp Thr Trp Arg Val Phe Cys Leu Leu Ala Val Ala Pro Gly
1               5                   10                  15

Ala His Ser Trp Ser His Pro Gln Phe Glu Lys Gln Val Gln Leu Val
            20                  25                  30

Gln Ser Gly Ala Glu Val Lys Lys Pro Gly Glu Ser Val Lys Val Ser
        35                  40                  45

Cys Lys Ala Ser Gly Tyr Thr Phe Thr Thr Tyr Leu His Trp Val
    50                  55                  60

Arg Gln Ala Pro Gly Gln Gly Leu Glu Trp Met Gly Trp Ile Tyr Pro
65                  70                  75                  80

Gly Asn Gly His Ala Gln Tyr Asn Glu Lys Phe Lys Gly Arg Val Thr
                85                  90                  95

Ile Thr Ala Asp Lys Ser Thr Ser Thr Ala Tyr Met Glu Leu Ser Ser
            100                 105                 110

Leu Arg Ser Glu Asp Thr Ala Val Tyr Tyr Cys Ala Arg Ser Trp Glu
        115                 120                 125

Gly Phe Pro Tyr Trp Gly Gln Gly Thr Val Thr Val Ser Ser Gly
    130                 135                 140

Gly Gly Gly Ser Gly Gly Gly Gly Ser Gly Gly Gly Gly Ser Gly Gly
145                 150                 155                 160

Gly Gly Ser Asp Ile Gln Met Thr Gln Ser Pro Ser Ser Leu Ser Ala
                165                 170                 175

Ser Val Gly Asp Arg Val Thr Ile Thr Cys Lys Ala Ser Gln Asn Val
            180                 185                 190

Gly Ile Asn Val Ala Trp Tyr Gln Gln Lys Pro Gly Lys Ala Pro Lys
        195                 200                 205
```

```
Leu Leu Ile Ser Ser Ala Ser Tyr Arg Tyr Ser Gly Val Pro Ser Arg
    210                 215                 220
Phe Ser Gly Ser Gly Ser Gly Thr Asp Phe Thr Leu Thr Ile Ser Ser
225                 230                 235                 240
Leu Gln Pro Glu Asp Phe Ala Thr Tyr Phe Cys Gln Gln Tyr Asp Thr
                245                 250                 255
Tyr Pro Phe Thr Phe Gly Gln Gly Thr Lys Val Glu Ile Lys Gly Gly
            260                 265                 270
Gly Gly Ser Gly Gly Gly Gly Ser Glu Pro Lys Ser Ser Asp Lys Thr
        275                 280                 285
His Thr Cys Pro Pro Cys Pro Ala Pro Glu Leu Leu Gly Gly Pro Ser
    290                 295                 300
Val Phe Leu Phe Pro Pro Lys Pro Lys Asp Thr Leu Met Ile Ser Arg
305                 310                 315                 320
Thr Pro Glu Val Thr Cys Val Val Asp Val Ser His Glu Asp Pro
                325                 330                 335
Glu Val Lys Phe Asn Trp Tyr Val Asp Gly Val Glu Val His Asn Ala
                340                 345                 350
Lys Thr Lys Pro Arg Glu Glu Gln Tyr Asn Ser Thr Tyr Arg Val Val
            355                 360                 365
Ser Val Leu Thr Val Leu His Gln Asp Trp Leu Asn Gly Lys Glu Tyr
        370                 375                 380
Lys Cys Lys Val Ser Asn Lys Ala Leu Pro Ala Pro Ile Glu Lys Thr
385                 390                 395                 400
Ile Ser Lys Ala Lys Gly Gln Pro Arg Glu Pro Gln Val Tyr Thr Leu
                405                 410                 415
Pro Pro Ser Gln Glu Glu Met Thr Lys Asn Gln Val Ser Leu Thr Cys
            420                 425                 430
Leu Val Lys Gly Phe Tyr Pro Ser Asp Ile Ala Val Glu Trp Glu Ser
        435                 440                 445
Asn Gly Gln Pro Glu Asn Asn Tyr Lys Thr Thr Pro Pro Val Leu Asp
450                 455                 460
Ser Asp Gly Ser Phe Phe Leu Tyr Ser Arg Leu Thr Val Asp Lys Ser
465                 470                 475                 480
Arg Trp Gln Glu Gly Asn Val Phe Ser Cys Ser Val Met His Glu Ala
                485                 490                 495
Leu His Asn His Tyr Thr Gln Lys Ser Leu Ser Leu Ser Leu Gly Gly
            500                 505                 510
Gly Gly Gly Ser Ala Ser Thr Lys Gly Pro Ser Val Phe Pro Leu Ala
        515                 520                 525
Pro Ser Ser Lys Ser Thr Ser Gly Gly Thr Ala Ala Leu Gly Cys Leu
530                 535                 540
Val Lys Asp Tyr Phe Pro Glu Pro Val Thr Val Ser Trp Asn Ser Gly
545                 550                 555                 560
Ala Leu Thr Ser Gly Val His Thr Phe Pro Ala Val Leu Gln Ser Ser
                565                 570                 575
Gly Leu Tyr Ser Leu Ser Ser Val Val Thr Val Pro Ser Ser Ser Leu
            580                 585                 590
Gly Thr Gln Thr Tyr Ile Cys Asn Val Asn His Lys Pro Ser Asn Thr
        595                 600                 605
Lys Val Asp Lys Lys Val Glu Pro
    610                 615
```

<210> SEQ ID NO 75
<211> LENGTH: 9
<212> TYPE: PRT
<213> ORGANISM: Artificial Sequence
<220> FEATURE:
<223> OTHER INFORMATION: Synthetic peptide

<400> SEQUENCE: 75

Leu His Asn His Tyr Val Thr Lys Ser
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic peptide

<400> SEQUENCE: 76

Val Tyr Ala Cys Ser Val Met His Glu
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic peptide

<400> SEQUENCE: 77

Leu His Asn His Tyr Thr Gln Lys Ser
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic peptide

<400> SEQUENCE: 78

Tyr Tyr Pro Ser Asp Val Ala Val Ser
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic peptide

<400> SEQUENCE: 79

Tyr Val Asp Lys Lys Val Glu Pro Lys
1               5

<210> SEQ ID NO 80
<211> LENGTH: 259
<212> TYPE: PRT
<213> ORGANISM: Artificial Sequence
<220> FEATURE:
<223> OTHER INFORMATION: Synthetic peptide: c0 (reference)

<400> SEQUENCE: 80

Met Asp Trp Thr Trp Arg Val Phe Cys Leu Leu Ala Val Ala Pro Gly
1               5                   10                  15

Ala His Ser Asp Tyr Lys Asp Asp Asp Lys Glu Pro Lys Ser Ser

```
            20                  25                  30
Asp Lys Thr His Thr Cys Pro Pro Cys Pro Ala Pro Glu Leu Leu Gly
                35                  40                  45
Gly Pro Ser Val Phe Leu Phe Pro Pro Lys Pro Lys Asp Thr Leu Met
            50                  55                  60
Ile Ser Arg Thr Pro Glu Val Thr Cys Val Val Val Asp Val Ser His
65                  70                  75                  80
Glu Asp Pro Glu Val Lys Phe Asn Trp Tyr Val Asp Gly Val Glu Val
                85                  90                  95
His Asn Ala Lys Thr Lys Pro Arg Glu Glu Gln Tyr Asn Ser Thr Tyr
                100                 105                 110
Arg Val Val Ser Val Leu Thr Val Leu His Gln Asp Trp Leu Asn Gly
            115                 120                 125
Lys Glu Tyr Lys Cys Lys Val Ser Asn Lys Ala Leu Pro Ala Pro Ile
        130                 135                 140
Glu Lys Thr Ile Ser Lys Ala Lys Arg Thr Val Ala Ala Pro Ser Val
145                 150                 155                 160
Phe Ile Phe Pro Pro Ser Asp Glu Gln Leu Lys Ser Gly Thr Ala Ser
                165                 170                 175
Val Val Cys Leu Leu Asn Asn Phe Tyr Pro Arg Glu Ala Lys Val Gln
                180                 185                 190
Trp Lys Val Asp Asn Ala Leu Gln Ser Gly Asn Ser Gln Glu Ser Val
            195                 200                 205
Thr Glu Gln Asp Ser Lys Asp Ser Thr Tyr Ser Leu Ser Ser Thr Leu
        210                 215                 220
Thr Leu Ser Lys Ala Asp Tyr Glu Lys His Lys Val Tyr Ala Cys Glu
225                 230                 235                 240
Val Thr His Gln Gly Leu Ser Ser Pro Val Thr Lys Ser Phe Asn Arg
                245                 250                 255
Gly Glu Cys

<210> SEQ ID NO 81
<211> LENGTH: 260
<212> TYPE: PRT
<213> ORGANISM: Artificial Sequence
<220> FEATURE:
<223> OTHER INFORMATION: Synthetic peptide: c1

<400> SEQUENCE: 81

Met Asp Trp Thr Trp Arg Val Phe Cys Leu Leu Ala Val Ala Pro Gly
1               5                   10                  15
Ala His Ser Asp Tyr Lys Asp Asp Asp Lys Glu Pro Lys Ser Ser
                20                  25                  30
Asp Lys Thr His Thr Cys Pro Pro Cys Pro Ala Pro Glu Leu Leu Gly
            35                  40                  45
Gly Pro Ser Val Phe Leu Phe Pro Pro Lys Pro Lys Asp Thr Leu Met
        50                  55                  60
Ile Ser Arg Thr Pro Glu Val Thr Cys Val Val Val Asp Val Ser His
65                  70                  75                  80
Glu Asp Pro Glu Val Lys Phe Asn Trp Tyr Val Asp Gly Val Glu Val
                85                  90                  95
His Asn Ala Lys Thr Lys Pro Arg Glu Glu Gln Tyr Asn Ser Thr Tyr
            100                 105                 110
Arg Val Val Ser Val Leu Thr Val Leu His Gln Asp Trp Leu Asn Gly
        115                 120                 125
```

```
Lys Glu Tyr Lys Cys Lys Val Ser Asn Lys Ala Leu Pro Ala Pro Ile
            130                 135                 140

Glu Lys Thr Ile Ser Lys Ala Lys Gly Gln Pro Arg Glu Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
            180                 185                 190

Trp Lys Val Asp Asn Ala Leu Gln Ser Gly Asn Ser Gln Glu Ser Val
            195                 200                 205

Thr Glu Gln Asp Ser Lys Asp Ser Thr Tyr Ser Leu Ser Ser Thr Leu
            210                 215                 220

Thr Leu Ser Lys Ala Asp Tyr Glu Lys His Lys Val Tyr Ala Cys Ser
225                 230                 235                 240

Val Met His Glu Ala Leu His Asn His Tyr Val Thr Lys Ser Phe Asn
                245                 250                 255

Arg Gly Glu Cys
            260

<210> SEQ ID NO 82
<211> LENGTH: 260
<212> TYPE: PRT
<213> ORGANISM: Artificial Sequence
<220> FEATURE:
<223> OTHER INFORMATION: Synthetic peptide: c2

<400> SEQUENCE: 82

Met Asp Trp Thr Trp Arg Val Phe Cys Leu Leu Ala Val Ala Pro Gly
1               5                   10                  15

Ala His Ser Asp Tyr Lys Asp Asp Asp Lys Glu Pro Lys Ser Ser
            20                  25                  30

Asp Lys Thr His Thr Cys Pro Pro Cys Pro Ala Pro Glu Leu Leu Gly
            35                  40                  45

Gly Pro Ser Val Phe Leu Phe Pro Pro Lys Pro Lys Asp Thr Leu Met
50                  55                  60

Ile Ser Arg Thr Pro Glu Val Thr Cys Val Val Val Asp Val Ser His
65                  70                  75                  80

Glu Asp Pro Glu Val Lys Phe Asn Trp Tyr Val Asp Gly Val Glu Val
                85                  90                  95

His Asn Ala Lys Thr Lys Pro Arg Glu Glu Gln Tyr Asn Ser Thr Tyr
            100                 105                 110

Arg Val Val Ser Val Leu Thr Val Leu His Gln Asp Trp Leu Asn Gly
            115                 120                 125

Lys Glu Tyr Lys Cys Lys Val Ser Asn Lys Ala Leu Pro Ala Pro Ile
            130                 135                 140

Glu Lys Thr Ile Ser Lys Ala Lys Gly Gln Pro Arg Glu Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Ser Asp Ile Ala Val Glu
            180                 185                 190

Trp Lys Val Asp Asn Ala Leu Gln Ser Gly Asn Ser Gln Glu Ser Val
            195                 200                 205

Thr Glu Gln Asp Ser Lys Asp Ser Thr Tyr Ser Leu Ser Ser Thr Leu
            210                 215                 220
```

```
Thr Leu Ser Lys Ala Asp Tyr Glu Lys His Lys Val Tyr Ala Cys Ser
225                 230                 235                 240

Val Met His Glu Ala Leu His Asn His Tyr Val Thr Lys Ser Phe Asn
                245                 250                 255

Arg Gly Glu Cys
            260

<210> SEQ ID NO 83
<211> LENGTH: 260
<212> TYPE: PRT
<213> ORGANISM: Artificial Sequence
<220> FEATURE:
<223> OTHER INFORMATION: Synthetic peptide: c3

<400> SEQUENCE: 83

Met Asp Trp Thr Trp Arg Val Phe Cys Leu Leu Ala Val Ala Pro Gly
1               5                   10                  15

Ala His Ser Asp Tyr Lys Asp Asp Asp Lys Glu Pro Lys Ser Ser
            20                  25                  30

Asp Lys Thr His Thr Cys Pro Pro Cys Pro Ala Pro Glu Leu Leu Gly
            35                  40                  45

Gly Pro Ser Val Phe Leu Phe Pro Pro Lys Pro Lys Asp Thr Leu Met
        50                  55                  60

Ile Ser Arg Thr Pro Glu Val Thr Cys Val Val Val Asp Val Ser His
65                  70                  75                  80

Glu Asp Pro Glu Val Lys Phe Asn Trp Tyr Val Asp Gly Val Glu Val
                85                  90                  95

His Asn Ala Lys Thr Lys Pro Arg Glu Glu Gln Tyr Asn Ser Thr Tyr
            100                 105                 110

Arg Val Val Ser Val Leu Thr Val Leu His Gln Asp Trp Leu Asn Gly
        115                 120                 125

Lys Glu Tyr Lys Cys Lys Val Ser Asn Lys Ala Leu Pro Ala Pro Ile
130                 135                 140

Glu Lys Thr Ile Ser Lys Ala Lys Gly Gln Pro Arg Glu Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Ser Asp Ile Ala Val Glu
            180                 185                 190

Trp Glu Ser Asn Gly Gln Pro Glu Ser Gly Asn Ser Gln Glu Ser Val
        195                 200                 205

Thr Glu Gln Asp Ser Lys Asp Ser Thr Tyr Ser Leu Ser Ser Thr Leu
210                 215                 220

Thr Leu Ser Lys Ala Asp Tyr Glu Lys His Lys Val Tyr Ala Cys Ser
225                 230                 235                 240

Val Met His Glu Ala Leu His Asn His Tyr Val Thr Lys Ser Phe Asn
                245                 250                 255

Arg Gly Glu Cys
            260

<210> SEQ ID NO 84
<211> LENGTH: 262
<212> TYPE: PRT
<213> ORGANISM: Artificial Sequence
<220> FEATURE:
<223> OTHER INFORMATION: Synthetic peptide: c4
```

<400> SEQUENCE: 84

```
Met Asp Trp Thr Trp Arg Val Phe Cys Leu Leu Ala Val Ala Pro Gly
1               5                   10                  15

Ala His Ser Asp Tyr Lys Asp Asp Asp Lys Glu Pro Lys Ser Ser
            20                  25                  30

Asp Lys Thr His Thr Cys Pro Pro Cys Pro Ala Pro Glu Leu Leu Gly
            35                  40                  45

Gly Pro Ser Val Phe Leu Phe Pro Pro Lys Pro Lys Asp Thr Leu Met
        50                  55                  60

Ile Ser Arg Thr Pro Glu Val Thr Cys Val Val Val Asp Val Ser His
65                  70                  75                  80

Glu Asp Pro Glu Val Lys Phe Asn Trp Tyr Val Asp Gly Val Glu Val
                85                  90                  95

His Asn Ala Lys Thr Lys Pro Arg Glu Glu Gln Tyr Asn Ser Thr Tyr
            100                 105                 110

Arg Val Val Ser Val Leu Thr Val Leu His Gln Asp Trp Leu Asn Gly
        115                 120                 125

Lys Glu Tyr Lys Cys Lys Val Ser Asn Lys Ala Leu Pro Ala Pro Ile
130                 135                 140

Glu Lys Thr Ile Ser Lys Ala Lys Gly Ser Gly Gln Pro Arg Glu Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Ser Val Met His Glu Ala Leu His Asn His Tyr Val Thr Lys Ser
                245                 250                 255

Phe Asn Arg Gly Glu Cys
            260
```

<210> SEQ ID NO 85
<211> LENGTH: 262
<212> TYPE: PRT
<213> ORGANISM: Artificial Sequence
<220> FEATURE:
<223> OTHER INFORMATION: Synthetic peptide: c5

<400> SEQUENCE: 85

```
Met Asp Trp Thr Trp Arg Val Phe Cys Leu Leu Ala Val Ala Pro Gly
1               5                   10                  15

Ala His Ser Asp Tyr Lys Asp Asp Asp Lys Glu Pro Lys Ser Ser
            20                  25                  30

Asp Lys Thr His Thr Cys Pro Pro Cys Pro Ala Pro Glu Leu Leu Gly
            35                  40                  45

Gly Pro Ser Val Phe Leu Phe Pro Pro Lys Pro Lys Asp Thr Leu Met
        50                  55                  60

Ile Ser Arg Thr Pro Glu Val Thr Cys Val Val Val Asp Val Ser His
65                  70                  75                  80

Glu Asp Pro Glu Val Lys Phe Asn Trp Tyr Val Asp Gly Val Glu Val
```

```
                  85                  90                  95

His Asn Ala Lys Thr Lys Pro Arg Glu Glu Gln Tyr Asn Ser Thr Tyr
            100                 105                 110

Arg Val Val Ser Val Leu Thr Val Leu His Gln Asp Trp Leu Asn Gly
            115                 120                 125

Lys Glu Tyr Lys Cys Lys Val Ser Asn Lys Ala Leu Pro Ala Pro Ile
            130                 135                 140

Glu Lys Thr Ile Ser Lys Ala Lys Gly Ser Gly Gln Pro Arg Glu Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Ser Asp Ile Ala
                180                 185                 190

Val Glu Trp Lys Val Asp Asn Ala Leu Gln Ser Gly Asn Ser Gln Glu
                195                 200                 205

Ser Val Thr Glu Gln Asp Ser Lys Asp Ser Thr Tyr Ser Leu Ser Ser
            210                 215                 220

Thr Leu Thr Leu Ser Lys Ala Asp Tyr Glu Lys His Lys Val Tyr Ala
225                 230                 235                 240

Cys Ser Val Met His Glu Ala Leu His Asn His Tyr Val Thr Lys Ser
                245                 250                 255

Phe Asn Arg Gly Glu Cys
            260

<210> SEQ ID NO 86
<211> LENGTH: 262
<212> TYPE: PRT
<213> ORGANISM: Artificial Sequence
<220> FEATURE:
<223> OTHER INFORMATION: Synthetic peptide: c6

<400> SEQUENCE: 86

Met Asp Trp Thr Trp Arg Val Phe Cys Leu Leu Ala Val Ala Pro Gly
1               5                   10                  15

Ala His Ser Asp Tyr Lys Asp Asp Asp Lys Glu Pro Lys Ser Ser
            20                  25                  30

Asp Lys Thr His Thr Cys Pro Pro Cys Pro Ala Pro Glu Leu Leu Gly
            35                  40                  45

Gly Pro Ser Val Phe Leu Phe Pro Pro Lys Pro Lys Asp Thr Leu Met
        50                  55                  60

Ile Ser Arg Thr Pro Glu Val Thr Cys Val Val Val Asp Val Ser His
65                  70                  75                  80

Glu Asp Pro Glu Val Lys Phe Asn Trp Tyr Val Asp Gly Val Glu Val
                85                  90                  95

His Asn Ala Lys Thr Lys Pro Arg Glu Glu Gln Tyr Asn Ser Thr Tyr
            100                 105                 110

Arg Val Val Ser Val Leu Thr Val Leu His Gln Asp Trp Leu Asn Gly
            115                 120                 125

Lys Glu Tyr Lys Cys Lys Val Ser Asn Lys Ala Leu Pro Ala Pro Ile
            130                 135                 140

Glu Lys Thr Ile Ser Lys Ala Lys Gly Ser Gly Gln Pro Arg Glu Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Ser Asp Ile Ala
```

```
            180                 185                 190
Val Glu Trp Glu Ser Asn Gly Gln Pro Glu Ser Gly Asn Ser Gln Glu
            195                 200                 205

Ser Val Thr Glu Gln Asp Ser Lys Asp Ser Thr Tyr Ser Leu Ser Ser
            210                 215                 220

Thr Leu Thr Leu Ser Lys Ala Asp Tyr Glu Lys His Lys Val Tyr Ala
225                 230                 235                 240

Cys Ser Val Met His Glu Ala Leu His Asn His Tyr Val Thr Lys Ser
                245                 250                 255

Phe Asn Arg Gly Glu Cys
                260

<210> SEQ ID NO 87
<211> LENGTH: 264
<212> TYPE: PRT
<213> ORGANISM: Artificial Sequence
<220> FEATURE:
<223> OTHER INFORMATION: Synthetic peptide: c7

<400> SEQUENCE: 87

Met Asp Trp Thr Trp Arg Val Phe Cys Leu Leu Ala Val Ala Pro Gly
1               5                   10                  15

Ala His Ser Asp Tyr Lys Asp Asp Asp Lys Glu Pro Lys Ser Ser
            20                  25                  30

Asp Lys Thr His Thr Cys Pro Pro Cys Pro Ala Pro Glu Leu Leu Gly
            35                  40                  45

Gly Pro Ser Val Phe Leu Phe Pro Pro Lys Pro Lys Asp Thr Leu Met
50                  55                  60

Ile Ser Arg Thr Pro Glu Val Thr Cys Val Val Val Asp Val Ser His
65                  70                  75                  80

Glu Asp Pro Glu Val Lys Phe Asn Trp Tyr Val Asp Gly Val Glu Val
                85                  90                  95

His Asn Ala Lys Thr Lys Pro Arg Glu Glu Gln Tyr Asn Ser Thr Tyr
            100                 105                 110

Arg Val Val Ser Val Leu Thr Val Leu His Gln Asp Trp Leu Asn Gly
            115                 120                 125

Lys Glu Tyr Lys Cys Lys Val Ser Asn Lys Ala Leu Pro Ala Pro Ile
130                 135                 140

Glu Lys Thr Ile Ser Lys Ala Lys Gly Gly Ser Gly Gln Pro Arg
145                 150                 155                 160

Glu Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Arg Glu
            180                 185                 190

Ala Lys Val Gln Trp Lys Val Asp Asn Ala Leu Gln Ser Gly Asn Ser
            195                 200                 205

Gln Glu Ser Val Thr Glu Gln Asp Ser Lys Asp Ser Thr Tyr Ser Leu
            210                 215                 220

Ser Ser Thr Leu Thr Leu Ser Lys Ala Asp Tyr Glu Lys His Lys Val
225                 230                 235                 240

Tyr Ala Cys Ser Val Met His Glu Ala Leu His Asn His Tyr Val Thr
                245                 250                 255

Lys Ser Phe Asn Arg Gly Glu Cys
                260
```

-continued

```
<210> SEQ ID NO 88
<211> LENGTH: 264
<212> TYPE: PRT
<213> ORGANISM: Artificial Sequence
<220> FEATURE:
<223> OTHER INFORMATION: Synthetic peptide: c8

<400> SEQUENCE: 88

Met Asp Trp Thr Trp Arg Val Phe Cys Leu Leu Ala Val Ala Pro Gly
1               5                   10                  15

Ala His Ser Asp Tyr Lys Asp Asp Asp Lys Glu Pro Lys Ser Ser
            20                  25                  30

Asp Lys Thr His Thr Cys Pro Pro Cys Pro Ala Pro Glu Leu Leu Gly
        35                  40                  45

Gly Pro Ser Val Phe Leu Phe Pro Pro Lys Pro Lys Asp Thr Leu Met
    50                  55                  60

Ile Ser Arg Thr Pro Glu Val Thr Cys Val Val Val Asp Val Ser His
65                  70                  75                  80

Glu Asp Pro Glu Val Lys Phe Asn Trp Tyr Val Asp Gly Val Glu Val
                85                  90                  95

His Asn Ala Lys Thr Lys Pro Arg Glu Glu Gln Tyr Asn Ser Thr Tyr
            100                 105                 110

Arg Val Val Ser Val Leu Thr Val Leu His Gln Asp Trp Leu Asn Gly
        115                 120                 125

Lys Glu Tyr Lys Cys Lys Val Ser Asn Lys Ala Leu Pro Ala Pro Ile
    130                 135                 140

Glu Lys Thr Ile Ser Lys Ala Lys Gly Gly Ser Gly Gln Pro Arg
145                 150                 155                 160

Glu Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Ser Asp
            180                 185                 190

Ile Ala Val Glu Trp Lys Val Asp Asn Ala Leu Gln Ser Gly Asn Ser
        195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Ser Val Met His Glu Ala Leu His Asn His Tyr Val Thr
                245                 250                 255

Lys Ser Phe Asn Arg Gly Glu Cys
            260

<210> SEQ ID NO 89
<211> LENGTH: 264
<212> TYPE: PRT
<213> ORGANISM: Artificial Sequence
<220> FEATURE:
<223> OTHER INFORMATION: Synthetic peptide: c9

<400> SEQUENCE: 89

Met Asp Trp Thr Trp Arg Val Phe Cys Leu Leu Ala Val Ala Pro Gly
1               5                   10                  15

Ala His Ser Asp Tyr Lys Asp Asp Asp Lys Glu Pro Lys Ser Ser
            20                  25                  30

Asp Lys Thr His Thr Cys Pro Pro Cys Pro Ala Pro Glu Leu Leu Gly
        35                  40                  45
```

Gly Pro Ser Val Phe Leu Phe Pro Pro Lys Pro Lys Asp Thr Leu Met
    50                  55                  60

Ile Ser Arg Thr Pro Glu Val Thr Cys Val Val Val Asp Val Ser His
65                  70                  75                  80

Glu Asp Pro Glu Val Lys Phe Asn Trp Tyr Val Asp Gly Val Glu Val
                85                  90                  95

His Asn Ala Lys Thr Lys Pro Arg Glu Glu Gln Tyr Asn Ser Thr Tyr
            100                 105                 110

Arg Val Val Ser Val Leu Thr Val Leu His Gln Asp Trp Leu Asn Gly
            115                 120                 125

Lys Glu Tyr Lys Cys Lys Val Ser Asn Lys Ala Leu Pro Ala Pro Ile
130                 135                 140

Glu Lys Thr Ile Ser Lys Ala Lys Gly Gly Ser Gly Gln Pro Arg
145                 150                 155                 160

Glu Pro Ser Val Phe Ile Phe Pro Pro Ser Asp Glu Gln Leu Lys Ser
                165                 170                 175

Gly Thr Ala Ser Val Val Cys Leu Leu Asn Asn Phe Tyr Pro Ser Asp
            180                 185                 190

Ile Ala Val Glu Trp Glu Ser Asn Gly Gln Pro Glu Ser Gly Asn Ser
            195                 200                 205

Gln Glu Ser Val Thr Glu Gln Asp Ser Lys Asp Ser Thr Tyr Ser Leu
    210                 215                 220

Ser Ser Thr Leu Thr Leu Ser Lys Ala Asp Tyr Glu Lys His Lys Val
225                 230                 235                 240

Tyr Ala Cys Ser Val Met His Glu Ala Leu His Asn His Tyr Val Thr
                245                 250                 255

Lys Ser Phe Asn Arg Gly Glu Cys
            260

<210> SEQ ID NO 90
<211> LENGTH: 508
<212> TYPE: PRT
<213> ORGANISM: Artificial Sequence
<220> FEATURE:
<223> OTHER INFORMATION: Synthetic peptide: d0(reference)

<400> SEQUENCE: 90

Met Asp Trp Thr Trp Arg Val Phe Cys Leu Leu Ala Val Ala Pro Gly
1               5                   10                  15

Ala His Ser Trp Ser His Pro Gln Phe Glu Lys Gln Val Gln Leu Val
            20                  25                  30

Gln Ser Gly Ala Glu Val Lys Lys Pro Gly Glu Ser Val Lys Val Ser
        35                  40                  45

Cys Lys Ala Ser Gly Tyr Thr Phe Thr Thr Tyr Leu His Trp Val
    50                  55                  60

Arg Gln Ala Pro Gly Gln Gly Leu Glu Trp Met Gly Trp Ile Tyr Pro
65                  70                  75                  80

Gly Asn Gly His Ala Gln Tyr Asn Glu Lys Phe Lys Gly Arg Val Thr
                85                  90                  95

Ile Thr Ala Asp Lys Ser Thr Ser Thr Ala Tyr Met Glu Leu Ser Ser
            100                 105                 110

Leu Arg Ser Glu Asp Thr Ala Val Tyr Tyr Cys Ala Arg Ser Trp Glu
            115                 120                 125

Gly Phe Pro Tyr Trp Gly Gln Gly Thr Thr Val Thr Val Ser Ser Gly
        130                 135                 140

```
Gly Gly Gly Ser Gly Gly Gly Ser Gly Gly Gly Ser Gly Gly
145                 150                 155                 160

Gly Gly Ser Asp Ile Gln Met Thr Gln Ser Pro Ser Ser Leu Ser Ala
            165                 170                 175

Ser Val Gly Asp Arg Val Thr Ile Thr Cys Lys Ala Ser Gln Asn Val
            180                 185                 190

Gly Ile Asn Val Ala Trp Tyr Gln Gln Lys Pro Gly Lys Ala Pro Lys
            195                 200                 205

Leu Leu Ile Ser Ser Ala Ser Tyr Arg Tyr Ser Gly Val Pro Ser Arg
    210                 215                 220

Phe Ser Gly Ser Gly Ser Gly Thr Asp Phe Thr Leu Thr Ile Ser Ser
225                 230                 235                 240

Leu Gln Pro Glu Asp Phe Ala Thr Tyr Phe Cys Gln Gln Tyr Asp Thr
            245                 250                 255

Tyr Pro Phe Thr Phe Gly Gln Gly Thr Lys Val Glu Ile Lys Gly Gly
            260                 265                 270

Gly Gly Ser Gly Gly Gly Ser Glu Pro Lys Ser Ser Asp Lys Thr
        275                 280                 285

His Thr Cys Pro Pro Cys Pro Ala Pro Glu Leu Leu Gly Gly Pro Ser
    290                 295                 300

Val Phe Leu Phe Pro Pro Lys Pro Lys Asp Thr Leu Met Ile Ser Arg
305                 310                 315                 320

Thr Pro Glu Val Thr Cys Val Val Val Asp Val Ser His Glu Asp Pro
            325                 330                 335

Glu Val Lys Phe Asn Trp Tyr Val Asp Gly Val Glu Val His Asn Ala
            340                 345                 350

Lys Thr Lys Pro Arg Glu Glu Gln Tyr Asn Ser Thr Tyr Arg Val Val
            355                 360                 365

Ser Val Leu Thr Val Leu His Gln Asp Trp Leu Asn Gly Lys Glu Tyr
    370                 375                 380

Lys Cys Lys Val Ser Asn Lys Ala Leu Pro Ala Pro Ile Glu Lys Thr
385                 390                 395                 400

Ile Ser Lys Ala Lys Ala Ser Thr Lys Gly Pro Ser Val Phe Pro Leu
            405                 410                 415

Ala Pro Ser Ser Lys Ser Thr Ser Gly Gly Thr Ala Ala Leu Gly Cys
            420                 425                 430

Leu Val Lys Asp Tyr Phe Pro Glu Pro Val Thr Val Ser Trp Asn Ser
            435                 440                 445

Gly Ala Leu Thr Ser Gly Val His Thr Phe Pro Ala Val Leu Gln Ser
    450                 455                 460

Ser Gly Leu Tyr Ser Leu Ser Ser Val Val Thr Val Pro Ser Ser Ser
465                 470                 475                 480

Leu Gly Thr Gln Thr Tyr Ile Cys Asn Val Asn His Lys Pro Ser Asn
            485                 490                 495

Thr Lys Val Asp Lys Lys Val Glu Pro Lys Ser Cys
            500                 505

<210> SEQ ID NO 91
<211> LENGTH: 509
<212> TYPE: PRT
<213> ORGANISM: Artificial Sequence
<220> FEATURE:
<223> OTHER INFORMATION: Synthetic peptide: d1

<400> SEQUENCE: 91
```

```
Met Asp Trp Thr Trp Arg Val Phe Cys Leu Leu Ala Val Ala Pro Gly
1               5                   10                  15
Ala His Ser Trp Ser His Pro Gln Phe Glu Lys Gln Val Gln Leu Val
            20                  25                  30
Gln Ser Gly Ala Glu Val Lys Lys Pro Gly Glu Ser Val Lys Val Ser
        35                  40                  45
Cys Lys Ala Ser Gly Tyr Thr Phe Thr Thr Tyr Leu His Trp Val
50                  55                  60
Arg Gln Ala Pro Gly Gln Gly Leu Glu Trp Met Gly Trp Ile Tyr Pro
65                  70                  75                  80
Gly Asn Gly His Ala Gln Tyr Asn Glu Lys Phe Lys Gly Arg Val Thr
            85                  90                  95
Ile Thr Ala Asp Lys Ser Thr Ser Thr Ala Tyr Met Glu Leu Ser Ser
            100                 105                 110
Leu Arg Ser Glu Asp Thr Ala Val Tyr Tyr Cys Ala Arg Ser Trp Glu
        115                 120                 125
Gly Phe Pro Tyr Trp Gly Gln Gly Thr Thr Val Thr Val Ser Ser Gly
    130                 135                 140
Gly Gly Ser Gly Gly Gly Gly Ser Gly Gly Gly Ser Gly Gly
145                 150                 155                 160
Gly Gly Ser Asp Ile Gln Met Thr Gln Ser Pro Ser Ser Leu Ser Ala
            165                 170                 175
Ser Val Gly Asp Arg Val Thr Ile Thr Cys Lys Ala Ser Gln Asn Val
            180                 185                 190
Gly Ile Asn Val Ala Trp Tyr Gln Gln Lys Pro Gly Lys Ala Pro Lys
            195                 200                 205
Leu Leu Ile Ser Ser Ala Ser Tyr Arg Tyr Ser Gly Val Pro Ser Arg
        210                 215                 220
Phe Ser Gly Ser Gly Ser Gly Thr Asp Phe Thr Leu Thr Ile Ser Ser
225                 230                 235                 240
Leu Gln Pro Glu Asp Phe Ala Thr Tyr Phe Cys Gln Gln Tyr Asp Thr
                245                 250                 255
Tyr Pro Phe Thr Phe Gly Gln Gly Thr Lys Val Glu Ile Lys Gly Gly
                260                 265                 270
Gly Gly Ser Gly Gly Gly Gly Ser Glu Pro Lys Ser Ser Asp Lys Thr
        275                 280                 285
His Thr Cys Pro Pro Cys Pro Ala Pro Glu Leu Leu Gly Gly Pro Ser
    290                 295                 300
Val Phe Leu Phe Pro Pro Lys Pro Lys Asp Thr Leu Met Ile Ser Arg
305                 310                 315                 320
Thr Pro Glu Val Thr Cys Val Val Val Asp Val Ser His Glu Asp Pro
                325                 330                 335
Glu Val Lys Phe Asn Trp Tyr Val Asp Gly Val Glu Val His Asn Ala
                340                 345                 350
Lys Thr Lys Pro Arg Glu Glu Gln Tyr Asn Ser Thr Tyr Arg Val Val
            355                 360                 365
Ser Val Leu Thr Val Leu His Gln Asp Trp Leu Asn Gly Lys Glu Tyr
        370                 375                 380
Lys Cys Lys Val Ser Asn Lys Ala Leu Pro Ala Pro Ile Glu Lys Thr
385                 390                 395                 400
Ile Ser Lys Ala Lys Gly Gln Pro Arg Glu Pro Ser Val Phe Pro Leu
                405                 410                 415
Ala Pro Ser Ser Lys Ser Thr Ser Gly Gly Thr Ala Ala Leu Gly Cys
```

```
                      420                 425                 430
Leu Val Lys Asp Tyr Phe Pro Glu Pro Val Thr Val Ser Trp Asn Ser
            435                 440                 445

Gly Ala Leu Thr Ser Gly Val His Thr Phe Pro Ala Val Leu Gln Ser
        450                 455                 460

Ser Gly Leu Tyr Ser Leu Ser Ser Val Val Thr Val Pro Ser Ser Ser
465                 470                 475                 480

Leu Gly Thr Gln Thr Tyr Ile Cys Asn Val Met His Glu Ala Leu His
                485                 490                 495

Asn His Tyr Val Asp Lys Lys Val Glu Pro Lys Ser Cys
                500                 505

<210> SEQ ID NO 92
<211> LENGTH: 509
<212> TYPE: PRT
<213> ORGANISM: Artificial Sequence
<220> FEATURE:
<223> OTHER INFORMATION: Synthetic peptide: d2

<400> SEQUENCE: 92

Met Asp Trp Thr Trp Arg Val Phe Cys Leu Leu Ala Val Ala Pro Gly
1               5                   10                  15

Ala His Ser Trp Ser His Pro Gln Phe Glu Lys Gln Val Gln Leu Val
            20                  25                  30

Gln Ser Gly Ala Glu Val Lys Lys Pro Gly Glu Ser Val Lys Val Ser
        35                  40                  45

Cys Lys Ala Ser Gly Tyr Thr Phe Thr Thr Tyr Leu His Trp Val
    50                  55                  60

Arg Gln Ala Pro Gly Gln Gly Leu Glu Trp Met Gly Trp Ile Tyr Pro
65                  70                  75                  80

Gly Asn Gly His Ala Gln Tyr Asn Glu Lys Phe Lys Gly Arg Val Thr
                85                  90                  95

Ile Thr Ala Asp Lys Ser Thr Ser Thr Ala Tyr Met Glu Leu Ser Ser
            100                 105                 110

Leu Arg Ser Glu Asp Thr Ala Val Tyr Tyr Cys Ala Arg Ser Trp Glu
        115                 120                 125

Gly Phe Pro Tyr Trp Gly Gln Gly Thr Thr Val Thr Val Ser Ser Gly
    130                 135                 140

Gly Gly Gly Ser Gly Gly Gly Gly Ser Gly Gly Gly Gly Ser Gly Gly
145                 150                 155                 160

Gly Gly Ser Asp Ile Gln Met Thr Gln Ser Pro Ser Ser Leu Ser Ala
                165                 170                 175

Ser Val Gly Asp Arg Val Thr Ile Thr Cys Lys Ala Ser Gln Asn Val
            180                 185                 190

Gly Ile Asn Val Ala Trp Tyr Gln Gln Lys Pro Gly Lys Ala Pro Lys
        195                 200                 205

Leu Leu Ile Ser Ser Ala Ser Tyr Arg Tyr Ser Gly Val Pro Ser Arg
    210                 215                 220

Phe Ser Gly Ser Gly Ser Gly Thr Asp Phe Thr Leu Thr Ile Ser Ser
225                 230                 235                 240

Leu Gln Pro Glu Asp Phe Ala Thr Tyr Phe Cys Gln Gln Tyr Asp Thr
                245                 250                 255

Tyr Pro Phe Thr Phe Gly Gln Gly Thr Lys Val Glu Ile Lys Gly Gly
            260                 265                 270

Gly Gly Ser Gly Gly Gly Gly Ser Glu Pro Lys Ser Ser Asp Lys Thr
```

```
                275                 280                 285
His Thr Cys Pro Pro Cys Pro Ala Pro Glu Leu Leu Gly Gly Pro Ser
    290                 295                 300

Val Phe Leu Phe Pro Pro Lys Pro Lys Asp Thr Leu Met Ile Ser Arg
305                 310                 315                 320

Thr Pro Glu Val Thr Cys Val Val Val Asp Val Ser His Glu Asp Pro
                325                 330                 335

Glu Val Lys Phe Asn Trp Tyr Val Asp Gly Val Glu Val His Asn Ala
            340                 345                 350

Lys Thr Lys Pro Arg Glu Glu Gln Tyr Asn Ser Thr Tyr Arg Val Val
        355                 360                 365

Ser Val Leu Thr Val Leu His Gln Asp Trp Leu Asn Gly Lys Glu Tyr
    370                 375                 380

Lys Cys Lys Val Ser Asn Lys Ala Leu Pro Ala Pro Ile Glu Lys Thr
385                 390                 395                 400

Ile Ser Lys Ala Lys Gly Gln Pro Arg Glu Pro Ser Val Phe Pro Leu
                405                 410                 415

Ala Pro Ser Ser Lys Ser Thr Ser Gly Gly Thr Ala Ala Leu Gly Cys
            420                 425                 430

Leu Val Lys Asp Tyr Tyr Pro Ser Asp Val Ala Val Ser Trp Asn Ser
        435                 440                 445

Gly Ala Leu Thr Ser Gly Val His Thr Phe Pro Ala Val Leu Gln Ser
    450                 455                 460

Ser Gly Leu Tyr Ser Leu Ser Ser Val Val Thr Val Pro Ser Ser Ser
465                 470                 475                 480

Leu Gly Thr Gln Thr Tyr Ile Cys Asn Val Met His Glu Ala Leu His
                485                 490                 495

Asn His Tyr Val Asp Lys Lys Val Glu Pro Lys Ser Cys
            500                 505

<210> SEQ ID NO 93
<211> LENGTH: 509
<212> TYPE: PRT
<213> ORGANISM: Artificial Sequence
<220> FEATURE:
<223> OTHER INFORMATION: Synthetic peptide: d3

<400> SEQUENCE: 93

Met Asp Trp Thr Trp Arg Val Phe Cys Leu Leu Ala Val Ala Pro Gly
1               5                   10                  15

Ala His Ser Trp Ser His Pro Gln Phe Glu Lys Gln Val Gln Leu Val
            20                  25                  30

Gln Ser Gly Ala Glu Val Lys Lys Pro Gly Glu Ser Val Lys Val Ser
        35                  40                  45

Cys Lys Ala Ser Gly Tyr Thr Phe Thr Thr Tyr Leu His Trp Val
    50                  55                  60

Arg Gln Ala Pro Gly Gln Gly Leu Glu Trp Met Gly Trp Ile Tyr Pro
65                  70                  75                  80

Gly Asn Gly His Ala Gln Tyr Asn Glu Lys Phe Lys Gly Arg Val Thr
                85                  90                  95

Ile Thr Ala Asp Lys Ser Thr Ser Thr Ala Tyr Met Glu Leu Ser Ser
            100                 105                 110

Leu Arg Ser Glu Asp Thr Ala Val Tyr Tyr Cys Ala Arg Ser Trp Glu
        115                 120                 125

Gly Phe Pro Tyr Trp Gly Gln Gly Thr Thr Val Thr Val Ser Ser Gly
```

-continued

```
            130                 135                 140
Gly Gly Gly Ser Gly Gly Gly Ser Gly Gly Gly Ser Gly Gly
145                 150                 155                 160

Gly Gly Ser Asp Ile Gln Met Thr Gln Ser Pro Ser Ser Leu Ser Ala
                165                 170                 175

Ser Val Gly Asp Arg Val Thr Ile Thr Cys Lys Ala Ser Gln Asn Val
                180                 185                 190

Gly Ile Asn Val Ala Trp Tyr Gln Gln Lys Pro Gly Lys Ala Pro Lys
            195                 200                 205

Leu Leu Ile Ser Ser Ala Ser Tyr Arg Tyr Ser Gly Val Pro Ser Arg
210                 215                 220

Phe Ser Gly Ser Gly Ser Gly Thr Asp Phe Thr Leu Thr Ile Ser Ser
225                 230                 235                 240

Leu Gln Pro Glu Asp Phe Ala Thr Tyr Phe Cys Gln Gln Tyr Asp Thr
                245                 250                 255

Tyr Pro Phe Thr Phe Gly Gln Gly Thr Lys Val Glu Ile Lys Gly Gly
                260                 265                 270

Gly Gly Ser Gly Gly Gly Gly Ser Glu Pro Lys Ser Ser Asp Lys Thr
            275                 280                 285

His Thr Cys Pro Pro Cys Pro Ala Pro Glu Leu Leu Gly Gly Pro Ser
290                 295                 300

Val Phe Leu Phe Pro Pro Lys Pro Lys Asp Thr Leu Met Ile Ser Arg
305                 310                 315                 320

Thr Pro Glu Val Thr Cys Val Val Val Asp Val Ser His Glu Asp Pro
                325                 330                 335

Glu Val Lys Phe Asn Trp Tyr Val Asp Gly Val Glu Val His Asn Ala
                340                 345                 350

Lys Thr Lys Pro Arg Glu Glu Gln Tyr Asn Ser Thr Tyr Arg Val Val
            355                 360                 365

Ser Val Leu Thr Val Leu His Gln Asp Trp Leu Asn Gly Lys Glu Tyr
370                 375                 380

Lys Cys Lys Val Ser Asn Lys Ala Leu Pro Ala Pro Ile Glu Lys Thr
385                 390                 395                 400

Ile Ser Lys Ala Lys Gly Gln Pro Arg Glu Pro Ser Val Phe Pro Leu
                405                 410                 415

Ala Pro Ser Ser Lys Ser Thr Ser Gly Gly Thr Ala Ala Leu Gly Cys
                420                 425                 430

Leu Val Lys Asp Phe Tyr Pro Ser Asp Ile Ala Val Glu Trp Glu Ser
            435                 440                 445

Gly Ala Leu Thr Ser Gly Val His Thr Phe Pro Ala Val Leu Gln Ser
450                 455                 460

Ser Gly Leu Tyr Ser Leu Ser Ser Val Val Thr Val Pro Ser Ser Ser
465                 470                 475                 480

Leu Gly Thr Gln Thr Tyr Ile Cys Ser Val Met His Glu Ala Leu His
                485                 490                 495

Asn His Tyr Val Gln Lys Ser Val Glu Pro Lys Ser Cys
            500                 505

<210> SEQ ID NO 94
<211> LENGTH: 510
<212> TYPE: PRT
<213> ORGANISM: Artificial Sequence
<220> FEATURE:
<223> OTHER INFORMATION: Synthetic peptide: d4
```

<400> SEQUENCE: 94

```
Met Asp Trp Thr Trp Arg Val Phe Cys Leu Leu Ala Val Ala Pro Gly
1               5                   10                  15

Ala His Ser Trp Ser His Pro Gln Phe Glu Lys Gln Val Gln Leu Val
            20                  25                  30

Gln Ser Gly Ala Glu Val Lys Lys Pro Gly Glu Ser Val Lys Val Ser
        35                  40                  45

Cys Lys Ala Ser Gly Tyr Thr Phe Thr Thr Tyr Tyr Leu His Trp Val
50                  55                  60

Arg Gln Ala Pro Gly Gln Gly Leu Glu Trp Met Gly Trp Ile Tyr Pro
65                  70                  75                  80

Gly Asn Gly His Ala Gln Tyr Asn Glu Lys Phe Lys Gly Arg Val Thr
                85                  90                  95

Ile Thr Ala Asp Lys Ser Thr Ser Thr Ala Tyr Met Glu Leu Ser Ser
            100                 105                 110

Leu Arg Ser Glu Asp Thr Ala Val Tyr Tyr Cys Ala Arg Ser Trp Glu
        115                 120                 125

Gly Phe Pro Tyr Trp Gly Gln Gly Thr Thr Val Thr Val Ser Ser Gly
130                 135                 140

Gly Gly Gly Ser Gly Gly Gly Gly Ser Gly Gly Gly Gly Ser Gly Gly
145                 150                 155                 160

Gly Gly Ser Asp Ile Gln Met Thr Gln Ser Pro Ser Ser Leu Ser Ala
                165                 170                 175

Ser Val Gly Asp Arg Val Thr Ile Thr Cys Lys Ala Ser Gln Asn Val
            180                 185                 190

Gly Ile Asn Val Ala Trp Tyr Gln Gln Lys Pro Gly Lys Ala Pro Lys
        195                 200                 205

Leu Leu Ile Ser Ser Ala Ser Tyr Arg Tyr Ser Gly Val Pro Ser Arg
210                 215                 220

Phe Ser Gly Ser Gly Ser Gly Thr Asp Phe Thr Leu Thr Ile Ser Ser
225                 230                 235                 240

Leu Gln Pro Glu Asp Phe Ala Thr Tyr Phe Cys Gln Gln Tyr Asp Thr
                245                 250                 255

Tyr Pro Phe Thr Phe Gly Gln Gly Thr Lys Val Glu Ile Lys Gly Gly
            260                 265                 270

Gly Gly Ser Gly Gly Gly Gly Ser Glu Pro Lys Ser Ser Asp Lys Thr
        275                 280                 285

His Thr Cys Pro Pro Cys Pro Ala Pro Glu Leu Leu Gly Gly Pro Ser
290                 295                 300

Val Phe Leu Phe Pro Pro Lys Pro Lys Asp Thr Leu Met Ile Ser Arg
305                 310                 315                 320

Thr Pro Glu Val Thr Cys Val Val Val Asp Val Ser His Glu Asp Pro
                325                 330                 335

Glu Val Lys Phe Asn Trp Tyr Val Asp Gly Val Glu Val His Asn Ala
            340                 345                 350

Lys Thr Lys Pro Arg Glu Glu Gln Tyr Asn Ser Thr Tyr Arg Val Val
        355                 360                 365

Ser Val Leu Thr Val Leu His Gln Asp Trp Leu Asn Gly Lys Glu Tyr
370                 375                 380

Lys Cys Lys Val Ser Asn Lys Ala Leu Pro Ala Pro Ile Glu Lys Thr
385                 390                 395                 400

Ile Ser Lys Ala Lys Gly Gln Pro Arg Glu Pro Ser Val Phe Pro Leu
                405                 410                 415
```

```
Ala Pro Ser Ser Lys Ser Thr Ser Gly Gly Thr Ala Ala Leu Gly Cys
            420                 425                 430

Leu Val Lys Asp Phe Tyr Pro Ser Asp Ile Ala Val Glu Trp Glu Ser
            435                 440                 445

Asn Gly Gln Pro Glu Asn Asn Tyr His Thr Phe Pro Ala Val Leu Gln
            450                 455                 460

Ser Ser Gly Leu Tyr Ser Leu Ser Ser Val Val Thr Val Pro Ser Ser
465                 470                 475                 480

Ser Leu Gly Thr Asn Thr Tyr Ile Cys Ser Val Met His Glu Ala Leu
            485                 490                 495

His Asn His Tyr Val Gln Lys Ser Val Glu Pro Lys Ser Cys
            500                 505                 510

<210> SEQ ID NO 95
<211> LENGTH: 511
<212> TYPE: PRT
<213> ORGANISM: Artificial Sequence
<220> FEATURE:
<223> OTHER INFORMATION: Synthetic peptide: d5

<400> SEQUENCE: 95

Met Asp Trp Thr Trp Arg Val Phe Cys Leu Leu Ala Val Ala Pro Gly
1               5                   10                  15

Ala His Ser Trp Ser His Pro Gln Phe Glu Lys Gln Val Gln Leu Val
            20                  25                  30

Gln Ser Gly Ala Glu Val Lys Lys Pro Gly Glu Ser Val Lys Val Ser
            35                  40                  45

Cys Lys Ala Ser Gly Tyr Thr Phe Thr Thr Tyr Tyr Leu His Trp Val
50                  55                  60

Arg Gln Ala Pro Gly Gln Gly Leu Glu Trp Met Gly Trp Ile Tyr Pro
65                  70                  75                  80

Gly Asn Gly His Ala Gln Tyr Asn Glu Lys Phe Lys Gly Arg Val Thr
            85                  90                  95

Ile Thr Ala Asp Lys Ser Thr Ser Thr Ala Tyr Met Glu Leu Ser Ser
            100                 105                 110

Leu Arg Ser Glu Asp Thr Ala Val Tyr Tyr Cys Ala Arg Ser Trp Glu
            115                 120                 125

Gly Phe Pro Tyr Trp Gly Gln Gly Thr Thr Val Thr Val Ser Ser Gly
            130                 135                 140

Gly Gly Gly Ser Gly Gly Gly Gly Ser Gly Gly Gly Gly Ser Gly Gly
145                 150                 155                 160

Gly Gly Ser Asp Ile Gln Met Thr Gln Ser Pro Ser Ser Leu Ser Ala
            165                 170                 175

Ser Val Gly Asp Arg Val Thr Ile Thr Cys Lys Ala Ser Gln Asn Val
            180                 185                 190

Gly Ile Asn Val Ala Trp Tyr Gln Gln Lys Pro Gly Lys Ala Pro Lys
            195                 200                 205

Leu Leu Ile Ser Ser Ala Ser Tyr Arg Tyr Ser Gly Val Pro Ser Arg
            210                 215                 220

Phe Ser Gly Ser Gly Ser Gly Thr Asp Phe Thr Leu Thr Ile Ser Ser
225                 230                 235                 240

Leu Gln Pro Glu Asp Phe Ala Thr Tyr Phe Cys Gln Gln Tyr Asp Thr
            245                 250                 255

Tyr Pro Phe Thr Phe Gly Gln Gly Thr Lys Val Glu Ile Lys Gly Gly
            260                 265                 270
```

```
Gly Gly Ser Gly Gly Gly Ser Glu Pro Lys Ser Asp Lys Thr
        275                 280                 285

His Thr Cys Pro Pro Cys Pro Ala Pro Glu Leu Leu Gly Gly Pro Ser
    290                 295                 300

Val Phe Leu Phe Pro Pro Lys Pro Lys Asp Thr Leu Met Ile Ser Arg
305                 310                 315                 320

Thr Pro Glu Val Thr Cys Val Val Val Asp Val Ser His Glu Asp Pro
                325                 330                 335

Glu Val Lys Phe Asn Trp Tyr Val Asp Gly Val Glu Val His Asn Ala
                340                 345                 350

Lys Thr Lys Pro Arg Glu Glu Gln Tyr Asn Ser Thr Tyr Arg Val Val
            355                 360                 365

Ser Val Leu Thr Val Leu His Gln Asp Trp Leu Asn Gly Lys Glu Tyr
        370                 375                 380

Lys Cys Lys Val Ser Asn Lys Ala Leu Pro Ala Pro Ile Glu Lys Thr
385                 390                 395                 400

Ile Ser Lys Ala Lys Gly Ser Gly Gln Pro Arg Glu Pro Ser Val Phe
                405                 410                 415

Pro Leu Ala Pro Ser Ser Lys Ser Thr Ser Gly Gly Thr Ala Ala Leu
                420                 425                 430

Gly Cys Leu Val Lys Asp Tyr Phe Pro Glu Pro Val Thr Val Ser Trp
            435                 440                 445

Asn Ser Gly Ala Leu Thr Ser Gly Val His Thr Phe Pro Ala Val Leu
        450                 455                 460

Gln Ser Ser Gly Leu Tyr Ser Leu Ser Ser Val Val Thr Val Pro Ser
465                 470                 475                 480

Ser Ser Leu Gly Thr Gln Thr Tyr Ile Cys Asn Val Met His Glu Ala
                485                 490                 495

Leu His Asn His Tyr Val Asp Lys Lys Val Glu Pro Lys Ser Cys
                500                 505                 510

<210> SEQ ID NO 96
<211> LENGTH: 511
<212> TYPE: PRT
<213> ORGANISM: Artificial Sequence
<220> FEATURE:
<223> OTHER INFORMATION: Synthetic peptide: d6

<400> SEQUENCE: 96

Met Asp Trp Thr Trp Arg Val Phe Cys Leu Leu Ala Val Ala Pro Gly
1               5                   10                  15

Ala His Ser Trp Ser His Pro Gln Phe Glu Lys Gln Val Gln Leu Val
                20                  25                  30

Gln Ser Gly Ala Glu Val Lys Lys Pro Gly Glu Ser Val Lys Val Ser
            35                  40                  45

Cys Lys Ala Ser Gly Tyr Thr Phe Thr Thr Tyr Leu His Trp Val
        50                  55                  60

Arg Gln Ala Pro Gly Gln Gly Leu Glu Trp Met Gly Trp Ile Tyr Pro
65                  70                  75                  80

Gly Asn Gly His Ala Gln Tyr Asn Glu Lys Phe Lys Gly Arg Val Thr
                85                  90                  95

Ile Thr Ala Asp Lys Ser Thr Ser Thr Ala Tyr Met Glu Leu Ser Ser
                100                 105                 110

Leu Arg Ser Glu Asp Thr Ala Val Tyr Tyr Cys Ala Arg Ser Trp Glu
            115                 120                 125
```

```
Gly Phe Pro Tyr Trp Gly Gln Gly Thr Thr Val Thr Val Ser Ser Gly
    130                 135                 140

Gly Gly Gly Ser Gly Gly Gly Ser Gly Gly Gly Ser Gly Gly
145                 150                 155                 160

Gly Gly Ser Asp Ile Gln Met Thr Gln Ser Pro Ser Ser Leu Ser Ala
                165                 170                 175

Ser Val Gly Asp Arg Val Thr Ile Thr Cys Lys Ala Ser Gln Asn Val
            180                 185                 190

Gly Ile Asn Val Ala Trp Tyr Gln Gln Lys Pro Gly Lys Ala Pro Lys
        195                 200                 205

Leu Leu Ile Ser Ser Ala Ser Tyr Arg Tyr Ser Gly Val Pro Ser Arg
    210                 215                 220

Phe Ser Gly Ser Gly Ser Gly Thr Asp Phe Thr Leu Thr Ile Ser Ser
225                 230                 235                 240

Leu Gln Pro Glu Asp Phe Ala Thr Tyr Phe Cys Gln Gln Tyr Asp Thr
                245                 250                 255

Tyr Pro Phe Thr Phe Gly Gln Gly Thr Lys Val Glu Ile Lys Gly Gly
            260                 265                 270

Gly Gly Ser Gly Gly Gly Ser Glu Pro Lys Ser Ser Asp Lys Thr
        275                 280                 285

His Thr Cys Pro Pro Cys Pro Ala Pro Glu Leu Leu Gly Gly Pro Ser
    290                 295                 300

Val Phe Leu Phe Pro Pro Lys Pro Lys Asp Thr Leu Met Ile Ser Arg
305                 310                 315                 320

Thr Pro Glu Val Thr Cys Val Val Val Asp Val Ser His Glu Asp Pro
                325                 330                 335

Glu Val Lys Phe Asn Trp Tyr Val Asp Gly Val Glu Val His Asn Ala
            340                 345                 350

Lys Thr Lys Pro Arg Glu Glu Gln Tyr Asn Ser Thr Tyr Arg Val Val
        355                 360                 365

Ser Val Leu Thr Val Leu His Gln Asp Trp Leu Asn Gly Lys Glu Tyr
    370                 375                 380

Lys Cys Lys Val Ser Asn Lys Ala Leu Pro Ala Pro Ile Glu Lys Thr
385                 390                 395                 400

Ile Ser Lys Ala Lys Gly Ser Gly Gln Pro Arg Glu Pro Ser Val Phe
                405                 410                 415

Pro Leu Ala Pro Ser Ser Lys Ser Thr Ser Gly Gly Thr Ala Ala Leu
            420                 425                 430

Gly Cys Leu Val Lys Asp Tyr Tyr Pro Ser Asp Val Ala Val Ser Trp
        435                 440                 445

Asn Ser Gly Ala Leu Thr Ser Gly Val His Thr Phe Pro Ala Val Leu
    450                 455                 460

Gln Ser Ser Gly Leu Tyr Ser Leu Ser Ser Val Val Thr Val Pro Ser
465                 470                 475                 480

Ser Ser Leu Gly Thr Gln Thr Tyr Ile Cys Asn Val Met His Glu Ala
                485                 490                 495

Leu His Asn His Tyr Val Asp Lys Lys Val Glu Pro Lys Ser Cys
            500                 505                 510

<210> SEQ ID NO 97
<211> LENGTH: 511
<212> TYPE: PRT
<213> ORGANISM: Artificial Sequence
<220> FEATURE:
```

<223> OTHER INFORMATION: Synthetic peptide: d7

<400> SEQUENCE: 97

```
Met Asp Trp Thr Trp Arg Val Phe Cys Leu Leu Ala Val Ala Pro Gly
1               5                   10                  15

Ala His Ser Trp Ser His Pro Gln Phe Glu Lys Gln Val Gln Leu Val
            20                  25                  30

Gln Ser Gly Ala Glu Val Lys Lys Pro Gly Glu Ser Val Lys Val Ser
        35                  40                  45

Cys Lys Ala Ser Gly Tyr Thr Phe Thr Thr Tyr Leu His Trp Val
50                  55                  60

Arg Gln Ala Pro Gly Gln Gly Leu Glu Trp Met Gly Trp Ile Tyr Pro
65                  70                  75                  80

Gly Asn Gly His Ala Gln Tyr Asn Glu Lys Phe Lys Gly Arg Val Thr
                85                  90                  95

Ile Thr Ala Asp Lys Ser Thr Ser Thr Ala Tyr Met Glu Leu Ser Ser
            100                 105                 110

Leu Arg Ser Glu Asp Thr Ala Val Tyr Tyr Cys Ala Arg Ser Trp Glu
        115                 120                 125

Gly Phe Pro Tyr Trp Gly Gln Gly Thr Thr Val Thr Val Ser Ser Gly
130                 135                 140

Gly Gly Gly Ser Gly Gly Gly Ser Gly Gly Gly Ser Gly Gly
145                 150                 155                 160

Gly Gly Ser Asp Ile Gln Met Thr Gln Ser Pro Ser Ser Leu Ser Ala
                165                 170                 175

Ser Val Gly Asp Arg Val Thr Ile Thr Cys Lys Ala Ser Gln Asn Val
            180                 185                 190

Gly Ile Asn Val Ala Trp Tyr Gln Gln Lys Pro Gly Lys Ala Pro Lys
        195                 200                 205

Leu Leu Ile Ser Ser Ala Ser Tyr Arg Tyr Ser Gly Val Pro Ser Arg
210                 215                 220

Phe Ser Gly Ser Gly Ser Gly Thr Asp Phe Thr Leu Thr Ile Ser Ser
225                 230                 235                 240

Leu Gln Pro Glu Asp Phe Ala Thr Tyr Phe Cys Gln Gln Tyr Asp Thr
                245                 250                 255

Tyr Pro Phe Thr Phe Gly Gln Gly Thr Lys Val Glu Ile Lys Gly Gly
            260                 265                 270

Gly Gly Ser Gly Gly Gly Ser Glu Pro Lys Ser Ser Asp Lys Thr
        275                 280                 285

His Thr Cys Pro Pro Cys Pro Ala Pro Glu Leu Leu Gly Gly Pro Ser
290                 295                 300

Val Phe Leu Phe Pro Pro Lys Pro Lys Asp Thr Leu Met Ile Ser Arg
305                 310                 315                 320

Thr Pro Glu Val Thr Cys Val Val Val Asp Val Ser His Glu Asp Pro
                325                 330                 335

Glu Val Lys Phe Asn Trp Tyr Val Asp Gly Val Glu Val His Asn Ala
            340                 345                 350

Lys Thr Lys Pro Arg Glu Glu Gln Tyr Asn Ser Thr Tyr Arg Val Val
        355                 360                 365

Ser Val Leu Thr Val Leu His Gln Asp Trp Leu Asn Gly Lys Glu Tyr
370                 375                 380

Lys Cys Lys Val Ser Asn Lys Ala Leu Pro Ala Pro Ile Glu Lys Thr
385                 390                 395                 400
```

```
Ile Ser Lys Ala Lys Gly Ser Gly Gln Pro Arg Glu Pro Ser Val Phe
                405                 410                 415

Pro Leu Ala Pro Ser Ser Lys Ser Thr Ser Gly Gly Thr Ala Ala Leu
            420                 425                 430

Gly Cys Leu Val Lys Asp Phe Tyr Pro Ser Asp Ile Ala Val Glu Trp
            435                 440                 445

Glu Ser Gly Ala Leu Thr Ser Gly Val His Thr Phe Pro Ala Val Leu
        450                 455                 460

Gln Ser Ser Gly Leu Tyr Ser Leu Ser Ser Val Val Thr Val Pro Ser
465                 470                 475                 480

Ser Ser Leu Gly Thr Gln Thr Tyr Ile Cys Ser Val Met His Glu Ala
                485                 490                 495

Leu His Asn His Tyr Val Gln Lys Ser Val Glu Pro Lys Ser Cys
                500                 505                 510

<210> SEQ ID NO 98
<211> LENGTH: 512
<212> TYPE: PRT
<213> ORGANISM: Artificial Sequence
<220> FEATURE:
<223> OTHER INFORMATION: Synthetic peptide: d8

<400> SEQUENCE: 98

Met Asp Trp Thr Trp Arg Val Phe Cys Leu Leu Ala Val Ala Pro Gly
1               5                   10                  15

Ala His Ser Trp Ser His Pro Gln Phe Glu Lys Gln Val Gln Leu Val
            20                  25                  30

Gln Ser Gly Ala Glu Val Lys Lys Pro Gly Glu Ser Val Lys Val Ser
        35                  40                  45

Cys Lys Ala Ser Gly Tyr Thr Phe Thr Thr Tyr Leu His Trp Val
    50                  55                  60

Arg Gln Ala Pro Gly Gln Gly Leu Glu Trp Met Gly Trp Ile Tyr Pro
65                  70                  75                  80

Gly Asn Gly His Ala Gln Tyr Asn Glu Lys Phe Lys Gly Arg Val Thr
                85                  90                  95

Ile Thr Ala Asp Lys Ser Thr Ser Thr Ala Tyr Met Glu Leu Ser Ser
            100                 105                 110

Leu Arg Ser Glu Asp Thr Ala Val Tyr Tyr Cys Ala Arg Ser Trp Glu
        115                 120                 125

Gly Phe Pro Tyr Trp Gly Gln Gly Thr Thr Val Thr Val Ser Ser Gly
    130                 135                 140

Gly Gly Gly Ser Gly Gly Gly Gly Ser Gly Gly Gly Gly Ser Gly Gly
145                 150                 155                 160

Gly Gly Ser Asp Ile Gln Met Thr Gln Ser Pro Ser Ser Leu Ser Ala
                165                 170                 175

Ser Val Gly Asp Arg Val Thr Ile Thr Cys Lys Ala Ser Gln Asn Val
            180                 185                 190

Gly Ile Asn Val Ala Trp Tyr Gln Gln Lys Pro Gly Lys Ala Pro Lys
        195                 200                 205

Leu Leu Ile Ser Ser Ala Ser Tyr Arg Tyr Ser Gly Val Pro Ser Arg
    210                 215                 220

Phe Ser Gly Ser Gly Ser Gly Thr Asp Phe Thr Leu Thr Ile Ser Ser
225                 230                 235                 240

Leu Gln Pro Glu Asp Phe Ala Thr Tyr Phe Cys Gln Gln Tyr Asp Thr
                245                 250                 255
```

Tyr Pro Phe Thr Phe Gly Gln Gly Thr Lys Val Glu Ile Lys Gly Gly
            260                 265                 270

Gly Gly Ser Gly Gly Gly Ser Glu Pro Lys Ser Ser Asp Lys Thr
    275                 280                 285

His Thr Cys Pro Pro Cys Pro Ala Pro Glu Leu Leu Gly Gly Pro Ser
290                 295                 300

Val Phe Leu Phe Pro Pro Lys Pro Lys Asp Thr Leu Met Ile Ser Arg
305                 310                 315                 320

Thr Pro Glu Val Thr Cys Val Val Val Asp Val Ser His Glu Asp Pro
                325                 330                 335

Glu Val Lys Phe Asn Trp Tyr Val Asp Gly Val Glu Val His Asn Ala
            340                 345                 350

Lys Thr Lys Pro Arg Glu Glu Gln Tyr Asn Ser Thr Tyr Arg Val Val
        355                 360                 365

Ser Val Leu Thr Val Leu His Gln Asp Trp Leu Asn Gly Lys Glu Tyr
370                 375                 380

Lys Cys Lys Val Ser Asn Lys Ala Leu Pro Ala Pro Ile Glu Lys Thr
385                 390                 395                 400

Ile Ser Lys Ala Lys Gly Ser Gly Gln Pro Arg Glu Pro Ser Val Phe
                405                 410                 415

Pro Leu Ala Pro Ser Ser Lys Ser Thr Ser Gly Gly Thr Ala Ala Leu
            420                 425                 430

Gly Cys Leu Val Lys Asp Phe Tyr Pro Ser Asp Ile Ala Val Glu Trp
        435                 440                 445

Glu Ser Asn Gly Gln Pro Glu Asn Asn Tyr His Thr Phe Pro Ala Val
450                 455                 460

Leu Gln Ser Ser Gly Leu Tyr Ser Leu Ser Val Val Thr Val Pro
465                 470                 475                 480

Ser Ser Ser Leu Gly Thr Asn Thr Tyr Ile Cys Ser Val Met His Glu
                485                 490                 495

Ala Leu His Asn His Tyr Val Gln Lys Ser Val Glu Pro Lys Ser Cys
            500                 505                 510

<210> SEQ ID NO 99
<211> LENGTH: 15
<212> TYPE: PRT
<213> ORGANISM: Homo sapiens
<220> FEATURE:
<221> NAME/KEY: misc_feature
<222> LOCATION: (1)..(15)
<223> OTHER INFORMATION: IgG3 middle region

<400> SEQUENCE: 99

Glu Pro Lys Ser Cys Asp Thr Pro Pro Cys Pro Arg Cys Pro
1               5                   10                  15

<210> SEQ ID NO 100
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

```
Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
                100                 105

<210> SEQ ID NO 101
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val
```